(12) United States Patent
Steele et al.

(10) Patent No.: US 11,618,906 B2
(45) Date of Patent: Apr. 4, 2023

(54) HYDROXYLATION TECHNIQUES

(71) Applicant: HYPHA DISCOVERY LTD., Abingdon (GB)

(72) Inventors: Jonathan Charles Paul Steele, Maidenhead (GB); Antonio De Riso, Uxbridge (GB); Francesco Falcioni, Manchester (GB); Richard Kerry Phipps, Aylesbury (GB); Stephen Keith Wrigley, High Wycombe (GB); Kinga Linda Nytko, Slough (GB); Vincent Poon, Bicester (GB); Sebastian Schulz, Dresden (DE); John Maxim Ward, London (GB); Mariacristina Bawn, Royston (GB)

(73) Assignee: HYPHA DISCOVERY LTD., Abingdon (GB)

( * ) Notice: Subject to any disclaimer, the term of this patent is extended or adjusted under 35 U.S.C. 154(b) by 0 days.

(21) Appl. No.: 17/055,353

(22) PCT Filed: May 14, 2019

(86) PCT No.: PCT/GB2019/051313
§ 371 (c)(1),
(2) Date: Nov. 13, 2020

(87) PCT Pub. No.: WO2019/220093
PCT Pub. Date: Nov. 21, 2019

(65) Prior Publication Data
US 2021/0230642 A1 Jul. 29, 2021

(30) Foreign Application Priority Data
May 14, 2018 (GB) ..................................... 1807815

(51) Int. Cl.
| | | |
|---|---|---|
| C12N 1/20 | (2006.01) | |
| C12P 7/66 | (2006.01) | |
| C12P 7/02 | (2006.01) | |
| C12P 17/16 | (2006.01) | |
| C12P 17/18 | (2006.01) | |

(52) U.S. Cl.
CPC .................. *C12P 7/02* (2013.01); *C12P 7/66* (2013.01); *C12P 17/165* (2013.01); *C12P 17/167* (2013.01); *C12P 17/182* (2013.01)

(58) Field of Classification Search
CPC ............. C12P 7/02; C12P 7/66; C12P 17/165; C12P 17/182; C12P 17/167; C12Y 114/00
USPC .......... 435/195, 189, 155, 156, 252.3, 320.1
See application file for complete search history.

(56) References Cited

U.S. PATENT DOCUMENTS

| 6,884,608 B2 | 4/2005 | Basch et al. |
| 2010/0313300 A1 | 12/2010 | Nakajima et al. |
| 2014/0038850 A1 | 2/2014 | Fasan et al. |

FOREIGN PATENT DOCUMENTS

| CN | 109022515 | 12/2018 |
| WO | 02/083062 | 10/2002 |
| WO | 02/092801 | 11/2002 |
| WO | 03/057830 | 7/2003 |
| WO | 2004/078978 | 9/2004 |
| WO | 2011/038313 | 3/2011 |
| WO | 2012/109586 | 8/2012 |
| WO | 2013/073775 | 5/2013 |
| WO | 2016/007623 | 1/2016 |
| WO | 2018/091885 | 5/2018 |

OTHER PUBLICATIONS

Basch, Jonathan et al., "Cloning and expression of a cytochrome P450 hydroxylase gene from Amycolatopsis orientalis: hydroxylation of epothilone B for the production of epothilone F", J Ind Microbiol Biotechnol, vol. 34, 2007, pp. 171-176.
International Search Report dated Sep. 13, 2019 in International (PCT) Application No. PCT/GB2019/051313.
Metal Ions in Life Sciences, vol. 3 "The Ubiquitous Roles of Cytochrome P450 Proteins", Sigel, A., Sigel, H and Sigel R.K.O. eds., John Wiley & Sons Ltd, 2007, pp. 1-667, XP055611890.
Kwun, Min Jung et al., "Draft Genome Sequence of *Amycolatopsis lurida* NRRL 2430, Producer of the Glycopeptide Family Antibiotic Ristocetin", Genome Announcements, Sep./Oct. 2014, vol. 2, Issue 5, e01050-14, p. 1.
Adam, Waldemar et al., "Biocatalytic Asymmetric Hydroxylation of Hydrocarbons with the Topsoil-Microorganism *Bacillus megaterium*", Journal of Organic Chemistry, 2000, vol. 65, No. 3, pp. 878-882.
Appleby, C.A. "A soluble haemoprotein P 450 from nitrogen-fixing Rhizobium bacteroids", Preliminary Notes, Biochimica et Biophysica Acta, 1967, vol. 147, No. 2, pp. 399-402.
Broadbent, D.A. et al., "Bacterial attack on phenolic ethers Electron acceptor-substrate binding proteins in bacterial O-dealkylases: purification and characterization of cytochrome $P450_{npd}$ of *Nocardia*", Microbios, 1974, vol. 9, pp. 119-130.
Danielson, P.B., "The Cytochrome P450 Superfamily: Biochemistry, Evolution and Drug Metabolism in Humans", Current Drug Metabolism, 2002, vol. 3, No. 6, pp. 561-597.
Dennig, A., "Engineering of cytochrome P450 monooxygenases for application in phenol synthesis", Aachen University, 2013, pp. 1-222.

(Continued)

*Primary Examiner* — Tekchand Saidha
*Assistant Examiner* — Mohammad Y Meah
(74) *Attorney, Agent, or Firm* — Wenderoth, Lind & Ponack, L.L.P.

(57) ABSTRACT

The use of a cytochrome P-450 enzyme comprising SEQ ID NO: 110, or a variant enzyme having at least 70% identity thereto and having CYP-450 activity, for the hydroxylation of an organic compound, wherein the amino acid residue at position 291 is not threonine.

20 Claims, 30 Drawing Sheets

Specification includes a Sequence Listing.

(56) References Cited

OTHER PUBLICATIONS

Di Nardo, Giovanna et al., "Optimization of the Bacterial Cytochrome P450 BM3 System for the Production of Human Drug Metabolites", International Journal of Molecular Sciences, 2012, vol. 13, pp. 15901-15924.
Fasan, Rudi, "Turning P450 Enzymes as Oxidation Catalysts", ACS Catalysis, 2012, vol. 2, pp. 647-666.
Girvan, Hazel M et al., "Applications of microbial cytochrome P450 enzymes in biotechnology and synthetic biology", Current Opinion in Chemical Biology, 2016, vol. 31, pp. 136-145.
Hanukoglu, Israel, "Electron Transfer Proteins of Cytochrome P450 Systems", Advances in Molecular and Cell Biology, 1996, vol. 14, pp. 29-56.
Hussain, Haitham A. et al., "Enhanced Heterologous Expression of Two *Streptomyces griseolus* Cytochrome P450s and *Streptomyces coelicolor* Ferredoxin Reductase as Potentially Efficient Hydroxylation Catalysts", Applied and Environmental Microbiology, Jan. 2003, vol. 69, No. 1, pp. 373-382.
Lamb, David C. et al., "The First Virally Encoded Cytochrome P450", Journal of Virology, Aug. 2009, vol. 83, No. 16, pp. 8266-8269.
Lamb, David C. et al., "Unusual properties of the cytochrome P450 superfamily", Philosophical Transactions of the Royal Society B, 2013, pp. 1-13.
Le Gal, Annabelle et al., "Diversity of selective environmental substrates for human cytochrome P450 2A6: alkoxyethers, nicotine, coumarin, N-nitrosodiethylamine, and N-nitrosobenzylmethylamine", Toxicology Letters, 2003, vol. 144, pp. 77-91.
Lepri, Susan et al., "Metabolism study and biological evaluation of bosentan derivatives", European Journal of Medicinal Chemistry, 2016, vol. 121, pp. 658-670.
Mäntylä, Antti et al., "Synthesis and antileishmanial activity of novel buparvaquone oxime derivatives", Bioorganic & Medicinal Chemistry, 2004, vol. 12, pp. 3497-3502.
Nakamura, Katsunori et al., "Coumarin Substrates for Cytochrome P450 2D6 Fluorescence Assays", Analytical Biochemistry, 2001, vol. 292, pp. 280-286.
Narhi, Linda Owers et al., "Characterization of a Catalytically Self-sufficient 119,000-Dalton Cytochrome P-450 Monooxygenase Induced by Barbiturates in *Bacillus megaterium*", Journal of Biological Chemistry, vol. 261, No. 10, 1986, pp. 7160-7169.
Roper, Laila et al., "Biocatalysis for Organic Chemists: Hydroxylations", Chapter 8, Organic Synthesis Using Biocatalysis, 2016, pp. 213-241.
Sariaslani, F. Sima et al., "Induction Of Cytochrome P-450 in *Streptomyces griseus* by Soybean Flour", Biochemical and Biophysical Research Communications, Dec. 15, 1986, vol. 141, No. 2, pp. 405-410.
Schwalb, Herzl et al., "Purification and characterization of pentobarbital-induced cytochrome P-450$_{BM-1}$ from *Bacillus megaterium* ATCC 14581", Biochimica et Biophysica Acta. 1985, vol. 838, pp. 302-311.
Shafiee, Ali et al., "Macrolide Antibiotic Biosynthesis: Isolation and Properties of Two Forms of 6-Deoxyerythronolide B Hydroxylase from *Saccharopolyspora erythraea* (*Streptomyces erythreus*)", Biochemistry, vol. 26, No. 19, 1987, pp. 6204-6210.

Yu, C-A. et al., "Cytochrome P-450$_{cam}$", The Journal of Biological Chemistry, 1974, vol. 249, No. 1, pp. 94-101.
UniProtKB/trEMBL entry A0A075VAF5 for Cytochrome P450, *Amycolatopsis japonica*, dated Oct. 25, 2017.
UniProtKB/trEMBL entry A0A093BCG8 for Cytochrome P450, *Amycolatopsis lurida*, dated Nov. 26, 2014.
International Search Report and Written Opinion of the International Searching Authority dated Jun. 23, 2020 in International (PCT) Application No. PCT/GB2019/053337.
International Search Report and Written Opinion of the International Searching Authority dated Feb. 26, 2021 in International (PCT) Application No. PCT/GB2020/052982.
Worsch, Anne et al., "A novel cytochrome P450 mono-oxygenase from *Streptomyces platensis* resembles activities of human drug metabolizing P450s", Biotechnology and Bioengineering, 2018, vol. 115(9), pp. 2156-2166.
Machida, Kazuhiro et al., "Increase in Pladienolide D Production Rate Using a *Streptomyces* Strain Overexpressing a Cytochrome P450 Gene", Journal of Bioscience and Bioengineering, 2008, vol. 105, No. 6, pp. 649-654.
Moody, Suzy C. et al., "CYP105- diverse structures, functions and roles in an intriguing family of enzymes in *Streptomyces*", Journal of Applied Microbiology, 2014, vol. 117(6), pp. 1549-1563.
Rudolf, Jeffrey D. et al., "Cytochromes P450 for natural product biosynthesis in *Streptomyces*: sequence, structure, and function", Natural Products Report, 2017, vol. 34(9), pp. 1141-1172.
Hayashi, Keiko et al., "Structure-based design of a highly active vitamin D hydroxylase from *Streptomyces griseolus* CYP105A1", Biochemistry, 2008, vol. 47(46), pp. 11964-11972 (Abstract only).
Sugimoto, Hiroshi et al., "Crystal Structure of CYP105A1 (P450SU-1) in Complex with 1α,25-Dihydroxyvitamin D$_3$", Biochemistry, 2008, vol. 47(13), pp. 4017-4027.
Ohta, Kazuo et al., "Production of Human Metabolites of Cyclosporin A, AM1, AM4N and AM9, by Microbial Conversion", Journal of Bioscience and Bioengineering, 2005, vol. 99, No. 4, pp. 390-395.
Sherwood, Emma J. et al., "Cloning and Analysis of the Planosporicin Lantibiotic Biosynthetic Gene Cluster of *Planomonospora alba*", Journal of Bacteriology, May 2013, vol. 195, No. 10, pp. 2309-2321.
Summers, D.K. et al., "Resolution of ColE1 dimers requires a DNA sequence implicated in the three-dimensional organization of the cer site", The EMBO Journal, 1988, vol. 7(3), pp. 851-858.
Thompson, Julie D. et al., "Clustal W: improving the sensitivity of progressive multiple sequence alignment through sequence weighting, position-specific gap penalties and weight matrix choice", Nucleic Acids Research, 1994, vol. 22, No. 22, pp. 4673-4680.
Xu, Lian-Hua et al., "Structural basis for the 4'-hydroxylation of diclofenac by a microbial cytochrome P450 monooxygenase", Appl. Microbiol. Biotech., Oct. 2014, 11 pages. DOI 10.1007/s00253-014-6148-y.
Yao, Qiuping et al., "Hydroxylation of Compactin (ML-236B) by CYP105D7 (SAV_7469) from *Streptomyces avermitilis*", J. Microbiol. Biotechnol., 2017, vol. 27(5), pp. 956-964.
Bell, Stephen G. et al., "Engineering the CYP101 system for in vivo oxidation of unnatural substrates", Protein Engineering, 2001, vol. 14, No. 10, pp. 797-802.
Kabumoto, Hiroki et al., "Directed Evolution of the Actinomycete Cytochrome P450 MoxA (CYP105) for Enhanced Activity", Biosci. Biotechnol. Biochem., 2009, vol. 73(9), pp. 1922-1927.
Liu, Ling et al., "Hydroxylation of flavanones by Cytocrhome P450 105D7 from *Streptomyces avermitilus*", J. Molec. Catalysis, 2016, vol. 132, pp. 91-97.

SEQ ID NO: 1

*ATGACTGACGTCGAGGAAACCACCGCGACCTTGCCGCTGGCCCGGAAATGCCCGTTTT*
*CGCCGCCGCCCGAATACGAACGGCTTCGCCGGGAAAGTCCGGTTTCCCGGGTCGGTC*
*TCCCGTCCGGTCAAACGGCTTGGGCGCTCACCCGGCTCGAAGACATCCGCGAAATGCT*
*GAGCAGCCCGCATTTCAGTTCCGACCGGCAGAGCCCGTCGTTCCCGCTGATGGTCGC*
*GCGGCAGATCCGCCGCGAGGACAAGCCGTTCCGCCCCTCCCTCATCGCGATGGATCC*
*GCCGGAACACAGCCGGGCCAGGCGTGACGTCGTCGGGGAATTCACCGTCAAGCGGAT*
*GAAGGCGCTCCAGCCGCGAATTCAGCAGATCGTCGACGAACATCTCGACGCCCTGCTC*
*GCGGGCCCCAAACCCGCCGATCTCGTCCAGGCGCTTTCCCTGCCCGTTCCCTCGCTG*
*GTGATCTGCGAACTGCTCGGCGTCCCCTATTCGGACCACGAGTTCTTCCAGTCCTGCA*
*GTTCCAGGATGCTCAGCCGGGAGGTCACCGCCGAAGAACGGATGACCGCGTTCGAGC*
*AGCTCGAAAACTATCTCGACGAACTGGTCACCAAGAAGGAGGCGAACGCCACCGAGGA*
*CGACCTCCTCGGCCGTCAGATCCTGAAACAGCGGGAAACGGGCGAGGCCGACCACGG*
*TGAACTCGTCGGGCTGGCGTTCCTGCTGCTCATCGCCGGACACGAGACCACGGCGAA*
*CATGATCTCGCTCGGCACGGTGACCCTGCTGGAGAATCCCGATCAGCTCGCGAAGATC*
*AAGGCAGACCCCGGCAAGACCCTCGCCGCCATCGAGGAACTCCTGCGGGTCTTCACG*
*ATCGCGGAAACGGCGACCTCACGCTTCGCCACGGCGGACGTCGAGATCGGCGGAACG*
*CTGATCCGCGCGGGGGAAGGGGTGGTGGGCCTGAGCAACGCGGGCAACCACGATCC*
*GGACGGCTTCGAGAACCCGGACACCTTCGACATCGAACGCGGCGCGGCATCACGT*
*CGCGTTCGGATTCGGGGTGCACCAGTGTCTCGGCCAGAACTTGGCGAGGTTGGAACTC*
*CAGATCGTCTTCGATACGTTGTTCCGGCGAGTGCCGGGCCTCCGGATCGCCGTTCCGG*
*TCGACGAACTGCCGTTCAAGCACGATTCGACGATCTACGGCCTCCACGCCCTTCCGGT*
*CACCTGGTAG*GAGGAGCC<u>ATGAAGATCATCGCGGACACCGGGAAATGCGTGGGCGCG</u>
<u>GGCCAGTGCGTGCTCACCGATCCCGATCTGTTCGATCAGAGCGAGGACGACGGAACG</u>
<u>GTCCTCGTGCTGAACGCCGAGCCTGAAGGCGAAGAGGCGGAAGAAAACGCCCGCACC</u>
<u>GCCGTGCACATCTGCCCGGGGCAGGCCTTGTCGCTCGCTTAA</u>TAGGAAGCTT*<u>ATGCCC</u>*
*<u>CGCCCTCTGCGGGTAGCCATCGTCGGATCCGGCCCGGCCGGGATCTACGCCGCCGAC</u>*
*<u>GCCCTGCTCAAGTCCGAAGTGGCCGCCGACCCCGGTGTTTCCATCGACATCTTCGAGC</u>*
*<u>GCATGCCCGCCCGTTCGGCCTCATCCGGTACGGCGTCGCGCCCGACCACCGCGGA</u>*
*<u>TCAAGGGCATCATCACGGCCCTCCACCAGGTGCTCGACAAGCCGCAGATCCGCCTCTT</u>*
*<u>CGGCAACGTGAACTACCCCACCGACGTCAGCCTGGACGATCTGCGCGCCTTCTACGAC</u>*
*<u>GGTGTGATCTTCGCCACCGGCGCCACGGCGGACCGGGACCTGTCCCTCCCGGGCATC</u>*
*<u>GACCTCGACGGCTCGTACGGCGCGGCCGACTTCGTCGCCTGGTACGACGGCCACCCC</u>*
*<u>GACTTCCCGCGCACCTGGCCGCTGGAGGCGGAGAAAGTCGCCGTCCTCGGTGTCGGC</u>*
*<u>AACGTCGCCCTGGACATCGCGCGCGTCCTCGCCAAGACGGCCGACGAGCTGCTGCCG</u>*
*<u>ACCGAGATCCCGCCGAACGTCTACGAGGGCCTCAAGGCCAACAAGGCGCTGGAGGTG</u>*
*<u>CACGTCTTCGGCCGCCGCGGCCCGGCGCAGGCGAAGTTCAGCCCGATGGAGCTGCG</u>*
*<u>GGAGCTGGACCACTCCCCAACATCGAGGTGATCGTCGACCCCGAGGACATCGACTAC</u>*
*<u>GACGAGGGCTCGATCGCGACCCGGCGCGGCAACAAGCAGGCCGACATGGTCGCCAA</u>*
*<u>GACCCTGGAGAACTGGGCGATCCGCGACGTCGGCGACCGGCCGCACAAGCTCTTCCT</u>*
*<u>GCACTTCTTCGAGTCGCCCGCGGAGATCCTCGGCGAGGACGGCAGGGTGACCGGCCT</u>*
*<u>GCGCACCGAGCGCACGGAGCTGGACGGCACGGGCAACGTCAAGGGCACCGGCGAGT</u>*
*<u>TCAAGGACTGGGACGTCCAGGCGGTCTACCGGGCCGTCGGCTACCTCTCCGACCAGC</u>*
*<u>TGCCCAAGCTGCCCTGGGACCTCGAGACGTGCACGGTCCCGGACGCGGGCGGCCGG</u>*
*<u>GTCGTCCAGGAGTCCGGCGAGCACCTCCAGTCGACGTACGTCACCGGCTGGATCCGG</u>*
*<u>CGCGGTCCGATCGGCCTGATCGGCCACACCAAGGGCGACGCCAACGAGACGGTGTCC</u>*
*<u>AACCTGCTGGACGACTACGCGAACGGCCGTCTCCAGACGCCCTCCTCCCCGCTCCC</u>*
*<u>GAGGCCGTGGACGCGTTCCTCGCCGAGCGGAACGTCCGCTTCACCACCTGGGACGGC</u>*
*<u>TGGTACCGGCTCGACGCCGCGGAGAAGGCGCAGGGCAACCGCACGGGCGTGAGCG</u>*
*<u>CGTGAAGTACGTCGAGCGCGAGGACATGCTCCGCGAGAGCGGCGCCTGA</u>*

*P450 (italics)*
<u>Ferredoxin (underline)</u>
*<u>Ferredoxin reductase (italics and underline)</u>*

Figure 1

Start and stop codons in bold

SEQ ID NO: 2 (amino acid sequence of AluC09 (404 aa))
MTDVEETTATLPLARKCPFSPPPEYERLRRESPVSRVGLPSGQTAWALTRLEDIREMLSS
PHFSSDRQSPSFPLMVARQIRREDKPFRPSLIAMDPPEHSRARRDVVGEFTVKRMKALQP
RIQQIVDEHLDALLAGPKPADLVQALSLPVPSLVICELLGVPYSDHEFFQSCSSRMLSRE
VTAEERMTAFEQLENYLDELVTKKEANATEDDLLGRQILKQRETGEADHGELVGLAFLLL
IAGHETTANMISLGTVTLLENPDQLAKIKADPGKTLAAIEELLRVFTIAETATSRFATAD
VEIGGTLIRAGEGVVGLSNAGNHDPDGFENPDTFDIERGARHHVAFGFGVHQCLGQNLAR
LELQIVFDTLFRRVPGLRIAVPVDELPFKHDSTIYGLHALPVTW- SEQ ID NO: 3 (amino acid sequence of AluF03 (64 aa))
MKIIADTGKCVGAGQCVLTDPDLFDQSEDDGTVLVLNAEPEGEEAEENARTAVHICPGQA
LSLA- SEQ ID NO: 4 (amino acid sequence of SCF15A (454 aa))
MPRPLRVAIVGSGPAGIYAADALLKSEVAADPGVSIDIFERMPAPFGLIRYGVAPDHPRI
KGIITALHQVLDKPQIRLFGNVNYPTDVSLDDLRAFYDGVIFATGATADRDLSLPGIDLD
GSYGAADFVAWYDGHPDFPRTWPLEAEKVAVLGVGNVALDIARVLAKTADELLPTEIPPN
VYEGLKANKALEVHVFGRRGPAQAKFSPMELRELDHSPNIEVIVDPEDIDYDEGSIATRR
GNKQADMVAKTLENWAIRDVGDRPHKLFLHFFESPAEILGEDGRVTGLRTERTELDGTGN
VKGTGEFKDWDVQAVYRAVGYLSDQLPKLPWDLETCTVPDAGGRVVQESGEHLQSTYVT
GWIRRGPIGLIGHTKGDANETVSNLLDDYANGRLQTPSSPAPEAVDAFLAERNVRFTTWDG
WYRLDAAEKAQGEPHGRERVKYVEREDMLRESGA- SEQ ID NO: 7 (nucleic acid sequence of aluC09M11)
ATGACTGACGTCGAGGAAACCACCGCGACCTTGCCGCTGGCCCGGAAATGCCCGTTTT
CGCCGCCGCCCGAATACGAACGGCTTCGCCGGGAAAGTCCGGTTTCCCGGGTCGGTC
TCCCGTCCGGTCAAACGGCTTGGGCGCTCACCCGGCTCGAAGACATCCGCGAAATGCT
GAGCAGCCCGCATTTCAGTTCCGACCGGCAGAGCCCGTCGTTCCCGCTGATGGTCGC
GCGGCAGATCCGCCGCGAGGACAAGCCGTTCCGCCCCTCCCTCATCGCGATGGATCC
GCCGGAACACAGCCGGGCCAGGCGTGACGTCGTCGGGGAATTCACCGTCAAGCGGAT
GAAGGCGCTCCAGCCGCGAATTCAGCAGATCGTCGACGAACATCTCGACGCCCTGCTC
GCGGGCCCCAAACCCGCCGATCTCGTCCAGGCGCTTTCCCTGCCCGTTCCCTCGCTG
GTGATCTGCGAACTGCTCGGCGTCCCCTATTCGGACCACGAGTTCTTCCAGTCCTGCA
GTTCCAGGATGCTCAGCCGGGAGGTCACCGCCGAAGAACGGATGACCGCGTTCGAGC
AGCTCGAAAACTATCTCGACGAACTGGTCACCAAGAAGGAGGCGAACGCCACCGAGGA
CGACCTCCTCGGCCGTCAGATCCTGAAACAGCGGGAAACGGGCGAGGCCGACCACGG
TGAACTCGTCGGGCTGGCGTTCCTGCTGCTCATCGCCGGACACGAGACCACGGCGAA
CATGATCTCGCTCGGCACGGTGACCCTGCTGGAGAATCCCGATCAGCTCGCGAAGATC
AAGGCAGACCCCGGCAAGACCCTCGCCGCCATCGAGGAACTCCTGCGGGTCTTCACG
ATCGCGGAAGATGCGACCTCACGCTTCGCCACGGCGGACGTCGAGATCGGCGGAACG
CTGATCCGCGCGGGGGAAGGGGTGGTGGGCCTGAGCAACGCGGGCAACCACGATCC
GGACGGCTTCGAGAACCCGGACACCTTCGACATCGAACGCGGCGCGCGGCATCACGT
CGCGTTCGGATTCGGGGTGCACCAGTGTCTCGGCCAGAACTTGGCGAGGTTGGAACTC
CAGATCGTCTTCGATACGTTGTTCCGGCGAGTGCCGGGCCTCCGGATCGCCGTTCCGG
TCGACGAACTGCCGTTCAAGCACGATTCGACGATCTACGGCCTCCACGCCCTTCCGGT
CACCTGGTAG SEQ ID NO: 8 (amino acid sequence of AluC09M11 (404aa))
MTDVEETTATLPLARKCPFSPPPEYERLRRESPVSRVGLPSGQTAWALTRLEDIREMLSSP
HFSSDRQSPSFPLMVARQIRREDKPFRPSLIAMDPPEHSRARRDVVGEFTVKRMKALQPRI
QQIVDEHLDALLAGPKPADLVQALSLPVPSLVICELLGVPYSDHEFFQSCSSRMLSREVTAE
ERMTAFEQLENYLDELVTKKEANATEDDLLGRQILKQRETGEADHGELVGLAFLLLIAGHET
TANMISLGTVTLLENPDQLAKIKADPGKTLAAIEELLRVFTIAEDATSRFATADVEIGGTLIRAG
EGVVGLSNAGNHDPDGFENPDTFDIERGARHHVAFGFGVHQCLGQNLARLELQIVFDTLFR
RVPGLRIAVPVDELPFKHDSTIYGLHALPVTW-

Figure 1 (continued)

SEQ ID NO: 11 (nucleic acid sequence of aluC09M12)
ATGACTGACGTCGAGGAAACCACCGCGACCTTGCCGCTGGCCCGGAAATGCCCGTTTT
CGCCGCCGCCCGAATACGAACGGCTTCGCCGGGAAAGTCCGGTTTCCCGGGTCGGTC
TCCCGTCCGGTCAAACGGCTTGGGCGCTCACCCGGCTCGAAGACATCCGCGAAATGCT
GAGCAGCCCGCATTTCAGTTCCGACCGGCAGAGCCCGTCGTTCCCGCTGATGGTCGC
GCGGCAGATCCGCCGCGAGGACAAGCCGTTCCGCCCCTCCCTCATCGCGATGGATCC
GCCGGAACACAGCCGGGCCAGGCGTGACGTCGTCGGGGAATTCACCGTCAAGCGGAT
GAAGGCGCTCCAGCCGCGAATTCAGCAGATCGTCGACGAACATCTCGACGCCCTGCTC
GCGGGCCCCAAACCCGCCGATCTCGTCCAGGCGCTTTCCCTGCCCGTTCCCTCGCTG
GTGATCTGCGAACTGCTCGGCGTCCCCTATTCGGACCACGAGTTCTTCCAGTCCTGCA
GTTCCAGGATGCTCAGCCGGGAGGTCACCGCCGAAGAACGGATGACCGCGTTCGAGC
AGCTCGAAAACTATCTCGACGAACTGGTCACCAAGAAGGAGGCGAACGCCACCGAGGA
CGACCTCCTCGGCCGTCAGATCCTGAAACAGCGGGAAACGGGCGAGGCCGACCACGG
TGAACTCGTCGGGCTGGCGTTCCTGCTGCTCATCGCCGGACACGAGACCACGGCGAA
CATGATCTCGCTCGGCACGGTGACCCTGCTGGAGAATCCCGATCAGCTCGCGAAGATC
AAGGCAGACCCCGGCAAGACCCTCGCCGCCATCGAGGAACTCCTGCGGGTCTTCACG
ATCGCGGAAGAAGCGACCTCACGCTTCGCCACGGCGGACGTCGAGATCGGCGGAACG
CTGATCCGCGCGGGGGAAGGGGTGGTGGGCCTGAGCAACGCGGGCAACCACGATCC
GGACGGCTTCGAGAACCCGGACACCTTCGACATCGAACGCGGCGCGCGGCATCACGT
CGCGTTCGGATTCGGGGTGCACCAGTGTCTCGGCCAGAACTTGGCGAGGTTGGAACTC
CAGATCGTCTTCGATACGTTGTTCCGGCGAGTGCCGGGCCTCCGGATCGCCGTTCCGG
TCGACGAACTGCCGTTCAAGCACGATTCGACGATCTACGGCCTCCACGCCCTTCCGGT
CACCTGGTAG SEQ ID NO: 12 (amino acid sequence of AluC09M12 (404aa))
MTDVEETTATLPLARKCPFSPPPEYERLRRESPVSRVGLPSGQTAWALTRLEDIREMLSSP
HFSSDRQSPSFPLMVARQIRREDKPFRPSLIAMDPPEHSRARRDVVGEFTVKRMKALQPRI
QQIVDEHLDALLAGPKPADLVQALSLPVPSLVICELLGVPYSDHEFFQSCSSRMLSREVTAE
ERMTAFEQLENYLDELVTKKEANATEDDLLGRQILKQRETGEADHGELVGLAFLLLIAGHET
TANMISLGTVTLLENPDQLAKIKADPGKTLAAIEELLRVFTIAEEATSRFATADVEIGGTLIRAG
EGVVGLSNAGNHDPDGFENPDTFDIERGARHHVAFGFGVHQCLGQNLARLELQIVFDTLFR
RVPGLRIAVPVDELPFKHDSTIYGLHALPVTW- SEQ ID NO: 15 (nucleic acid sequence of aluC09M17)
ATGACTGACGTCGAGGAAACCACCGCGACCTTGCCGCTGGCCCGGAAATGCCCGTTTT
CGCCGCCGCCCGAATACGAACGGCTTCGCCGGGAAAGTCCGGTTTCCCGGGTCGGTC
TCCCGTCCGGTCAAACGGCTTGGGCGCTCACCCGGCTCGAAGACATCCGCGAAATGCT
GAGCAGCCCGCATTTCAGTTCCGACCGGCAGAGCCCGTCGTTCCCGCTGATGGTCGC
GCGGCAGATCCGCCGCGAGGACAAGCCGTTCCGCCCCTCCCTCATCGCGATGGATCC
GCCGGAACACAGCCGGGCCAGGCGTGACGTCGTCGGGGAATTCACCGTCAAGCGGAT
GAAGGCGCTCCAGCCGCGAATTCAGCAGATCGTCGACGAACATCTCGACGCCCTGCTC
GCGGGCCCCAAACCCGCCGATCTCGTCCAGGCGCTTTCCCTGCCCGTTCCCTCGCTG
GTGATCTGCGAACTGCTCGGCGTCCCCTATTCGGACCACGAGTTCTTCCAGTCCTGCA
GTTCCAGGATGCTCAGCCGGGAGGTCACCGCCGAAGAACGGATGACCGCGTTCGAGC
AGCTCGAAAACTATCTCGACGAACTGGTCACCAAGAAGGAGGCGAACGCCACCGAGGA
CGACCTCCTCGGCCGTCAGATCCTGAAACAGCGGGAAACGGGCGAGGCCGACCACGG
TGAACTCGTCGGGCTGGCGTTCCTGCTGCTCATCGCCGGACACGAGACCACGGCGAA
CATGATCTCGCTCGGCACGGTGACCCTGCTGGAGAATCCCGATCAGCTCGCGAAGATC
AAGGCAGACCCCGGCAAGACCCTCGCCGCCATCGAGGAACTCCTGCGGGTCTTCACG
ATCGCGGAAAACGCGACCTCACGCTTCGCCACGGCGGACGTCGAGATCGGCGGAACG
CTGATCCGCGCGGGGGAAGGGGTGGTGGGCCTGAGCAACGCGGGCAACCACGATCC
GGACGGCTTCGAGAACCCGGACACCTTCGACATCGAACGCGGCGCGCGGCATCACGT
CGCGTTCGGATTCGGGGTGCACCAGTGTCTCGGCCAGAACTTGGCGAGGTTGGAACTC
CAGATCGTCTTCGATACGTTGTTCCGGCGAGTGCCGGGCCTCCGGATCGCCGTTCCGG
TCGACGAACTGCCGTTCAAGCACGATTCGACGATCTACGGCCTCCACGCCCTTCCGGT
CACCTGGTAG SEQ ID NO: 16 (amino acid sequence of AluC09M17 (404aa))

Figure 1 (continued)

MTDVEETTATLPLARKCPFSPPPEYERLRRESPVSRVGLPSGQTAWALTRLEDIREMLSSP
HFSSDRQSPSFPLMVARQIRREDKPFRPSLIAMDPPEHSRARRDVVGEFTVKRMKALQPRI
QQIVDEHLDALLAGPKPADLVQALSLPVPSLVICELLGVPYSDHEFFQSCSSRMLSREVTAE
ERMTAFEQLENYLDELVTKKEANATEDDLLGRQILKQRETGEADHGELVGLAFLLLIAGHET
TANMISLGTVTLLENPDQLAKIKADPGKTLAAIEELLRVFTIAENATSRFATADVEIGGTLIRAG
EGVVGLSNAGNHDPDGFENPDTFDIERGARHHVAFGFGVHQCLGQNLARLELQIVFDTLFR
RVPGLRIAVPVDELPFKHDSTIYGLHALPVTW-

SEQ ID NO: 19 (nucleic acid sequence of aluC09M18)
ATGACTGACGTCGAGGAAACCACCGCGACCTTGCCGCTGGCCCGGAAATGCCCGTTTT
CGCCGCCGCCCGAATACGAACGGCTTCGCCGGGAAAGTCCGGTTTCCCGGGTCGGTC
TCCCGTCCGGTCAAACGGCTTGGGCGCTCACCCGGCTCGAAGACATCCGCGAAATGCT
GAGCAGCCCGCATTTCAGTTCCGACCGGCAGAGCCCGTCGTTCCCGCTGATGGTCGC
GCGGCAGATCCGCCGCGAGGACAAGCCGTTCCGCCCCTCCCTCATCGCGATGGATCC
GCCGGAACACAGCCGGGCCAGGCGTGACGTCGTCGGGGAATTCACCGTCAAGCGGAT
GAAGGCGCTCCAGCCGCGAATTCAGCAGATCGTCGACGAACATCTCGACGCCCTGCTC
GCGGGCCCCAAACCCGCCGATCTCGTCCAGGCGCTTTCCCTGCCCGTTCCCTCGCTG
GTGATCTGCGAACTGCTCGGCGTCCCCTATTCGGACCACGAGTTCTTCCAGTCCTGCA
GTTCCAGGATGCTCAGCCGGGAGGTCACCGCCGAAGAACGGATGACCGCGTTCGAGC
AGCTCGAAAACTATCTCGACGAACTGGTCACCAAGAAGGAGGCGAACGCCACCGAGGA
CGACCTCCTCGGCCGTCAGATCCTGAAACAGCGGGAAACGGGCGAGGCCGACCACGG
TGAACTCGTCGGGCTGGCGTTCCTGCTGCTCATCGCCGGACACGAGACCACGGCGAA
CATGATCTCGCTCGGCACGGTGACCCTGCTGGAGAATCCCGATCAGCTCGCGAAGATC
AAGGCAGACCCCGGCAAGACCCTCGCCGCCATCGAGGAACTCCTGCGGGTCTTCACG
ATCGCGGAACAGGCGACCTCACGCTTCGCCACGGCGGACGTCGAGATCGGCGGAACG
CTGATCCGCGCGGGGAAGGGGTGGTGGGCCTGAGCAACGCGGGCAACCACGATCC
GGACGGCTTCGAGAACCCGGACACCTTCGACATCGAACGCGGCGCGCGGCATCACGT
CGCGTTCGGATTCGGGGTGCACCAGTGTCTCGGCCAGAACTTGGCGAGGTTGGAACTC
CAGATCGTCTTCGATACGTTGTTCCGGCGAGTGCCGGGCCTCCGGATCGCCGTTCCGG
TCGACGAACTGCCGTTCAAGCACGATTCGACGATCTACGGCCTCCACGCCCTTCCGGT
CACCTGGTAG SEQ ID NO: 20 (amino acid sequence of AluC09M18 (404aa))
MTDVEETTATLPLARKCPFSPPPEYERLRRESPVSRVGLPSGQTAWALTRLEDIREMLSSP
HFSSDRQSPSFPLMVARQIRREDKPFRPSLIAMDPPEHSRARRDVVGEFTVKRMKALQPRI
QQIVDEHLDALLAGPKPADLVQALSLPVPSLVICELLGVPYSDHEFFQSCSSRMLSREVTAE
ERMTAFEQLENYLDELVTKKEANATEDDLLGRQILKQRETGEADHGELVGLAFLLLIAGHET
TANMISLGTVTLLENPDQLAKIKADPGKTLAAIEELLRVFTIAEQATSRFATADVEIGGTLIRAG
EGVVGLSNAGNHDPDGFENPDTFDIERGARHHVAFGFGVHQCLGQNLARLELQIVFDTLFR
RVPGLRIAVPVDELPFKHDSTIYGLHALPVTW- SEQ ID NO: 23 (nucleic acid sequence of aluC09M19)
ATGACTGACGTCGAGGAAACCACCGCGACCTTGCCGCTGGCCCGGAAATGCCCGTTTT
CGCCGCCGCCCGAATACGAACGGCTTCGCCGGGAAAGTCCGGTTTCCCGGGTCGGTC
TCCCGTCCGGTCAAACGGCTTGGGCGCTCACCCGGCTCGAAGACATCCGCGAAATGCT
GAGCAGCCCGCATTTCAGTTCCGACCGGCAGAGCCCGTCGTTCCCGCTGATGGTCGC
GCGGCAGATCCGCCGCGAGGACAAGCCGTTCCGCCCCTCCCTCATCGCGATGGATCC
GCCGGAACACAGCCGGGCCAGGCGTGACGTCGTCGGGGAATTCACCGTCAAGCGGAT
GAAGGCGCTCCAGCCGCGAATTCAGCAGATCGTCGACGAACATCTCGACGCCCTGCTC
GCGGGCCCCAAACCCGCCGATCTCGTCCAGGCGCTTTCCCTGCCCGTTCCCTCGCTG
GTGATCTGCGAACTGCTCGGCGTCCCCTATTCGGACCACGAGTTCTTCCAGTCCTGCA
GTTCCAGGATGCTCAGCCGGGAGGTCACCGCCGAAGAACGGATGACCGCGTTCGAGC
AGCTCGAAAACTATCTCGACGAACTGGTCACCAAGAAGGAGGCGAACGCCACCGAGGA
CGACCTCCTCGGCCGTCAGATCCTGAAACAGCGGGAAACGGGCGAGGCCGACCACGG
TGAACTCGTCGGGCTGGCGTTCCTGCTGCTCATCGCCGGACACGAGACCACGGCGAA
CATGATCTCGCTCGGCACGGTGACCCTGCTGGAGAATCCCGATCAGCTCGCGAAGATC
AAGGCAGACCCCGGCAAGACCCTCGCCGCCATCGAGGAACTCCTGCGGGTCTTCACG ATCGCGGAAGCGGCGACCTCACGCTTCGCCACGGCGGACGTCGAGATCGGCGGAACG
CTGATCCGCGCGGGGGAAGGGGTGGTGGGCCTGAGCAACGCGGGCAACCACGATCC
GGACGGCTTCGAGAACCCGGACACCTTCGACATCGAACGCGGCGCGCGGCATCACGT
CGCGTTCGGATTCGGGGTGCACCAGTGTCTCGGCCAGAACTTGGCGAGGTTGGAACTC
CAGATCGTCTTCGATACGTTGTTCCGGCGAGTGCCGGGCCTCCGGATCGCCGTTCCGG
TCGACGAACTGCCGTTCAAGCACGATTCGACGATCTACGGCCTCCACGCCCTTCCGGT
CACCTGGTAG SEQ ID NO: 24 (amino acid sequence of AluC09M19 (404aa))
MTDVEETTATLPLARKCPFSPPPEYERLRRESPVSRVGLPSGQTAWALTRLEDIREMLSSP
HFSSDRQSPSFPLMVARQIRREDKPFRPSLIAMDPPEHSRARRDVVGEFTVKRMKALQPRI
QQIVDEHLDALLAGPKPADLVQALSLPVPSLVICELLGVPYSDHEFFQSCSSRMLSREVTAE
ERMTAFEQLENYLDELVTKKEANATEDDLLGRQILKQRETGEADHGELVGLAFLLLIAGHET
TANMISLGTVTLLENPDQLAKIKADPGKTLAAIEELLRVFTIAEAATSRFATADVEIGGTLIRAG
EGVVGLSNAGNHDPDGFENPDTFDIERGARHHVAFGFGVHQCLGQNLARLELQIVFDTLFR
RVPGLRIAVPVDELPFKHDSTIYGLHALPVTW- SEQ ID NO: 27 (nucleic acid sequence of aluC09M20)
ATGACTGACGTCGAGGAAACCACCGCGACCTTGCCGCTGGCCCGGAAATGCCCGTTTT
CGCCGCCGCCCGAATACGAACGGCTTCGCCGGGAAAGTCCGGTTTCCCGGGTCGGTC
TCCCGTCCGGTCAAACGGCTTGGGCGCTCACCCGGCTCGAAGACATCCGCGAAATGCT
GAGCAGCCCGCATTTCAGTTCCGACCGGCAGAGCCCGTCGTTCCCGCTGATGGTCGC
GCGGCAGATCCGCCGCGAGGACAAGCCGTTCCGCCCCTCCCTCATCGCGATGGATCC
GCCGGAACACAGCCGGGCCAGGCGTGACGTCGTCGGGGAATTCACCGTCAAGCGGAT
GAAGGCGCTCCAGCCGCGAATTCAGCAGATCGTCGACGAACATCTCGACGCCCTGCTC
GCGGGCCCCAAACCCGCCGATCTCGTCCAGGCGCTTTCCCTGCCCGTTCCCTCGCTG
GTGATCTGCGAACTGCTCGGCGTCCCCTATTCGGACCACGAGTTCTTCCAGTCCTGCA
GTTCCAGGATGCTCAGCCGGGAGGTCACCGCCGAAGAACGGATGACCGCGTTCGAGC
AGCTCGAAAACTATCTCGACGAACTGGTCACCAAGAAGGAGGCGAACGCCACCGAGGA
CGACCTCCTCGGCCGTCAGATCCTGAAACAGCGGGAAACGGGCGAGGCCGACCACGG
TGAACTCGTCGGGCTGGCGTTCCTGCTGCTCATCGCCGGACACGAGACCACGGCGAA
CATGATCTCGCTCGGCACGGTGACCCTGCTGGAGAATCCCGATCAGCTCGCGAAGATC
AAGGCAGACCCCGGCAAGACCCTCGCCGCCATCGAGGAACTCCTGCGGGTCTTCACG
ATCGCGGAAGTGGCGACCTCACGCTTCGCCACGGCGGACGTCGAGATCGGCGGAACG
CTGATCCGCGCGGGGGAAGGGGTGGTGGGCCTGAGCAACGCGGGCAACCACGATCC
GGACGGCTTCGAGAACCCGGACACCTTCGACATCGAACGCGGCGCGCGGCATCACGT
CGCGTTCGGATTCGGGGTGCACCAGTGTCTCGGCCAGAACTTGGCGAGGTTGGAACTC
CAGATCGTCTTCGATACGTTGTTCCGGCGAGTGCCGGGCCTCCGGATCGCCGTTCCGG
TCGACGAACTGCCGTTCAAGCACGATTCGACGATCTACGGCCTCCACGCCCTTCCGGT
CACCTGGTAG SEQ ID NO: 28 (amino acid sequence of AluC09M20 (404aa))
MTDVEETTATLPLARKCPFSPPPEYERLRRESPVSRVGLPSGQTAWALTRLEDIREMLSSP
HFSSDRQSPSFPLMVARQIRREDKPFRPSLIAMDPPEHSRARRDVVGEFTVKRMKALQPRI
QQIVDEHLDALLAGPKPADLVQALSLPVPSLVICELLGVPYSDHEFFQSCSSRMLSREVTAE
ERMTAFEQLENYLDELVTKKEANATEDDLLGRQILKQRETGEADHGELVGLAFLLLIAGHET
TANMISLGTVTLLENPDQLAKIKADPGKTLAAIEELLRVFTIAEVATSRFATADVEIGGTLIRAG
EGVVGLSNAGNHDPDGFENPDTFDIERGARHHVAFGFGVHQCLGQNLARLELQIVFDTLFR
RVPGLRIAVPVDELPFKHDSTIYGLHALPVTW- SEQ ID NO: 31 (nucleic acid sequence of aluC09M21)
ATGACTGACGTCGAGGAAACCACCGCGACCTTGCCGCTGGCCCGGAAATGCCCGTTTT
CGCCGCCGCCCGAATACGAACGGCTTCGCCGGGAAAGTCCGGTTTCCCGGGTCGGTC
TCCCGTCCGGTCAAACGGCTTGGGCGCTCACCCGGCTCGAAGACATCCGCGAAATGCT
GAGCAGCCCGCATTTCAGTTCCGACCGGCAGAGCCCGTCGTTCCCGCTGATGGTCGC
GCGGCAGATCCGCCGCGAGGACAAGCCGTTCCGCCCCTCCCTCATCGCGATGGATCC
GCCGGAACACAGCCGGGCCAGGCGTGACGTCGTCGGGGAATTCACCGTCAAGCGGAT
GAAGGCGCTCCAGCCGCGAATTCAGCAGATCGTCGACGAACATCTCGACGCCCTGCTC

Figure 1 (continued)

GCGGGCCCCAAACCCGCCGATCTCGTCCAGGCGCTTTCCCTGCCCGTTCCCTCGCTG
GTGATCTGCGAACTGCTCGGCGTCCCTATTCGGACCACGAGTTCTTCCAGTCCTGCA
GTTCCAGGATGCTCAGCCGGGAGGTCACCGCCGAAGAACGGATGACCGCGTTCGAGC
AGCTCGAAAACTATCTCGACGAACTGGTCACCAAGAAGGAGGCGAACGCCACCGAGGA
CGACCTCCTCGGCCGTCAGATCCTGAAACAGCGGGAAACGGGCGAGGCCGACCACGG
TGAACTCGTCGGGCTGGCGTTCCTGCTGCTCATCGCCGGACACGAGACCACGGCGAA
CATGATCTCGCTCGGCACGGTGACCCTGCTGGAGAATCCCGATCAGCTCGCGAAGATC
AAGGCAGACCCCGGCAAGACCCTCGCCGCCATCGAGGAACTCCTGCGGGTCTTCACG
ATCGCGGAATATGCGACCTCACGCTTCGCCACGGCGGACGTCGAGATCGGCGGAACG
CTGATCCGCGCGGGGGAAGGGGTGGTGGGCCTGAGCAACGCGGGCAACCACGATCC
GGACGGCTTCGAGAACCCGGACACCTTCGACATCGAACGCGGCGCGCGGCATCACGT
CGCGTTCGGATTCGGGGTGCACCAGTGTCTCGGCCAGAACTTGGCGAGGTTGGAACTC
CAGATCGTCTTCGATACGTTGTTCCGGCGAGTGCCGGGCCTCCGGATCGCCGTTCCGG
TCGACGAACTGCCGTTCAAGCACGATTCGACGATCTACGGCCTCCACGCCCTTCCGGT
CACCTGGTAG

SEQ ID NO: 32 (amino acid sequence of AluC09M21 (404aa))
MTDVEETTATLPLARKCPFSPPPEYERLRRESPVSRVGLPSGQTAWALTRLEDIREMLSSP
HFSSDRQSPSFPLMVARQIRREDKPFRPSLIAMDPPEHSRARRDVVGEFTVKRMKALQPRI
QQIVDEHLDALLAGPKPADLVQALSLPVPSLVICELLGVPYSDHEFFQSCSSRMLSREVTAE
ERMTAFEQLENYLDELVTKKEANATEDDLLGRQILKQRETGEADHGELVGLAFLLLIAGHET
TANMISLGTVTLLENPDQLAKIKADPGKTLAAIEELLRVFTIAEYATSRFATADVEIGGTLIRAG
EGVVGLSNAGNHDPDGFENPDTFDIERGARHHVAFGFGVHQCLGQNLARLELQIVFDTLFR
RVPGLRIAVPVDELPFKHDSTIYGLHALPVTW- SEQ ID NO: 35 (nucleic acid sequence of aluC09M31)
ATGACTGACGTCGAGGAAACCACCGCGACCTTGCCGCTGGCCCGGAAATGCCCGTTTT
CGCCGCCGCCCGAATACGAACGGCTTCGCCGGGAAAGTCCGGTTTCCCGGGTCGGTC
TCCCGTCCGGTCAAACGGCTTGGGCGCTCACCCGGCTCGAAGACATCCGCGAAATGCT
GAGCAGCCCGCATTTCAGTTCCGACCGGCAGAGCCCGTCGTTCCCGCTGATGGTCGC
GCGGCAGATCCGCCGCGAGGACAAGCCGTTCCGCCCCTCCCTCATCGCGATGGATCC
GCCGGAACACAGCCGGGCCAGGCGTGACGTCGTCGGGGAATTCACCGTCAAGCGGAT
GAAGGCGCTCCAGCCGCGAATTCAGCAGATCGTCGACGAACATCTCGACGCCCTGCTC
GCGGGCCCCAAACCCGCCGATCTCGTCCAGGCGCTTTCCCTGCCCGTTCCCTCGCTG
GTGATCTGCGAACTGCTCGGCGTCCCTATTCGGACCACGAGTTCTTCCAGTCCTGCA
GTTCCAGGATGCTCAGCCGGGAGGTCACCGCCGAAGAACGGATGACCGCGTTCGAGC
AGCTCGAAAACTATCTCGACGAACTGGTCACCAAGAAGGAGGCGAACGCCACCGAGGA
CGACCTCCTCGGCCGTCAGATCCTGAAACAGCGGGAAACGGGCGAGGCCGACCACGG
TGAACTCGTCGGGCTGGCGTTCCTGCTGCTCATCGCCGGACACGAGACCACGGCGAA
CATGATCTCGCTCGGCACGGTGACCCTGCTGGAGAATCCCGATCAGCTCGCGAAGATC
AAGGCAGACCCCGGCAAGACCCTCGCCGCCATCGAGGAACTCCTGCGGGTCTTCACG
ATCGCGGAAAGCGCGACCTCACGCTTCGCCACGGCGGACGTCGAGATCGGCGGAACG
CTGATCCGCGCGGGGGAAGGGGTGGTGGGCCTGAGCAACGCGGGCAACCACGATCC
GGACGGCTTCGAGAACCCGGACACCTTCGACATCGAACGCGGCGCGCGGCATCACGT
CGCGTTCGGATTCGGGGTGCACCAGTGTCTCGGCCAGAACTTGGCGAGGTTGGAACTC
CAGATCGTCTTCGATACGTTGTTCCGGCGAGTGCCGGGCCTCCGGATCGCCGTTCCGG
TCGACGAACTGCCGTTCAAGCACGATTCGACGATCTACGGCCTCCACGCCCTTCCGGT
CACCTGGTAG SEQ ID NO: 36 (amino acid sequence of AluC09M31 (404aa))
MTDVEETTATLPLARKCPFSPPPEYERLRRESPVSRVGLPSGQTAWALTRLEDIREMLSSP
HFSSDRQSPSFPLMVARQIRREDKPFRPSLIAMDPPEHSRARRDVVGEFTVKRMKALQPRI
QQIVDEHLDALLAGPKPADLVQALSLPVPSLVICELLGVPYSDHEFFQSCSSRMLSREVTAE
ERMTAFEQLENYLDELVTKKEANATEDDLLGRQILKQRETGEADHGELVGLAFLLLIAGHET
TANMISLGTVTLLENPDQLAKIKADPGKTLAAIEELLRVFTIAESATSRFATADVEIGGTLIRAG
EGVVGLSNAGNHDPDGFENPDTFDIERGARHHVAFGFGVHQCLGQNLARLELQIVFDTLFR
RVPGLRIAVPVDELPFKHDSTIYGLHALPVTW-

Figure 1 (continued)

SEQ ID NO 39 (nucleic acid sequence of aluC09M32)
ATGACTGACGTCGAGGAAACCACCGCGACCTTGCCGCTGGCCCGGAAATGCCCGTTTT
CGCCGCCGCCCGAATACGAACGGCTTCGCCGGGAAAGTCCGGTTTCCCGGGTCGGTC
TCCCGTCCGGTCAAACGGCTTGGGCGCTCACCCGGCTCGAAGACATCCGCGAAATGCT
GAGCAGCCCGCATTTCAGTTCCGACCGGCAGAGCCCGTCGTTCCCGCTGATGGTCGC
GCGGCAGATCCGCCGCGAGGACAAGCCGTTCCGCCCCTCCCTCATCGCGATGGATCC
GCCGGAACACAGCCGGGCCAGGCGTGACGTCGTCGGGGAATTCACCGTCAAGCGGAT
GAAGGCGCTCCAGCCGCGAATTCAGCAGATCGTCGACGAACATCTCGACGCCCTGCTC
GCGGGCCCCAAACCCGCCGATCTCGTCCAGGCGCTTTCCCTGCCCGTTCCCTCGCTG
GTGATCTGCGAACTGCTCGGCGTCCCTATTCGGACCACGAGTTCTTCCAGTCCTGCA
GTTCCAGGATGCTCAGCCGGGAGGTCACCGCCGAAGAACGGATGACCGCGTTCGAGC
AGCTCGAAAACTATCTCGACGAACTGGTCACCAAGAAGGAGGCGAACGCCACCGAGGA
CGACCTCCTCGGCCGTCAGATCCTGAAACAGCGGGAAACGGGCGAGGCCGACCACGG
TGAACTCGTCGGGCTGGCGTTCCTGCTGCTCATCGCCGGACACGAGACCACGGCGAA
CATGATCTCGCTCGGCACGGTGACCCTGCTGGAGAATCCCGATCAGCTCGCGAAGATC
AAGGCAGACCCCGGCAAGACCCTCGCCGCCATCGAGGAACTCCTGCGGGTCTTCACG
ATCGCGGAACTGGCGACCTCACGCTTCGCCACGGCGGACGTCGAGATCGGCGGAACG
CTGATCCGCGCGGGGGAAGGGGTGGTGGGCCTGAGCAACGCGGGCAACCACGATCC
GGACGGCTTCGAGAACCCGGACACCTTCGACATCGAACGCGGCGCGCGGCATCACGT
CGCGTTCGGATTCGGGGTGCACCAGTGTCTCGGCCAGAACTTGGCGAGGTTGGAACTC
CAGATCGTCTTCGATACGTTGTTCCGGCGAGTGCCGGGCCTCCGGATCGCCGTTCCGG
TCGACGAACTGCCGTTCAAGCACGATTCGACGATCTACGGCCTCCACGCCCTTCCGGT
CACCTGGTAG SEQ ID NO: 40 (amino acid sequence of AluC09M32 (404aa))
MTDVEETTATLPLARKCPFSPPPEYERLRRESPVSRVGLPSGQTAWALTRLEDIREMLSSP
HFSSDRQSPSFPLMVARQIRREDKPFRPSLIAMDPPEHSRARRDVVGEFTVKRMKALQPRI
QQIVDEHLDALLAGPKPADLVQALSLPVPSLVICELLGVPYSDHEFFQSCSSRMLSREVTAE
ERMTAFEQLENYLDELVTKKEANATEDDLLGRQILKQRETGEADHGELVGLAFLLLIAGHET
TANMISLGTVTLLENPDQLAKIKADPGKTLAAIEELLRVFTIAELATSRFATADVEIGGTLIRAG
EGVVGLSNAGNHDPDGFENPDTFDIERGARHHVAFGFGVHQCLGQNLARLELQIVFDTLFR
RVPGLRIAVPVDELPFKHDSTIYGLHALPVTW- SEQ ID NO: 43 (nucleic acid sequence of aluC09M33)
ATGACTGACGTCGAGGAAACCACCGCGACCTTGCCGCTGGCCCGGAAATGCCCGTTTT
CGCCGCCGCCCGAATACGAACGGCTTCGCCGGGAAAGTCCGGTTTCCCGGGTCGGTC
TCCCGTCCGGTCAAACGGCTTGGGCGCTCACCCGGCTCGAAGACATCCGCGAAATGCT
GAGCAGCCCGCATTTCAGTTCCGACCGGCAGAGCCCGTCGTTCCCGCTGATGGTCGC
GCGGCAGATCCGCCGCGAGGACAAGCCGTTCCGCCCCTCCCTCATCGCGATGGATCC
GCCGGAACACAGCCGGGCCAGGCGTGACGTCGTCGGGGAATTCACCGTCAAGCGGAT
GAAGGCGCTCCAGCCGCGAATTCAGCAGATCGTCGACGAACATCTCGACGCCCTGCTC
GCGGGCCCCAAACCCGCCGATCTCGTCCAGGCGCTTTCCCTGCCCGTTCCCTCGCTG
GTGATCTGCGAACTGCTCGGCGTCCCTATTCGGACCACGAGTTCTTCCAGTCCTGCA
GTTCCAGGATGCTCAGCCGGGAGGTCACCGCCGAAGAACGGATGACCGCGTTCGAGC
AGCTCGAAAACTATCTCGACGAACTGGTCACCAAGAAGGAGGCGAACGCCACCGAGGA
CGACCTCCTCGGCCGTCAGATCCTGAAACAGCGGGAAACGGGCGAGGCCGACCACGG
TGAACTCGTCGGGCTGGCGTTCCTGCTGCTCATCGCCGGACACGAGACCACGGCGAA
CATGATCTCGCTCGGCACGGTGACCCTGCTGGAGAATCCCGATCAGCTCGCGAAGATC
AAGGCAGACCCCGGCAAGACCCTCGCCGCCATCGAGGAACTCCTGCGGGTCTTCACG
ATCGCGGAAATTGCGACCTCACGCTTCGCCACGGCGGACGTCGAGATCGGCGGAACG
CTGATCCGCGCGGGGGAAGGGGTGGTGGGCCTGAGCAACGCGGGCAACCACGATCC
GGACGGCTTCGAGAACCCGGACACCTTCGACATCGAACGCGGCGCGCGGCATCACGT
CGCGTTCGGATTCGGGGTGCACCAGTGTCTCGGCCAGAACTTGGCGAGGTTGGAACTC
CAGATCGTCTTCGATACGTTGTTCCGGCGAGTGCCGGGCCTCCGGATCGCCGTTCCGG
TCGACGAACTGCCGTTCAAGCACGATTCGACGATCTACGGCCTCCACGCCCTTCCGGT
CACCTGGTAG SEQ ID NO: 44 (amino acid sequence of AluC09M33 (404aa))

Figure 1 (continued)

MTDVEETTATLPLARKCPFSPPPEYERLRRESPVSRVGLPSGQTAWALTRLEDIREMLSSP
HFSSDRQSPSFPLMVARQIRREDKPFRPSLIAMDPPEHSRARRDVVGEFTVKRMKALQPRI
QQIVDEHLDALLAGPKPADLVQALSLPVPSLVICELLGVPYSDHEFFQSCSSRMLSREVTAE
ERMTAFEQLENYLDELVTKKEANATEDDLLGRQILKQRETGEADHGELVGLAFLLLIAGHET
TANMISLGTVTLLENPDQLAKIKADPGKTLAAIEELLRVFTIAEIATSRFATADVEIGGTLIRAGE
GVVGLSNAGNHDPDGFENPDTFDIERGARHHVAFGFGVHQCLGQNLARLELQIVFDTLFRR
VPGLRIAVPVDELPFKHDSTIYGLHALPVTW-

SEQ ID NO: 47 (nucleic acid sequence of aluC09M34)
ATGACTGACGTCGAGGAAACCACCGCGACCTTGCCGCTGGCCCGGAAATGCCCGTTTT
CGCCGCCGCCCGAATACGAACGGCTTCGCCGGGAAAGTCCGGTTTCCCGGGTCGGTC
TCCCGTCCGGTCAAACGGCTTGGGCGCTCACCCGGCTCGAAGACATCCGCGAAATGCT
GAGCAGCCCGCATTTCAGTTCCGACCGGCAGAGCCCGTCGTTCCCGCTGATGGTCGC
GCGGCAGATCCGCCGCGAGGACAAGCCGTTCCGCCCCTCCCTCATCGCGATGGATCC
GCCGGAACACAGCCGGGCCAGGCGTGACGTCGTCGGGGAATTCACCGTCAAGCGGAT
GAAGGCGCTCCAGCCGCGAATTCAGCAGATCGTCGACGAACATCTCGACGCCCTGCTC
GCGGGCCCCAAACCCGCCGATCTCGTCCAGGCGCTTTCCCTGCCCGTTCCCTCGCTG
GTGATCTGCGAACTGCTCGGCGTCCCTATTCGGACCACGAGTTCTTCCAGTCCTGCA
GTTCCAGGATGCTCAGCCGGGAGGTCACCGCCGAAGAACGGATGACCGCGTTCGAGC
AGCTCGAAAACTATCTCGACGAACTGGTCACCAAGAAGGAGGCGAACGCCACCGAGGA
CGACCTCCTCGGCCGTCAGATCCTGAAACAGCGGGAAACGGGCGAGGCCGACCACGG
TGAACTCGTCGGGCTGGCGTTCCTGCTGCTCATCGCCGGACACGAGACCACGGCGAA
CATGATCTCGCTCGGCACGGTGACCCTGCTGGAGAATCCCGATCAGCTCGCGAAGATC
AAGGCAGACCCCGGCAAGACCCTCGCCGCCATCGAGGAACTCCTGCGGGTCTTCACG
ATCGCGGAAATGGCGACCTCACGCTTCGCCACGGCGGACGTCGAGATCGGCGGAACG
CTGATCCGCGCGGGGAAGGGGTGGTGGGCCTGAGCAACGCGGGCAACCACGATCC
GGACGGCTTCGAGAACCCGGACACCTTCGACATCGAACGCGGCGCGCGGCATCACGT
CGCGTTCGGATTCGGGGTGCACCAGTGTCTCGGCCAGAACTTGGCGAGGTTGGAACTC
CAGATCGTCTTCGATACGTTGTTCCGGCGAGTGCCGGGCCTCCGGATCGCCGTTCCGG
TCGACGAACTGCCGTTCAAGCACGATTCGACGATCTACGGCCTCCACGCCCTTCCGGT
CACCTGGTAG SEQ ID NO: 48 (amino acid sequence of AluC09M34 (404aa))
MTDVEETTATLPLARKCPFSPPPEYERLRRESPVSRVGLPSGQTAWALTRLEDIREMLSSP
HFSSDRQSPSFPLMVARQIRREDKPFRPSLIAMDPPEHSRARRDVVGEFTVKRMKALQPRI
QQIVDEHLDALLAGPKPADLVQALSLPVPSLVICELLGVPYSDHEFFQSCSSRMLSREVTAE
ERMTAFEQLENYLDELVTKKEANATEDDLLGRQILKQRETGEADHGELVGLAFLLLIAGHET
TANMISLGTVTLLENPDQLAKIKADPGKTLAAIEELLRVFTIAEMATSRFATADVEIGGTLIRAG
EGVVGLSNAGNHDPDGFENPDTFDIERGARHHVAFGFGVHQCLGQNLARLELQIVFDTLFR
RVPGLRIAVPVDELPFKHDSTIYGLHALPVTW- SEQ ID NO: 51 (nucleic acid sequence of aluC09M35)
ATGACTGACGTCGAGGAAACCACCGCGACCTTGCCGCTGGCCCGGAAATGCCCGTTTT
CGCCGCCGCCCGAATACGAACGGCTTCGCCGGGAAAGTCCGGTTTCCCGGGTCGGTC
TCCCGTCCGGTCAAACGGCTTGGGCGCTCACCCGGCTCGAAGACATCCGCGAAATGCT
GAGCAGCCCGCATTTCAGTTCCGACCGGCAGAGCCCGTCGTTCCCGCTGATGGTCGC
GCGGCAGATCCGCCGCGAGGACAAGCCGTTCCGCCCCTCCCTCATCGCGATGGATCC
GCCGGAACACAGCCGGGCCAGGCGTGACGTCGTCGGGGAATTCACCGTCAAGCGGAT
GAAGGCGCTCCAGCCGCGAATTCAGCAGATCGTCGACGAACATCTCGACGCCCTGCTC
GCGGGCCCCAAACCCGCCGATCTCGTCCAGGCGCTTTCCCTGCCCGTTCCCTCGCTG
GTGATCTGCGAACTGCTCGGCGTCCCTATTCGGACCACGAGTTCTTCCAGTCCTGCA
GTTCCAGGATGCTCAGCCGGGAGGTCACCGCCGAAGAACGGATGACCGCGTTCGAGC
AGCTCGAAAACTATCTCGACGAACTGGTCACCAAGAAGGAGGCGAACGCCACCGAGGA
CGACCTCCTCGGCCGTCAGATCCTGAAACAGCGGGAAACGGGCGAGGCCGACCACGG
TGAACTCGTCGGGCTGGCGTTCCTGCTGCTCATCGCCGGACACGAGACCACGGCGAA
CATGATCTCGCTCGGCACGGTGACCCTGCTGGAGAATCCCGATCAGCTCGCGAAGATC
AAGGCAGACCCCGGCAAGACCCTCGCCGCCATCGAGGAACTCCTGCGGGTCTTCACG
ATCGCGGAACCGGCGACCTCACGCTTCGCCACGGCGGACGTCGAGATCGGCGGAACG

Figure 1 (continued)

CTGATCCGCGCGGGGGAAGGGGTGGTGGGCCTGAGCAACGCGGGCAACCACGATCC
GGACGGCTTCGAGAACCCGGACACCTTCGACATCGAACGCGGCGCGCGGCATCACGT
CGCGTTCGGATTCGGGGTGCACCAGTGTCTCGGCCAGAACTTGGCGAGGTTGGAACTC
CAGATCGTCTTCGATACGTTGTTCCGGCGAGTGCCGGGCCTCCGGATCGCCGTTCCGG
TCGACGAACTGCCGTTCAAGCACGATTCGACGATCTACGGCCTCCACGCCCTTCCGGT
CACCTGGTAG

SEQ ID NO: 52 (amino acid sequence of AluC09M35 (404aa))
MTDVEETTATLPLARKCPFSPPPEYERLRRESPVSRVGLPSGQTAWALTRLEDIREMLSSP
HFSSDRQSPSFPLMVARQIRREDKPFRPSLIAMDPPEHSRARRDVVGEFTVKRMKALQPRI
QQIVDEHLDALLAGPKPADLVQALSLPVPSLVICELLGVPYSDHEFFQSCSSRMLSREVTAE
ERMTAFEQLENYLDELVTKKEANATEDDLLGRQILKQRETGEADHGELVGLAFLLLIAGHET
TANMISLGTVTLLENPDQLAKIKADPGKTLAAIEELLRVFTIAEPATSRFATADVEIGGTLIRAG
EGVVGLSNAGNHDPDGFENPDTFDIERGARHHVAFGFGVHQCLGQNLARLELQIVFDTLFR
RVPGLRIAVPVDELPFKHDSTIYGLHALPVTW- SEQ ID NO: 55 (nucleic acid sequence of aluC09M36)
ATGACTGACGTCGAGGAAACCACCGCGACCTTGCCGCTGGCCCGGAAATGCCCGTTTT
CGCCGCCGCCCGAATACGAACGGCTTCGCCGGGAAAGTCCGGTTTCCCGGGTCGGTC
TCCCGTCCGGTCAAACGGCTTGGGCGCTCACCCGGCTCGAAGACATCCGCGAAATGCT
GAGCAGCCCGCATTTCAGTTCCGACCGGCAGAGCCCGTCGTTCCCGCTGATGGTCGC
GCGGCAGATCCGCCGCGAGGACAAGCCGTTCCGCCCCTCCCTCATCGCGATGGATCC
GCCGGAACACAGCCGGGCCAGGCGTGACGTCGTCGGGGAATTCACCGTCAAGCGGAT
GAAGGCGCTCCAGCCGCGAATTCAGCAGATCGTCGACGAACATCTCGACGCCCTGCTC
GCGGGCCCCAAACCCGCCGATCTCGTCCAGGCGCTTTCCCTGCCCGTTCCCTCGCTG
GTGATCTGCGAACTGCTCGGCGTCCCTATTCGGACCACGAGTTCTTCCAGTCCTGCA
GTTCCAGGATGCTCAGCCGGGAGGTCACCGCCGAAGAACGGATGACCGCGTTCGAGC
AGCTCGAAAACTATCTCGACGAACTGGTCACCAAGAAGGAGGCGAACGCCACCGAGGA
CGACCTCCTCGGCCGTCAGATCCTGAAACAGCGGGAAACGGGCGAGGCCGACCACGG
TGAACTCGTCGGGCTGGCGTTCCTGCTGCTCATCGCCGGACACGAGACCACGGCGAA
CATGATCTCGCTCGGCACGGTGACCCTGCTGGAGAATCCCGATCAGCTCGCGAAGATC
AAGGCAGACCCCGGCAAGACCCTCGCCGCCATCGAGGAACTCCTGCGGGTCTTCACG
ATCGCGGAATTTGCGACCTCACGCTTCGCCACGGCGGACGTCGAGATCGGCGGAACG
CTGATCCGCGCGGGGGAAGGGGTGGTGGGCCTGAGCAACGCGGGCAACCACGATCC
GGACGGCTTCGAGAACCCGGACACCTTCGACATCGAACGCGGCGCGCGGCATCACGT
CGCGTTCGGATTCGGGGTGCACCAGTGTCTCGGCCAGAACTTGGCGAGGTTGGAACTC
CAGATCGTCTTCGATACGTTGTTCCGGCGAGTGCCGGGCCTCCGGATCGCCGTTCCGG
TCGACGAACTGCCGTTCAAGCACGATTCGACGATCTACGGCCTCCACGCCCTTCCGGT
CACCTGGTAG SEQ ID NO: 56 (amino acid sequence of AluC09M36 (404aa))
MTDVEETTATLPLARKCPFSPPPEYERLRRESPVSRVGLPSGQTAWALTRLEDIREMLSSP
HFSSDRQSPSFPLMVARQIRREDKPFRPSLIAMDPPEHSRARRDVVGEFTVKRMKALQPRI
QQIVDEHLDALLAGPKPADLVQALSLPVPSLVICELLGVPYSDHEFFQSCSSRMLSREVTAE
ERMTAFEQLENYLDELVTKKEANATEDDLLGRQILKQRETGEADHGELVGLAFLLLIAGHET
TANMISLGTVTLLENPDQLAKIKADPGKTLAAIEELLRVFTIAEFATSRFATADVEIGGTLIRAG
EGVVGLSNAGNHDPDGFENPDTFDIERGARHHVAFGFGVHQCLGQNLARLELQIVFDTLFR
RVPGLRIAVPVDELPFKHDSTIYGLHALPVTW- SEQ ID NO: 59 (nucleic acid sequence of aluC09M37)
ATGACTGACGTCGAGGAAACCACCGCGACCTTGCCGCTGGCCCGGAAATGCCCGTTTT
CGCCGCCGCCCGAATACGAACGGCTTCGCCGGGAAAGTCCGGTTTCCCGGGTCGGTC
TCCCGTCCGGTCAAACGGCTTGGGCGCTCACCCGGCTCGAAGACATCCGCGAAATGCT
GAGCAGCCCGCATTTCAGTTCCGACCGGCAGAGCCCGTCGTTCCCGCTGATGGTCGC
GCGGCAGATCCGCCGCGAGGACAAGCCGTTCCGCCCCTCCCTCATCGCGATGGATCC
GCCGGAACACAGCCGGGCCAGGCGTGACGTCGTCGGGGAATTCACCGTCAAGCGGAT
GAAGGCGCTCCAGCCGCGAATTCAGCAGATCGTCGACGAACATCTCGACGCCCTGCTC
GCGGGCCCCAAACCCGCCGATCTCGTCCAGGCGCTTTCCCTGCCCGTTCCCTCGCTG

Figure 1 (continued)

GTGATCTGCGAACTGCTCGGCGTCCCTATTCGGACCACGAGTTCTTCCAGTCCTGCA
GTTCCAGGATGCTCAGCCGGGAGGTCACCGCCGAAGAACGGATGACCGCGTTCGAGC
AGCTCGAAAACTATCTCGACGAACTGGTCACCAAGAAGGAGGCGAACGCCACCGAGGA
CGACCTCCTCGGCCGTCAGATCCTGAAACAGCGGGAAACGGGCGAGGCCGACCACGG
TGAACTCGTCGGGCTGGCGTTCCTGCTGCTCATCGCCGGACACGAGACCACGGCGAA
CATGATCTCGCTCGGCACGGTGACCCTGCTGGAGAATCCCGATCAGCTCGCGAAGATC
AAGGCAGACCCCGGCAAGACCCTCGCCGCCATCGAGGAACTCCTGCGGGTCTTCACG
ATCGCGGAATGGGCGACCTCACGCTTCGCCACGGCGGACGTCGAGATCGGCGGAACG
CTGATCCGCGCGGGGAAGGGGTGGTGGGCCTGAGCAACGCGGGCAACCACGATCC
GGACGGCTTCGAGAACCCGGACACCTTCGACATCGAACGCGGCGCGCGGCATCACGT
CGCGTTCGGATTCGGGGTGCACCAGTGTCTCGGCCAGAACTTGGCGAGGTTGGAACTC
CAGATCGTCTTCGATACGTTGTTCCGGCGAGTGCCGGGCCTCCGGATCGCCGTTCCGG
TCGACGAACTGCCGTTCAAGCACGATTCGACGATCTACGGCCTCCACGCCCTTCCGGT
CACCTGGTAG

SEQ ID NO: 60 (amino acid sequence of AluC09M37 (404aa))
MTDVEETTATLPLARKCPFSPPPEYERLRRESPVSRVGLPSGQTAWALTRLEDIREMLSSP
HFSSDRQSPSFPLMVARQIRREDKPFRPSLIAMDPPEHSRARRDVVGEFTVKRMKALQPRI
QQIVDEHLDALLAGPKPADLVQALSLPVPSLVICELLGVPYSDHEFFQSCSSRMLSREVTAE
ERMTAFEQLENYLDELVTKKEANATEDDLLGRQILKQRETGEADHGELVGLAFLLLIAGHET
TANMISLGTVTLLENPDQLAKIKADPGKTLAAIEELLRVFTIAEWATSRFATADVEIGGTLIRAG
EGVVGLSNAGNHDPDGFENPDTFDIERGARHHVAFGFGVHQCLGQNLARLELQIVFDTLFR
RVPGLRIAVPVDELPFKHDSTIYGLHALPVTW- SEQ ID NO: 63 (nucleic acid sequence of aluC09M38)
ATGACTGACGTCGAGGAAACCACCGCGACCTTGCCGCTGGCCCGGAAATGCCCGTTTT
CGCCGCCGCCCGAATACGAACGGCTTCGCCGGGAAAGTCCGGTTTCCCGGGTCGGTC
TCCCGTCCGGTCAAACGGCTTGGGCGCTCACCCGGCTCGAAGACATCCGCGAAATGCT
GAGCAGCCCGCATTTCAGTTCCGACCGGCAGAGCCCGTCGTTCCCGCTGATGGTCGC
GCGGCAGATCCGCCGCGAGGACAAGCCGTTCCGCCCCTCCCTCATCGCGATGGATCC
GCCGGAACACAGCCGGGCCAGGCGTGACGTCGTCGGGGAATTCACCGTCAAGCGGAT
GAAGGCGCTCCAGCCGCGAATTCAGCAGATCGTCGACGAACATCTCGACGCCCTGCTC
GCGGGCCCCAAACCCGCCGATCTCGTCCAGGCGCTTTCCCTGCCCGTTCCCTCGCTG
GTGATCTGCGAACTGCTCGGCGTCCCTATTCGGACCACGAGTTCTTCCAGTCCTGCA
GTTCCAGGATGCTCAGCCGGGAGGTCACCGCCGAAGAACGGATGACCGCGTTCGAGC
AGCTCGAAAACTATCTCGACGAACTGGTCACCAAGAAGGAGGCGAACGCCACCGAGGA
CGACCTCCTCGGCCGTCAGATCCTGAAACAGCGGGAAACGGGCGAGGCCGACCACGG
TGAACTCGTCGGGCTGGCGTTCCTGCTGCTCATCGCCGGACACGAGACCACGGCGAA
CATGATCTCGCTCGGCACGGTGACCCTGCTGGAGAATCCCGATCAGCTCGCGAAGATC
AAGGCAGACCCCGGCAAGACCCTCGCCGCCATCGAGGAACTCCTGCGGGTCTTCACG
ATCGCGGAACATGCGACCTCACGCTTCGCCACGGCGGACGTCGAGATCGGCGGAACG
CTGATCCGCGCGGGGAAGGGGTGGTGGGCCTGAGCAACGCGGGCAACCACGATCC
GGACGGCTTCGAGAACCCGGACACCTTCGACATCGAACGCGGCGCGCGGCATCACGT
CGCGTTCGGATTCGGGGTGCACCAGTGTCTCGGCCAGAACTTGGCGAGGTTGGAACTC
CAGATCGTCTTCGATACGTTGTTCCGGCGAGTGCCGGGCCTCCGGATCGCCGTTCCGG
TCGACGAACTGCCGTTCAAGCACGATTCGACGATCTACGGCCTCCACGCCCTTCCGGT
CACCTGGTAG SEQ ID NO: 64 (amino acid sequence of AluC09M38 (404aa))
MTDVEETTATLPLARKCPFSPPPEYERLRRESPVSRVGLPSGQTAWALTRLEDIREMLSSP
HFSSDRQSPSFPLMVARQIRREDKPFRPSLIAMDPPEHSRARRDVVGEFTVKRMKALQPRI
QQIVDEHLDALLAGPKPADLVQALSLPVPSLVICELLGVPYSDHEFFQSCSSRMLSREVTAE
ERMTAFEQLENYLDELVTKKEANATEDDLLGRQILKQRETGEADHGELVGLAFLLLIAGHET
TANMISLGTVTLLENPDQLAKIKADPGKTLAAIEELLRVFTIAEHATSRFATADVEIGGTLIRAG
EGVVGLSNAGNHDPDGFENPDTFDIERGARHHVAFGFGVHQCLGQNLARLELQIVFDTLFR
RVPGLRIAVPVDELPFKHDSTIYGLHALPVTW- SEQ ID NO: 67 (nucleic acid sequence of aluC09M39)

Figure 1 (continued)

ATGACTGACGTCGAGGAAACCACCGCGACCTTGCCGCTGGCCCGGAAATGCCCGTTTT
CGCCGCCGCCCGAATACGAACGGCTTCGCCGGGAAAGTCCGGTTTCCCGGGTCGGTC
TCCCGTCCGGTCAAACGGCTTGGGCGCTCACCCGGCTCGAAGACATCCGCGAAATGCT
GAGCAGCCCGCATTTCAGTTCCGACCGGCAGAGCCCGTCGTTCCCGCTGATGGTCGC
GCGGCAGATCCGCCGCGAGGACAAGCCGTTCCGCCCCTCCCTCATCGCGATGGATCC
GCCGGAACACAGCCGGGCCAGGCGTGACGTCGTCGGGGAATTCACCGTCAAGCGGAT
GAAGGCGCTCCAGCCGCGAATTCAGCAGATCGTCGACGAACATCTCGACGCCCTGCTC
GCGGGCCCCAAACCCGCCGATCTCGTCCAGGCGCTTTCCCTGCCCGTTCCCTCGCTG
GTGATCTGCGAACTGCTCGGCGTCCCCTATTCGGACCACGAGTTCTTCCAGTCCTGCA
GTTCCAGGATGCTCAGCCGGGAGGTCACCGCCGAAGAACGGATGACCGCGTTCGAGC
AGCTCGAAAACTATCTCGACGAACTGGTCACCAAGAAGGAGGCGAACGCCACCGAGGA
CGACCTCCTCGGCCGTCAGATCCTGAAACAGCGGGAAACGGGCGAGGCCGACCACGG
TGAACTCGTCGGGCTGGCGTTCCTGCTGCTCATCGCCGGACACGAGACCACGGCGAA
CATGATCTCGCTCGGCACGGTGACCCTGCTGGAGAATCCCGATCAGCTCGCGAAGATC
AAGGCAGACCCCGGCAAGACCCTCGCCGCCATCGAGGAACTCCTGCGGGTCTTCACG
ATCGCGGAAAAAGCGACCTCACGCTTCGCCACGGCGGACGTCGAGATCGGCGGAACG
CTGATCCGCGCGGGGGAAGGGGTGGTGGGCCTGAGCAACGCGGGCAACCACGATCC
GGACGGCTTCGAGAACCCGGACACCTTCGACATCGAACGCGGCGCGCGGCATCACGT
CGCGTTCGGATTCGGGGTGCACCAGTGTCTCGGCCAGAACTTGGCGAGGTTGGAACTC
CAGATCGTCTTCGATACGTTGTTCCGGCGAGTGCCGGGCCTCCGGATCGCCGTTCCGG
TCGACGAACTGCCGTTCAAGCACGATTCGACGATCTACGGCCTCCACGCCCTTCCGGT
CACCTGGTAG

SEQ ID NO: 68 (amino acid sequence of AluC09M39 (404aa))
MTDVEETTATLPLARKCPFSPPPEYERLRRESPVSRVGLPSGQTAWALTRLEDIREMLSSP
HFSSDRQSPSFPLMVARQIRREDKPFRPSLIAMDPPEHSRARRDVVGEFTVKRMKALQPRI
QQIVDEHLDALLAGPKPADLVQALSLPVPSLVICELLGVPYSDHEFFQSCSSRMLSREVTAE
ERMTAFEQLENYLDELVTKKEANATEDDLLGRQILKQRETGEADHGELVGLAFLLLIAGHET
TANMISLGTVTLLENPDQLAKIKADPGKTLAAIEELLRVFTIAEKATSRFATADVEIGGTLIRAG
EGVVGLSNAGNHDPDGFENPDTFDIERGARHHVAFGFGVHQCLGQNLARLELQIVFDTLFR
RVPGLRIAVPVDELPFKHDSTIYGLHALPVTW- SEQ ID NO: 71 (nucleic acid sequence of aluC09M40)
ATGACTGACGTCGAGGAAACCACCGCGACCTTGCCGCTGGCCCGGAAATGCCCGTTTT
CGCCGCCGCCCGAATACGAACGGCTTCGCCGGGAAAGTCCGGTTTCCCGGGTCGGTC
TCCCGTCCGGTCAAACGGCTTGGGCGCTCACCCGGCTCGAAGACATCCGCGAAATGCT
GAGCAGCCCGCATTTCAGTTCCGACCGGCAGAGCCCGTCGTTCCCGCTGATGGTCGC
GCGGCAGATCCGCCGCGAGGACAAGCCGTTCCGCCCCTCCCTCATCGCGATGGATCC
GCCGGAACACAGCCGGGCCAGGCGTGACGTCGTCGGGGAATTCACCGTCAAGCGGAT
GAAGGCGCTCCAGCCGCGAATTCAGCAGATCGTCGACGAACATCTCGACGCCCTGCTC
GCGGGCCCCAAACCCGCCGATCTCGTCCAGGCGCTTTCCCTGCCCGTTCCCTCGCTG
GTGATCTGCGAACTGCTCGGCGTCCCCTATTCGGACCACGAGTTCTTCCAGTCCTGCA
GTTCCAGGATGCTCAGCCGGGAGGTCACCGCCGAAGAACGGATGACCGCGTTCGAGC
AGCTCGAAAACTATCTCGACGAACTGGTCACCAAGAAGGAGGCGAACGCCACCGAGGA
CGACCTCCTCGGCCGTCAGATCCTGAAACAGCGGGAAACGGGCGAGGCCGACCACGG
TGAACTCGTCGGGCTGGCGTTCCTGCTGCTCATCGCCGGACACGAGACCACGGCGAA
CATGATCTCGCTCGGCACGGTGACCCTGCTGGAGAATCCCGATCAGCTCGCGAAGATC
AAGGCAGACCCCGGCAAGACCCTCGCCGCCATCGAGGAACTCCTGCGGGTCTTCACG
ATCGCGGAACGCGCGACCTCACGCTTCGCCACGGCGGACGTCGAGATCGGCGGAACG
CTGATCCGCGCGGGGGAAGGGGTGGTGGGCCTGAGCAACGCGGGCAACCACGATCC
GGACGGCTTCGAGAACCCGGACACCTTCGACATCGAACGCGGCGCGCGGCATCACGT
CGCGTTCGGATTCGGGGTGCACCAGTGTCTCGGCCAGAACTTGGCGAGGTTGGAACTC
CAGATCGTCTTCGATACGTTGTTCCGGCGAGTGCCGGGCCTCCGGATCGCCGTTCCGG
TCGACGAACTGCCGTTCAAGCACGATTCGACGATCTACGGCCTCCACGCCCTTCCGGT
CACCTGGTAG SEQ ID NO: 72 (amino acid sequence of AluC09M40 (404aa))

Figure 1 (continued)

MTDVEETTATLPLARKCPFSPPPEYERLRRESPVSRVGLPSGQTAWALTRLEDIREMLSSP
HFSSDRQSPSFPLMVARQIRREDKPFRPSLIAMDPPEHSRARRDVVGEFTVKRMKALQPRI
QQIVDEHLDALLAGPKPADLVQALSLPVPSLVICELLGVPYSDHEFFQSCSSRMLSREVTAE
ERMTAFEQLENYLDELVTKKEANATEDDLLGRQILKQRETGEADHGELVGLAFLLLIAGHET
TANMISLGTVTLLENPDQLAKIKADPGKTLAAIEELLRVFTIAERATSRFATADVEIGGTLIRAG
EGVVGLSNAGNHDPDGFENPDTFDIERGARHHVAFGFGVHQCLGQNLARLELQIVFDTLFR
RVPGLRIAVPVDELPFKHDSTIYGLHALPVTW-

SEQ ID NO: 75 (nucleic acid sequence of aluC09M22)
ATGACTGACGTCGAGGAAACCACCGCGACCTTGCCGCTGGCCCGGAAATGCCCGTTTT
CGCCGCCGCCCGAATACGAACGGCTTCGCCGGGAAAGTCCGGTTTCCCGGGTCGGTC
TCCCGTCCGGTCAAACGGCTTGGTGGCTCACCCGGCTCGAAGACATCCGCGAAATGCT
GAGCAGCCCGCATTTCAGTTCCGACCGGCAGAGCCCGTCGTTCCCGCTGATGGTCGC
GCGGCAGATCCGCCGCGAGGACAAGCCGTTCCGCCCCTCCCTCATCGCGATGGATCC
GCCGGAACACAGCCGGGCCAGGCGTGACGTCGTCGGGGAATTCACCGTCAAGCGGAT
GAAGGCGCTCCAGCCGCGAATTCAGCAGATCGTCGACGAACATCTCGACGCCCTGCTC
GCGGGCCCCAAACCCGCCGATCTCGTCCAGGCGCTTTCCCTGCCCGTTCCCTCGCTG
GTGATCTGCGAACTGCTCGGCGTCCCTATTCGGACCACGAGTTCTTCCAGTCCTGCA
GTTCCAGGATGCTCAGCCGGGAGGTCACCGCCGAAGAACGGATGACCGCGTTCGAGC
AGCTCGAAAACTATCTCGACGAACTGGTCACCAAGAAGGAGGCGAACGCCACCGAGGA
CGACCTCCTCGGCCGTCAGATCCTGAAACAGCGGGAAACGGGCGAGGCCGACCACGG
TGAACTCGTCGGGCTGGCGTTCCTGCTGCTCATCGCCGGACACGAGACCACGGCGAA
CATGATCTCGCTCGGCACGGTGACCCTGCTGGAGAATCCCGATCAGCTCGCGAAGATC
AAGGCAGACCCCGGCAAGACCCTCGCCGCCATCGAGGAACTCCTGCGGGTCTTCACG
ATCGCGGAAGAAGCGACCTCACGCTTCGCCACGGCGGACGTCGAGATCGGCGGAACG
CTGATCCGCGCGGGGAAGGGGTGGTGGGCCTGAGCAACGCGGGCAACCACGATCC
GGACGGCTTCGAGAACCCGGACACCTTCGACATCGAACGCGGCGCGCGGCATCACGT
CGCGTTCGGATTCGGGGTGCACCAGTGTCTCGGCCAGAACTTGGCGAGGTTGGAACTC
CAGATCGTCTTCGATACGTTGTTCCGGCGAGTGCCGGGCCTCCGGATCGCCGTTCCGG
TCGACGAACTGCCGTTCAAGCACGATTCGACGATCTACGGCCTCCACGCCCTTCCGGT
CACCTGGTAG SEQ ID NO: 76 (amino acid sequence of AluC09M22 (404aa))
MTDVEETTATLPLARKCPFSPPPEYERLRRESPVSRVGLPSGQTAWWLTRLEDIREMLSSP
HFSSDRQSPSFPLMVARQIRREDKPFRPSLIAMDPPEHSRARRDVVGEFTVKRMKALQPRI
QQIVDEHLDALLAGPKPADLVQALSLPVPSLVICELLGVPYSDHEFFQSCSSRMLSREVTAE
ERMTAFEQLENYLDELVTKKEANATEDDLLGRQILKQRETGEADHGELVGLAFLLLIAGHET
TANMISLGTVTLLENPDQLAKIKADPGKTLAAIEELLRVFTIAEEEATSRFATADVEIGGTLIRAG
EGVVGLSNAGNHDPDGFENPDTFDIERGARHHVAFGFGVHQCLGQNLARLELQIVFDTLFR
RVPGLRIAVPVDELPFKHDSTIYGLHALPVTW- SEQ ID NO: 79 (nucleic acid sequence of aluC09M23)
ATGACTGACGTCGAGGAAACCACCGCGACCTTGCCGCTGGCCCGGAAATGCCCGTTTT
CGCCGCCGCCCGAATACGAACGGCTTCGCCGGGAAAGTCCGGTTTCCCGGGTCGGTC
TCCCGTCCGGTCAAACGGCTTGGTTTCTCACCCGGCTCGAAGACATCCGCGAAATGCT
GAGCAGCCCGCATTTCAGTTCCGACCGGCAGAGCCCGTCGTTCCCGCTGATGGTCGC
GCGGCAGATCCGCCGCGAGGACAAGCCGTTCCGCCCCTCCCTCATCGCGATGGATCC
GCCGGAACACAGCCGGGCCAGGCGTGACGTCGTCGGGGAATTCACCGTCAAGCGGAT
GAAGGCGCTCCAGCCGCGAATTCAGCAGATCGTCGACGAACATCTCGACGCCCTGCTC
GCGGGCCCCAAACCCGCCGATCTCGTCCAGGCGCTTTCCCTGCCCGTTCCCTCGCTG
GTGATCTGCGAACTGCTCGGCGTCCCTATTCGGACCACGAGTTCTTCCAGTCCTGCA
GTTCCAGGATGCTCAGCCGGGAGGTCACCGCCGAAGAACGGATGACCGCGTTCGAGC
AGCTCGAAAACTATCTCGACGAACTGGTCACCAAGAAGGAGGCGAACGCCACCGAGGA
CGACCTCCTCGGCCGTCAGATCCTGAAACAGCGGGAAACGGGCGAGGCCGACCACGG
TGAACTCGTCGGGCTGGCGTTCCTGCTGCTCATCGCCGGACACGAGACCACGGCGAA
CATGATCTCGCTCGGCACGGTGACCCTGCTGGAGAATCCCGATCAGCTCGCGAAGATC
AAGGCAGACCCCGGCAAGACCCTCGCCGCCATCGAGGAACTCCTGCGGGTCTTCACG
ATCGCGGAAGAAGCGACCTCACGCTTCGCCACGGCGGACGTCGAGATCGGCGGAACG CTGATCCGCGCGGGGGAAGGGGTGGTGGGCCTGAGCAACGCGGGCAACCACGATCC
GGACGGCTTCGAGAACCCGGACACCTTCGACATCGAACGCGGCGCGCGGCATCACGT
CGCGTTCGGATTCGGGGTGCACCAGTGTCTCGGCCAGAACTTGGCGAGGTTGGAACTC
CAGATCGTCTTCGATACGTTGTTCCGGCGAGTGCCGGGCCTCCGGATCGCCGTTCCGG
TCGACGAACTGCCGTTCAAGCACGATTCGACGATCTACGGCCTCCACGCCCTTCCGGT
CACCTGGTAG SEQ ID NO: 80 (amino acid sequence of AluC09M23 (404aa))
MTDVEETTATLPLARKCPFSPPPEYERLRRESPVSRVGLPSGQTAWFLTRLEDIREMLSSP
HFSSDRQSPSFPLMVARQIRREDKPFRPSLIAMDPPEHSRARRDVVGEFTVKRMKALQPRI
QQIVDEHLDALLAGPKPADLVQALSLPVPSLVICELLGVPYSDHEFFQSCSSRMLSREVTAE
ERMTAFEQLENYLDELVTKKEANATEDDLLGRQILKQRETGEADHGELVGLAFLLLIAGHET
TANMISLGTVTLLENPDQLAKIKADPGKTLAAIEELLRVFTIAEEATSRFATADVEIGGTLIRAG
EGVVGLSNAGNHDPDGFENPDTFDIERGARHHVAFGFGVHQCLGQNLARLELQIVFDTLFR
RVPGLRIAVPVDELPFKHDSTIYGLHALPVTW- SEQ ID NO: 83 (nucleic acid sequence of aluC09M24)
ATGACTGACGTCGAGGAAACCACCGCGACCTTGCCGCTGGCCCGGAAATGCCCGTTTT
CGCCGCCGCCCGAATACGAACGGCTTCGCCGGGAAAGTCCGGTTTCCCGGGTCGGTC
TCCCGTCCGGTCAAACGGCTTGGATTCTCACCCGGCTCGAAGACATCCGCGAAATGCT
GAGCAGCCCGCATTTCAGTTCCGACCGGCAGAGCCCGTCGTTCCCGCTGATGGTCGC
GCGGCAGATCCGCCGCGAGGACAAGCCGTTCCGCCCCTCCCTCATCGCGATGGATCC
GCCGGAACACAGCCGGGCCAGGCGTGACGTCGTCGGGGAATTCACCGTCAAGCGGAT
GAAGGCGCTCCAGCCGCGAATTCAGCAGATCGTCGACGAACATCTCGACGCCCTGCTC
GCGGGCCCCAAACCCGCCGATCTCGTCCAGGCGCTTTCCCTGCCCGTTCCCTCGCTG
GTGATCTGCGAACTGCTCGGCGTCCCTATTCGGACCACGAGTTCTTCCAGTCCTGCA
GTTCCAGGATGCTCAGCCGGGAGGTCACCGCCGAAGAACGGATGACCGCGTTCGAGC
AGCTCGAAAACTATCTCGACGAACTGGTCACCAAGAAGGAGGCGAACGCCACCGAGGA
CGACCTCCTCGGCCGTCAGATCCTGAAACAGCGGGAAACGGGCGAGGCCGACCACGG
TGAACTCGTCGGGCTGGCGTTCCTGCTGCTCATCGCCGGACACGAGACCACGGCGAA
CATGATCTCGCTCGGCACGGTGACCCTGCTGGAGAATCCCGATCAGCTCGCGAAGATC
AAGGCAGACCCCGGCAAGACCCTCGCCGCCATCGAGGAACTCCTGCGGGTCTTCACG
ATCGCGGAAGAAGCGACCTCACGCTTCGCCACGGCGGACGTCGAGATCGGCGGAACG
CTGATCCGCGCGGGGGAAGGGGTGGTGGGCCTGAGCAACGCGGGCAACCACGATCC
GGACGGCTTCGAGAACCCGGACACCTTCGACATCGAACGCGGCGCGCGGCATCACGT
CGCGTTCGGATTCGGGGTGCACCAGTGTCTCGGCCAGAACTTGGCGAGGTTGGAACTC
CAGATCGTCTTCGATACGTTGTTCCGGCGAGTGCCGGGCCTCCGGATCGCCGTTCCGG
TCGACGAACTGCCGTTCAAGCACGATTCGACGATCTACGGCCTCCACGCCCTTCCGGT
CACCTGGTAG SEQ ID NO: 84 (amino acid sequence of AluC09M24 (404aa))
MTDVEETTATLPLARKCPFSPPPEYERLRRESPVSRVGLPSGQTAWILTRLEDIREMLSSPH
FSSDRQSPSFPLMVARQIRREDKPFRPSLIAMDPPEHSRARRDVVGEFTVKRMKALQPRIQ
QIVDEHLDALLAGPKPADLVQALSLPVPSLVICELLGVPYSDHEFFQSCSSRMLSREVTAEE
RMTAFEQLENYLDELVTKKEANATEDDLLGRQILKQRETGEADHGELVGLAFLLLIAGHETT
ANMISLGTVTLLENPDQLAKIKADPGKTLAAIEELLRVFTIAEEATSRFATADVEIGGTLIRAGE
GVVGLSNAGNHDPDGFENPDTFDIERGARHHVAFGFGVHQCLGQNLARLELQIVFDTLFRR
VPGLRIAVPVDELPFKHDSTIYGLHALPVTW- SEQ ID NO: 87 (nucleic acid sequence of aluC09M25)
ATGACTGACGTCGAGGAAACCACCGCGACCTTGCCGCTGGCCCGGAAATGCCCGTTTT
CGCCGCCGCCCGAATACGAACGGCTTCGCCGGGAAAGTCCGGTTTCCCGGGTCGGTC
TCCCGTCCGGTCAAACGGCTTGGGCGCTCACCCGGCTCGAAGACATCCGCGAAATGCT
GAGCAGCCCGCATTTCAGTTCCGACCGGCAGAGCCCGTCGTTCCCGCTGTTTGTCGCG
CGGCAGATCCGCCGCGAGGACAAGCCGTTCCGCCCCTCCCTCATCGCGATGGATCCG
CCGGAACACAGCCGGGCCAGGCGTGACGTCGTCGGGGAATTCACCGTCAAGCGGATG
AAGGCGCTCCAGCCGCGAATTCAGCAGATCGTCGACGAACATCTCGACGCCCTGCTCG
CGGGCCCCAAACCCGCCGATCTCGTCCAGGCGCTTTCCCTGCCCGTTCCCTCGCTGGT

Figure 1 (continued)

GATCTGCGAACTGCTCGGCGTCCCCTATTCGGACCACGAGTTCTTCCAGTCCTGCAGTT
CCAGGATGCTCAGCCGGGAGGTCACCGCCGAAGAACGGATGACCGCGTTCGAGCAGC
TCGAAAACTATCTCGACGAACTGGTCACCAAGAAGGAGGCGAACGCCACCGAGGACGA
CCTCCTCGGCCGTCAGATCCTGAAACAGCGGGAAACGGGCGAGGCCGACCACGGTGA
ACTCGTCGGGCTGGCGTTCCTGCTGCTCATCGCCGGACACGAGACCACGGCGAACAT
GATCTCGCTCGGCACGGTGACCCTGCTGGAGAATCCCGATCAGCTCGCGAAGATCAAG
GCAGACCCCGGCAAGACCCTCGCCGCCATCGAGGAACTCCTGCGGGTCTTCACGATC
GCGGAAGAAGCGACCTCACGCTTCGCCACGGCGGACGTCGAGATCGGCGGAACGCTG
ATCCGCGCGGGGAAGGGGTGGTGGGCCTGAGCAACGCGGGCAACCACGATCCGGA
CGGCTTCGAGAACCCGGACACCTTCGACATCGAACGCGGCGCGCGGCATCACGTCGC
GTTCGGATTCGGGGTGCACCAGTGTCTCGGCCAGAACTTGGCGAGGTTGGAACTCCAG
ATCGTCTTCGATACGTTGTTCCGGCGAGTGCCGGGCCTCCGGATCGCCGTTCCGGTCG
ACGAACTGCCGTTCAAGCACGATTCGACGATCTACGGCCTCCACGCCCTTCCGGTCAC
CTGGTAG

SEQ ID NO: 88 (amino acid sequence of AluC09M25 (404aa))
MTDVEETTATLPLARKCPFSPPPEYERLRRESPVSRVGLPSGQTAWALTRLEDIREMLSSP
HFSSDRQSPSFPLFVARQIRREDKPFRPSLIAMDPPEHSRARRDVVGEFTVKRMKALQPRI
QQIVDEHLDALLAGPKPADLVQALSLPVPSLVICELLGVPYSDHEFFQSCSSRMLSREVTAE
ERMTAFEQLENYLDELVTKKEANATEDDLLGRQILKQRETGEADHGELVGLAFLLLIAGHET
TANMISLGTVTLLENPDQLAKIKADPGKTLAAIEELLRVFTIAEEEATSRFATADVEIGGTLIRAG
EGVVGLSNAGNHDPDGFENPDTFDIERGARHHVAFGFGVHQCLGQNLARLELQIVFDTLFR
RVPGLRIAVPVDELPFKHDSTIYGLHALPVTW- SEQ ID NO: 91 (nucleic acid sequence of aluC09M26)
ATGACTGACGTCGAGGAAACCACCGCGACCTTGCCGCTGGCCCGGAAATGCCCGTTTT
CGCCGCCGCCCGAATACGAACGGCTTCGCCGGGAAAGTCCGGTTTCCCGGGTCGGTC
TCCCGTCCGGTCAAACGGCTTGGGCGCTCACCCGGCTCGAAGACATCCGCGAAATGCT
GAGCAGCCCGCATTTCAGTTCCGACCGGCAGAGCCCGTCGTTCCCGCTGTGGGTCGC
GCGGCAGATCCGCCGCGAGGACAAGCCGTTCCGCCCCTCCCTCATCGCGATGGATCC
GCCGGAACACAGCCGGGCCAGGCGTGACGTCGTCGGGGAATTCACCGTCAAGCGGAT
GAAGGCGCTCCAGCCGCGAATTCAGCAGATCGTCGACGAACATCTCGACGCCCTGCTC
GCGGGCCCCAAACCCGCCGATCTCGTCCAGGCGCTTTCCCTGCCCGTTCCCTCGCTG
GTGATCTGCGAACTGCTCGGCGTCCCCTATTCGGACCACGAGTTCTTCCAGTCCTGCA
GTTCCAGGATGCTCAGCCGGGAGGTCACCGCCGAAGAACGGATGACCGCGTTCGAGC
AGCTCGAAAACTATCTCGACGAACTGGTCACCAAGAAGGAGGCGAACGCCACCGAGGA
CGACCTCCTCGGCCGTCAGATCCTGAAACAGCGGGAAACGGGCGAGGCCGACCACGG
TGAACTCGTCGGGCTGGCGTTCCTGCTGCTCATCGCCGGACACGAGACCACGGCGAA
CATGATCTCGCTCGGCACGGTGACCCTGCTGGAGAATCCCGATCAGCTCGCGAAGATC
AAGGCAGACCCCGGCAAGACCCTCGCCGCCATCGAGGAACTCCTGCGGGTCTTCACG
ATCGCGGAAGAAGCGACCTCACGCTTCGCCACGGCGGACGTCGAGATCGGCGGAACG
CTGATCCGCGCGGGGAAGGGGTGGTGGGCCTGAGCAACGCGGGCAACCACGATCC
GGACGGCTTCGAGAACCCGGACACCTTCGACATCGAACGCGGCGCGCGGCATCACGT
CGCGTTCGGATTCGGGGTGCACCAGTGTCTCGGCCAGAACTTGGCGAGGTTGGAACTC
CAGATCGTCTTCGATACGTTGTTCCGGCGAGTGCCGGGCCTCCGGATCGCCGTTCCGG
TCGACGAACTGCCGTTCAAGCACGATTCGACGATCTACGGCCTCCACGCCCTTCCGGT
CACCTGGTAG SEQ ID NO: 92 (amino acid sequence of AluC09M26 (404aa))
MTDVEETTATLPLARKCPFSPPPEYERLRRESPVSRVGLPSGQTAWALTRLEDIREMLSSP
HFSSDRQSPSFPLVVARQIRREDKPFRPSLIAMDPPEHSRARRDVVGEFTVKRMKALQPRI
QQIVDEHLDALLAGPKPADLVQALSLPVPSLVICELLGVPYSDHEFFQSCSSRMLSREVTAE
ERMTAFEQLENYLDELVTKKEANATEDDLLGRQILKQRETGEADHGELVGLAFLLLIAGHET
TANMISLGTVTLLENPDQLAKIKADPGKTLAAIEELLRVFTIAEEEATSRFATADVEIGGTLIRAG
EGVVGLSNAGNHDPDGFENPDTFDIERGARHHVAFGFGVHQCLGQNLARLELQIVFDTLFR
RVPGLRIAVPVDELPFKHDSTIYGLHALPVTW- SEQ ID NO: 95 (nucleic acid sequence of aluC09M27)

Figure 1 (continued)

ATGACTGACGTCGAGGAAACCACCGCGACCTTGCCGCTGGCCCGGAAATGCCCGTTTT
CGCCGCCGCCCGAATACGAACGGCTTCGCCGGGAAAGTCCGGTTTCCCGGGTCGGTC
TCCCGTCCGGTCAAACGGCTTGGGCGCTCACCCGGCTCGAAGACATCCGCGAAATGCT
GAGCAGCCCGCATTTCAGTTCCGACCGGCAGAGCCCGTCGTTCCCGCTGGCGGTCGC
GCGGCAGATCCGCCGCGAGGACAAGCCGTTCCGCCCCTCCCTCATCGCGATGGATCC
GCCGGAACACAGCCGGGCCAGGCGTGACGTCGTCGGGGAATTCACCGTCAAGCGGAT
GAAGGCGCTCCAGCCGCGAATTCAGCAGATCGTCGACGAACATCTCGACGCCCTGCTC
GCGGGCCCCAAACCCGCCGATCTCGTCCAGGCGCTTTCCCTGCCCGTTCCCTCGCTG
GTGATCTGCGAACTGCTCGGCGTCCCCTATTCGGACCACGAGTTCTTCCAGTCCTGCA
GTTCCAGGATGCTCAGCCGGGAGGTCACCGCCGAAGAACGGATGACCGCGTTCGAGC
AGCTCGAAAACTATCTCGACGAACTGGTCACCAAGAAGGAGGCGAACGCCACCGAGGA
CGACCTCCTCGGCCGTCAGATCCTGAAACAGCGGGAAACGGGCGAGGCCGACCACGG
TGAACTCGTCGGGCTGGCGTTCCTGCTGCTCATCGCCGGACACGAGACCACGGCGAA
CATGATCTCGCTCGGCACGGTGACCCTGCTGGAGAATCCCGATCAGCTCGCGAAGATC
AAGGCAGACCCCGGCAAGACCCTCGCCGCCATCGAGGAACTCCTGCGGGTCTTCACG
ATCGCGGAAGAAGCGACCTCACGCTTCGCCACGGCGGACGTCGAGATCGGCGGAACG
CTGATCCGCGCGGGGGAAGGGGTGGTGGGCCTGAGCAACGCGGGCAACCACGATCC
GGACGGCTTCGAGAACCCGGACACCTTCGACATCGAACGCGGCGCGCGGCATCACGT
CGCGTTCGGATTCGGGGTGCACCAGTGTCTCGGCCAGAACTTGGCGAGGTTGGAACTC
CAGATCGTCTTCGATACGTTGTTCCGGCGAGTGCCGGGCCTCCGGATCGCCGTTCCGG
TCGACGAACTGCCGTTCAAGCACGATTCGACGATCTACGGCCTCCACGCCCTTCCGGT
CACCTGGTAG

SEQ ID NO: 96 (amino acid sequence of AluC09M27 (404aa))
MTDVEETTATLPLARKCPFSPPPEYERLRRESPVSRVGLPSGQTAWALTRLEDIREMLSSP
HFSSDRQSPSFPLAVARQIRREDKPFRPSLIAMDPPEHSRARRDVVGEFTVKRMKALQPRI
QQIVDEHLDALLAGPKPADLVQALSLPVPSLVICELLGVPYSDHEFFQSCSSRMLSREVTAE
ERMTAFEQLENYLDELVTKKEANATEDDLLGRQILKQRETGEADHGELVGLAFLLLIAGHET
TANMISLGTVTLLENPDQLAKIKADPGKTLAAIEELLRVFTIAEEATSRFATADVEIGGTLIRAG
EGVVGLSNAGNHDPDGFENPDTFDIERGARHHVAFGFGVHQCLGQNLARLELQIVFDTLFR
RVPGLRIAVPVDELPFKHDSTIYGLHALPVTW- SEQ ID NO: 99 (nucleic acid sequence of aluC09M28)
ATGACTGACGTCGAGGAAACCACCGCGACCTTGCCGCTGGCCCGGAAATGCCCGTTTT
CGCCGCCGCCCGAATACGAACGGCTTCGCCGGGAAAGTCCGGTTTCCCGGGTCGGTC
TCCCGTCCGGTCAAACGGCTTGGGCGCTCACCCGGCTCGAAGACATCCGCGAAATGCT
GAGCAGCCCGCATTTCAGTTCCGACCGGCAGAGCCCGTCGTTCCCGCTGATGGTCGC
GCGGCAGATCCGCCGCGAGGACAAGCCGTTCCGCCCCTCCCTCATCGCGATGGATCC
GCCGGAACACAGCCGGGCCAGGCGTGACGTCGTCGGGGAATTCACCGTCAAGCGGAT
GAAGGCGCTCCAGCCGCGAATTCAGCAGATCGTCGACGAACATCTCGACGCCCTGCTC
GCGGGCCCCAAACCCGCCGATCTCGTCCAGGCGCTTTCCCTGCCCGTTCCCTCGCTG
GTGATCTGCGAACTGCTCGGCGTCCCCTATTCGGACCACGAGTTCTTCCAGTCCTGCA
GTTCCAGGATGCTCAGCCGGGAGGTCACCGCCGAAGAACGGATGACCGCGTTCGAGC
AGCTCGAAAACTATCTCGACGAACTGGTCACCAAGAAGGAGGCGAACGCCACCGAGGA
CGACCTCCTCGGCCGTCAGATCCTGAAACAGCGGGAAACGGGCGAGGCCGACCACGG
TGAACTCGTCGGGCTGGCGTTCCTGCTGCTCATCGCCGGACACGAGACCACGGCGAA
CATGATCTCGCTCGGCACGGTGACCCTGCTGGAGAATCCCGATCAGCTCGCGAAGATC
AAGGCAGACCCCGGCAAGACCCTCGCCGCCATCGAGGAACTCCTGCGGGTCTTCACG
ATCGCGGAAGAAGCGACCTCACGCTTCGCCACGGCGGACGTCGAGATCGGCGGAACG
CTGATCCGCGCGGGGGAAGGGGTGATTGGCCTGAGCAACGCGGGCAACCACGATCCG
GACGGCTTCGAGAACCCGGACACCTTCGACATCGAACGCGGCGCGCGGCATCACGTC
GCGTTCGGATTCGGGGTGCACCAGTGTCTCGGCCAGAACTTGGCGAGGTTGGAACTCC
AGATCGTCTTCGATACGTTGTTCCGGCGAGTGCCGGGCCTCCGGATCGCCGTTCCGGT
CGACGAACTGCCGTTCAAGCACGATTCGACGATCTACGGCCTCCACGCCCTTCCGGTC
ACCTGGTAG SEQ ID NO: 100 (amino acid sequence of AluC09M28 (404aa))

Figure 1 (continued)

MTDVEETTATLPLARKCPFSPPPEYERLRRESPVSRVGLPSGQTAWALTRLEDIREMLSSP
HFSSDRQSPSFPLMVARQIRREDKPFRPSLIAMDPPEHSRARRDVVGEFTVKRMKALQPRI
QQIVDEHLDALLAGPKPADLVQALSLPVPSLVICELLGVPYSDHEFFQSCSSRMLSREVTAE
ERMTAFEQLENYLDELVTKKEANATEDDLLGRQILKQRETGEADHGELVGLAFLLLIAGHET
TANMISLGTVTLLENPDQLAKIKADPGKTLAAIEELLRVFTIAEEEATSRFATADVEIGGTLIRAG
EGVIGLSNAGNHDPDGFENPDTFDIERGARHHVAFGFGVHQCLGQNLARLELQIVFDTLFR
RVPGLRIAVPVDELPFKHDSTIYGLHALPVTW-

SEQ ID NO: 103 (nucleic acid sequence of aluC09M29)
ATGACTGACGTCGAGGAAACCACCGCGACCTTGCCGCTGGCCCGGAAATGCCCGTTTT
CGCCGCCGCCCGAATACGAACGGCTTCGCCGGGAAAGTCCGGTTTCCCGGGTCGGTC
TCCCGTCCGGTCAAACGGCTTGGGCGCTCACCCGGCTCGAAGACATCCGCGAAATGCT
GAGCAGCCCGCATTTCAGTTCCGACCGGCAGAGCCCGTCGTTCCCGCTGATGGTCGC
GCGGCAGATCCGCCGCGAGGACAAGCCGTTCCGCCCCTCCCTCATCGCGATGGATCC
GCCGGAACACAGCCGGGCCAGGCGTGACGTCGTCGGGGAATTCACCGTCAAGCGGAT
GAAGGCGCTCCAGCCGCGAATTCAGCAGATCGTCGACGAACATCTCGACGCCCTGCTC
GCGGGCCCCAAACCCGCCGATCTCGTCCAGGCGCTTTCCCTGCCCGTTCCCTCGCTG
GTGATCTGCGAACTGCTCGGCGTCCCTATTCGGACCACGAGTTCTTCCAGTCCTGCA
GTTCCAGGATGCTCAGCCGGGAGGTCACCGCCGAAGAACGGATGACCGCGTTCGAGC
AGCTCGAAAACTATCTCGACGAACTGGTCACCAAGAAGGAGGCGAACGCCACCGAGGA
CGACCTCCTCGGCCGTCAGATCCTGAAACAGCGGGAAACGGGCGAGGCCGACCACGG
TGAACTCGTCGGGCTGGCGTTCCTGCTGCTCATCGCCGGACACGAGACCACGGCGAA
CATGATCTCGCTCGGCACGGTGACCCTGCTGGAGAATCCCGATCAGCTCGCGAAGATC
AAGGCAGACCCCGGCAAGACCCTCGCCGCCATCGAGGAACTCCTGCGGGTCTTCACG
ATCGCGGAAGAAGCGACCTCACGCTTCGCCACGGCGGACGTCGAGATCGGCGGAACG
CTGATCCGCGCGGGGGAAGGGGTGGCGGGCCTGAGCAACGCGGGCAACCACGATCC
GGACGGCTTCGAGAACCCGGACACCTTCGACATCGAACGCGGCGCGCGGCATCACGT
CGCGTTCGGATTCGGGGTGCACCAGTGTCTCGGCCAGAACTTGGCGAGGTTGGAACTC
CAGATCGTCTTCGATACGTTGTTCCGGCGAGTGCCGGGCCTCCGGATCGCCGTTCCGG
TCGACGAACTGCCGTTCAAGCACGATTCGACGATCTACGGCCTCCACGCCCTTCCGGT
CACCTGGTAG SEQ ID NO: 104 (amino acid sequence of AluC09M29 (404aa))
MTDVEETTATLPLARKCPFSPPPEYERLRRESPVSRVGLPSGQTAWALTRLEDIREMLSSP
HFSSDRQSPSFPLMVARQIRREDKPFRPSLIAMDPPEHSRARRDVVGEFTVKRMKALQPRI
QQIVDEHLDALLAGPKPADLVQALSLPVPSLVICELLGVPYSDHEFFQSCSSRMLSREVTAE
ERMTAFEQLENYLDELVTKKEANATEDDLLGRQILKQRETGEADHGELVGLAFLLLIAGHET
TANMISLGTVTLLENPDQLAKIKADPGKTLAAIEELLRVFTIAEEEATSRFATADVEIGGTLIRAG
EGVAGLSNAGNHDPDGFENPDTFDIERGARHHVAFGFGVHQCLGQNLARLELQIVFDTLFR
RVPGLRIAVPVDELPFKHDSTIYGLHALPVTW- SEQ ID NO: 107 (nucleic acid sequence of aluC09M30)
ATGACTGACGTCGAGGAAACCACCGCGACCTTGCCGCTGGCCCGGAAATGCCCGTTTT
CGCCGCCGCCCGAATACGAACGGCTTCGCCGGGAAAGTCCGGTTTCCCGGGTCGGTC
TCCCGTCCGGTCAAACGGCTTGGGCGCTCACCCGGCTCGAAGACATCCGCGAAATGCT
GAGCAGCCCGCATTTCAGTTCCGACCGGCAGAGCCCGTCGTTCCCGCTGATGGTCGC
GCGGCAGATCCGCCGCGAGGACAAGCCGTTCCGCCCCTCCCTCATCGCGATGGATCC
GCCGGAACACAGCCGGGCCAGGCGTGACGTCGTCGGGGAATTCACCGTCAAGCGGAT
GAAGGCGCTCCAGCCGCGAATTCAGCAGATCGTCGACGAACATCTCGACGCCCTGCTC
GCGGGCCCCAAACCCGCCGATCTCGTCCAGGCGCTTTCCCTGCCCGTTCCCTCGCTG
GTGATCTGCGAACTGCTCGGCGTCCCTATTCGGACCACGAGTTCTTCCAGTCCTGCA
GTTCCAGGATGCTCAGCCGGGAGGTCACCGCCGAAGAACGGATGACCGCGTTCGAGC
AGCTCGAAAACTATCTCGACGAACTGGTCACCAAGAAGGAGGCGAACGCCACCGAGGA
CGACCTCCTCGGCCGTCAGATCCTGAAACAGCGGGAAACGGGCGAGGCCGACCACGG
TGAACTCGTCGGGCTGGCGTTCCTGCTGCTCATCGCCGGACACGAGACCACGGCGAA
CATGATCTCGCTCGGCACGGTGACCCTGCTGGAGAATCCCGATCAGCTCGCGAAGATC
AAGGCAGACCCCGGCAAGACCCTCGCCGCCATCGAGGAACTCCTGCGGGTCTTCACG
ATCGCGGAAGAAGCGACCTCACGCTTCGCCACGGCGGACGTCGAGATCGGCGGAACG CTGATCCGCGCGGGGGAAGGGGTGCTGGGCCTGAGCAACGCGGGCAACCACGATCC
GGACGGCTTCGAGAACCCGGACACCTTCGACATCGAACGCGGCGCGCGGCATCACGT
CGCGTTCGGATTCGGGGTGCACCAGTGTCTCGGCCAGAACTTGGCGAGGTTGGAACTC
CAGATCGTCTTCGATACGTTGTTCCGGCGAGTGCCGGGCCTCCGGATCGCCGTTCCGG
TCGACGAACTGCCGTTCAAGCACGATTCGACGATCTACGGCCTCCACGCCCTTCCGGT
CACCTGGTAG SEQ ID NO: 108 (amino acid sequence of AluC09M30 (404aa))
MTDVEETTATLPLARKCPFSPPPEYERLRRESPVSRVGLPSGQTAWALTRLEDIREMLSSP
HFSSDRQSPSFPLMVARQIRREDKPFRPSLIAMDPPEHSRARRDVVGEFTVKRMKALQPRI
QQIVDEHLDALLAGPKPADLVQALSLPVPSLVICELLGVPYSDHEFFQSCSSRMLSREVTAE
ERMTAFEQLENYLDELVTKKEANATEDDLLGRQILKQRETGEADHGELVGLAFLLLIAGHET
TANMISLGTVTLLENPDQLAKIKADPGKTLAAIEELLRVFTIAEEATSRFATADVEIGGTLIRAG
EGVLGLSNAGNHDPDGFENPDTFDIERGARHHVAFGFGVHQCLGQNLARLELQIVFDTLFR
RVPGLRIAVPVDELPFKHDSTIYGLHALPVTW- SEQ ID NO: 109 (variable codon for T291, A47, M75 or V315)
atgactgacg tcgaggaaac caccgcgacc ttgccgctgg cccggaaatg cccgttttcg     60
ccgccgcccg aatacgaacg gcttcgccgg gaaagtccgg tttcccgggt cggtctcccg     120
tccggtcaaa cggcttgggc nnncacccgg ctcgaagaca tccgcgaaat gctgagcagc     180
ccgcatttca gttccgaccg gcagagcccg tcgttcccgc tgnnngtcgc gcggcagatc     240
cgccgcgagg acaagccgtt ccgcccctcc ctcatcgcga tggatccgcc ggaacacagc     300
cgggccaggc gtgacgtcgt cggggaattc accgtcaagc ggatgaaggc gctccagccg     360
cgaattcagc agatcgtcga cgaacatctc gacgccctgc tcgcgggccc caaacccgcc     420
gatctcgtcc aggcgctttc cctgccgtt ccctcgctgg tgatctgcga actgctcggc     480
gtcccctatt cggaccacga gttcttccag tcctgcagtt ccaggatgct cagccgggag     540
gtcaccgccg aagaacggat gaccgcgttc gagcagctcg aaaactatct cgacgaactg     600
gtcaccaaga aggaggcgaa cgccaccgag gacgacctcc tcggccgtca gatcctgaaa     660
cagcgggaaa cgggcgaggc cgaccacggt gaactcgtcg gctggcgtt cctgctgctc     720 atcgccggac acgagaccac ggcgaacatg atctcgctcg gcacggtgac cctgctggag     780
aatcccgatc agctcgcgaa gatcaaggca gaccccggca agaccctcgc cgccatcgag     840
gaactcctgc gggtcttcac gatcgcggaa nnngcgacct cacgcttcgc cacggcggac     900
gtcgagatcg gcggaacgct gatccgcgcg ggggaagggg tgnnnggcct gagcaacgcg     960
ggcaaccacg atccggacgg cttcgagaac ccggacacct cgacatcga acgcggcgcg     1020 cggcatcacg tcgcgttcgg attcggggtg caccagtgtc tcggccagaa cttggcgagg     1080
ttggaactcc agatcgtctt cgatacgttg ttccggcgag tgccgggcct ccggatcgcc     1140
gttccggtcg acgaactgcc gttcaagcac gattcgacga tctacggcct ccacgccctt     1200
ccggtcacct ggtaggagga gccatgaaga tcatcgcgga caccgggaaa tgcgtgggcg     1260

Figure 1 (continued)

cgggccagtg cgtgctcacc gatcccgatc tgttcgatca gagcgaggac gacggaacgg    1320
tcctcgtgct gaacgccgag cctgaaggcg aagaggcgga agaaaacgcc cgcaccgccg    1380
tgcacatctg cccggggcag gccttgtcgc tcgcttaa

SEQ ID NO: 110 (variable residue for T291, A47, M75 or V315)
Met Thr Asp Val Glu Glu Thr Thr Ala Thr Leu Pro Leu Ala Arg Lys
1               5                   10                  15

Cys Pro Phe Ser Pro Pro Glu Tyr Glu Arg Leu Arg Arg Glu Ser
            20                  25                  30

Pro Val Ser Arg Val Gly Leu Pro Ser Gly Gln Thr Ala Trp Xaa Leu
            35                  40                  45

Thr Arg Leu Glu Asp Ile Arg Glu Met Leu Ser Ser Pro His Phe Ser
            50                  55                  60

Ser Asp Arg Gln Ser Pro Ser Phe Pro Leu Xaa Val Ala Arg Gln Ile
65                  70                  75                  80

Arg Arg Glu Asp Lys Pro Phe Arg Pro Ser Leu Ile Ala Met Asp Pro
                85                  90                  95

Pro Glu His Ser Arg Ala Arg Arg Asp Val Val Gly Glu Phe Thr Val
            100                 105                 110

Lys Arg Met Lys Ala Leu Gln Pro Arg Ile Gln Gln Ile Val Asp Glu
            115                 120                 125

His Leu Asp Ala Leu Leu Ala Gly Pro Lys Pro Ala Asp Leu Val Gln
            130                 135                 140

Ala Leu Ser Leu Pro Val Pro Ser Leu Val Ile Cys Glu Leu Leu Gly
145                 150                 155                 160

Val Pro Tyr Ser Asp His Glu Phe Phe Gln Ser Cys Ser Ser Arg Met
                165                 170                 175

Leu Ser Arg Glu Val Thr Ala Glu Glu Arg Met Thr Ala Phe Glu Gln
            180                 185                 190

Leu Glu Asn Tyr Leu Asp Glu Leu Val Thr Lys Lys Glu Ala Asn Ala
            195                 200                 205

Figure 1 (continued)

Thr Glu Asp Asp Leu Leu Gly Arg Gln Ile Leu Lys Gln Arg Glu Thr
210 215 220

Gly Glu Ala Asp His Gly Glu Leu Val Gly Leu Ala Phe Leu Leu Leu
225 230 235 240

Ile Ala Gly His Glu Thr Thr Ala Asn Met Ile Ser Leu Gly Thr Val
245 250 255

Thr Leu Leu Glu Asn Pro Asp Gln Leu Ala Lys Ile Lys Ala Asp Pro
260 265 270

Gly Lys Thr Leu Ala Ala Ile Glu Glu Leu Leu Arg Val Phe Thr Ile
275 280 285

Ala Glu Xaa Ala Thr Ser Arg Phe Ala Thr Ala Asp Val Glu Ile Gly
290 295 300

Gly Thr Leu Ile Arg Ala Gly Glu Gly Val Xaa Gly Leu Ser Asn Ala
305 310 315 320

Gly Asn His Asp Pro Asp Gly Phe Glu Asn Pro Asp Thr Phe Asp Ile
325 330 335

Glu Arg Gly Ala Arg His His Val Ala Phe Gly Phe Gly Val His Gln
340 345 350

Cys Leu Gly Gln Asn Leu Ala Arg Leu Glu Leu Gln Ile Val Phe Asp
355 360 365

Thr Leu Phe Arg Arg Val Pro Gly Leu Arg Ile Ala Val Pro Val Asp
370 375 380

Glu Leu Pro Phe Lys His Asp Ser Thr Ile Tyr Gly Leu His Ala Leu
385 390 395 400

Pro Val Thr Trp

Figure 1 (continued)

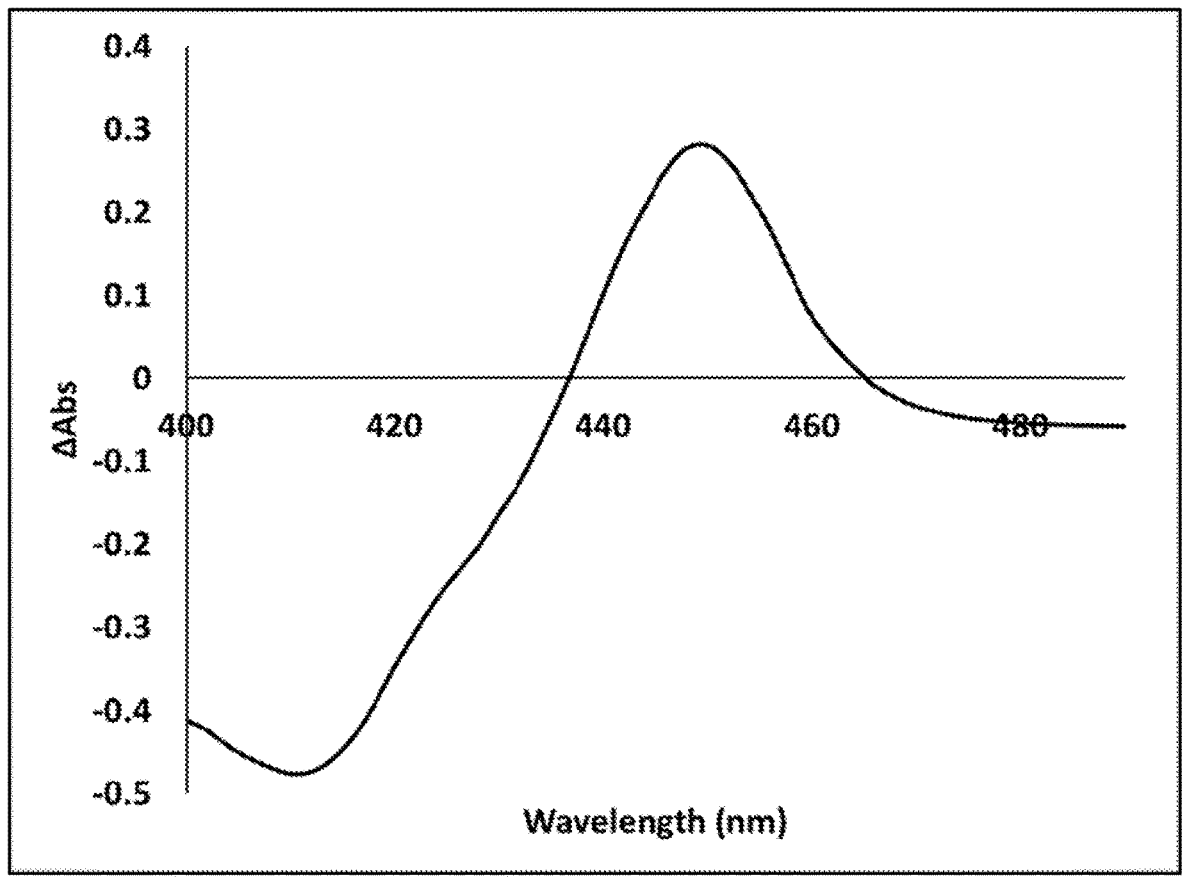
Figure 2: carbon monoxide difference spectrum for CYP aluC09M11

UPLC chromatograms with UV detection at 275 nm showing the hydroxylation of diclofenac catalysed by, from top to bottom: cytochrome P450 aluC09 and mutants aluC09M11, aluC09M12, aluC09M17, aluC09M18 and aluC09M19.

UPLC chromatograms with UV detection at 275 nm showing the hydroxylation of diclofenac catalysed by, from top to bottom: cytochrome P450 mutants aluC09M20, aluC09M24, aluC09M30, aluC09M31, aluC09M33 and aluC09M34.

UPLC chromatograms with UV detection at 275 nm showing the hydroxylation of diclofenac catalysed by, from top to bottom: cytochrome P450 mutants aluC09M35, aluC09M36, aluC09M37, aluC09M38, aluC09M39 and aluC09M40.

Selected UPLC chromatograms with UV detection at 275 nm showing the hydroxylation of flufenamic acid catalysed by, from top to bottom: cytochrome P450 aluC09 and mutants aluC09M18, aluC09M35 and aluC09M39.

UPLC chromatograms with UV detection at 275 nm showing the hydroxylation of aceclofenac catalysed by, from top to bottom: cytochrome P450 aluC09 and mutants aluC09M11, aluC09M12, aluC09M17, aluC09M18 and aluC09M19.

UPLC chromatograms with UV detection at 275 nm showing the hydroxylation of aceclofenac catalysed by, from top to bottom: cytochrome P450 mutants aluC09M20, aluC09M24, aluC09M30, aluC09M31, aluC09M33 and aluC09M34.

UPLC chromatograms with UV detection at 275 nm showing the hydroxylation of aceclofenac catalysed by, from top to bottom: cytochrome P450 mutants aluC09M35, aluC09M36, aluC09M37, aluC09M38, aluC09M39 and aluC09M40.

UPLC chromatograms with UV detection at 300 nm showing the metabolism of napropamide catalysed by, from top to bottom: cytochrome P450 aluC09 and mutants aluC09M34, aluC09M36, aluC09M38.

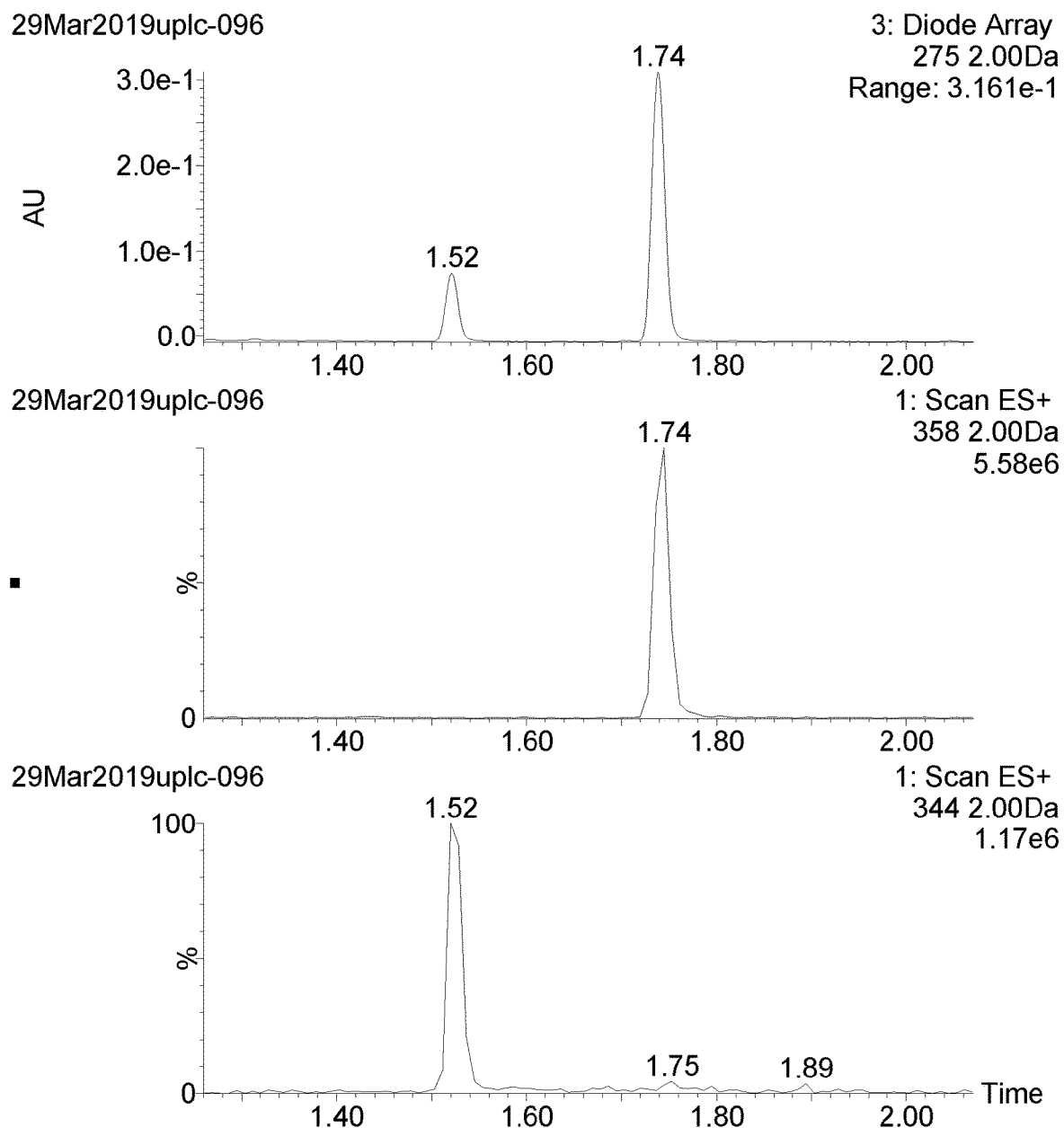

UPLC chromatograms showing the O-demethylation of indomethacin catalysed by cytochrome P450 mutant aluC09M36, as a representative example. Top to bottom: $UV_{275nm}$ chromatogram, extracted ion chromatogram for parent molecular ion ($[M+H]^+$ m/z358), extracted ion chromatogram for O-demethyl-indomethacin product molecular ion ($[M+H]^+$ m/z344). Parent indomethacin eluted at 1.74 minutes and the O-demethyl-indomethacin product elutes at 1.52 minutes.

Figure 7

Structural formulae of selected compounds employed in Example 5, and products thereof. Diclofenac (a), flufenamic acid (b), aceclofenac (c), napropamide (d) and indomethacin (e).

SEQUENCE LISTING

<160> NUMBER OF SEQ ID NOS: 110

<210> SEQ ID NO 1
<211> LENGTH: 2793
<212> TYPE: DNA
<213> ORGANISM: Amycolatopsis lurida

```
<400> SEQUENCE: 1
atgactgacg tcgaggaaac caccgcgacc ttgccgctgg cccggaaatg cccgttttcg      60
ccgccgcccg aatacgaacg gcttcgccgg gaaagtccgg tttcccgggt cggtctcccg     120
tccggtcaaa cggcttgggc gctcacccgg ctcgaagaca tccgcgaaat gctgagcagc     180
ccgcatttca gttccgaccg gcagagcccg tcgttcccgc tgatggtcgc gcggcagatc     240
cgccgcgagg acaagccgtt ccgcccctcc ctcatcgcga tggatccgcc ggaacacagc     300
cgggccaggc gtgacgtcgt cggggaattc accgtcaagc ggatgaaggc gctccagccg     360
cgaattcagc agatcgtcga cgaacatctc gacgccctgc tcgcgggccc caaacccgcc     420
gatctcgtcc aggcgctttc cctgccgtt ccctcgctgg tgatctgcga actgctcggc     480
gtcccctatt cggaccacga gttcttccag tcctgcagtt ccaggatgct cagccgggag     540
gtcaccgccg aagaacggat gaccgcgttc gagcagctcg aaaactatct cgacgaactg     600
gtcaccaaga aggaggcgaa cgccaccgag gacgacctcc tcggccgtca gatcctgaaa     660
cagcgggaaa cgggcgaggc cgaccacggt gaactcgtcg gctggcgtt cctgctgctc     720
atcgccggac acgagaccac ggcgaacatg atctcgctcg gcacggtgac cctgctggag     780
aatcccgatc agctcgcgaa gatcaaggca gaccccggca agaccctcgc cgccatcgag     840
gaactcctgc gggtcttcac gatcgcggaa acggcgacct cacgcttcgc cacggcggac     900
gtcgagatcg gcggaacgct gatccgcgcg ggggaagggg tggtgggcct gagcaacgcg     960
ggcaaccacg atccggacgg cttcgagaac ccggacacct tcgacatcga acgcggcgcg    1020
cggcatcacg tcgcgttcgg attcggggtg caccagtgtc tcggccagaa cttggcgagg    1080
ttggaactcc agatcgtctt cgatacgttg ttccggcgag tgccgggcct ccggatcgcc    1140
gttccggtcg acgaactgcc gttcaagcac gattcgacga tctacggcct ccacgcccct    1200
ccggtcacct ggtaggagga gccatgaaga tcatcgcgga caccgggaaa tgcgtgggcg    1260
cgggccagtg cgtgctcacc gatcccgatc tgttcgatca gagcgaggac gacggaacgg    1320
tcctcgtgct gaacgccgag cctgaaggcg aagaggcgga agaaaacgcc cgcaccgccg    1380
tgcacatctg cccggggcag gccttgtcgc tcgcttaata ggaagcttat gccccgccct    1440
ctgcgggtag ccatcgtcgg atccggcccg gcgggatct acgccgccga cgccctgctc    1500
aagtccgaag tggccgccga ccccggtgtt tccatcgaca tcttcgagcg catgcccgcc    1560
ccgttcggcc tcatccggta cggcgtcgcg cccgaccacc gcgggatcaa gggcatcatc    1620
acggccctcc accaggtgct cgacaagccg cagatccgcc tcttcggcaa cgtgaactac    1680
cccaccgacg tcagcctgga cgatctgcgc gccttctacg acggtgtgat cttcgccacc    1740
ggcgccacgg cggaccggga cctgtccctc ccgggcatcg acctcgacgg ctcgtacggc    1800
gcggccgact tcgtcgcctg gtacgacggc caccccgact tcccgcgcac ctggccgctg    1860
gaggcggaga agtcgccgt cctcggtgtc ggcaacgtcg ccctggacat cgcgcgcgtc    1920
ctcgccaaga cggccgacga gctgctgccg accgagatcc cgccgaacgt ctacgagggc    1980
ctcaaggcca acaaggcgct ggaggtgcac gtcttcggcc gccgcggccc ggcgcaggcg    2040
aagttcagcc cgatggagct gcgggagctg accactcccc caacatcga ggtgatcgtc     2100
gaccccgagg acatcgacta cgacgagggc tcgatcgcga cccggcgcgg caacaagcag    2160
gccgacatgg tcgccaagac cctggagaac tgggcgatcc gcgacgtcgg cgaccggccg    2220
cacaagctct tcctgcactt cttcgagtcg cccgcgcgaga tcctcggcga ggacggcagg    2280
gtgaccggcc tgcgcaccga gcgcacggag ctggacggca cgggcaacgt caagggcacc    2340
```

```
ggcgagttca aggactggga cgtccaggcg gtctaccggg ccgtcggcta cctctccgac    2400
cagctgccca agctgccctg ggacctcgag acgtgcacgg tcccggacgc gggcggccgg    2460
gtcgtccagg agtccggcga gcacctccag tcgacgtacg tcaccggctg gatccggcgc    2520
ggtccgatcg gcctgatcgg ccacaccaag ggcgacgcca acgagacggt gtccaacctg    2580
ctggacgact acgcgaacgg ccgtctccag acgccctcct ccccgctcc cgaggccgtg    2640 gacgcgttcc tcgccgagcg gaacgtccgc ttcaccacct gggacggctg gtaccggctc    2700
gacgccgcgg agaaggcgca gggcgaaccg cacgggcgtg agcgcgtgaa gtacgtcgag    2760
cgcgaggaca tgctccgcga gagcggcgcc tga                                2793
```

<210> SEQ ID NO 2
<211> LENGTH: 404
<212> TYPE: PRT
<213> ORGANISM: Amycolatopsis lurida

<400> SEQUENCE: 2

```
Met Thr Asp Val Glu Glu Thr Thr Ala Thr Leu Pro Leu Ala Arg Lys
1               5                   10                  15

Cys Pro Phe Ser Pro Pro Glu Tyr Glu Arg Leu Arg Arg Glu Ser
            20                  25                  30

Pro Val Ser Arg Val Gly Leu Pro Ser Gly Gln Thr Ala Trp Ala Leu
        35                  40                  45

Thr Arg Leu Glu Asp Ile Arg Glu Met Leu Ser Ser Pro His Phe Ser
    50                  55                  60

Ser Asp Arg Gln Ser Pro Ser Phe Pro Leu Met Val Ala Arg Gln Ile
65                  70                  75                  80

Arg Arg Glu Asp Lys Pro Phe Arg Pro Ser Leu Ile Ala Met Asp Pro
                85                  90                  95

Pro Glu His Ser Arg Ala Arg Arg Asp Val Val Gly Glu Phe Thr Val
            100                 105                 110

Lys Arg Met Lys Ala Leu Gln Pro Arg Ile Gln Gln Ile Val Asp Glu
        115                 120                 125

His Leu Asp Ala Leu Leu Ala Gly Pro Lys Pro Ala Asp Leu Val Gln
    130                 135                 140

Ala Leu Ser Leu Pro Val Pro Ser Leu Val Ile Cys Glu Leu Leu Gly
145                 150                 155                 160

Val Pro Tyr Ser Asp His Glu Phe Phe Gln Ser Cys Ser Ser Arg Met
                165                 170                 175

Leu Ser Arg Glu Val Thr Ala Glu Glu Arg Met Thr Ala Phe Glu Gln
            180                 185                 190

Leu Glu Asn Tyr Leu Asp Glu Leu Val Thr Lys Lys Glu Ala Asn Ala
        195                 200                 205

Thr Glu Asp Asp Leu Leu Gly Arg Gln Ile Leu Lys Gln Arg Glu Thr
    210                 215                 220

Gly Glu Ala Asp His Gly Glu Leu Val Gly Leu Ala Phe Leu Leu Leu
225                 230                 235                 240

Ile Ala Gly His Glu Thr Thr Ala Asn Met Ile Ser Leu Gly Thr Val
                245                 250                 255

Thr Leu Leu Glu Asn Pro Asp Gln Leu Ala Lys Ile Lys Ala Asp Pro
            260                 265                 270

Gly Lys Thr Leu Ala Ala Ile Glu Glu Leu Leu Arg Val Phe Thr Ile
        275                 280                 285
```

```
Ala Glu Thr Ala Thr Ser Arg Phe Ala Thr Ala Asp Val Glu Ile Gly
            290                 295                 300
Gly Thr Leu Ile Arg Ala Gly Glu Gly Val Val Gly Leu Ser Asn Ala
305                 310                 315                 320
Gly Asn His Asp Pro Asp Gly Phe Glu Asn Pro Asp Thr Phe Asp Ile
                325                 330                 335
Glu Arg Gly Ala Arg His His Val Ala Phe Gly Phe Gly Val His Gln
            340                 345                 350
Cys Leu Gly Gln Asn Leu Ala Arg Leu Glu Leu Gln Ile Val Phe Asp
                355                 360                 365
Thr Leu Phe Arg Arg Val Pro Gly Leu Arg Ile Ala Val Pro Val Asp
370                 375                 380
Glu Leu Pro Phe Lys His Asp Ser Thr Ile Tyr Gly Leu His Ala Leu
385                 390                 395                 400
Pro Val Thr Trp

<210> SEQ ID NO 3
<211> LENGTH: 64
<212> TYPE: PRT
<213> ORGANISM: Amycolatopsis lurida

<400> SEQUENCE: 3

Met Lys Ile Ile Ala Asp Thr Gly Lys Cys Val Gly Ala Gly Gln Cys
1               5                   10                  15
Val Leu Thr Asp Pro Asp Leu Phe Asp Gln Ser Glu Asp Gly Thr
            20                  25                  30
Val Leu Val Leu Asn Ala Glu Pro Glu Gly Glu Ala Glu Glu Asn
            35                  40                  45
Ala Arg Thr Ala Val His Ile Cys Pro Gly Gln Ala Leu Ser Leu Ala
            50                  55                  60

<210> SEQ ID NO 4
<211> LENGTH: 454
<212> TYPE: PRT
<213> ORGANISM: Amycolatopsis lurida

<400> SEQUENCE: 4

Met Pro Arg Pro Leu Arg Val Ala Ile Val Gly Ser Gly Pro Ala Gly
1               5                   10                  15
Ile Tyr Ala Ala Asp Ala Leu Leu Lys Ser Glu Val Ala Ala Asp Pro
            20                  25                  30
Gly Val Ser Ile Asp Ile Phe Glu Arg Met Pro Ala Pro Phe Gly Leu
            35                  40                  45
Ile Arg Tyr Gly Val Ala Pro Asp His Pro Arg Ile Lys Gly Ile Ile
50                  55                  60
Thr Ala Leu His Gln Val Leu Asp Lys Pro Gln Ile Arg Leu Phe Gly
65                  70                  75                  80
Asn Val Asn Tyr Pro Thr Asp Val Ser Leu Asp Asp Leu Arg Ala Phe
                85                  90                  95
Tyr Asp Gly Val Ile Phe Ala Thr Gly Ala Thr Ala Asp Arg Asp Leu
            100                 105                 110
Ser Leu Pro Gly Ile Asp Leu Asp Gly Ser Tyr Gly Ala Ala Asp Phe
            115                 120                 125
Val Ala Trp Tyr Asp Gly His Pro Asp Phe Pro Arg Thr Trp Pro Leu
130                 135                 140
```

Glu Ala Glu Lys Val Ala Val Leu Gly Val Gly Asn Val Ala Leu Asp
145                 150                 155                 160

Ile Ala Arg Val Leu Ala Lys Thr Ala Asp Glu Leu Pro Thr Glu
            165                 170                 175

Ile Pro Pro Asn Val Tyr Glu Gly Leu Lys Ala Asn Lys Ala Leu Glu
                180                 185                 190

Val His Val Phe Gly Arg Arg Gly Pro Ala Gln Ala Lys Phe Ser Pro
            195                 200                 205

Met Glu Leu Arg Glu Leu Asp His Ser Pro Asn Ile Glu Val Ile Val
210                 215                 220

Asp Pro Glu Asp Ile Asp Tyr Asp Glu Gly Ser Ile Ala Thr Arg Arg
225                 230                 235                 240

Gly Asn Lys Gln Ala Asp Met Val Ala Lys Thr Leu Glu Asn Trp Ala
            245                 250                 255

Ile Arg Asp Val Gly Asp Arg Pro His Lys Leu Phe Leu His Phe Phe
            260                 265                 270

Glu Ser Pro Ala Glu Ile Leu Gly Glu Asp Gly Arg Val Thr Gly Leu
        275                 280                 285

Arg Thr Glu Arg Thr Glu Leu Asp Gly Thr Gly Asn Val Lys Gly Thr
290                 295                 300

Gly Glu Phe Lys Asp Trp Asp Val Gln Ala Val Tyr Arg Ala Val Gly
305                 310                 315                 320

Tyr Leu Ser Asp Gln Leu Pro Lys Leu Pro Trp Asp Leu Glu Thr Cys
            325                 330                 335

Thr Val Pro Asp Ala Gly Gly Arg Val Val Gln Glu Ser Gly Glu His
            340                 345                 350

Leu Gln Ser Thr Tyr Val Thr Gly Trp Ile Arg Arg Gly Pro Ile Gly
        355                 360                 365

Leu Ile Gly His Thr Lys Gly Asp Ala Asn Glu Thr Val Ser Asn Leu
370                 375                 380

Leu Asp Asp Tyr Ala Asn Gly Arg Leu Gln Thr Pro Ser Ser Pro Ala
385                 390                 395                 400

Pro Glu Ala Val Asp Ala Phe Leu Ala Glu Arg Asn Val Arg Phe Thr
            405                 410                 415

Thr Trp Asp Gly Trp Tyr Arg Leu Asp Ala Ala Glu Lys Ala Gln Gly
            420                 425                 430

Glu Pro His Gly Arg Glu Arg Val Lys Tyr Val Glu Arg Glu Asp Met
            435                 440                 445

Leu Arg Glu Ser Gly Ala
        450

<210> SEQ ID NO 5
<211> LENGTH: 23
<212> TYPE: DNA
<213> ORGANISM: Artifical Sequence
<220> FEATURE:
<223> OTHER INFORMATION: Designed primer sequence used for amplification
      and mutagenesis of position T291 in P450aluC09 to produce Mutant
      11 (T291D)

<400> SEQUENCE: 5
gatcgcggaa gatgcgacct cac                                          23

<210> SEQ ID NO 6
<211> LENGTH: 23
<212> TYPE: DNA

<213> ORGANISM: Artifical Sequence
<220> FEATURE:
<223> OTHER INFORMATION: Designed primer sequence used for amplification and mutagenesis of position T291 in P450aluC09 to produce Mutant 11 (T291D)

<400> SEQUENCE: 6

```
gtgaggtcgc atcttccgcg atc                                               23
```

<210> SEQ ID NO 7
<211> LENGTH: 1215
<212> TYPE: DNA
<213> ORGANISM: Amycolatopsis lurida

<400> SEQUENCE: 7

```
atgactgacg tcgaggaaac caccgcgacc ttgccgctgg cccggaaatg cccgttttcg      60
ccgccgcccg aatacgaacg gcttcgccgg gaaagtccgg tttccgggt cggtctcccg      120
tccggtcaaa cggcttgggc gctcaccccgg ctcgaagaca tccgcgaaat gctgagcagc   180
ccgcatttca gttccgaccg gcagagcccg tcgttcccgc tgatggtcgc gcggcagatc    240
cgccgcgagg acaagccgtt ccgcccctcc ctcatcgcga tggatccgcc ggaacacagc    300
cgggccaggc gtgacgtcgt cggggaattc accgtcaagc ggatgaaggc gctccagccg    360
cgaattcagc agatcgtcga cgaacatctc gacgccctgc tcgcgggccc caaacccgcc    420
gatctcgtcc aggcgctttc cctgcccgtt ccctcgctgg tgatctgcga actgctcggc    480
gtcccctatt cggaccacga gttcttccag tcctgcagtt ccaggatgct cagccgggag    540
gtcaccgccg aagaacggat gaccgcgttc gagcagctcg aaaactatct cgacgaactg    600
gtcaccaaga aggaggcgaa cgccaccgag gacgacctcc tcggccgtca gatcctgaaa    660
cagcgggaaa cgggcgaggc cgaccacggt gaactcgtcg ggctggcgtt cctgctgctc    720
atcgccggac acgagaccac ggcgaacatg atctcgctcg gcacggtgac cctgctggag    780
aatcccgatc agctcgcgaa gatcaaggca gaccccggca agaccctcgc cgccatcgag    840
gaactcctgc gggtcttcac gatcgcggaa gatgcgacct cacgcttcgc cacggcggac    900
gtcgagatcg gcgaacgct gatccgcgcg ggggaagggg tggtgggcct gagcaacgcg    960
ggcaaccacg atccggacgg cttcgagaac ccggacacct tcgacatcga acgcggcgcg   1020
cggcatcacg tcgcgttcgg attcggggtg caccagtgtc tcggccagaa cttggcgagg   1080
ttggaactcc agatcgtctt cgatacgttg ttccggcgag tgccgggcct ccggatcgcc   1140
gttccggtcg acgaactgcc gttcaagcac gattcgacga tctacggcct ccacgcccttt   1200
ccggtcacct ggtag                                                     1215
```

<210> SEQ ID NO 8
<211> LENGTH: 404
<212> TYPE: PRT
<213> ORGANISM: Amycolatopsis lurida

<400> SEQUENCE: 8

```
Met Thr Asp Val Glu Glu Thr Thr Ala Thr Leu Pro Leu Ala Arg Lys
1               5                   10                  15

Cys Pro Phe Ser Pro Pro Glu Tyr Glu Arg Leu Arg Arg Glu Ser
            20                  25                  30

Pro Val Ser Arg Val Gly Leu Pro Ser Gly Gln Thr Ala Trp Ala Leu
        35                  40                  45

Thr Arg Leu Glu Asp Ile Arg Glu Met Leu Ser Ser Pro His Phe Ser
    50                  55                  60
```

Ser Asp Arg Gln Ser Pro Ser Phe Pro Leu Met Val Ala Arg Gln Ile
65                  70                  75                  80

Arg Arg Glu Asp Lys Pro Phe Arg Pro Ser Leu Ile Ala Met Asp Pro
            85                  90                  95

Pro Glu His Ser Arg Ala Arg Asp Val Val Gly Glu Phe Thr Val
            100                 105                 110

Lys Arg Met Lys Ala Leu Gln Pro Arg Ile Gln Gln Ile Val Asp Glu
            115                 120                 125

His Leu Asp Ala Leu Leu Ala Gly Pro Lys Pro Ala Asp Leu Val Gln
        130                 135                 140

Ala Leu Ser Leu Pro Val Pro Ser Leu Val Ile Cys Glu Leu Leu Gly
145                 150                 155                 160

Val Pro Tyr Ser Asp His Glu Phe Phe Gln Ser Cys Ser Ser Arg Met
                165                 170                 175

Leu Ser Arg Glu Val Thr Ala Glu Glu Arg Met Thr Ala Phe Glu Gln
            180                 185                 190

Leu Glu Asn Tyr Leu Asp Glu Leu Val Thr Lys Lys Glu Ala Asn Ala
        195                 200                 205

Thr Glu Asp Asp Leu Leu Gly Arg Gln Ile Leu Lys Gln Arg Glu Thr
    210                 215                 220

Gly Glu Ala Asp His Gly Glu Leu Val Gly Leu Ala Phe Leu Leu Leu
225                 230                 235                 240

Ile Ala Gly His Glu Thr Thr Ala Asn Met Ile Ser Leu Gly Thr Val
                245                 250                 255

Thr Leu Leu Glu Asn Pro Asp Gln Leu Ala Lys Ile Lys Ala Asp Pro
            260                 265                 270

Gly Lys Thr Leu Ala Ala Ile Glu Glu Leu Leu Arg Val Phe Thr Ile
        275                 280                 285

Ala Glu Asp Ala Thr Ser Arg Phe Ala Thr Ala Asp Val Glu Ile Gly
290                 295                 300

Gly Thr Leu Ile Arg Ala Gly Glu Gly Val Val Gly Leu Ser Asn Ala
305                 310                 315                 320

Gly Asn His Asp Pro Asp Gly Phe Glu Asn Pro Asp Thr Phe Asp Ile
                325                 330                 335

Glu Arg Gly Ala Arg His His Val Ala Phe Gly Phe Gly Val His Gln
            340                 345                 350

Cys Leu Gly Gln Asn Leu Ala Arg Leu Glu Leu Gln Ile Val Phe Asp
        355                 360                 365

Thr Leu Phe Arg Arg Val Pro Gly Leu Arg Ile Ala Val Pro Val Asp
    370                 375                 380

Glu Leu Pro Phe Lys His Asp Ser Thr Ile Tyr Gly Leu His Ala Leu
385                 390                 395                 400

Pro Val Thr Trp

<210> SEQ ID NO 9
<211> LENGTH: 23
<212> TYPE: DNA
<213> ORGANISM: Artifical Sequence
<220> FEATURE:
<223> OTHER INFORMATION: Designed primer sequence used for amplification
      and mutagenesis of position T291 in P450aluC09 to produce Mutant
      12 (T291E)

<400> SEQUENCE: 9
gatcgcggaa gaagcgacct cac                                           23

<210> SEQ ID NO 10
<211> LENGTH: 23
<212> TYPE: DNA
<213> ORGANISM: Artifical Sequence
<220> FEATURE:
<223> OTHER INFORMATION: Designed primer sequence used for amplification
and mutagenesis of position T291 in P450aluC09 to produce Mutant
12 (T291E)

<400> SEQUENCE: 10
gtgaggtcgc ttcttccgcg atc                                          23

<210> SEQ ID NO 11
<211> LENGTH: 1215
<212> TYPE: DNA
<213> ORGANISM: Amycolatopsis lurida

<400> SEQUENCE: 11
atgactgacg tcgaggaaac caccgcgacc ttgccgctgg cccggaaatg cccgttttcg    60
ccgccgcccg aatacgaacg gcttcgccgg gaaagtccgg tttcccgggt cggtctcccg   120
tccggtcaaa cggcttgggc gctcacccgg ctcgaagaca tccgcgaaat gctgagcagc   180
ccgcatttca gttccgaccg gcagagcccg tcgttcccgc tgatggtcgc gcggcagatc   240
cgccgcgagg acaagccgtt ccgcccctcc ctcatcgcga tggatccgcc ggaacacagc   300
cgggccaggc gtgacgtcgt cggggaattc accgtcaagc ggatgaaggc gctccagccg   360
cgaattcagc agatcgtcga cgaacatctc gacgccctgc tcgcgggccc caaacccgcc   420
gatctcgtcc aggcgctttc cctgcccgtt ccctcgctgg tgatctgcga actgctcggc   480
gtcccctatt cggaccacga gttcttccag tcctgcagtt ccaggatgct cagccgggag   540
gtcaccgccg aagaacggat gaccgcgttc gagcagctcg aaaactatct cgacgaactg   600
gtcaccaaga aggaggcgaa cgccaccgag gacgacctcc tcggccgtca gatcctgaaa   660
cagcgggaaa cgggcgaggc cgaccacggt gaactcgtcg ggctggcgtt cctgctgctc   720
atcgccggac acgagaccac ggcgaacatg atctcgctcg gcacggtgac cctgctggag   780
aatcccgatc agctcgcgaa gatcaaggca gaccccggca agaccctcgc cgccatcgag   840
gaactcctgc gggtcttcac gatcgcggaa gaagcgacct cacgcttcgc cacggcggac   900
gtcgagatcg gcggaacgct gatccgcgcg ggggaagggg tggtgggcct gagcaacgcg   960
ggcaaccacg atccggacgg cttcgagaac ccggacacct tcgacatcga acgcggcgcg  1020
cggcatcacg tcgcgttcgg attcggggtg caccagtgtc tcggccagaa cttggcgagg  1080
ttggaactcc agatcgtctt cgatacgttg ttccggcgag tgccgggcct ccggatcgcc  1140
gttccggtcg acgaactgcc gttcaagcac gattcgacga tctacggcct ccacgccctt  1200
ccggtcacct ggtag                                                  1215

<210> SEQ ID NO 12
<211> LENGTH: 404
<212> TYPE: PRT
<213> ORGANISM: Amycolatopsis lurida

<400> SEQUENCE: 12

Met Thr Asp Val Glu Glu Thr Thr Ala Thr Leu Pro Leu Ala Arg Lys
1               5                   10                  15

Cys Pro Phe Ser Pro Pro Glu Tyr Glu Arg Leu Arg Arg Glu Ser
            20                  25                  30

Pro Val Ser Arg Val Gly Leu Pro Ser Gly Gln Thr Ala Trp Ala Leu
            35                  40                  45

Thr Arg Leu Glu Asp Ile Arg Glu Met Leu Ser Ser Pro His Phe Ser
 50                  55                  60

Ser Asp Arg Gln Ser Pro Ser Phe Pro Leu Met Val Ala Arg Gln Ile
 65                  70                  75                  80

Arg Arg Glu Asp Lys Pro Phe Arg Pro Ser Leu Ile Ala Met Asp Pro
                 85                  90                  95

Pro Glu His Ser Arg Ala Arg Arg Asp Val Val Gly Glu Phe Thr Val
            100                 105                 110

Lys Arg Met Lys Ala Leu Gln Pro Arg Ile Gln Gln Ile Val Asp Glu
            115                 120                 125

His Leu Asp Ala Leu Leu Ala Gly Pro Lys Pro Ala Asp Leu Val Gln
130                 135                 140

Ala Leu Ser Leu Pro Val Pro Ser Leu Val Ile Cys Glu Leu Leu Gly
145                 150                 155                 160

Val Pro Tyr Ser Asp His Glu Phe Phe Gln Ser Cys Ser Ser Arg Met
                165                 170                 175

Leu Ser Arg Glu Val Thr Ala Glu Glu Arg Met Thr Ala Phe Glu Gln
            180                 185                 190

Leu Glu Asn Tyr Leu Asp Glu Leu Val Thr Lys Lys Glu Ala Asn Ala
        195                 200                 205

Thr Glu Asp Asp Leu Leu Gly Arg Gln Ile Leu Lys Gln Arg Glu Thr
    210                 215                 220

Gly Glu Ala Asp His Gly Glu Leu Val Gly Leu Ala Phe Leu Leu Leu
225                 230                 235                 240

Ile Ala Gly His Glu Thr Thr Ala Asn Met Ile Ser Leu Gly Thr Val
                245                 250                 255

Thr Leu Leu Glu Asn Pro Asp Gln Leu Ala Lys Ile Lys Ala Asp Pro
            260                 265                 270

Gly Lys Thr Leu Ala Ala Ile Glu Glu Leu Leu Arg Val Phe Thr Ile
        275                 280                 285

Ala Glu Glu Ala Thr Ser Arg Phe Ala Thr Ala Asp Val Glu Ile Gly
    290                 295                 300

Gly Thr Leu Ile Arg Ala Gly Glu Gly Val Val Gly Leu Ser Asn Ala
305                 310                 315                 320

Gly Asn His Asp Pro Asp Gly Phe Glu Asn Pro Asp Thr Phe Asp Ile
                325                 330                 335

Glu Arg Gly Ala Arg His His Val Ala Phe Gly Phe Gly Val His Gln
            340                 345                 350

Cys Leu Gly Gln Asn Leu Ala Arg Leu Glu Leu Gln Ile Val Phe Asp
        355                 360                 365

Thr Leu Phe Arg Arg Val Pro Gly Leu Arg Ile Ala Val Pro Val Asp
    370                 375                 380

Glu Leu Pro Phe Lys His Asp Ser Thr Ile Tyr Gly Leu His Ala Leu
385                 390                 395                 400

Pro Val Thr Trp

<210> SEQ ID NO 13
<211> LENGTH: 23
<212> TYPE: DNA
<213> ORGANISM: Artifical Sequence
<220> FEATURE:

<223> OTHER INFORMATION: Designed primer sequence used for amplification
and mutagenesis of position T291 in P450aluC09 to produce Mutant
17 (T291N)

<400> SEQUENCE: 13
gatcgcggaa aacgcgacct cac                                              23

<210> SEQ ID NO 14
<211> LENGTH: 23
<212> TYPE: DNA
<213> ORGANISM: Artifical Sequence
<220> FEATURE:
<223> OTHER INFORMATION: Designed primer sequence used for amplification
and mutagenesis of position T291 in P450aluC09 to produce Mutant
17 (T291N)

<400> SEQUENCE: 14
gtgaggtcgc gttttccgcg atc                                              23

<210> SEQ ID NO 15
<211> LENGTH: 1215
<212> TYPE: DNA
<213> ORGANISM: Amycolatopsis lurida

<400> SEQUENCE: 15
atgactgacg tcgaggaaac caccgcgacc ttgccgctgg cccggaaatg cccgttttcg      60
ccgccgcccg aatacgaacg gcttcgccgg gaaagtccgg tttcccgggt cggtctcccg     120
tccggtcaaa cggcttgggc gctcacccgg ctcgaagaca tccgcgaaat gctgagcagc     180
ccgcatttca gttccgaccg gcagagcccg tcgttcccgc tgatggtcgc gcggcagatc     240
cgccgcgagg acaagccgtt ccgcccctcc ctcatcgcga tggatccgcc ggaacacagc     300
cgggccaggc gtgacgtcgt cggggaattc accgtcaagc ggatgaaggc gctccagccg     360
cgaattcagc agatcgtcga cgaacatctc gacgccctgc tcgcgggccc caaacccgcc     420
gatctcgtcc aggcgctttc cctgcccgtt ccctcgctgg tgatctgcga actgctcggc     480
gtcccctatt cggaccacga gttcttccag tcctgcagtt ccaggatgct cagccgggag     540
gtcaccgccg aagaacggat gaccgcgttc gagcagctcg aaaactatct cgacgaactg     600
gtcaccaaga aggaggcgaa cgccaccgag gacgacctcc tcggccgtca gatcctgaaa     660
cagcgggaaa cgggcgaggc cgaccacggt gaactcgtcg ggctggcgtt cctgctgctc     720
atcgccggac acgagaccac ggcgaacatg atctcgctcg gcacggtgac cctgctggag     780
aatcccgatc agctcgcgaa gatcaaggca gaccccggca agaccctcgc cgccatcgag     840
gaactcctgc gggtcttcac gatcgcggaa aacgcgacct cacgcttcgc cacggcggac     900
gtcgagatcg gcggaacgct gatccgcgcg ggggaagggg tggtgggcct gagcaacgcg     960
ggcaaccacg atccggacgg cttcgagaac ccggacacct cgacatcga acgcggcgcg    1020 cggcatcacg tcgcgttcgg attcggggtg ccagtgtc tcggccagaa cttggcgagg    1080
ttggaactcc agatcgtctt cgatacgttg ttccggcgag tgccgggcct ccggatcgcc    1140
gttccggtcg acgaactgcc gttcaagcac gattcgacga tctacggcct ccacgcccctt    1200 ccggtcacct ggtag                                                    1215

<210> SEQ ID NO 16
<211> LENGTH: 404
<212> TYPE: PRT
<213> ORGANISM: Amycolatopsis lurida

<400> SEQUENCE: 16

```
Met Thr Asp Val Glu Thr Thr Ala Thr Leu Pro Leu Ala Arg Lys
1               5                   10                  15

Cys Pro Phe Ser Pro Pro Glu Tyr Glu Arg Leu Arg Arg Glu Ser
                20                  25                  30

Pro Val Ser Arg Val Gly Leu Pro Ser Gly Gln Thr Ala Trp Ala Leu
                35                  40                  45

Thr Arg Leu Glu Asp Ile Arg Glu Met Leu Ser Ser Pro His Phe Ser
            50                  55                  60

Ser Asp Arg Gln Ser Pro Ser Phe Pro Leu Met Val Ala Arg Gln Ile
65                  70                  75                  80

Arg Arg Glu Asp Lys Pro Phe Arg Pro Ser Leu Ile Ala Met Asp Pro
                85                  90                  95

Pro Glu His Ser Arg Ala Arg Arg Asp Val Val Gly Glu Phe Thr Val
                100                 105                 110

Lys Arg Met Lys Ala Leu Gln Pro Arg Ile Gln Gln Ile Val Asp Glu
            115                 120                 125

His Leu Asp Ala Leu Leu Ala Gly Pro Lys Pro Ala Asp Leu Val Gln
        130                 135                 140

Ala Leu Ser Leu Pro Val Pro Ser Leu Val Ile Cys Glu Leu Leu Gly
145                 150                 155                 160

Val Pro Tyr Ser Asp His Glu Phe Phe Gln Ser Cys Ser Ser Arg Met
                165                 170                 175

Leu Ser Arg Glu Val Thr Ala Glu Glu Arg Met Thr Ala Phe Glu Gln
            180                 185                 190

Leu Glu Asn Tyr Leu Asp Glu Leu Val Thr Lys Lys Glu Ala Asn Ala
        195                 200                 205

Thr Glu Asp Asp Leu Leu Gly Arg Gln Ile Leu Lys Gln Arg Glu Thr
    210                 215                 220

Gly Glu Ala Asp His Gly Glu Leu Val Gly Leu Ala Phe Leu Leu Leu
225                 230                 235                 240

Ile Ala Gly His Glu Thr Thr Ala Asn Met Ile Ser Leu Gly Thr Val
                245                 250                 255

Thr Leu Leu Glu Asn Pro Asp Gln Leu Ala Lys Ile Lys Ala Asp Pro
            260                 265                 270

Gly Lys Thr Leu Ala Ala Ile Glu Glu Leu Leu Arg Val Phe Thr Ile
        275                 280                 285

Ala Glu Asn Ala Thr Ser Arg Phe Ala Thr Ala Asp Val Glu Ile Gly
    290                 295                 300

Gly Thr Leu Ile Arg Ala Gly Glu Gly Val Val Gly Leu Ser Asn Ala
305                 310                 315                 320

Gly Asn His Asp Pro Asp Gly Phe Glu Asn Pro Asp Thr Phe Asp Ile
                325                 330                 335

Glu Arg Gly Ala Arg His His Val Ala Phe Gly Phe Gly Val His Gln
            340                 345                 350

Cys Leu Gly Gln Asn Leu Ala Arg Leu Glu Leu Gln Ile Val Phe Asp
        355                 360                 365

Thr Leu Phe Arg Arg Val Pro Gly Leu Arg Ile Ala Val Pro Val Asp
    370                 375                 380

Glu Leu Pro Phe Lys His Asp Ser Thr Ile Tyr Gly Leu His Ala Leu
385                 390                 395                 400

Pro Val Thr Trp
```

<210> SEQ ID NO 17
<211> LENGTH: 23
<212> TYPE: DNA
<213> ORGANISM: Artifical Sequence
<220> FEATURE:
<223> OTHER INFORMATION: Designed primer sequence used for amplification and mutagenesis of position T291 in P450aluC09 to produce Mutant 18 (T291Q)

<400> SEQUENCE: 17
gatcgcggaa caggcgacct cac        23

<210> SEQ ID NO 18
<211> LENGTH: 23
<212> TYPE: DNA
<213> ORGANISM: Artifical Sequence
<220> FEATURE:
<223> OTHER INFORMATION: Designed primer sequence used for amplification and mutagenesis of position T291 in P450aluC09 to produce Mutant 18 (T291Q)

<400> SEQUENCE: 18
gtgaggtcgc ctgttccgcg atc        23

<210> SEQ ID NO 19
<211> LENGTH: 1215
<212> TYPE: DNA
<213> ORGANISM: Amycolatopsis lurida

<400> SEQUENCE: 19

```
atgactgacg tcgaggaaac caccgcgacc ttgccgctgg cccggaaatg cccgttttcg      60
ccgccgcccg aatacgaacg gcttcgccgg gaaagtccgg tttccgggt cggtctcccg     120
tccggtcaaa cggcttgggc gctcacccgg ctcgaagaca tccgcgaaat gctgagcagc     180
ccgcatttca gttccgaccg gcagagcccg tcgttcccgc tgatggtcgc gcggcagatc     240
cgccgcgagg acaagccgtt ccgccccctcc ctcatcgcga tggatccgcc ggaacacagc     300
cgggccaggc gtgacgtcgt cggggaattc accgtcaagc ggatgaaggc gctccagccg     360
cgaattcagc agatcgtcga cgaacatctc gacgccctgc tcgcgggccc caaacccgcc     420
gatctcgtcc aggcgctttc cctgcccgtt ccctcgctgg tgatctgcga actgctcggc     480
gtcccctatt cggaccacga gttcttccag tcctgcagtt ccaggatgct cagcggggag     540
gtcaccgccg aagaacggat daccgcgttc gagcagctcg aaaactatct cgacgaactg     600
gtcaccaaga aggaggcgaa cgccaccgag gacgacctcc tcggccgtca gatcctgaaa     660
cagcgggaaa cgggcgaggc cgaccacggt gaactcgtcg ggctggcgtt cctgctgctc     720
atcgccggac acgagaccac ggcgaacatg atctcgctcg gcacggtgac cctgctggag     780
aatcccgatc agctcgcgaa gatcaaggca gaccccggca gaccctcgc cgccatcgag     840
gaactcctgc gggtcttcac gatcgcggaa caggcgacct cacgcttcgc cacggcggac     900
gtcgagatcg gcggaacgct gatccgcgcg ggggaagggg tggtgggcct gagcaacgcg     960
ggcaaccacg atccggacgg cttcgagaac ccggacacct tcgacatcga acgcggcgcg    1020
cggcatcacg tcgcgttcgg attcggggtg caccagtgtc tcggccagaa cttggcgagg    1080
ttggaactcc agatcgtcct cgatacgttg ttccggcgag tgccgggcct ccggatcgcc    1140
gttccggtcg acgaactgcc gttcaagcac gattcgacga tctacggcct ccacgcccctt    1200
ccggtcacct ggtag                              1215
```

```
<210> SEQ ID NO 20
<211> LENGTH: 404
<212> TYPE: PRT
<213> ORGANISM: Amycolatopsis lurida

<400> SEQUENCE: 20
```

Met Thr Asp Val Glu Thr Thr Ala Thr Leu Pro Leu Ala Arg Lys
1               5                   10                  15

Cys Pro Phe Ser Pro Pro Glu Tyr Glu Arg Leu Arg Arg Glu Ser
            20                  25                  30

Pro Val Ser Arg Val Gly Leu Pro Ser Gly Gln Thr Ala Trp Ala Leu
        35                  40                  45

Thr Arg Leu Glu Asp Ile Arg Glu Met Leu Ser Ser Pro His Phe Ser
50                  55                  60

Ser Asp Arg Gln Ser Pro Ser Phe Pro Leu Met Val Ala Arg Gln Ile
65                  70                  75                  80

Arg Arg Glu Asp Lys Pro Phe Arg Pro Ser Leu Ile Ala Met Asp Pro
                85                  90                  95

Pro Glu His Ser Arg Ala Arg Arg Asp Val Val Gly Glu Phe Thr Val
            100                 105                 110

Lys Arg Met Lys Ala Leu Gln Pro Arg Ile Gln Gln Ile Val Asp Glu
        115                 120                 125

His Leu Asp Ala Leu Leu Ala Gly Pro Lys Pro Ala Asp Leu Val Gln
130                 135                 140

Ala Leu Ser Leu Pro Val Pro Ser Leu Val Ile Cys Glu Leu Leu Gly
145                 150                 155                 160

Val Pro Tyr Ser Asp His Glu Phe Phe Gln Ser Cys Ser Ser Arg Met
                165                 170                 175

Leu Ser Arg Glu Val Thr Ala Glu Arg Met Thr Ala Phe Glu Gln
            180                 185                 190

Leu Glu Asn Tyr Leu Asp Glu Leu Val Thr Lys Lys Glu Ala Asn Ala
        195                 200                 205

Thr Glu Asp Asp Leu Leu Gly Arg Gln Ile Leu Lys Gln Arg Glu Thr
210                 215                 220

Gly Glu Ala Asp His Gly Glu Leu Val Gly Leu Ala Phe Leu Leu Leu
225                 230                 235                 240

Ile Ala Gly His Glu Thr Thr Ala Asn Met Ile Ser Leu Gly Thr Val
                245                 250                 255

Thr Leu Leu Glu Asn Pro Asp Gln Leu Ala Lys Ile Lys Ala Asp Pro
            260                 265                 270

Gly Lys Thr Leu Ala Ala Ile Glu Glu Leu Leu Arg Val Phe Thr Ile
        275                 280                 285

Ala Glu Gln Ala Thr Ser Arg Phe Ala Thr Ala Asp Val Glu Ile Gly
        290                 295                 300

Gly Thr Leu Ile Arg Ala Gly Glu Gly Val Val Gly Leu Ser Asn Ala
305                 310                 315                 320

Gly Asn His Asp Pro Asp Gly Phe Glu Asn Pro Asp Thr Phe Asp Ile
                325                 330                 335

Glu Arg Gly Ala Arg His His Val Ala Phe Gly Phe Gly Val His Gln
            340                 345                 350

Cys Leu Gly Gln Asn Leu Ala Arg Leu Glu Leu Gln Ile Val Phe Asp
        355                 360                 365

Thr Leu Phe Arg Arg Val Pro Gly Leu Arg Ile Ala Val Pro Val Asp
370                 375                 380

```
Glu Leu Pro Phe Lys His Asp Ser Thr Ile Tyr Gly Leu His Ala Leu
385                 390                 395                 400

Pro Val Thr Trp

<210> SEQ ID NO 21
<211> LENGTH: 23
<212> TYPE: DNA
<213> ORGANISM: Artifical Sequence
<220> FEATURE:
<223> OTHER INFORMATION: Designed primer sequence used for amplification
      and mutagenesis of position T291 in P450aluC09 to produce Mutant
      19 (T291A)

<400> SEQUENCE: 21
gatcgcggaa gcggcgacct cac                                          23

<210> SEQ ID NO 22
<211> LENGTH: 23
<212> TYPE: DNA
<213> ORGANISM: Artifical Sequence
<220> FEATURE:
<223> OTHER INFORMATION: Designed primer sequence used for amplification
      and mutagenesis of position T291 in P450aluC09 to produce Mutant
      19 (T291A)

<400> SEQUENCE: 22
gtgaggtcgc cgcttccgcg atc                                          23

<210> SEQ ID NO 23
<211> LENGTH: 1215
<212> TYPE: DNA
<213> ORGANISM: Amycolatopsis lurida

<400> SEQUENCE: 23
atgactgacg tcgaggaaac caccgcgacc ttgccgctgg cccggaaatg cccgttttcg    60
ccgccgcccg aatacgaacg gcttcgccgg gaaagtccgg tttcccgggt cggtctcccg   120
tccggtcaaa cggcttgggc gctcacccgg ctcgaagaca tccgcgaaat gctgagcagc   180
ccgcatttca gttccgaccg gcagagcccg tcgttcccgc tgatggtcgc gcggcagatc   240
cgccgcgagg acaagccgtt ccgcccctcc ctcatcgcga tggatccgcc ggaacacagc   300
cggggccagg cgtgacgtcgt cggggaattc accgtcaagc ggatgaaggc gctccagccg   360
cgaattcagc agatcgtcga cgaacatctc gacgccctgc tcgcgggccc caaacccgcc   420
gatctcgtcc aggcgctttc cctgccgtt ccctcgctgg tgatctgcga actgctcggc   480
gtcccctatt cggaccacga gttcttccag tcctgcagtt ccaggatgct cagccgggag   540
gtcaccgccg aagaacggat gaccgcgttc gagcagctcg aaaactatct cgacgaactg   600
gtcaccaaga aggaggcgaa cgccaccgag gacgacctcc tcggccgtca gatcctgaaa   660
cagcgggaaa cgggcgaggc cgaccacggt gaactcgtcg ggctggcgtt cctgctgctc   720
atcgccggac acgagaccac ggcgaacatg atctcgctcg gcacggtgac cctgctggag   780
aatcccgatc agctcgcgaa gatcaaggca gaccccggca agaccctcgc cgccatcgag   840
gaactcctgc gggtcttcac gatcgcggaa gcggcgacct cacgcttcgc cacggcggac   900
gtcgagatcg gcggaacgct gatccgcgcg ggggaagggg tggtgggcct gagcaacgcg   960
ggcaaccacg atccggacgg cttcgagaac ccggacacct tcgacatcga acgcggcgcg  1020
cggcatcacg tcgcgttcgg attcggggtg caccagtgtc tcggccagaa cttggcgagg  1080
ttggaactcc agatcgtctt cgatacgttg ttccggcgag tgccgggcct ccggatcgcc  1140
```

-continued

```
gttccggtcg acgaactgcc gttcaagcac gattcgacga tctacggcct ccacgccctt    1200
ccggtcacct ggtag                                                     1215
```

<210> SEQ ID NO 24
<211> LENGTH: 404
<212> TYPE: PRT
<213> ORGANISM: Amycolatopsis lurida

<400> SEQUENCE: 24

```
Met Thr Asp Val Glu Glu Thr Thr Ala Thr Leu Pro Leu Ala Arg Lys
1               5                   10                  15

Cys Pro Phe Ser Pro Pro Glu Tyr Glu Arg Leu Arg Arg Glu Ser
            20                  25                  30

Pro Val Ser Arg Val Gly Leu Pro Ser Gly Gln Thr Ala Trp Ala Leu
            35                  40                  45

Thr Arg Leu Glu Asp Ile Arg Glu Met Leu Ser Ser Pro His Phe Ser
        50                  55                  60

Ser Asp Arg Gln Ser Pro Ser Phe Pro Leu Met Val Ala Arg Gln Ile
65                  70                  75                  80

Arg Arg Glu Asp Lys Pro Phe Arg Pro Ser Leu Ile Ala Met Asp Pro
                85                  90                  95

Pro Glu His Ser Arg Ala Arg Arg Asp Val Val Gly Glu Phe Thr Val
            100                 105                 110

Lys Arg Met Lys Ala Leu Gln Pro Arg Ile Gln Gln Ile Val Asp Glu
        115                 120                 125

His Leu Asp Ala Leu Leu Ala Gly Pro Lys Pro Ala Asp Leu Val Gln
    130                 135                 140

Ala Leu Ser Leu Pro Val Pro Ser Leu Val Ile Cys Glu Leu Leu Gly
145                 150                 155                 160

Val Pro Tyr Ser Asp His Glu Phe Phe Gln Ser Cys Ser Ser Arg Met
                165                 170                 175

Leu Ser Arg Glu Val Thr Ala Glu Glu Arg Met Thr Ala Phe Glu Gln
            180                 185                 190

Leu Glu Asn Tyr Leu Asp Glu Leu Val Thr Lys Lys Glu Ala Asn Ala
        195                 200                 205

Thr Glu Asp Asp Leu Leu Gly Arg Gln Ile Leu Lys Gln Arg Glu Thr
    210                 215                 220

Gly Glu Ala Asp His Gly Glu Leu Val Gly Leu Ala Phe Leu Leu Leu
225                 230                 235                 240

Ile Ala Gly His Glu Thr Thr Ala Asn Met Ile Ser Leu Gly Thr Val
                245                 250                 255

Thr Leu Leu Glu Asn Pro Asp Gln Leu Ala Lys Ile Lys Ala Asp Pro
            260                 265                 270

Gly Lys Thr Leu Ala Ala Ile Glu Glu Leu Leu Arg Val Phe Thr Ile
        275                 280                 285

Ala Glu Ala Ala Thr Ser Arg Phe Ala Thr Ala Asp Val Glu Ile Gly
    290                 295                 300

Gly Thr Leu Ile Arg Ala Gly Glu Gly Val Val Gly Leu Ser Asn Ala
305                 310                 315                 320

Gly Asn His Asp Pro Asp Gly Phe Glu Asn Pro Asp Thr Phe Asp Ile
                325                 330                 335

Glu Arg Gly Ala Arg His His Val Ala Phe Gly Phe Gly Val His Gln
            340                 345                 350
```

Cys Leu Gly Gln Asn Leu Ala Arg Leu Glu Leu Gln Ile Val Phe Asp
            355                 360                 365

Thr Leu Phe Arg Arg Val Pro Gly Leu Arg Ile Ala Val Pro Val Asp
    370                 375                 380

Glu Leu Pro Phe Lys His Asp Ser Thr Ile Tyr Gly Leu His Ala Leu
385                 390                 395                 400

Pro Val Thr Trp

<210> SEQ ID NO 25
<211> LENGTH: 23
<212> TYPE: DNA
<213> ORGANISM: Artifical Sequence
<220> FEATURE:
<223> OTHER INFORMATION: Designed primer sequence used for amplification
      and mutagenesis of position T291 in P450aluC09 to produce Mutant
      20 (T291V)

<400> SEQUENCE: 25
gatcgcggaa gtggcgacct cac                                             23

<210> SEQ ID NO 26
<211> LENGTH: 23
<212> TYPE: DNA
<213> ORGANISM: Artifical Sequence
<220> FEATURE:
<223> OTHER INFORMATION: Designed primer sequence used for amplification
      and mutagenesis of position T291 in P450aluC09 to produce Mutant
      20 (T291V)

<400> SEQUENCE: 26
gtgaggtcgc cacttccgcg atc                                             23

<210> SEQ ID NO 27
<211> LENGTH: 1215
<212> TYPE: DNA
<213> ORGANISM: Amycolatopsis lurida

<400> SEQUENCE: 27
atgactgacg tcgaggaaac caccgcgacc ttgccgctgg cccggaaatg cccgttttcg      60
ccgccgcccg aatacgaacg gcttcgccgg gaaagtccgg tttcccgggt cggtctcccg     120
tccggtcaaa cggcttgggc gctcacccgg ctcgaagaca tccgcgaaat gctgagcagc     180
ccgcatttca gttccgaccg gcagagcccg tcgttcccgc tgatggtcgc gcggcagatc     240
cgccgcgagg acaagccgtt ccgcccctcc ctcatcgcga tggatccgcc ggaacacagc     300
cgggccaggc gtgacgtcgt cggggaattc accgtcaagc ggatgaaggc gctccagccg     360
cgaattcagc agatcgtcga cgaacatctc gacgccctgc tcgcgggccc caaacccgcc     420
gatctcgtcc aggcgctttc cctgccgtt cctcgctgg tgatctgcga actgctcggc      480
gtcccctatt cggaccacga gttcttccag tcctgcagtt ccaggatgct cagccgggag     540
gtcaccgccg aagaacggat gaccgcgttc gagcagctcg aaaactatct cgacgaactg     600
gtcaccaaga aggaggcgaa cgccaccgag gacgacctcc tcggccgtca gatcctgaaa     660
cagcgggaaa cgggcgaggc cgaccacggt gaactcgtcg ggctggcgtt cctgctgctc     720
atcgccggac acgagaccac ggcgaacatg atctcgctcg gcacggtgac cctgctggag     780
aatcccgatc agctcgcgaa gatcaaggca gaccccggca agaccctcgc cgccatcgag     840
gaactcctgc gggtcttcac gatcgcggaa gtggcgacct cacgcttcgc cacggcggac     900
gtcgagatcg gcggaacgct gatccgcgcg ggggaagggg tggtgggcct gagcaacgcg     960

-continued

```
ggcaaccacg atccggacgg cttcgagaac ccggacacct tcgacatcga acgcggcgcg    1020
cggcatcacg tcgcgttcgg attcggggtg caccagtgtc tcggccagaa cttggcgagg    1080
ttggaactcc agatcgtctt cgatacgttg ttccggcgag tgccgggcct ccggatcgcc    1140
gttccggtcg acgaactgcc gttcaagcac gattcgacga tctacggcct ccacgccctt    1200
ccggtcacct ggtag                                                     1215
```

<210> SEQ ID NO 28
<211> LENGTH: 404
<212> TYPE: PRT
<213> ORGANISM: Amycolatopsis lurida

<400> SEQUENCE: 28

```
Met Thr Asp Val Glu Glu Thr Thr Ala Thr Leu Pro Leu Ala Arg Lys
1               5                   10                  15

Cys Pro Phe Ser Pro Pro Glu Tyr Glu Arg Leu Arg Arg Glu Ser
            20                  25                  30

Pro Val Ser Arg Val Gly Leu Pro Ser Gly Gln Thr Ala Trp Ala Leu
        35                  40                  45

Thr Arg Leu Glu Asp Ile Arg Glu Met Leu Ser Ser Pro His Phe Ser
    50                  55                  60

Ser Asp Arg Gln Ser Pro Ser Phe Pro Leu Met Val Ala Arg Gln Ile
65                  70                  75                  80

Arg Arg Glu Asp Lys Pro Phe Arg Pro Ser Leu Ile Ala Met Asp Pro
                85                  90                  95

Pro Glu His Ser Arg Ala Arg Arg Asp Val Val Gly Glu Phe Thr Val
            100                 105                 110

Lys Arg Met Lys Ala Leu Gln Pro Arg Ile Gln Gln Ile Val Asp Glu
        115                 120                 125

His Leu Asp Ala Leu Leu Ala Gly Pro Lys Pro Ala Asp Leu Val Gln
    130                 135                 140

Ala Leu Ser Leu Pro Val Pro Ser Leu Val Ile Cys Glu Leu Leu Gly
145                 150                 155                 160

Val Pro Tyr Ser Asp His Glu Phe Phe Gln Ser Cys Ser Ser Arg Met
                165                 170                 175

Leu Ser Arg Glu Val Thr Ala Glu Arg Met Thr Ala Phe Glu Gln
            180                 185                 190

Leu Glu Asn Tyr Leu Asp Glu Leu Val Thr Lys Lys Glu Ala Asn Ala
        195                 200                 205

Thr Glu Asp Asp Leu Leu Gly Arg Gln Ile Leu Lys Gln Arg Glu Thr
    210                 215                 220

Gly Glu Ala Asp His Gly Glu Leu Val Gly Leu Ala Phe Leu Leu Leu
225                 230                 235                 240

Ile Ala Gly His Glu Thr Thr Ala Asn Met Ile Ser Leu Gly Thr Val
                245                 250                 255

Thr Leu Leu Glu Asn Pro Asp Gln Leu Ala Lys Ile Lys Ala Asp Pro
            260                 265                 270

Gly Lys Thr Leu Ala Ala Ile Glu Glu Leu Leu Arg Val Phe Thr Ile
        275                 280                 285

Ala Glu Val Ala Thr Ser Arg Phe Ala Thr Ala Asp Val Glu Ile Gly
    290                 295                 300

Gly Thr Leu Ile Arg Ala Gly Glu Gly Val Val Gly Leu Ser Asn Ala
305                 310                 315                 320
```

Gly Asn His Asp Pro Asp Gly Phe Glu Asn Pro Asp Thr Phe Asp Ile
            325                 330                 335

Glu Arg Gly Ala Arg His His Val Ala Phe Gly Phe Val His Gln
        340                 345                 350

Cys Leu Gly Gln Asn Leu Ala Arg Leu Glu Leu Gln Ile Val Phe Asp
            355                 360                 365

Thr Leu Phe Arg Arg Val Pro Gly Leu Arg Ile Ala Val Pro Val Asp
    370                 375                 380

Glu Leu Pro Phe Lys His Asp Ser Thr Ile Tyr Gly Leu His Ala Leu
385                 390                 395                 400

Pro Val Thr Trp

<210> SEQ ID NO 29
<211> LENGTH: 23
<212> TYPE: DNA
<213> ORGANISM: Artifical Sequence
<220> FEATURE:
<223> OTHER INFORMATION: Designed primer sequence used for amplification
      and mutagenesis of position T291 in P450aluC09 to produce Mutant
      21 (T291Y)

<400> SEQUENCE: 29
gatcgcggaa tatgcgacct cac                                         23

<210> SEQ ID NO 30
<211> LENGTH: 23
<212> TYPE: DNA
<213> ORGANISM: Artifical Sequence
<220> FEATURE:
<223> OTHER INFORMATION: Designed primer sequence used for amplification
      and mutagenesis of position T291 in P450aluC09 to produce Mutant
      21 (T291Y)

<400> SEQUENCE: 30
gtgaggtcgc atattccgcg atc                                         23

<210> SEQ ID NO 31
<211> LENGTH: 1215
<212> TYPE: DNA
<213> ORGANISM: Amycolatopsis lurida

<400> SEQUENCE: 31
atgactgacg tcgaggaaac caccgcgacc ttgccgctgg cccggaaatg cccgttttcg    60
ccgccgcccg aatacgaacg gcttcgccgg gaaagtccgg tttcccgggt cggtctcccg   120
tccggtcaaa cggcttgggc gctcacccgg ctcgaagaca tccgcgaaat gctgagcagc   180
ccgcatttca gttccgaccg gcagagcccg tcgttcccgc tgatggtcgc gcggcagatc   240
cgccgcgagg acaagccgtt ccgcccctcc ctcatcgcga tggatccgcc ggaacacagc   300
cgggccaggc gtgacgtcgt cggggaattc accgtcaagc ggatgaaggc gctccagccg   360
cgaattcagc agatcgtcga cgaacatctc gacgccctgc tcgcgggccc caaacccgcc   420
gatctcgtcc aggcgctttc cctgcccgtt ccctcgctgg tgatctgcga actgctcggc   480 gtccccctatt cggaccacga gttcttccag tcctgcagtt ccaggatgct cagccgggag   540
gtcaccgccg aagaacggat gaccgcgttc gagcagctcg aaaactatct cgacgaactg   600
gtcaccaaga aggaggcgaa cgccaccgag gacgacctcc tcggccgtca gatcctgaaa   660
cagcgggaaa cgggcgaggc cgaccacggt gaactcgtcg ggctggcgtt cctgctgctc   720
atcgccggac acgagaccac ggcgaacatg atctcgctcg gcacggtgac cctgctggag   780

```
aatcccgatc agctcgcgaa gatcaaggca gaccccggca agaccctcgc cgccatcgag      840
gaactcctgc gggtcttcac gatcgcggaa tatgcgacct cacgcttcgc cacggcggac      900
gtcgagatcg gcggaacgct gatccgcgcg ggggaagggg tggtgggcct gagcaacgcg      960
ggcaaccacg atccggacgg cttcgagaac ccggacacct cgacatcga acgcggcgcg     1020 cggcatcacg tcgcgttcgg attcggggtg caccagtgtc tcggccagaa cttggcgagg     1080
ttggaactcc agatcgtctt cgatacgttg ttccggcgag tgccgggcct ccggatcgcc     1140
gttccggtcg acgaactgcc gttcaagcac gattcgacga tctacggcct ccacgccctt     1200
ccggtcacct ggtag                                                      1215
```

<210> SEQ ID NO 32
<211> LENGTH: 404
<212> TYPE: PRT
<213> ORGANISM: Amycolatopsis lurida

<400> SEQUENCE: 32

```
Met Thr Asp Val Glu Glu Thr Thr Ala Thr Leu Pro Leu Ala Arg Lys
1               5                   10                  15

Cys Pro Phe Ser Pro Pro Glu Tyr Glu Arg Leu Arg Arg Glu Ser
            20                  25                  30

Pro Val Ser Arg Val Gly Leu Pro Ser Gly Gln Thr Ala Trp Ala Leu
        35                  40                  45

Thr Arg Leu Glu Asp Ile Arg Glu Met Leu Ser Ser Pro His Phe Ser
    50                  55                  60

Ser Asp Arg Gln Ser Pro Ser Phe Pro Leu Met Val Ala Arg Gln Ile
65                  70                  75                  80

Arg Arg Glu Asp Lys Pro Phe Arg Pro Ser Leu Ile Ala Met Asp Pro
                85                  90                  95

Pro Glu His Ser Arg Ala Arg Arg Asp Val Val Gly Glu Phe Thr Val
            100                 105                 110

Lys Arg Met Lys Ala Leu Gln Pro Arg Ile Gln Gln Ile Val Asp Glu
        115                 120                 125

His Leu Asp Ala Leu Leu Ala Gly Pro Lys Pro Ala Asp Leu Val Gln
    130                 135                 140

Ala Leu Ser Leu Pro Val Pro Ser Leu Val Ile Cys Glu Leu Leu Gly
145                 150                 155                 160

Val Pro Tyr Ser Asp His Glu Phe Phe Gln Ser Cys Ser Ser Arg Met
                165                 170                 175

Leu Ser Arg Glu Val Thr Ala Glu Glu Arg Met Thr Ala Phe Glu Gln
            180                 185                 190

Leu Glu Asn Tyr Leu Asp Glu Leu Val Thr Lys Lys Glu Ala Asn Ala
        195                 200                 205

Thr Glu Asp Asp Leu Leu Gly Arg Gln Ile Leu Lys Gln Arg Glu Thr
    210                 215                 220

Gly Glu Ala Asp His Gly Glu Leu Val Gly Leu Ala Phe Leu Leu Leu
225                 230                 235                 240

Ile Ala Gly His Glu Thr Thr Ala Asn Met Ile Ser Leu Gly Thr Val
                245                 250                 255

Thr Leu Leu Glu Asn Pro Asp Gln Leu Ala Lys Ile Lys Ala Asp Pro
            260                 265                 270

Gly Lys Thr Leu Ala Ala Ile Glu Glu Leu Leu Arg Val Phe Thr Ile
        275                 280                 285
```

```
Ala Glu Tyr Ala Thr Ser Arg Phe Ala Thr Ala Asp Val Glu Ile Gly
        290                 295                 300
Gly Thr Leu Ile Arg Ala Gly Glu Gly Val Val Gly Leu Ser Asn Ala
305                 310                 315                 320
Gly Asn His Asp Pro Asp Gly Phe Glu Asn Pro Asp Thr Phe Asp Ile
                325                 330                 335
Glu Arg Gly Ala Arg His His Val Ala Phe Gly Phe Gly Val His Gln
            340                 345                 350
Cys Leu Gly Gln Asn Leu Ala Arg Leu Glu Leu Gln Ile Val Phe Asp
        355                 360                 365
Thr Leu Phe Arg Arg Val Pro Gly Leu Arg Ile Ala Val Pro Val Asp
370                 375                 380
Glu Leu Pro Phe Lys His Asp Ser Thr Ile Tyr Gly Leu His Ala Leu
385                 390                 395                 400
Pro Val Thr Trp

<210> SEQ ID NO 33
<211> LENGTH: 23
<212> TYPE: DNA
<213> ORGANISM: Artifical Sequence
<220> FEATURE:
<223> OTHER INFORMATION: Designed primer sequence used for amplification
      and mutagenesis of position T291 in P450aluC09 to produce Mutant
      31 (T291S)

<400> SEQUENCE: 33
gatcgcggaa agcgcgacct cac                                          23

<210> SEQ ID NO 34
<211> LENGTH: 23
<212> TYPE: DNA
<213> ORGANISM: Artifical Sequence
<220> FEATURE:
<223> OTHER INFORMATION: Designed primer sequence used for amplification
      and mutagenesis of position T291 in P450aluC09 to produce Mutant
      31 (T291S)

<400> SEQUENCE: 34
gtgaggtcgc gctttccgcg atc                                          23

<210> SEQ ID NO 35
<211> LENGTH: 1215
<212> TYPE: DNA
<213> ORGANISM: Amycolatopsis lurida

<400> SEQUENCE: 35
atgactgacg tcgaggaaac caccgcgacc ttgccgctgg cccggaaatg cccgttttcg    60
ccgccgcccg aatacgaacg gcttcgccgg gaaagtccgg tttcccgggt cggtctcccg   120
tccggtcaaa cggcttgggc gctcacccgg ctcgaagaca tccgcgaaat gctgagcagc   180
ccgcatttca gttccgaccg gcagagcccg tcgttcccgc tgatggtcgc gcggcagatc   240
cgccgcgagg acaagccgtt ccgcccctcc ctcatcgcga tggatccgcc ggaacacagc   300
cgggccaggc gtgacgtcgt cggggaattc accgtcaagc ggatgaaggc gctccagccg   360
cgaattcagc agatcgtcga cgaacatctc gacgccctgc tcgcgggccc caaacccgcc   420
gatctcgtcc aggcgctttc cctgcccgtt ccctcgctgg tgatctgcga actgctcggc   480 gtccccctatt cggaccacga gttcttccag tcctgcagtt ccaggatgct cagcggggag   540
gtcaccgccg aagaacggat gaccgcgttc gagcagctcg aaaactatct cgacgaactg   600
```

```
gtcaccaaga aggaggcgaa cgccaccgag gacgacctcc tcggccgtca gatcctgaaa      660
cagcgggaaa cgggcgaggc cgaccacggt gaactcgtcg ggctggcgtt cctgctgctc      720
atcgccggac acgagaccac ggcgaacatg atctcgctcg gcacggtgac cctgctggag      780
aatcccgatc agctcgcgaa gatcaaggca gaccccggca agaccctcgc cgccatcgag      840
gaactcctgc gggtcttcac gatcgcggaa agcgcgacct cacgcttcgc cacggcggac      900
gtcgagatcg gcgaacgct gatccgcgcg ggggaagggg tggtgggcct gagcaacgcg      960
ggcaaccacg atccggacgg cttcgagaac ccggacacct cgacatcga acgcggcgcg     1020 cggcatcacg tcgcgttcgg attcggggtg caccagtgtc tcggccagaa cttggcgagg     1080
ttggaactcc agatcgtctt cgatacgttg ttccggcgag tgccgggcct ccggatcgcc     1140
gttccggtcg acgaactgcc gttcaagcac gattcgacga tctacggcct ccacgccctt     1200
ccggtcacct ggtag                                                      1215
```

<210> SEQ ID NO 36
<211> LENGTH: 404
<212> TYPE: PRT
<213> ORGANISM: Amycolatopsis lurida

<400> SEQUENCE: 36

```
Met Thr Asp Val Glu Glu Thr Thr Ala Thr Leu Pro Leu Ala Arg Lys
1               5                   10                  15

Cys Pro Phe Ser Pro Pro Glu Tyr Glu Arg Leu Arg Arg Glu Ser
            20                  25                  30

Pro Val Ser Arg Val Gly Leu Pro Ser Gly Gln Thr Ala Trp Ala Leu
        35                  40                  45

Thr Arg Leu Glu Asp Ile Arg Glu Met Leu Ser Ser Pro His Phe Ser
    50                  55                  60

Ser Asp Arg Gln Ser Pro Ser Phe Pro Leu Met Val Ala Arg Gln Ile
65                  70                  75                  80

Arg Arg Glu Asp Lys Pro Phe Arg Pro Ser Leu Ile Ala Met Asp Pro
                85                  90                  95

Pro Glu His Ser Arg Ala Arg Asp Val Val Gly Glu Phe Thr Val
            100                 105                 110

Lys Arg Met Lys Ala Leu Gln Pro Arg Ile Gln Gln Ile Val Asp Glu
        115                 120                 125

His Leu Asp Ala Leu Leu Ala Gly Pro Lys Pro Ala Asp Leu Val Gln
    130                 135                 140

Ala Leu Ser Leu Pro Val Pro Ser Leu Val Ile Cys Glu Leu Leu Gly
145                 150                 155                 160

Val Pro Tyr Ser Asp His Glu Phe Phe Gln Ser Cys Ser Ser Arg Met
                165                 170                 175

Leu Ser Arg Glu Val Thr Ala Glu Glu Arg Met Thr Ala Phe Glu Gln
            180                 185                 190

Leu Glu Asn Tyr Leu Asp Glu Leu Val Thr Lys Lys Glu Ala Asn Ala
        195                 200                 205

Thr Glu Asp Asp Leu Leu Gly Arg Gln Ile Leu Lys Gln Arg Glu Thr
    210                 215                 220

Gly Glu Ala Asp His Gly Glu Leu Val Gly Leu Ala Phe Leu Leu Leu
225                 230                 235                 240

Ile Ala Gly His Glu Thr Thr Ala Asn Met Ile Ser Leu Gly Thr Val
                245                 250                 255
```

```
Thr Leu Leu Glu Asn Pro Asp Gln Leu Ala Lys Ile Lys Ala Asp Pro
            260                 265                 270

Gly Lys Thr Leu Ala Ala Ile Glu Glu Leu Leu Arg Val Phe Thr Ile
        275                 280                 285

Ala Glu Ser Ala Thr Ser Arg Phe Ala Thr Ala Asp Val Glu Ile Gly
    290                 295                 300

Gly Thr Leu Ile Arg Ala Gly Glu Gly Val Val Gly Leu Ser Asn Ala
305                 310                 315                 320

Gly Asn His Asp Pro Asp Gly Phe Glu Asn Pro Asp Thr Phe Asp Ile
                325                 330                 335

Glu Arg Gly Ala Arg His His Val Ala Phe Gly Phe Gly Val His Gln
            340                 345                 350

Cys Leu Gly Gln Asn Leu Ala Arg Leu Glu Leu Gln Ile Val Phe Asp
        355                 360                 365

Thr Leu Phe Arg Arg Val Pro Gly Leu Arg Ile Ala Val Pro Val Asp
    370                 375                 380

Glu Leu Pro Phe Lys His Asp Ser Thr Ile Tyr Gly Leu His Ala Leu
385                 390                 395                 400

Pro Val Thr Trp

<210> SEQ ID NO 37
<211> LENGTH: 23
<212> TYPE: DNA
<213> ORGANISM: Artificial Sequence
<220> FEATURE:
<223> OTHER INFORMATION: Designed primer sequence used for amplification
      and mutagenesis of position T291 in P450aluC09 to produce Mutant
      32 (T291L)

<400> SEQUENCE: 37
gatcgcggaa ctggcgacct cac                                              23

<210> SEQ ID NO 38
<211> LENGTH: 23
<212> TYPE: DNA
<213> ORGANISM: Artificial Sequence
<220> FEATURE:
<223> OTHER INFORMATION: Designed primer sequence used for amplification
      and mutagenesis of position T291 in P450aluC09 to produce Mutant
      32 (T291L)

<400> SEQUENCE: 38
gtgaggtcgc cagttccgcg atc                                              23

<210> SEQ ID NO 39
<211> LENGTH: 1215
<212> TYPE: DNA
<213> ORGANISM: Amycolatopsis lurida

<400> SEQUENCE: 39
atgactgacg tcgaggaaac caccgcgacc ttgccgctgg cccggaaatg cccgttttcg      60
ccgccgcccg aatacgaacg gcttcgccgg gaaagtccgg tttcccgggt cggtctcccg     120
tccggtcaaa cggcttgggc gctcaccccg ctcgaagaca tccgcgaaat gctgagcagc     180
ccgcatttca gttccgaccg gcagagcccg tcgttcccgc tgatggtcgc gcggcagatc     240
cgccgcgagg acaagccgtt ccgcccctcc ctcatcgcga tggatccgcc ggaacacagc     300
cgggccaggc gtgacgtcgt cggggaattc accgtcaagc ggatgaaggc gctccagccg     360
cgaattcagc agatcgtcga cgaacatctc gacgccctgc tcgcgggccc caaacccgcc     420
```

-continued

```
gatctcgtcc aggcgctttc cctgcccgtt ccctcgctgg tgatctgcga actgctcggc    480
gtccccattc ggaccacga gttcttccag tcctgcagtt ccaggatgct cagccgggag    540
gtcaccgccg aagaacggat gaccgcgttc gagcagctcg aaaactatct cgacgaactg    600
gtcaccaaga aggaggcgaa cgccaccgag gacgacctcc tcggccgtca gatcctgaaa    660
cagcgggaaa cgggcgaggc cgaccacggt gaactcgtcg ggctggcgtt cctgctgctc    720
atcgccggac acgagaccac ggcgaacatg atctcgctcg gcacggtgac cctgctggag    780
aatcccgatc agctcgcgaa gatcaaggca gaccccggca agaccctcgc cgccatcgag    840
gaactcctgc gggtcttcac gatcgcggaa ctggcgacct cacgcttcgc cacggcggac    900
gtcgagatcg gcggaacgct gatccgcgcg ggggaagggg tggtgggcct gagcaacgcg    960
ggcaaccacg atccggacgg cttcgagaac ccggacacct cgacatcga acgcggcgcg   1020 cggcatcacg tcgcgttcgg attcggggtg caccagtgtc tcggccagaa cttggcgagg   1080
ttggaactcc agatcgtctt cgatacgttg ttccggcgag tgccgggcct ccggatcgcc   1140
gttccggtcg acgaactgcc gttcaagcac gattcgacga tctacggcct ccacgccctt   1200
ccggtcacct ggtag                                                    1215
```

<210> SEQ ID NO 40
<211> LENGTH: 404
<212> TYPE: PRT
<213> ORGANISM: Amycolatopsis lurida

<400> SEQUENCE: 40

```
Met Thr Asp Val Glu Glu Thr Thr Ala Thr Leu Pro Leu Ala Arg Lys
1               5                   10                  15

Cys Pro Phe Ser Pro Pro Glu Tyr Glu Arg Leu Arg Arg Glu Ser
            20                  25                  30

Pro Val Ser Arg Val Gly Leu Pro Ser Gly Gln Thr Ala Trp Ala Leu
        35                  40                  45

Thr Arg Leu Glu Asp Ile Arg Glu Met Leu Ser Ser Pro His Phe Ser
    50                  55                  60

Ser Asp Arg Gln Ser Pro Ser Phe Pro Leu Met Val Ala Arg Gln Ile
65                  70                  75                  80

Arg Arg Glu Asp Lys Pro Phe Arg Pro Ser Leu Ile Ala Met Asp Pro
                85                  90                  95

Pro Glu His Ser Arg Ala Arg Arg Asp Val Val Gly Glu Phe Thr Val
            100                 105                 110

Lys Arg Met Lys Ala Leu Gln Pro Arg Ile Gln Gln Ile Val Asp Glu
        115                 120                 125

His Leu Asp Ala Leu Leu Ala Gly Pro Lys Pro Ala Asp Leu Val Gln
    130                 135                 140

Ala Leu Ser Leu Pro Val Pro Ser Leu Val Ile Cys Glu Leu Leu Gly
145                 150                 155                 160

Val Pro Tyr Ser Asp His Glu Phe Phe Gln Ser Cys Ser Ser Arg Met
                165                 170                 175

Leu Ser Arg Glu Val Thr Ala Glu Glu Arg Met Thr Ala Phe Glu Gln
            180                 185                 190

Leu Glu Asn Tyr Leu Asp Glu Leu Val Thr Lys Glu Ala Asn Ala
        195                 200                 205

Thr Glu Asp Asp Leu Leu Gly Arg Gln Ile Leu Lys Gln Arg Glu Thr
    210                 215                 220
```

Gly Glu Ala Asp His Gly Glu Leu Val Gly Leu Ala Phe Leu Leu Leu
225                 230                 235                 240

Ile Ala Gly His Glu Thr Thr Ala Asn Met Ile Ser Leu Gly Thr Val
            245                 250                 255

Thr Leu Leu Glu Asn Pro Asp Gln Leu Ala Lys Ile Lys Ala Asp Pro
        260                 265                 270

Gly Lys Thr Leu Ala Ala Ile Glu Glu Leu Leu Arg Val Phe Thr Ile
    275                 280                 285

Ala Glu Leu Ala Thr Ser Arg Phe Ala Thr Ala Asp Val Glu Ile Gly
        290                 295                 300

Gly Thr Leu Ile Arg Ala Gly Glu Gly Val Val Gly Leu Ser Asn Ala
305                 310                 315                 320

Gly Asn His Asp Pro Asp Gly Phe Glu Asn Pro Asp Thr Phe Asp Ile
            325                 330                 335

Glu Arg Gly Ala Arg His His Val Ala Phe Gly Phe Gly Val His Gln
        340                 345                 350

Cys Leu Gly Gln Asn Leu Ala Arg Leu Glu Leu Gln Ile Val Phe Asp
    355                 360                 365

Thr Leu Phe Arg Arg Val Pro Gly Leu Arg Ile Ala Val Pro Val Asp
        370                 375                 380

Glu Leu Pro Phe Lys His Asp Ser Thr Ile Tyr Gly Leu His Ala Leu
385                 390                 395                 400

Pro Val Thr Trp

<210> SEQ ID NO 41
<211> LENGTH: 23
<212> TYPE: DNA
<213> ORGANISM: Artifical Sequence
<220> FEATURE:
<223> OTHER INFORMATION: Designed primer sequence used for amplification
      and mutagenesis of position T291 in P450aluC09 to produce Mutant
      33 (T291I)

<400> SEQUENCE: 41
gatcgcggaa attgcgacct cac                                         23

<210> SEQ ID NO 42
<211> LENGTH: 23
<212> TYPE: DNA
<213> ORGANISM: Artifical Sequence
<220> FEATURE:
<223> OTHER INFORMATION: Designed primer sequence used for amplification
      and mutagenesis of position T291 in P450aluC09 to produce Mutant
      33 (T291I)

<400> SEQUENCE: 42
gtgaggtcgc aatttccgcg atc                                         23

<210> SEQ ID NO 43
<211> LENGTH: 1215
<212> TYPE: DNA
<213> ORGANISM: Amycolatopsis lurida

<400> SEQUENCE: 43
atgactgacg tcgaggaaac caccgcgacc ttgccgctgg cccggaaatg cccgtttcg     60 ccgccgcccg aatacgaacg gcttcgccgg gaaagtccgg tttcccgggt cggtctcccg    120
tccggtcaaa cggcttgggc gctcacccgg ctcgaagaca tccgcgaaat gctgagcagc    180
ccgcatttca gttccgaccg gcagagcccg tcgttcccgc tgatggtcgc gcggcagatc    240

```
cgccgcgagg acaagccgtt ccgcccctcc ctcatcgcga tggatccgcc ggaacacagc    300
cgggccaggc gtgacgtcgt cggggaattc accgtcaagc ggatgaaggc gctccagccg    360
cgaattcagc agatcgtcga cgaacatctc gacgccctgc tcgcgggccc caaacccgcc    420
gatctcgtcc aggcgctttc cctgccgtt ccctcgctgg tgatctgcga actgctcggc    480
gtcccctatt cggaccacga gttcttccag tcctgcagtt ccaggatgct cagccgggag    540
gtcaccgccg aagaacggat gaccgcgttc gagcagctcg aaaactatct cgacgaactg    600
gtcaccaaga aggaggcgaa cgccaccgag gacgacctcc tcggccgtca gatcctgaaa    660
cagcgggaaa cgggcgaggc cgaccacggt gaactcgtcg ggctggcgtt cctgctgctc    720
atcgccggac acgagaccac ggcgaacatg atctcgctcg gcacggtgac cctgctggag    780
aatcccgatc agctcgcgaa gatcaaggca gaccccggca agaccctcgc cgccatcgag    840
gaactcctgc gggtcttcac gatcgcggaa attgcgacct cacgcttcgc cacggcggac    900
gtcgagatcg gcggaacgct gatccgcgcg ggggaagggg tggtgggcct gagcaacgcg    960
ggcaaccacg atccggacgg cttcgagaac ccggacacct tcgacatcga acgcggcgcg   1020
cggcatcacg tcgcgttcgg attcggggtg caccagtgtc tcggccagaa cttggcgagg   1080
ttggaactcc agatcgtctt cgatacgttg ttccggcgag tgccgggcct ccggatcgcc   1140
gttccggtcg acgaactgcc gttcaagcac gattcgacga tctacggcct ccacgccctt   1200
ccggtcacct ggtag                                                    1215
```

<210> SEQ ID NO 44
<211> LENGTH: 404
<212> TYPE: PRT
<213> ORGANISM: Amycolatopsis lurida

<400> SEQUENCE: 44

```
Met Thr Asp Val Glu Glu Thr Thr Ala Thr Leu Pro Leu Ala Arg Lys
1               5                   10                  15

Cys Pro Phe Ser Pro Pro Glu Tyr Glu Arg Leu Arg Arg Glu Ser
            20                  25                  30

Pro Val Ser Arg Val Gly Leu Pro Ser Gly Gln Thr Ala Trp Ala Leu
        35                  40                  45

Thr Arg Leu Glu Asp Ile Arg Glu Met Leu Ser Ser Pro His Phe Ser
    50                  55                  60

Ser Asp Arg Gln Ser Pro Ser Phe Pro Leu Met Val Ala Arg Gln Ile
65                  70                  75                  80

Arg Arg Glu Asp Lys Pro Phe Arg Pro Ser Leu Ile Ala Met Asp Pro
                85                  90                  95

Pro Glu His Ser Arg Ala Arg Arg Asp Val Val Gly Glu Phe Thr Val
            100                 105                 110

Lys Arg Met Lys Ala Leu Gln Pro Arg Ile Gln Gln Ile Val Asp Glu
        115                 120                 125

His Leu Asp Ala Leu Leu Ala Gly Pro Lys Pro Ala Asp Leu Val Gln
    130                 135                 140

Ala Leu Ser Leu Pro Val Pro Ser Leu Val Ile Cys Glu Leu Leu Gly
145                 150                 155                 160

Val Pro Tyr Ser Asp His Glu Phe Phe Gln Ser Cys Ser Ser Arg Met
                165                 170                 175

Leu Ser Arg Glu Val Thr Ala Glu Glu Arg Met Thr Ala Phe Glu Gln
            180                 185                 190
```

Leu Glu Asn Tyr Leu Asp Glu Leu Val Thr Lys Lys Glu Ala Asn Ala
        195                 200                 205

Thr Glu Asp Asp Leu Leu Gly Arg Gln Ile Leu Lys Gln Arg Glu Thr
    210                 215                 220

Gly Glu Ala Asp His Gly Glu Leu Val Gly Leu Ala Phe Leu Leu Leu
225                 230                 235                 240

Ile Ala Gly His Glu Thr Thr Ala Asn Met Ile Ser Leu Gly Thr Val
                245                 250                 255

Thr Leu Leu Glu Asn Pro Asp Gln Leu Ala Lys Ile Lys Ala Asp Pro
        260                 265                 270

Gly Lys Thr Leu Ala Ala Ile Glu Glu Leu Leu Arg Val Phe Thr Ile
    275                 280                 285

Ala Glu Ile Ala Thr Ser Arg Phe Ala Thr Ala Asp Val Glu Ile Gly
        290                 295                 300

Gly Thr Leu Ile Arg Ala Gly Glu Gly Val Val Gly Leu Ser Asn Ala
305                 310                 315                 320

Gly Asn His Asp Pro Asp Gly Phe Glu Asn Pro Asp Thr Phe Asp Ile
                325                 330                 335

Glu Arg Gly Ala Arg His His Val Ala Phe Gly Phe Gly Val His Gln
        340                 345                 350

Cys Leu Gly Gln Asn Leu Ala Arg Leu Glu Leu Gln Ile Val Phe Asp
        355                 360                 365

Thr Leu Phe Arg Arg Val Pro Gly Leu Arg Ile Ala Val Pro Val Asp
    370                 375                 380

Glu Leu Pro Phe Lys His Asp Ser Thr Ile Tyr Gly Leu His Ala Leu
385                 390                 395                 400

Pro Val Thr Trp

<210> SEQ ID NO 45
<211> LENGTH: 23
<212> TYPE: DNA
<213> ORGANISM: Artifical Sequence
<220> FEATURE:
<223> OTHER INFORMATION: Designed primer sequence used for amplification
      and mutagenesis of position T291 in P450aluC09 to produce Mutant
      34 (T291M)

<400> SEQUENCE: 45
gatcgcggaa atggcgacct cac                                              23

<210> SEQ ID NO 46
<211> LENGTH: 23
<212> TYPE: DNA
<213> ORGANISM: Artifical Sequence
<220> FEATURE:
<223> OTHER INFORMATION: Designed primer sequence used for amplification
      and mutagenesis of position T291 in P450aluC09 to produce Mutant
      34 (T291M)

<400> SEQUENCE: 46
gtgaggtcgc catttccgcg atc                                              23

<210> SEQ ID NO 47
<211> LENGTH: 1215
<212> TYPE: DNA
<213> ORGANISM: Amycolatopsis lurida

<400> SEQUENCE: 47

```
atgactgacg tcgaggaaac caccgcgacc ttgccgctgg cccggaaatg cccgttttcg      60
ccgccgcccg aatacgaacg gcttcgccgg gaaagtccgg tttcccgggt cggtctcccg     120
tccggtcaaa cggcttgggc gctcacccgg ctcgaagaca tccgcgaaat gctgagcagc     180
ccgcatttca gttccgaccg gcagagcccg tcgttcccgc tgatggtcgc gcggcagatc     240
cgccgcgagg acaagccgtt ccgcccctcc ctcatcgcga tggatccgcc ggaacacagc     300
cgggccaggc gtgacgtcgt cggggaattc accgtcaagc ggatgaaggc gctccagccg     360
cgaattcagc agatcgtcga cgaacatctc gacgccctgc tcgcgggccc caaacccgcc     420
gatctcgtcc aggcgctttc cctgcccgtt ccctcgctgg tgatctgcga actgctcggc     480
gtccctatt cggaccacga gttcttccag tcctgcagtt ccaggatgct cagccgggag     540
gtcaccgccg aagaacggat gaccgcgttc gagcagctcg aaaactatct cgacgaactg     600
gtcaccaaga aggaggcgaa cgccaccgag gacgacctcc tcggccgtca gatcctgaaa     660
cagcgggaaa cgggcgaggc cgaccacggt gaactcgtcg ggctggcgtt cctgctgctc     720
atcgccggac acgagaccac ggcgaacatg atctcgctcg gcacggtgac cctgctggag     780
aatcccgatc agctcgcgaa gatcaaggca gaccccggca agaccctcgc cgccatcgag     840
gaactcctgc gggtcttcac gatcgcggaa atggcgacct cacgcttcgc cacggcggac     900
gtcgagatcg gcggaacgct gatccgcgcg ggggaagggg tggtgggcct gagcaacgcg     960
ggcaaccacg atccggacgg cttcgagaac ccggacacct tcgacatcga acgcggcgcg    1020
cggcatcacg tcgcgttcgg attcggggtg caccagtgtc tcggccagaa cttggcgagg    1080
ttggaactcc agatcgtctt cgatacgttg ttcggcgag tgccgggcct ccggatcgcc    1140
gttccggtcg acgaactgcc gttcaagcac gattcgacga tctacggcct ccacgcccctt    1200
ccggtcacct ggtag                                                     1215
```

<210> SEQ ID NO 48
<211> LENGTH: 404
<212> TYPE: PRT
<213> ORGANISM: Amycolatopsis lurida

<400> SEQUENCE: 48

```
Met Thr Asp Val Glu Glu Thr Thr Ala Thr Leu Pro Leu Ala Arg Lys
1               5                   10                  15

Cys Pro Phe Ser Pro Pro Glu Tyr Glu Arg Leu Arg Arg Glu Ser
            20                  25                  30

Pro Val Ser Arg Val Gly Leu Pro Ser Gly Gln Thr Ala Trp Ala Leu
        35                  40                  45

Thr Arg Leu Glu Asp Ile Arg Glu Met Leu Ser Ser Pro His Phe Ser
    50                  55                  60

Ser Asp Arg Gln Ser Pro Ser Phe Pro Leu Met Val Ala Arg Gln Ile
65                  70                  75                  80

Arg Arg Glu Asp Lys Pro Phe Arg Pro Ser Leu Ile Ala Met Asp Pro
                85                  90                  95

Pro Glu His Ser Arg Ala Arg Arg Asp Val Val Gly Glu Phe Thr Val
            100                 105                 110

Lys Arg Met Lys Ala Leu Gln Pro Arg Ile Gln Gln Ile Val Asp Glu
        115                 120                 125

His Leu Asp Ala Leu Leu Ala Gly Pro Lys Pro Ala Asp Leu Val Gln
    130                 135                 140
```

```
Ala Leu Ser Leu Pro Val Pro Ser Leu Val Ile Cys Glu Leu Leu Gly
145                 150                 155                 160

Val Pro Tyr Ser Asp His Glu Phe Phe Gln Ser Cys Ser Ser Arg Met
            165                 170                 175

Leu Ser Arg Glu Val Thr Ala Glu Arg Met Thr Ala Phe Glu Gln
        180                 185                 190

Leu Glu Asn Tyr Leu Asp Glu Leu Val Thr Lys Lys Glu Ala Asn Ala
            195                 200                 205

Thr Glu Asp Asp Leu Leu Gly Arg Gln Ile Leu Lys Gln Arg Glu Thr
        210                 215                 220

Gly Glu Ala Asp His Gly Glu Leu Val Gly Leu Ala Phe Leu Leu Leu
225                 230                 235                 240

Ile Ala Gly His Glu Thr Thr Ala Asn Met Ile Ser Leu Gly Thr Val
                245                 250                 255

Thr Leu Leu Glu Asn Pro Asp Gln Leu Ala Lys Ile Lys Ala Asp Pro
            260                 265                 270

Gly Lys Thr Leu Ala Ala Ile Glu Glu Leu Leu Arg Val Phe Thr Ile
        275                 280                 285

Ala Glu Met Ala Thr Ser Arg Phe Ala Thr Ala Asp Val Glu Ile Gly
290                 295                 300

Gly Thr Leu Ile Arg Ala Gly Glu Gly Val Val Gly Leu Ser Asn Ala
305                 310                 315                 320

Gly Asn His Asp Pro Asp Gly Phe Glu Asn Pro Asp Thr Phe Asp Ile
                325                 330                 335

Glu Arg Gly Ala Arg His His Val Ala Phe Gly Phe Gly Val His Gln
            340                 345                 350

Cys Leu Gly Gln Asn Leu Ala Arg Leu Glu Leu Gln Ile Val Phe Asp
        355                 360                 365

Thr Leu Phe Arg Arg Val Pro Gly Leu Arg Ile Ala Val Pro Val Asp
        370                 375                 380

Glu Leu Pro Phe Lys His Asp Ser Thr Ile Tyr Gly Leu His Ala Leu
385                 390                 395                 400

Pro Val Thr Trp

<210> SEQ ID NO 49
<211> LENGTH: 23
<212> TYPE: DNA
<213> ORGANISM: Artifical Sequence
<220> FEATURE:
<223> OTHER INFORMATION: Designed primer sequence used for amplification
      and mutagenesis of position T291 in P450aluC09 to produce Mutant
      35 (T291P)

<400> SEQUENCE: 49
gatcgcggaa ccggcgacct cac                                            23

<210> SEQ ID NO 50
<211> LENGTH: 23
<212> TYPE: DNA
<213> ORGANISM: Artifical Sequence
<220> FEATURE:
<223> OTHER INFORMATION: Designed primer sequence used for amplification
      and mutagenesis of position T291 in P450aluC09 to produce Mutant
      35 (T291P)

<400> SEQUENCE: 50
gtgaggtcgc cggttccgcg atc                                            23
```

<210> SEQ ID NO 51
<211> LENGTH: 1215
<212> TYPE: DNA
<213> ORGANISM: Amycolatopsis lurida

<400> SEQUENCE: 51

```
atgactgacg tcgaggaaac caccgcgacc ttgccgctgg cccggaaatg cccgttttcg      60
ccgccgcccg aatacgaacg gcttcgccgg gaaagtccgg tttccgggt cggtctcccg     120
tccggtcaaa cggcttgggc gctcacccgg ctcgaagaca tccgcgaaat gctgagcagc     180
ccgcatttca gttccgaccg gcagagcccg tcgttcccgc tgatggtcgc gcggcagatc     240
cgccgcgagg acaagccgtt ccgcccctcc ctcatcgcga tggatccgcc ggaacacagc     300
cgggccaggc gtgacgtcgt cggggaattc accgtcaagc ggatgaaggc gctccagccg     360
cgaattcagc agatcgtcga cgaacatctc gacgccctgc tcgcgggccc caaacccgcc     420
gatctcgtcc aggcgctttc cctgccgtt ccctcgctgg tgatctgcga actgctcggc     480
gtccctatt cggaccacga gttcttccag tcctgcagtt ccaggatgct cagccgggag     540
gtcaccgccg aagaacggat gaccgcgttc gagcagctcg aaaactatct cgacgaactg     600
gtcaccaaga aggaggcgaa cgccaccgag gacgacctcc tcggccgtca gatcctgaaa     660
cagcgggaaa cgggcgaggc cgaccacggt gaactcgtcg ggctggcgtt cctgctgctc     720
atcgccggac acgagaccac ggcgaacatg atctcgctcg gcacggtgac cctgctggag     780
aatcccgatc agctcgcgaa gatcaaggca gaccccggca agaccctcgc cgccatcgag     840
gaactcctgc gggtcttcac gatcgcggaa ccggcgacct cacgcttcgc cacggcggac     900
gtcgagatcg gcggaacgct gatccgcgcg ggggaagggg tggtgggcct gagcaacgcg     960
ggcaaccacg atccggacgg cttcgagaac ccggacacct tcgacatcga acgcggcgcg    1020
cggcatcacg tcgcgttcgg attcggggtg caccagtgtc tcggccagaa cttggcgagg    1080
ttggaactcc agatcgtctt cgatacgttg ttccggcgag tgccgggcct ccggatcgcc    1140
gttccggtcg acgaactgcc gttcaagcac gattcgacga tctacggcct ccacgcccct    1200
ccggtcacct ggtag                                                     1215
```

<210> SEQ ID NO 52
<211> LENGTH: 404
<212> TYPE: PRT
<213> ORGANISM: Amycolatopsis lurida

<400> SEQUENCE: 52

```
Met Thr Asp Val Glu Glu Thr Thr Ala Thr Leu Pro Leu Ala Arg Lys
1               5                   10                  15

Cys Pro Phe Ser Pro Pro Glu Tyr Glu Arg Leu Arg Arg Glu Ser
            20                  25                  30

Pro Val Ser Arg Val Gly Leu Pro Ser Gly Gln Thr Ala Trp Ala Leu
        35                  40                  45

Thr Arg Leu Glu Asp Ile Arg Glu Met Leu Ser Ser Pro His Phe Ser
    50                  55                  60

Ser Asp Arg Gln Ser Pro Ser Phe Pro Leu Met Val Ala Arg Gln Ile
65                  70                  75                  80

Arg Arg Glu Asp Lys Pro Phe Arg Pro Ser Leu Ile Ala Met Asp Pro
                85                  90                  95

Pro Glu His Ser Arg Ala Arg Arg Asp Val Val Gly Glu Phe Thr Val
            100                 105                 110
```

Lys Arg Met Lys Ala Leu Gln Pro Arg Ile Gln Gln Ile Val Asp Glu
            115                 120                 125

His Leu Asp Ala Leu Leu Ala Gly Pro Lys Pro Ala Asp Leu Val Gln
        130                 135                 140

Ala Leu Ser Leu Pro Val Pro Ser Leu Val Ile Cys Glu Leu Leu Gly
145                 150                 155                 160

Val Pro Tyr Ser Asp His Glu Phe Phe Gln Ser Cys Ser Ser Arg Met
                165                 170                 175

Leu Ser Arg Glu Val Thr Ala Glu Arg Met Thr Ala Phe Glu Gln
            180                 185                 190

Leu Glu Asn Tyr Leu Asp Glu Leu Val Thr Lys Lys Glu Ala Asn Ala
        195                 200                 205

Thr Glu Asp Asp Leu Leu Gly Arg Gln Ile Leu Lys Gln Arg Glu Thr
    210                 215                 220

Gly Glu Ala Asp His Gly Glu Leu Val Gly Leu Ala Phe Leu Leu Leu
225                 230                 235                 240

Ile Ala Gly His Glu Thr Thr Ala Asn Met Ile Ser Leu Gly Thr Val
                245                 250                 255

Thr Leu Leu Glu Asn Pro Asp Gln Leu Ala Lys Ile Lys Ala Asp Pro
            260                 265                 270

Gly Lys Thr Leu Ala Ala Ile Glu Glu Leu Leu Arg Val Phe Thr Ile
        275                 280                 285

Ala Glu Pro Ala Thr Ser Arg Phe Ala Thr Ala Asp Val Glu Ile Gly
    290                 295                 300

Gly Thr Leu Ile Arg Ala Gly Glu Gly Val Val Gly Leu Ser Asn Ala
305                 310                 315                 320

Gly Asn His Asp Pro Asp Gly Phe Glu Asn Pro Asp Thr Phe Asp Ile
                325                 330                 335

Glu Arg Gly Ala Arg His His Val Ala Phe Gly Phe Gly Val His Gln
            340                 345                 350

Cys Leu Gly Gln Asn Leu Ala Arg Leu Glu Leu Gln Ile Val Phe Asp
        355                 360                 365

Thr Leu Phe Arg Arg Val Pro Gly Leu Arg Ile Ala Val Pro Val Asp
    370                 375                 380

Glu Leu Pro Phe Lys His Asp Ser Thr Ile Tyr Gly Leu His Ala Leu
385                 390                 395                 400

Pro Val Thr Trp

<210> SEQ ID NO 53
<211> LENGTH: 23
<212> TYPE: DNA
<213> ORGANISM: Artificial Sequence
<220> FEATURE:
<223> OTHER INFORMATION: Designed primer sequence used for amplification
    and mutagenesis of position T291 in P450aluC09 to produce Mutant
    36 (T291F)

<400> SEQUENCE: 53
gatcgcggaa tttgcgacct cac                                           23

<210> SEQ ID NO 54
<211> LENGTH: 23
<212> TYPE: DNA
<213> ORGANISM: Artificial Sequence
<220> FEATURE:
<223> OTHER INFORMATION: Designed primer sequence used for amplification
    and mutagenesis of position T291 in P450aluC09 to produce Mutant
    36 (T291F)

<400> SEQUENCE: 54
gtgaggtcgc aaattccgcg atc                                    23

<210> SEQ ID NO 55
<211> LENGTH: 1215
<212> TYPE: DNA
<213> ORGANISM: Amycolatopsis lurida

<400> SEQUENCE: 55
atgactgacg tcgaggaaac caccgcgacc ttgccgctgg cccggaaatg cccgttttcg     60
ccgccgcccg aatacgaacg gcttcgccgg gaaagtccgg tttcccgggt cggtctcccg    120
tccggtcaaa cggcttgggc gctcacccgg ctcgaagaca tccgcgaaat gctgagcagc    180
ccgcatttca gttccgaccg gcagagcccg tcgttcccgc tgatggtcgc gcggcagatc    240
cgccgcgagg acaagccgtt ccgcccctcc ctcatcgcga tggatccgcc ggaacacagc    300
cgggccaggc gtgacgtcgt cggggaattc accgtcaagc ggatgaaggc gctccagccg    360
cgaattcagc agatcgtcga cgaacatctc gacgccctgc tcgcgggccc caaacccgcc    420
gatctcgtcc aggcgctttc cctgccgtt cctcgctgg tgatctgcga actgctcggc    480
gtcccctatt cggaccacga gttcttccag tcctgcagtt ccaggatgct cagccgggag    540
gtcaccgccg aagaacggat gaccgcgttc gagcagctcg aaaactatct cgacgaactg    600
gtcaccaaga aggaggcgaa cgccaccgag gacgacctcc tcggccgtca gatcctgaaa    660
cagcgggaaa cgggcgaggc cgaccacggt gaactcgtcg ggctggcgtt cctgctgctc    720
atcgccggac acgagaccac ggcgaacatg atctcgctcg gcacggtgac cctgctggag    780
aatcccgatc agctcgcgaa gatcaaggca gaccccggca agaccctcgc cgccatcgag    840
gaactcctgc gggtcttcac gatcgcgaa tttgcgacct cacgcttcgc cacggcggac    900
gtcgagatcg gcggaacgct gatccgcgcg ggggaagggg tggtgggcct gagcaacgcg    960
ggcaaccacg atccggacgg cttcgagaac ccggacacct tcgacatcga acgcggcgcg   1020
cggcatcacg tcgcgttcgg attcggggtg caccagtgtc tcggccagaa cttggcgagg   1080
ttggaactcc agatcgtctt cgatacgttg ttccggcgag tgccgggcct ccggatcgcc   1140
gttccggtcg acgaactgcc gttcaagcac gattcgacga tctacggcct ccacgccctt   1200
ccggtcacct ggtag                                                   1215

<210> SEQ ID NO 56
<211> LENGTH: 404
<212> TYPE: PRT
<213> ORGANISM: Amycolatopsis lurida

<400> SEQUENCE: 56

Met Thr Asp Val Glu Glu Thr Thr Ala Thr Leu Pro Leu Ala Arg Lys
1               5                   10                  15

Cys Pro Phe Ser Pro Pro Glu Tyr Glu Arg Leu Arg Arg Glu Ser
            20                  25                  30

Pro Val Ser Arg Val Gly Leu Pro Ser Gly Gln Thr Ala Trp Ala Leu
        35                  40                  45

Thr Arg Leu Glu Asp Ile Arg Glu Met Leu Ser Ser Pro His Phe Ser
    50                  55                  60

Ser Asp Arg Gln Ser Pro Ser Phe Pro Leu Met Val Ala Arg Gln Ile
65                  70                  75                  80

Arg Arg Glu Asp Lys Pro Phe Arg Pro Ser Leu Ile Ala Met Asp Pro
            85                  90                  95

Pro Glu His Ser Arg Ala Arg Arg Asp Val Val Gly Glu Phe Thr Val
100                 105                 110

Lys Arg Met Lys Ala Leu Gln Pro Arg Ile Gln Gln Ile Val Asp Glu
        115                 120                 125

His Leu Asp Ala Leu Leu Ala Gly Pro Lys Pro Ala Asp Leu Val Gln
    130                 135                 140

Ala Leu Ser Leu Pro Val Pro Ser Leu Val Ile Cys Glu Leu Leu Gly
145                 150                 155                 160

Val Pro Tyr Ser Asp His Glu Phe Phe Gln Ser Cys Ser Ser Arg Met
                165                 170                 175

Leu Ser Arg Glu Val Thr Ala Glu Arg Met Thr Ala Phe Glu Gln
            180                 185                 190

Leu Glu Asn Tyr Leu Asp Glu Leu Val Thr Lys Lys Glu Ala Asn Ala
        195                 200                 205

Thr Glu Asp Asp Leu Leu Gly Arg Gln Ile Leu Lys Gln Arg Glu Thr
    210                 215                 220

Gly Glu Ala Asp His Gly Glu Leu Val Gly Leu Ala Phe Leu Leu Leu
225                 230                 235                 240

Ile Ala Gly His Glu Thr Thr Ala Asn Met Ile Ser Leu Gly Thr Val
                245                 250                 255

Thr Leu Leu Glu Asn Pro Asp Gln Leu Ala Lys Ile Lys Ala Asp Pro
            260                 265                 270

Gly Lys Thr Leu Ala Ala Ile Glu Glu Leu Leu Arg Val Phe Thr Ile
        275                 280                 285

Ala Glu Phe Ala Thr Ser Arg Phe Ala Thr Ala Asp Val Glu Ile Gly
    290                 295                 300

Gly Thr Leu Ile Arg Ala Gly Glu Gly Val Val Gly Leu Ser Asn Ala
305                 310                 315                 320

Gly Asn His Asp Pro Asp Gly Phe Glu Asn Pro Asp Thr Phe Asp Ile
                325                 330                 335

Glu Arg Gly Ala Arg His His Val Ala Phe Gly Phe Gly Val His Gln
            340                 345                 350

Cys Leu Gly Gln Asn Leu Ala Arg Leu Glu Leu Gln Ile Val Phe Asp
        355                 360                 365

Thr Leu Phe Arg Arg Val Pro Gly Leu Arg Ile Ala Val Pro Val Asp
    370                 375                 380

Glu Leu Pro Phe Lys His Asp Ser Thr Ile Tyr Gly Leu His Ala Leu
385                 390                 395                 400

Pro Val Thr Trp

<210> SEQ ID NO 57
<211> LENGTH: 23
<212> TYPE: DNA
<213> ORGANISM: Artifical Sequence
<220> FEATURE:
<223> OTHER INFORMATION: Designed primer sequence used for amplification
      and mutagenesis of position T291 in P450aluC09 to produce Mutant
      37 (T291W)

<400> SEQUENCE: 57
gatcgcggaa tgggcgacct cac                                           23

<210> SEQ ID NO 58

<211> LENGTH: 23
<212> TYPE: DNA
<213> ORGANISM: Artifical Sequence
<220> FEATURE:
<223> OTHER INFORMATION: Designed primer sequence used for amplification
and mutagenesis of position T291 in P450aluC09 to produce Mutant
37 (T291W)

<400> SEQUENCE: 58
gtgaggtcgc ccattccgcg atc                                          23

<210> SEQ ID NO 59
<211> LENGTH: 1215
<212> TYPE: DNA
<213> ORGANISM: Amycolatopsis lurida

<400> SEQUENCE: 59
atgactgacg tcgaggaaac caccgcgacc ttgccgctgg cccggaaatg cccgttttcg      60
ccgccgcccg aatacgaacg gcttcgccgg gaaagtccgg tttccgggt cggtctcccg     120 tccggtcaaa cggcttgggc gctcacccgg ctcgaagaca tccgcgaaat gctgagcagc     180
ccgcatttca gttccgaccg gcagagcccg tcgttcccgc tgatggtcgc gcggcagatc     240
cgccgcgagg acaagccgtt ccgccctcc ctcatcgcga tggatccgcc ggaacacagc     300
cgggccaggc gtgacgtcgt cggggaattc accgtcaagc ggatgaaggc gctccagccg     360
cgaattcagc agatcgtcga cgaacatctc gacgccctgc tcgcgggccc caaacccgcc     420
gatctcgtcc aggcgctttc cctgcccgtt ccctcgctgg tgatctgcga actgctcggc     480
gtcccctatt cggaccacga gttcttccag tcctgcagtt ccaggatgct cagccgggag     540
gtcaccgccg aagaacggat gaccgcgttc gagcagctcg aaaactatct cgacgaactg     600
gtcaccaaga aggaggcgaa cgccaccgag gacgacctcc tcggccgtca gatcctgaaa     660
cagcgggaaa cgggcgaggc cgaccacggt gaactcgtcg ggctggcgtt cctgctgctc     720
atcgccggac acgagaccac ggcgaacatg atctcgctcg gcacggtgac cctgctggag     780
aatcccgatc agctcgcgaa gatcaaggca gaccccggca agaccctcgc cgccatcgag     840
gaactcctgc gggtcttcac gatcgcggaa tgggcgacct cacgcttcgc cacggcggac     900
gtcgagatcg gcggaacgct gatccgcgcg ggggaagggg tggtgggcct gagcaacgcg     960
ggcaaccacg atccggacgg cttcgagaac ccggacacct cgacatcga acgcggcgcg    1020 cggcatcacg tcgcgttcgg attcggggtg caccagtgtc tcggccagaa cttggcgagg    1080
ttggaactcc agatcgtctt cgatacgttg ttccggcgag tgccgggcct ccggatcgcc    1140
gttccggtcg acgaactgcc gttcaagcac gattcgacga tctacggcct ccacgcccct    1200
ccggtcacct ggtag                                                    1215

<210> SEQ ID NO 60
<211> LENGTH: 404
<212> TYPE: PRT
<213> ORGANISM: Amycolatopsis lurida

<400> SEQUENCE: 60

Met Thr Asp Val Glu Glu Thr Thr Ala Thr Leu Pro Leu Ala Arg Lys
1               5                   10                  15

Cys Pro Phe Ser Pro Pro Glu Tyr Glu Arg Leu Arg Arg Glu Ser
            20                  25                  30

Pro Val Ser Arg Val Gly Leu Pro Ser Gly Gln Thr Ala Trp Ala Leu
        35                  40                  45

```
Thr Arg Leu Glu Asp Ile Arg Glu Met Leu Ser Ser Pro His Phe Ser
 50                  55                  60

Ser Asp Arg Gln Ser Pro Ser Phe Pro Leu Met Val Ala Arg Gln Ile
 65                  70                  75                  80

Arg Arg Glu Asp Lys Pro Phe Arg Pro Ser Leu Ile Ala Met Asp Pro
                 85                  90                  95

Pro Glu His Ser Arg Ala Arg Arg Asp Val Val Gly Glu Phe Thr Val
             100                 105                 110

Lys Arg Met Lys Ala Leu Gln Pro Arg Ile Gln Gln Ile Val Asp Glu
         115                 120                 125

His Leu Asp Ala Leu Leu Ala Gly Pro Lys Pro Ala Asp Leu Val Gln
130                 135                 140

Ala Leu Ser Leu Pro Val Pro Ser Leu Val Ile Cys Glu Leu Leu Gly
145                 150                 155                 160

Val Pro Tyr Ser Asp His Glu Phe Phe Gln Ser Cys Ser Ser Arg Met
                165                 170                 175

Leu Ser Arg Glu Val Thr Ala Glu Glu Arg Met Thr Ala Phe Glu Gln
            180                 185                 190

Leu Glu Asn Tyr Leu Asp Glu Leu Val Thr Lys Lys Glu Ala Asn Ala
        195                 200                 205

Thr Glu Asp Asp Leu Leu Gly Arg Gln Ile Leu Lys Gln Arg Glu Thr
210                 215                 220

Gly Glu Ala Asp His Gly Glu Leu Val Gly Leu Ala Phe Leu Leu Leu
225                 230                 235                 240

Ile Ala Gly His Glu Thr Thr Ala Asn Met Ile Ser Leu Gly Thr Val
                245                 250                 255

Thr Leu Leu Glu Asn Pro Asp Gln Leu Ala Lys Ile Lys Ala Asp Pro
            260                 265                 270

Gly Lys Thr Leu Ala Ala Ile Glu Glu Leu Leu Arg Val Phe Thr Ile
        275                 280                 285

Ala Glu Trp Ala Thr Ser Arg Phe Ala Thr Ala Asp Val Glu Ile Gly
290                 295                 300

Gly Thr Leu Ile Arg Ala Gly Glu Gly Val Val Gly Leu Ser Asn Ala
305                 310                 315                 320

Gly Asn His Asp Pro Asp Gly Phe Glu Asn Pro Asp Thr Phe Asp Ile
                325                 330                 335

Glu Arg Gly Ala Arg His His Val Ala Phe Gly Phe Gly Val His Gln
            340                 345                 350

Cys Leu Gly Gln Asn Leu Ala Arg Leu Glu Leu Gln Ile Val Phe Asp
        355                 360                 365

Thr Leu Phe Arg Arg Val Pro Gly Leu Arg Ile Ala Val Pro Val Asp
370                 375                 380

Glu Leu Pro Phe Lys His Asp Ser Thr Ile Tyr Gly Leu His Ala Leu
385                 390                 395                 400

Pro Val Thr Trp

<210> SEQ ID NO 61
<211> LENGTH: 23
<212> TYPE: DNA
<213> ORGANISM: Artifical Sequence
<220> FEATURE:
<223> OTHER INFORMATION: Designed primer sequence used for amplification
      and mutagenesis of position T291 in P450aluC09 to produce Mutant
      38 (T291H)
```

<400> SEQUENCE: 61
gatcgcggaa catgcgacct cac                                              23

<210> SEQ ID NO 62
<211> LENGTH: 23
<212> TYPE: DNA
<213> ORGANISM: Artifical Sequence
<220> FEATURE:
<223> OTHER INFORMATION: Designed primer sequence used for amplification
      and mutagenesis of position T291 in P450aluC09 to produce Mutant
      38 (T291H)

<400> SEQUENCE: 62
gtgaggtcgc atgttccgcg atc                                              23

<210> SEQ ID NO 63
<211> LENGTH: 1215
<212> TYPE: DNA
<213> ORGANISM: Amycolatopsis lurida

<400> SEQUENCE: 63
atgactgacg tcgaggaaac caccgcgacc ttgccgctgg cccggaaatg cccgttttcg      60
ccgccgcccg aatacgaacg gcttcgccgg gaaagtccgg tttcccgggt cggtctcccg     120
tccggtcaaa cggcttgggc gctcacccgg ctcgaagaca tccgcgaaat gctgagcagc     180
ccgcatttca gttccgaccg gcagagcccg tcgttcccgc tgatggtcgc gcggcagatc     240
cgccgcgagg acaagccgtt ccgcccctcc ctcatcgcga tggatccgcc ggaacacagc     300
cgggccaggc gtgacgtcgt cggggaattc accgtcaagc ggatgaaggc gctccagccg     360
cgaattcagc agatcgtcga cgaacatctc gacgccctgc tcgcgggccc caaacccgcc     420
gatctcgtcc aggcgctttc cctgccgtt cctcgctgg tgatctgcga actgctcggc      480
gtcccctatt cggaccacga gttcttccag tcctgcagtt ccaggatgct cagccgggag     540
gtcaccgccg aagaacggat gaccgcgttc gagcagctcg aaaactatct cgacgaactg     600
gtcaccaaga aggaggcgaa cgccaccgag gacgacctcc tcggccgtca gatcctgaaa     660
cagcgggaaa cgggcgaggc cgaccacggt gaactcgtcg gctggcgtt cctgctgctc      720 atcgccggac acgagaccac ggcgaacatg atctcgctcg gcacggtgac cctgctggag     780
aatcccgatc agctcgcgaa gatcaaggca gaccccggca agaccctcgc cgccatcgag     840
gaactcctgc gggtcttcac gatcgcggaa catgcgacct cacgcttcgc cacggcggac     900
gtcgagatcg gcggaacgct gatccgcgcg gggaagggg tggtgggcct gagcaacgcg      960
ggcaaccacg atccggacgg cttcgagaac ccggacacct tcgacatcga acgcggcgcg    1020
cggcatcacg tcgcgttcgg attcggggtg caccagtgtc tcggccagaa cttggcgagg    1080
ttggaactcc agatcgtctt cgatacgttg ttccggcgag tgccgggcct ccggatcgcc    1140
gttccggtcg acgaactgcc gttcaagcac gattcgacga tctacggcct ccacgccctt    1200
ccggtcacct ggtag                                                    1215

<210> SEQ ID NO 64
<211> LENGTH: 404
<212> TYPE: PRT
<213> ORGANISM: Amycolatopsis lurida

<400> SEQUENCE: 64

Met Thr Asp Val Glu Glu Thr Thr Ala Thr Leu Pro Leu Ala Arg Lys
1               5                   10                  15

-continued

Cys Pro Phe Ser Pro Pro Pro Glu Tyr Glu Arg Leu Arg Arg Glu Ser
              20                  25                  30

Pro Val Ser Arg Val Gly Leu Pro Ser Gly Gln Thr Ala Trp Ala Leu
          35                  40                  45

Thr Arg Leu Glu Asp Ile Arg Glu Met Leu Ser Ser Pro His Phe Ser
 50                  55                  60

Ser Asp Arg Gln Ser Pro Ser Phe Pro Leu Met Val Ala Arg Gln Ile
 65                  70                  75                  80

Arg Arg Glu Asp Lys Pro Phe Arg Pro Ser Leu Ile Ala Met Asp Pro
              85                  90                  95

Pro Glu His Ser Arg Ala Arg Arg Asp Val Val Gly Glu Phe Thr Val
             100                 105                 110

Lys Arg Met Lys Ala Leu Gln Pro Arg Ile Gln Gln Ile Val Asp Glu
             115                 120                 125

His Leu Asp Ala Leu Leu Ala Gly Pro Lys Pro Ala Asp Leu Val Gln
 130                 135                 140

Ala Leu Ser Leu Pro Val Pro Ser Leu Val Ile Cys Glu Leu Leu Gly
145                 150                 155                 160

Val Pro Tyr Ser Asp His Glu Phe Phe Gln Ser Cys Ser Ser Arg Met
             165                 170                 175

Leu Ser Arg Glu Val Thr Ala Glu Arg Met Thr Ala Phe Glu Gln
             180                 185                 190

Leu Glu Asn Tyr Leu Asp Glu Leu Val Thr Lys Lys Glu Ala Asn Ala
             195                 200                 205

Thr Glu Asp Asp Leu Leu Gly Arg Gln Ile Leu Lys Gln Arg Glu Thr
 210                 215                 220

Gly Glu Ala Asp His Gly Glu Leu Val Gly Leu Ala Phe Leu Leu Leu
225                 230                 235                 240

Ile Ala Gly His Glu Thr Thr Ala Asn Met Ile Ser Leu Gly Thr Val
             245                 250                 255

Thr Leu Leu Glu Asn Pro Asp Gln Leu Ala Lys Ile Lys Ala Asp Pro
             260                 265                 270

Gly Lys Thr Leu Ala Ala Ile Glu Glu Leu Leu Arg Val Phe Thr Ile
             275                 280                 285

Ala Glu His Ala Thr Ser Arg Phe Ala Thr Ala Asp Val Glu Ile Gly
             290                 295                 300

Gly Thr Leu Ile Arg Ala Gly Glu Gly Val Val Gly Leu Ser Asn Ala
305                 310                 315                 320

Gly Asn His Asp Pro Asp Gly Phe Glu Asn Pro Asp Thr Phe Asp Ile
             325                 330                 335

Glu Arg Gly Ala Arg His His Val Ala Phe Gly Phe Gly Val His Gln
             340                 345                 350

Cys Leu Gly Gln Asn Leu Ala Arg Leu Glu Leu Gln Ile Val Phe Asp
             355                 360                 365

Thr Leu Phe Arg Arg Val Pro Gly Leu Arg Ile Ala Val Pro Val Asp
             370                 375                 380

Glu Leu Pro Phe Lys His Asp Ser Thr Ile Tyr Gly Leu His Ala Leu
385                 390                 395                 400

Pro Val Thr Trp

<210> SEQ ID NO 65
<211> LENGTH: 23
<212> TYPE: DNA

```
<213> ORGANISM: Artifical Sequence
<220> FEATURE:
<223> OTHER INFORMATION: Designed primer sequence used for amplification
      and mutagenesis of position T291 in P450aluC09 to produce Mutant
      39 (T291K)

<400> SEQUENCE: 65
gatcgcggaa aaagcgacct cac                                              23

<210> SEQ ID NO 66
<211> LENGTH: 23
<212> TYPE: DNA
<213> ORGANISM: Artifical Sequence
<220> FEATURE:
<223> OTHER INFORMATION: Designed primer sequence used for amplification
      and mutagenesis of position T291 in P450aluC09 to produce Mutant
      39 (T291K)

<400> SEQUENCE: 66
gtgaggtcgc tttttccgcg atc                                              23

<210> SEQ ID NO 67
<211> LENGTH: 1215
<212> TYPE: DNA
<213> ORGANISM: Amycolatopsis lurida

<400> SEQUENCE: 67
atgactgacg tcgaggaaac caccgcgacc ttgccgctgg cccggaaatg cccgttttcg       60
ccgccgcccg aatacgaacg gcttcgccgg gaaagtccgg tttcccgggt cggtctcccg      120
tccggtcaaa cggcttgggc gctcacccgg ctcgaagaca tccgcgaaat gctgagcagc      180
ccgcatttca gttccgaccg gcagagcccg tcgttcccgc tgatggtcgc gcggcagatc      240
cgccgcgagg acaagccgtt ccgcccctcc ctcatcgcga tggatccgcc ggaacacagc      300
cgggccaggc gtgacgtcgt cggggaattc accgtcaagc ggatgaaggc gctccagccg      360
cgaattcagc agatcgtcga cgaacatctc gacgccctgc tcgcgggccc caaacccgcc      420
gatctcgtcc aggcgctttc cctgcccgtt ccctcgctgg tgatctgcga actgctcggc      480 gtccccctatt cggaccacga gttcttccag tcctgcagtt ccaggatgct cagccgggag      540
gtcaccgccg aagaacggat gaccgcgttc gagcagctcg aaaactatct cgacgaactg      600
gtcaccaaga aggaggcgaa cgccaccgag gacgacctcc tcggccgtca gatcctgaaa      660
cagcgggaaa cgggcgaggc cgaccacggt gaactcgtcg ggctggcgtt cctgctgctc      720
atcgccggac acgagaccac ggcgaacatg atctcgctcg gcacggtgac cctgctggag      780
aatcccgatc agctcgcgaa gatcaaggca gaccccggca agaccctcgc cgccatcgag      840
gaactcctgc gggtcttcac gatcgcggaa aaagcgacct cacgcttcgc cacggcggac      900
gtcgagatcg gcggaacgct gatccgcgcg ggggaagggg tggtgggcct gagcaacgcg      960
ggcaaccacg atccggacgg cttcgagaac ccggacacct tcgacatcga acgcggcgcg     1020
cggcatcacg tcgcgttcgg attcggggtg ccagtgtc tcggccagaa cttggcgagg      1080
ttggaactcc agatcgtctt cgatacgttg ttccggcgag tgccgggcct ccggatcgcc     1140
gttccggtcg acgaactgcc gttcaagcac gattcgacga tctacggcct ccacgccctt     1200
ccggtcacct ggtag                                                       1215

<210> SEQ ID NO 68
<211> LENGTH: 404
<212> TYPE: PRT
<213> ORGANISM: Amycolatopsis lurida
```

<400> SEQUENCE: 68

```
Met Thr Asp Val Glu Thr Thr Ala Thr Leu Pro Leu Ala Arg Lys
1               5                   10                  15

Cys Pro Phe Ser Pro Pro Glu Tyr Glu Arg Leu Arg Arg Glu Ser
            20                  25                  30

Pro Val Ser Arg Val Gly Leu Pro Ser Gly Gln Thr Ala Trp Ala Leu
        35                  40                  45

Thr Arg Leu Glu Asp Ile Arg Glu Met Leu Ser Ser Pro His Phe Ser
    50                  55                  60

Ser Asp Arg Gln Ser Pro Ser Phe Pro Leu Met Val Ala Arg Gln Ile
65                  70                  75                  80

Arg Arg Glu Asp Lys Pro Phe Arg Pro Ser Leu Ile Ala Met Asp Pro
                85                  90                  95

Pro Glu His Ser Arg Ala Arg Arg Asp Val Val Gly Glu Phe Thr Val
            100                 105                 110

Lys Arg Met Lys Ala Leu Gln Pro Arg Ile Gln Gln Ile Val Asp Glu
        115                 120                 125

His Leu Asp Ala Leu Leu Ala Gly Pro Lys Pro Ala Asp Leu Val Gln
    130                 135                 140

Ala Leu Ser Leu Pro Val Pro Ser Leu Val Ile Cys Glu Leu Leu Gly
145                 150                 155                 160

Val Pro Tyr Ser Asp His Glu Phe Phe Gln Ser Cys Ser Ser Arg Met
                165                 170                 175

Leu Ser Arg Glu Val Thr Ala Glu Glu Arg Met Thr Ala Phe Glu Gln
            180                 185                 190

Leu Glu Asn Tyr Leu Asp Glu Leu Val Thr Lys Lys Glu Ala Asn Ala
        195                 200                 205

Thr Glu Asp Asp Leu Leu Gly Arg Gln Ile Leu Lys Gln Arg Glu Thr
    210                 215                 220

Gly Glu Ala Asp His Gly Glu Leu Val Gly Leu Ala Phe Leu Leu Leu
225                 230                 235                 240

Ile Ala Gly His Glu Thr Thr Ala Asn Met Ile Ser Leu Gly Thr Val
                245                 250                 255

Thr Leu Leu Glu Asn Pro Asp Gln Leu Ala Lys Ile Lys Ala Asp Pro
            260                 265                 270

Gly Lys Thr Leu Ala Ala Ile Glu Glu Leu Leu Arg Val Phe Thr Ile
        275                 280                 285

Ala Glu Lys Ala Thr Ser Arg Phe Ala Thr Ala Asp Val Glu Ile Gly
    290                 295                 300

Gly Thr Leu Ile Arg Ala Gly Glu Gly Val Val Gly Leu Ser Asn Ala
305                 310                 315                 320

Gly Asn His Asp Pro Asp Gly Phe Glu Asn Pro Asp Thr Phe Asp Ile
                325                 330                 335

Glu Arg Gly Ala Arg His His Val Ala Phe Gly Phe Gly Val His Gln
            340                 345                 350

Cys Leu Gly Gln Asn Leu Ala Arg Leu Glu Leu Gln Ile Val Phe Asp
        355                 360                 365

Thr Leu Phe Arg Arg Val Pro Gly Leu Arg Ile Ala Val Pro Val Asp
    370                 375                 380

Glu Leu Pro Phe Lys His Asp Ser Thr Ile Tyr Gly Leu His Ala Leu
385                 390                 395                 400

Pro Val Thr Trp
```

<210> SEQ ID NO 69
<211> LENGTH: 23
<212> TYPE: DNA
<213> ORGANISM: Artifical Sequence
<220> FEATURE:
<223> OTHER INFORMATION: Designed primer sequence used for amplification and mutagenesis of position T291 in P450aluC09 to produce Mutant 40 (T291R)

<400> SEQUENCE: 69
gatcgcggaa cgcgcgacct cac                                          23

<210> SEQ ID NO 70
<211> LENGTH: 23
<212> TYPE: DNA
<213> ORGANISM: Artifical Sequence
<220> FEATURE:
<223> OTHER INFORMATION: Designed primer sequence used for amplification and mutagenesis of position T291 in P450aluC09 to produce Mutant 40 (T291R)

<400> SEQUENCE: 70
gtgaggtcgc gcgttccgcg atc                                          23

<210> SEQ ID NO 71
<211> LENGTH: 1215
<212> TYPE: DNA
<213> ORGANISM: Amycolatopsis lurida

<400> SEQUENCE: 71
atgactgacg tcgaggaaac caccgcgacc ttgccgctgg cccggaaatg cccgttttcg      60
ccgccgcccg aatacgaacg gcttcgccgg gaaagtccgg tttccgggt cggtctcccg      120 tccggtcaaa cggcttgggc gctcaccegg ctcgaagaca tccgcgaaat gctgagcagc      180
ccgcatttca gttccgaccg gcagagcccg tcgttcccgc tgatggtcgc gcggcagatc      240
cgccgcgagg acaagccgtt ccgcccctcc ctcatcgcga tggatccgcc ggaacacagc      300
cgggccaggc gtgacgtcgt cggggaattc accgtcaagc ggatgaaggc gctccagccg      360
cgaattcagc agatcgtcga cgaacatctc gacgccctgc tcgcgggccc caaacccgcc      420
gatctcgtcc aggcgctttc cctgcccgtt ccctcgctgg tgatctgcga actgctcggc      480 gtccccctatt cggaccacga gttcttccag tcctgcagtt ccaggatgct cagccgggag      540
gtcaccgccg aagaacggat daccgcgttc gagcagctcg aaaactatct cgacgaactg      600
gtcaccaaga aggaggcgaa cgccaccgag gacgacctcc tcggccgtca gatcctgaaa      660
cagcgggaaa cgggcgaggc cgaccacggt gaactcgtcg ggctggcgtt cctgctgctc      720
atcgccggac acgagaccac ggcgaacatg atctcgctcg gcacggtgac cctgctggag      780
aatcccgatc agctcgcgaa gatcaaggca gaccccggca agaccctcgc cgccatcgag      840
gaactcctgc gggtcttcac gatcgcggaa cgcgcgacct cacgcttcgc cacggcggac      900
gtcgagatcg gcggaacgct gatccgcgcg ggggaagggg tggtgggcct gagcaacgcg      960
ggcaaccacg atccggacgg cttcgagaac ccggacacct tcgacatcga acgcggcgcg      1020
cggcatcacg tcgcgttcgg attcggggtg caccagtgtc tcggccagaa cttggcgagg      1080
ttggaactcc agatcgtcct cgatacgttg ttccggcgag tgccgggcct ccggatcgcc      1140
gttccggtcg acgaactgcc gttcaagcac gattcgacga tctacggcct ccacgccctt      1200
ccggtcacct ggtag                                                    1215

<210> SEQ ID NO 72
<211> LENGTH: 404
<212> TYPE: PRT
<213> ORGANISM: Amycolatopsis lurida

<400> SEQUENCE: 72

```
Met Thr Asp Val Glu Thr Thr Ala Thr Leu Pro Leu Ala Arg Lys
1               5                   10                  15

Cys Pro Phe Ser Pro Pro Glu Tyr Glu Arg Leu Arg Arg Glu Ser
                20                  25                  30

Pro Val Ser Arg Val Gly Leu Pro Ser Gly Gln Thr Ala Trp Ala Leu
                35                  40                  45

Thr Arg Leu Glu Asp Ile Arg Glu Met Leu Ser Ser Pro His Phe Ser
            50                  55                  60

Ser Asp Arg Gln Ser Pro Ser Phe Pro Leu Met Val Ala Arg Gln Ile
65                  70                  75                  80

Arg Arg Glu Asp Lys Pro Phe Arg Pro Ser Leu Ile Ala Met Asp Pro
                85                  90                  95

Pro Glu His Ser Arg Ala Arg Arg Asp Val Val Gly Glu Phe Thr Val
                100                 105                 110

Lys Arg Met Lys Ala Leu Gln Pro Arg Ile Gln Gln Ile Val Asp Glu
                115                 120                 125

His Leu Asp Ala Leu Leu Ala Gly Pro Lys Pro Ala Asp Leu Val Gln
                130                 135                 140

Ala Leu Ser Leu Pro Val Pro Ser Leu Val Ile Cys Glu Leu Leu Gly
145                 150                 155                 160

Val Pro Tyr Ser Asp His Glu Phe Phe Gln Ser Cys Ser Ser Arg Met
                165                 170                 175

Leu Ser Arg Glu Val Thr Ala Glu Glu Arg Met Thr Ala Phe Glu Gln
                180                 185                 190

Leu Glu Asn Tyr Leu Asp Glu Leu Val Thr Lys Lys Glu Ala Asn Ala
                195                 200                 205

Thr Glu Asp Asp Leu Leu Gly Arg Gln Ile Leu Lys Gln Arg Glu Thr
                210                 215                 220

Gly Glu Ala Asp His Gly Glu Leu Val Gly Leu Ala Phe Leu Leu Leu
225                 230                 235                 240

Ile Ala Gly His Glu Thr Thr Ala Asn Met Ile Ser Leu Gly Thr Val
                245                 250                 255

Thr Leu Leu Glu Asn Pro Asp Gln Leu Ala Lys Ile Lys Ala Asp Pro
                260                 265                 270

Gly Lys Thr Leu Ala Ala Ile Glu Glu Leu Leu Arg Val Phe Thr Ile
                275                 280                 285

Ala Glu Arg Ala Thr Ser Arg Phe Ala Thr Ala Asp Val Glu Ile Gly
                290                 295                 300

Gly Thr Leu Ile Arg Ala Gly Glu Gly Val Val Gly Leu Ser Asn Ala
305                 310                 315                 320

Gly Asn His Asp Pro Asp Gly Phe Glu Asn Pro Asp Thr Phe Asp Ile
                325                 330                 335

Glu Arg Gly Ala Arg His His Val Ala Phe Gly Phe Gly Val His Gln
                340                 345                 350

Cys Leu Gly Gln Asn Leu Ala Arg Leu Glu Leu Gln Ile Val Phe Asp
                355                 360                 365

Thr Leu Phe Arg Arg Val Pro Gly Leu Arg Ile Ala Val Pro Val Asp
                370                 375                 380
```

```
Glu Leu Pro Phe Lys His Asp Ser Thr Ile Tyr Gly Leu His Ala Leu
385                 390                 395                 400

Pro Val Thr Trp
```

<210> SEQ ID NO 73
<211> LENGTH: 23
<212> TYPE: DNA
<213> ORGANISM: Artifical Sequence
<220> FEATURE:
<223> OTHER INFORMATION: Designed primer sequence used for amplification
      and mutagenesis of Mutant 12 (T291E) to produce the double point
      mutant; Mutant 22 (T291E, A47W)

<400> SEQUENCE: 73
aacggcttgg tggctcaccc ggc                                            23

<210> SEQ ID NO 74
<211> LENGTH: 23
<212> TYPE: DNA
<213> ORGANISM: Artifical Sequence
<220> FEATURE:
<223> OTHER INFORMATION: Designed primer sequence used for amplification
      and mutagenesis of Mutant 12 (T291E) to produce a double point
      mutant; Mutant 22 (T291E, A47W)

<400> SEQUENCE: 74
gccgggtgag ccaccaagcc gtt                                            23

<210> SEQ ID NO 75
<211> LENGTH: 1215
<212> TYPE: DNA
<213> ORGANISM: Amycolatopsis lurida

<400> SEQUENCE: 75
atgactgacg tcgaggaaac caccgcgacc ttgccgctgg cccggaaatg cccgttttcg    60
ccgccgcccg aatacgaacg gcttcgccgg gaaagtccgg tttcccgggt cggtctcccg   120
tccggtcaaa cggcttggtg gctcacccgg ctcgaagaca tccgcgaaat gctgagcagc   180
ccgcatttca gttccgaccg gcagagcccg tcgttcccgc tgatggtcgc gcggcagatc   240
cgccgcgagg acaagccgtt ccgccctcc ctcatcgcga tggatccgcc ggaacacagc   300
cggggccaggc gtgacgtcgt cggggaattc accgtcaagc ggatgaaggc gctccagccg   360
cgaattcagc agatcgtcga cgaacatctc gacgccctgc tcgcgggccc caaacccgcc   420
gatctcgtcc aggcgctttc cctgccgtt ccctcgctgg tgatctgcga actgctcggc   480
gtccccctatt cggaccacga gttcttccag tcctgcagtt ccaggatgct cagccgggag   540
gtcaccgccg aagaacggat gaccgcgttc gagcagctcg aaaactatct cgacgaactg   600
gtcaccaaga aggaggcgaa cgccaccgag gacgacctcc tcggccgtca gatcctgaaa   660
cagcgggaaa cgggcgaggc cgaccacggt gaactcgtcg ggctggcgtt cctgctgctc   720
atcgccggac acgagaccac ggcgaacatg atctcgctcg gcacggtgac cctgctggag   780
aatcccgatc agctcgcgaa gatcaaggca gaccccggca gaccctcgc cgccatcgag   840
gaactcctgc gggtcttcac gatcgcgaa gaagcgacct cacgcttcgc cacggcggac   900
gtcgagatcg gcggaacgct gatccgcgcg ggggaagggg tggtgggcct gagcaacgcg   960
ggcaaccacg atccggacgg cttcgagaac ccggacacct tcgacatcga acgcggcgcg  1020
cggcatcacg tcgcgttcgg attcggggtg caccagtgtc tcggccagaa cttggcgagg  1080
ttggaactcc agatcgtctt cgatacgttg ttccggcgag tgccgggcct ccggatcgcc  1140
```

```
gttccggtcg acgaactgcc gttcaagcac gattcgacga tctacggcct ccacgccctt    1200
ccggtcacct ggtag                                                     1215
```

<210> SEQ ID NO 76
<211> LENGTH: 404
<212> TYPE: PRT
<213> ORGANISM: Amycolatopsis lurida

<400> SEQUENCE: 76

```
Met Thr Asp Val Glu Glu Thr Thr Ala Thr Leu Pro Leu Ala Arg Lys
1               5                   10                  15

Cys Pro Phe Ser Pro Pro Glu Tyr Glu Arg Leu Arg Arg Glu Ser
            20                  25                  30

Pro Val Ser Arg Val Gly Leu Pro Ser Gly Gln Thr Ala Trp Trp Leu
        35                  40                  45

Thr Arg Leu Glu Asp Ile Arg Glu Met Leu Ser Ser Pro His Phe Ser
    50                  55                  60

Ser Asp Arg Gln Ser Pro Ser Phe Pro Leu Met Val Ala Arg Gln Ile
65                  70                  75                  80

Arg Arg Glu Asp Lys Pro Phe Arg Pro Ser Leu Ile Ala Met Asp Pro
                85                  90                  95

Pro Glu His Ser Arg Ala Arg Arg Asp Val Val Gly Glu Phe Thr Val
            100                 105                 110

Lys Arg Met Lys Ala Leu Gln Pro Arg Ile Gln Gln Ile Val Asp Glu
        115                 120                 125

His Leu Asp Ala Leu Leu Ala Gly Pro Lys Pro Ala Asp Leu Val Gln
    130                 135                 140

Ala Leu Ser Leu Pro Val Pro Ser Leu Val Ile Cys Glu Leu Leu Gly
145                 150                 155                 160

Val Pro Tyr Ser Asp His Glu Phe Phe Gln Ser Cys Ser Ser Arg Met
                165                 170                 175

Leu Ser Arg Glu Val Thr Ala Glu Glu Arg Met Thr Ala Phe Glu Gln
            180                 185                 190

Leu Glu Asn Tyr Leu Asp Glu Leu Val Thr Lys Lys Glu Ala Asn Ala
        195                 200                 205

Thr Glu Asp Asp Leu Leu Gly Arg Gln Ile Leu Lys Gln Arg Glu Thr
    210                 215                 220

Gly Glu Ala Asp His Gly Glu Leu Val Gly Leu Ala Phe Leu Leu Leu
225                 230                 235                 240

Ile Ala Gly His Glu Thr Thr Ala Asn Met Ile Ser Leu Gly Thr Val
                245                 250                 255

Thr Leu Leu Glu Asn Pro Asp Gln Leu Ala Lys Ile Lys Ala Asp Pro
            260                 265                 270

Gly Lys Thr Leu Ala Ala Ile Glu Glu Leu Leu Arg Val Phe Thr Ile
        275                 280                 285

Ala Glu Glu Ala Thr Ser Arg Phe Ala Thr Ala Asp Val Glu Ile Gly
    290                 295                 300

Gly Thr Leu Ile Arg Ala Gly Glu Gly Val Val Gly Leu Ser Asn Ala
305                 310                 315                 320

Gly Asn His Asp Pro Asp Gly Phe Glu Asn Pro Asp Thr Phe Asp Ile
                325                 330                 335

Glu Arg Gly Ala Arg His His Val Ala Phe Gly Phe Gly Val His Gln
            340                 345                 350
```

```
Cys Leu Gly Gln Asn Leu Ala Arg Leu Glu Leu Gln Ile Val Phe Asp
            355                 360                 365

Thr Leu Phe Arg Arg Val Pro Gly Leu Arg Ile Ala Val Pro Val Asp
        370                 375                 380

Glu Leu Pro Phe Lys His Asp Ser Thr Ile Tyr Gly Leu His Ala Leu
385                 390                 395                 400

Pro Val Thr Trp

<210> SEQ ID NO 77
<211> LENGTH: 23
<212> TYPE: DNA
<213> ORGANISM: Artifical Sequence
<220> FEATURE:
<223> OTHER INFORMATION: Designed primer sequence used for amplification
      and mutagenesis of Mutant 12 (T291E) to produce a double point
      mutant; Mutant 23 (T291E, A47F)

<400> SEQUENCE: 77
aacggcttgg tttctcaccc ggc                                              23

<210> SEQ ID NO 78
<211> LENGTH: 23
<212> TYPE: DNA
<213> ORGANISM: Artifical Sequence
<220> FEATURE:
<223> OTHER INFORMATION: Designed primer sequence used for amplification
      and mutagenesis of Mutant 12 (T291E) to produce a double point
      mutant; Mutant 23 (T291E, A47F)

<400> SEQUENCE: 78
gccgggtgag aaaccaagcc gtt                                              23

<210> SEQ ID NO 79
<211> LENGTH: 1215
<212> TYPE: DNA
<213> ORGANISM: Amycolatopsis lurida

<400> SEQUENCE: 79
atgactgacg tcgaggaaac caccgcgacc ttgccgctgg cccggaaatg cccgttttcg      60
ccgccgcccg aatacgaacg gcttcgccgg gaaagtccgg tttcccgggt cggtctcccg     120
tccggtcaaa cggcttggtt tctcacccgg ctcgaagaca tccgcgaaat gctgagcagc     180
ccgcatttca gttccgaccg gcagagcccg tcgttcccgc tgatggtcgc gcggcagatc     240
cgccgcgagg acaagccgtt ccgcccctcc ctcatcgcga tggatccgcc ggaacacagc     300
cgggccaggc gtgacgtcgt cggggaattc accgtcaagc ggatgaaggc gctccagccg     360
cgaattcagc agatcgtcga cgaacatctc gacgccctgc tcgcgggccc caaacccgcc     420
gatctcgtcc aggcgctttc cctgccgtt cctcgctgg tgatctgcga actgctcggc      480
gtcccctatt cggaccacga gttcttccag tcctgcagtt ccaggatgct cagccgggag     540
gtcaccgccg aagaacggat gaccgcgttc gagcagctcg aaaactatct cgacgaactg     600
gtcaccaaga aggaggcgaa cgccaccgag gacgacctcc tcggccgtca gatcctgaaa     660
cagcgggaaa cgggcgaggc cgaccacggt gaactcgtcg ggctggcgtt cctgctgctc     720
atcgccggac acgagaccac ggcgaacatg atctcgctcg gcacggtgac cctgctggag     780
aatcccgatc agctcgcgaa gatcaaggca gaccccggca agaccctcgc cgccatcgag     840
gaactcctgc gggtcttcac gatcgcgaa gaagcgacct cacgcttcgc cacggcggac     900
gtcgagatcg gcggaacgct gatccgcgcg ggggaagggg tggtgggcct gagcaacgcg     960
```

-continued

```
ggcaaccacg atccggacgg cttcgagaac ccggacacct tcgacatcga acgcggcgcg    1020
cggcatcacg tcgcgttcgg attcggggtg caccagtgtc tcggccagaa cttggcgagg    1080
ttggaactcc agatcgtctt cgatacgttg ttccggcgag tgccgggcct ccggatcgcc    1140
gttccggtcg acgaactgcc gttcaagcac gattcgacga tctacggcct ccacgccctt    1200
ccggtcacct ggtag                                                    1215
```

<210> SEQ ID NO 80
<211> LENGTH: 404
<212> TYPE: PRT
<213> ORGANISM: Amycolatopsis lurida

<400> SEQUENCE: 80

| Met | Thr | Asp | Val | Glu | Glu | Thr | Thr | Ala | Thr | Leu | Pro | Leu | Ala | Arg | Lys |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Cys | Pro | Phe | Ser | Pro | Pro | Glu | Tyr | Glu | Arg | Leu | Arg | Arg | Glu | Ser |
|-----|-----|-----|-----|-----|-----|-----|-----|-----|-----|-----|-----|-----|-----|-----|
|     |     |     | 20  |     |     |     | 25  |     |     |     | 30  |     |     |     |

Pro Val Ser Arg Val Gly Leu Pro Ser Gly Gln Thr Ala Trp Phe Leu
             35                  40                  45

Thr Arg Leu Glu Asp Ile Arg Glu Met Leu Ser Ser Pro His Phe Ser
 50                  55                  60

Ser Asp Arg Gln Ser Pro Ser Phe Pro Leu Met Val Ala Arg Gln Ile
 65                  70                  75                  80

Arg Arg Glu Asp Lys Pro Phe Arg Pro Ser Leu Ile Ala Met Asp Pro
                 85                  90                  95

Pro Glu His Ser Arg Ala Arg Arg Asp Val Val Gly Glu Phe Thr Val
            100                 105                 110

Lys Arg Met Lys Ala Leu Gln Pro Arg Ile Gln Gln Ile Val Asp Glu
        115                 120                 125

His Leu Asp Ala Leu Leu Ala Gly Pro Lys Pro Ala Asp Leu Val Gln
130                 135                 140

Ala Leu Ser Leu Pro Val Pro Ser Leu Val Ile Cys Glu Leu Leu Gly
145                 150                 155                 160

Val Pro Tyr Ser Asp His Glu Phe Phe Gln Ser Cys Ser Ser Arg Met
                165                 170                 175

Leu Ser Arg Glu Val Thr Ala Glu Glu Arg Met Thr Ala Phe Glu Gln
            180                 185                 190

Leu Glu Asn Tyr Leu Asp Glu Leu Val Thr Lys Glu Ala Asn Ala
        195                 200                 205

Thr Glu Asp Asp Leu Leu Gly Arg Gln Ile Leu Lys Gln Arg Glu Thr
210                 215                 220

Gly Glu Ala Asp His Gly Glu Leu Val Gly Leu Ala Phe Leu Leu Leu
225                 230                 235                 240

Ile Ala Gly His Glu Thr Thr Ala Asn Met Ile Ser Leu Gly Thr Val
                245                 250                 255

Thr Leu Leu Glu Asn Pro Asp Gln Leu Ala Lys Ile Lys Ala Asp Pro
            260                 265                 270

Gly Lys Thr Leu Ala Ala Ile Glu Glu Leu Leu Arg Val Phe Thr Ile
        275                 280                 285

Ala Glu Glu Ala Thr Ser Arg Phe Ala Thr Ala Asp Val Glu Ile Gly
    290                 295                 300

Gly Thr Leu Ile Arg Ala Gly Glu Gly Val Val Gly Leu Ser Asn Ala
305                 310                 315                 320

```
Gly Asn His Asp Pro Asp Gly Phe Glu Asn Pro Asp Thr Phe Asp Ile
            325                 330                 335

Glu Arg Gly Ala Arg His His Val Ala Phe Gly Phe Val His Gln
        340                 345                 350

Cys Leu Gly Gln Asn Leu Ala Arg Leu Glu Leu Gln Ile Val Phe Asp
            355                 360                 365

Thr Leu Phe Arg Arg Val Pro Gly Leu Arg Ile Ala Val Pro Val Asp
    370                 375                 380

Glu Leu Pro Phe Lys His Asp Ser Thr Ile Tyr Gly Leu His Ala Leu
385                 390                 395                 400

Pro Val Thr Trp
```

<210> SEQ ID NO 81
<211> LENGTH: 23
<212> TYPE: DNA
<213> ORGANISM: Artifical Sequence
<220> FEATURE:
<223> OTHER INFORMATION: Designed primer sequence used for amplification and mutagenesis of Mutant 12 (T291E) to produce a double point mutant; Mutant 24 (T291E, A47I)

<400> SEQUENCE: 81
aacggcttgg attctcaccc ggc                                          23

<210> SEQ ID NO 82
<211> LENGTH: 23
<212> TYPE: DNA
<213> ORGANISM: Artifical Sequence
<220> FEATURE:
<223> OTHER INFORMATION: Designed primer sequence used for amplification and mutagenesis of Mutant 12 (T291E) to produce a double point mutant; Mutant 24 (T291E, A47I)

<400> SEQUENCE: 82
gccgggtgag aatccaagcc gtt                                          23

<210> SEQ ID NO 83
<211> LENGTH: 1215
<212> TYPE: DNA
<213> ORGANISM: Amycolatopsis lurida

<400> SEQUENCE: 83
atgactgacg tcgaggaaac caccgcgacc ttgccgctgg cccggaaatg cccgttttcg    60
ccgccgcccg aatacgaacg gcttcgccgg gaaagtccgg tttcccgggt cggtctcccg   120
tccggtcaaa cggcttggat tctcacccgg ctcgaagaca tccgcgaaat gctgagcagc   180
ccgcatttca gttccgaccg gcagagcccg tcgttcccgc tgatggtcgc gcggcagatc   240
cgccgcgagg acaagccgtt ccgcccctcc ctcatcgcga tggatccgcc ggaacacagc   300
cgggccaggc gtgacgtcgt cggggaattc accgtcaagc ggatgaaggc gctccagccg   360
cgaattcagc agatcgtcga cgaacatctc gacgccctgc tcgcgggccc caaacccgcc   420
gatctcgtcc aggcgctttc cctgcccgtt ccctcgctgg tgatctgcga actgctcggc   480
gtcccctatt cggaccacga gttcttccag tcctgcagtt ccaggatgct cagccgggag   540
gtcaccgccg aagaacggat gaccgcgttc gagcagctcg aaaactatct cgacgaactg   600
gtcaccaaga aggaggcgaa cgccaccgag gacgacctcc tcggccgtca gatcctgaaa   660 cagcggggaaa cgggcgaggc cgaccacggt gaactcgtcg gctggcgtt cctgctgctc   720 atcgccggac acgagaccac ggcgaacatg atctcgctcg gcacggtgac cctgctggag   780
```

```
aatcccgatc agctcgcgaa gatcaaggca gaccccggca agaccctcgc cgccatcgag    840
gaactcctgc gggtcttcac gatcgcggaa gaagcgacct cacgcttcgc cacggcggac    900
gtcgagatcg gcggaacgct gatccgcgcg ggggaagggg tggtgggcct gagcaacgcg    960
ggcaaccacg atccggacgg cttcgagaac ccggacacct cgacatcga acgcggcgcg   1020 cggcatcacg tcgcgttcgg attcggggtg caccagtgtc tcggccagaa cttggcgagg   1080
ttggaactcc agatcgtctt cgatacgttg ttccggcgag tgccgggcct ccggatcgcc   1140
gttccggtcg acgaactgcc gttcaagcac gattcgacga tctacggcct ccacgccctt   1200
ccggtcacct ggtag                                                    1215
```

<210> SEQ ID NO 84
<211> LENGTH: 404
<212> TYPE: PRT
<213> ORGANISM: Amycolatopsis lurida

<400> SEQUENCE: 84

```
Met Thr Asp Val Glu Glu Thr Thr Ala Thr Leu Pro Leu Ala Arg Lys
1               5                   10                  15

Cys Pro Phe Ser Pro Pro Glu Tyr Glu Arg Leu Arg Arg Glu Ser
            20                  25                  30

Pro Val Ser Arg Val Gly Leu Pro Ser Gly Gln Thr Ala Trp Ile Leu
        35                  40                  45

Thr Arg Leu Glu Asp Ile Arg Glu Met Leu Ser Ser Pro His Phe Ser
    50                  55                  60

Ser Asp Arg Gln Ser Pro Ser Phe Pro Leu Met Val Ala Arg Gln Ile
65                  70                  75                  80

Arg Arg Glu Asp Lys Pro Phe Arg Pro Ser Leu Ile Ala Met Asp Pro
                85                  90                  95

Pro Glu His Ser Arg Ala Arg Arg Asp Val Val Gly Glu Phe Thr Val
            100                 105                 110

Lys Arg Met Lys Ala Leu Gln Pro Arg Ile Gln Gln Ile Val Asp Glu
        115                 120                 125

His Leu Asp Ala Leu Leu Ala Gly Pro Lys Pro Ala Asp Leu Val Gln
    130                 135                 140

Ala Leu Ser Leu Pro Val Pro Ser Leu Val Ile Cys Glu Leu Leu Gly
145                 150                 155                 160

Val Pro Tyr Ser Asp His Glu Phe Phe Gln Ser Cys Ser Ser Arg Met
                165                 170                 175

Leu Ser Arg Glu Val Thr Ala Glu Glu Arg Met Thr Ala Phe Glu Gln
            180                 185                 190

Leu Glu Asn Tyr Leu Asp Glu Leu Val Thr Lys Lys Glu Ala Asn Ala
        195                 200                 205

Thr Glu Asp Asp Leu Leu Gly Arg Gln Ile Leu Lys Gln Arg Glu Thr
    210                 215                 220

Gly Glu Ala Asp His Gly Glu Leu Val Gly Leu Ala Phe Leu Leu Leu
225                 230                 235                 240

Ile Ala Gly His Glu Thr Thr Ala Asn Met Ile Ser Leu Gly Thr Val
                245                 250                 255

Thr Leu Leu Glu Asn Pro Asp Gln Leu Ala Lys Ile Lys Ala Asp Pro
            260                 265                 270

Gly Lys Thr Leu Ala Ala Ile Glu Glu Leu Leu Arg Val Phe Thr Ile
        275                 280                 285
```

```
Ala Glu Glu Ala Thr Ser Arg Phe Ala Thr Ala Asp Val Glu Ile Gly
            290                 295                 300

Gly Thr Leu Ile Arg Ala Gly Glu Gly Val Val Gly Leu Ser Asn Ala
305                 310                 315                 320

Gly Asn His Asp Pro Asp Gly Phe Glu Asn Pro Asp Thr Phe Asp Ile
                325                 330                 335

Glu Arg Gly Ala Arg His His Val Ala Phe Gly Phe Gly Val His Gln
                340                 345                 350

Cys Leu Gly Gln Asn Leu Ala Arg Leu Glu Leu Gln Ile Val Phe Asp
                355                 360                 365

Thr Leu Phe Arg Arg Val Pro Gly Leu Arg Ile Ala Val Pro Val Asp
370                 375                 380

Glu Leu Pro Phe Lys His Asp Ser Thr Ile Tyr Gly Leu His Ala Leu
385                 390                 395                 400

Pro Val Thr Trp

<210> SEQ ID NO 85
<211> LENGTH: 23
<212> TYPE: DNA
<213> ORGANISM: Artificial Sequence
<220> FEATURE:
<223> OTHER INFORMATION: Designed primer sequence used for amplification
      and mutagenesis of Mutant 12 (T291E) to produce a double point
      mutant; Mutant 25 (T291E, M75F)

<400> SEQUENCE: 85
gttcccgctg tttgtcgcgc ggc                                             23

<210> SEQ ID NO 86
<211> LENGTH: 23
<212> TYPE: DNA
<213> ORGANISM: Artifical Sequence
<220> FEATURE:
<223> OTHER INFORMATION: Designed primer sequence used for amplification
      and mutagenesis of Mutant 12 (T291E) to produce a double point
      mutant; Mutant 25 (T291E, M75F)

<400> SEQUENCE: 86
gccgcgcgac aaacagcggg aac                                             23

<210> SEQ ID NO 87
<211> LENGTH: 1215
<212> TYPE: DNA
<213> ORGANISM: Amycolatopsis lurida

<400> SEQUENCE: 87
atgactgacg tcgaggaaac caccgcgacc ttgccgctgg cccggaaatg cccgttttcg     60
ccgccgcccg aatacgaacg gcttcgccgg gaaagtccgg tttcccgggt cggtctcccg    120
tccggtcaaa cggcttgggc gctcacccgg ctcgaagaca tccgcgaaat gctgagcagc    180
ccgcatttca gttccgaccg gcagagcccg tcgttcccgc tgtttgtcgc gcggcagatc    240
cgccgcgagg acaagccgtt ccgcccctcc ctcatcgcga tggatccgcc ggaacacagc    300
cgggccaggc gtgacgtcgt cggggaattc accgtcaagc ggatgaaggc gctccagccg    360
cgaattcagc agatcgtcga cgaacatctc gacgccctgc tcgcgggccc caaacccgcc    420
gatctcgtcc aggcgctttc cctgcccgtt ccctcgctgg tgatctgcga actgctcggc    480 gtccctatt cggaccacga gttcttccag tcctgcagtt ccaggatgct cagcggggag    540
gtcaccgccg aagaacggat gaccgcgttc gagcagctcg aaaactatct cgacgaactg    600
```

```
gtcaccaaga aggaggcgaa cgccaccgag gacgacctcc tcggccgtca gatcctgaaa    660
cagcgggaaa cgggcgaggc cgaccacggt gaactcgtcg ggctggcgtt cctgctgctc    720
atcgccggac acgagaccac ggcgaacatg atctcgctcg gcacggtgac cctgctggag    780
aatcccgatc agctcgcgaa gatcaaggca gaccccggca agaccctcgc cgccatcgag    840
gaactcctgc gggtcttcac gatcgcggaa gaagcgacct cacgcttcgc cacggcggac    900
gtcgagatcg gcgaacgct gatccgcgcg ggggaagggg tggtgggcct gagcaacgcg    960
ggcaaccacg atccggacgg cttcgagaac ccggacacct tcgacatcga acgcggcgcg   1020
cggcatcacg tcgcgttcgg attcggggtg caccagtgtc tcggccagaa cttggcgagg   1080
ttggaactcc agatcgtctt cgatacgttg ttccggcgag tgccgggcct ccggatcgcc   1140
gttccggtcg acgaactgcc gttcaagcac gattcgacga tctacggcct ccacgcccct   1200
ccggtcacct ggtag                                                    1215
```

<210> SEQ ID NO 88
<211> LENGTH: 404
<212> TYPE: PRT
<213> ORGANISM: Amycolatopsis lurida

<400> SEQUENCE: 88

```
Met Thr Asp Val Glu Glu Thr Thr Ala Thr Leu Pro Leu Ala Arg Lys
1               5                   10                  15

Cys Pro Phe Ser Pro Pro Glu Tyr Glu Arg Leu Arg Arg Glu Ser
            20                  25                  30

Pro Val Ser Arg Val Gly Leu Pro Ser Gly Gln Thr Ala Trp Ala Leu
        35                  40                  45

Thr Arg Leu Glu Asp Ile Arg Glu Met Leu Ser Ser Pro His Phe Ser
    50                  55                  60

Ser Asp Arg Gln Ser Pro Ser Phe Pro Leu Phe Val Ala Arg Gln Ile
65                  70                  75                  80

Arg Arg Glu Asp Lys Pro Phe Arg Pro Ser Leu Ile Ala Met Asp Pro
                85                  90                  95

Pro Glu His Ser Arg Ala Arg Asp Val Val Gly Glu Phe Thr Val
            100                 105                 110

Lys Arg Met Lys Ala Leu Gln Pro Arg Ile Gln Gln Ile Val Asp Glu
        115                 120                 125

His Leu Asp Ala Leu Leu Ala Gly Pro Lys Pro Ala Asp Leu Val Gln
    130                 135                 140

Ala Leu Ser Leu Pro Val Pro Ser Leu Val Ile Cys Glu Leu Leu Gly
145                 150                 155                 160

Val Pro Tyr Ser Asp His Glu Phe Phe Gln Ser Cys Ser Ser Arg Met
                165                 170                 175

Leu Ser Arg Glu Val Thr Ala Glu Glu Arg Met Thr Ala Phe Glu Gln
            180                 185                 190

Leu Glu Asn Tyr Leu Asp Glu Leu Val Thr Lys Lys Glu Ala Asn Ala
        195                 200                 205

Thr Glu Asp Asp Leu Leu Gly Arg Gln Ile Leu Lys Gln Arg Glu Thr
    210                 215                 220

Gly Glu Ala Asp His Gly Glu Leu Val Gly Leu Ala Phe Leu Leu Leu
225                 230                 235                 240

Ile Ala Gly His Glu Thr Thr Ala Asn Met Ile Ser Leu Gly Thr Val
                245                 250                 255
```

```
Thr Leu Leu Glu Asn Pro Asp Gln Leu Ala Lys Ile Lys Ala Asp Pro
            260                 265                 270
Gly Lys Thr Leu Ala Ala Ile Glu Glu Leu Leu Arg Val Phe Thr Ile
        275                 280                 285
Ala Glu Glu Ala Thr Ser Arg Phe Ala Thr Ala Asp Val Glu Ile Gly
    290                 295                 300
Gly Thr Leu Ile Arg Ala Gly Glu Gly Val Val Gly Leu Ser Asn Ala
305                 310                 315                 320
Gly Asn His Asp Pro Asp Gly Phe Glu Asn Pro Asp Thr Phe Asp Ile
                325                 330                 335
Glu Arg Gly Ala Arg His His Val Ala Phe Gly Phe Gly Val His Gln
            340                 345                 350
Cys Leu Gly Gln Asn Leu Ala Arg Leu Glu Leu Gln Ile Val Phe Asp
        355                 360                 365
Thr Leu Phe Arg Arg Val Pro Gly Leu Arg Ile Ala Val Pro Val Asp
    370                 375                 380
Glu Leu Pro Phe Lys His Asp Ser Thr Ile Tyr Gly Leu His Ala Leu
385                 390                 395                 400

Pro Val Thr Trp

<210> SEQ ID NO 89
<211> LENGTH: 23
<212> TYPE: DNA
<213> ORGANISM: Artificial Sequence
<220> FEATURE:
<223> OTHER INFORMATION: Designed primer sequence used for amplification
      and mutagenesis of Mutant 12 (T291E) to produce a double point
      mutant; Mutant 26 (T291E, M75W)

<400> SEQUENCE: 89
gttcccgctg tgggtcgcgc ggc                                         23

<210> SEQ ID NO 90
<211> LENGTH: 23
<212> TYPE: DNA
<213> ORGANISM: Artificial Sequence
<220> FEATURE:
<223> OTHER INFORMATION: Designed primer sequence used for amplification
      and mutagenesis of Mutant 12 (T291E) to produce a double point
      mutant; Mutant 26 (T291E, M75W)

<400> SEQUENCE: 90
gccgcgcgac ccacagcggg aac                                         23

<210> SEQ ID NO 91
<211> LENGTH: 1215
<212> TYPE: DNA
<213> ORGANISM: Amycolatopsis lurida

<400> SEQUENCE: 91
atgactgacg tcgaggaaac caccgcgacc ttgccgctgg cccggaaatg cccgttttcg    60
ccgccgcccg aatacgaacg gcttcgccgg gaaagtccgg tttcccgggt cggtctcccg   120
tccggtcaaa cggcttgggc gctcacccgg ctcgaagaca tccgcgaaat gctgagcagc   180
ccgcatttca gttccgaccg gcagagcccg tcgttcccgc tgtgggtcgc gcggcagatc   240
cgccgcgagg acaagccgtt cgcccctcc ctcatcgcga tggatccgcc ggaacacagc   300
cgggccaggc gtgacgtcgt cggggaattc accgtcaagc ggatgaaggc gctccagccg   360
cgaattcagc agatcgtcga cgaacatctc gacgccctgc tcgcgggccc caaacccgcc   420
```

```
gatctcgtcc aggcgctttc cctgcccgtt ccctcgctgg tgatctgcga actgctcggc    480 gtccctatt cggaccacga gttcttccag tcctgcagtt ccaggatgct cagccgggag    540
gtcaccgccg aagaacggat gaccgcgttc gagcagctcg aaaactatct cgacgaactg    600
gtcaccaaga aggaggcgaa cgccaccgag gacgacctcc tcggccgtca gatcctgaaa    660
cagcgggaaa cgggcgaggc cgaccacggt gaactcgtcg ggctggcgtt cctgctgctc    720
atcgccggac acgagaccac ggcgaacatg atctcgctcg gcacggtgac cctgctggag    780
aatcccgatc agctcgcgaa gatcaaggca gaccccggca agaccctcgc cgccatcgag    840
gaactcctgc gggtcttcac gatcgcggaa gaagcgacct cacgcttcgc cacggcggac    900
gtcgagatcg gcggaacgct gatccgcgcg ggggaagggg tggtgggcct gagcaacgcg    960
ggcaaccacg atccggacgg cttcgagaac ccggacacct tcgacatcga acgcggcgcg   1020
cggcatcacg tcgcgttcgg attcggggtg caccagtgtc tcggccagaa cttggcgagg   1080
ttggaactcc agatcgtctt cgatacgttg ttccggcgag tgccgggcct ccggatcgcc   1140
gttccggtcg acgaactgcc gttcaagcac gattcgacga tctacggcct ccacgccctt   1200
ccggtcacct ggtag                                                    1215
```

<210> SEQ ID NO 92
<211> LENGTH: 404
<212> TYPE: PRT
<213> ORGANISM: Amycolatopsis lurida

<400> SEQUENCE: 92

```
Met Thr Asp Val Glu Glu Thr Thr Ala Thr Leu Pro Leu Ala Arg Lys
1               5                   10                  15

Cys Pro Phe Ser Pro Pro Glu Tyr Glu Arg Leu Arg Arg Glu Ser
            20                  25                  30

Pro Val Ser Arg Val Gly Leu Pro Ser Gly Gln Thr Ala Trp Ala Leu
        35                  40                  45

Thr Arg Leu Glu Asp Ile Arg Glu Met Leu Ser Ser Pro His Phe Ser
    50                  55                  60

Ser Asp Arg Gln Ser Pro Ser Phe Pro Leu Trp Val Ala Arg Gln Ile
65                  70                  75                  80

Arg Arg Glu Asp Lys Pro Phe Arg Pro Ser Leu Ile Ala Met Asp Pro
                85                  90                  95

Pro Glu His Ser Arg Ala Arg Arg Asp Val Val Gly Glu Phe Thr Val
            100                 105                 110

Lys Arg Met Lys Ala Leu Gln Pro Arg Ile Gln Gln Ile Val Asp Glu
        115                 120                 125

His Leu Asp Ala Leu Leu Ala Gly Pro Lys Pro Ala Asp Leu Val Gln
    130                 135                 140

Ala Leu Ser Leu Pro Val Pro Ser Leu Val Ile Cys Glu Leu Leu Gly
145                 150                 155                 160

Val Pro Tyr Ser Asp His Glu Phe Phe Gln Ser Cys Ser Ser Arg Met
                165                 170                 175

Leu Ser Arg Glu Val Thr Ala Glu Glu Arg Met Thr Ala Phe Glu Gln
            180                 185                 190

Leu Glu Asn Tyr Leu Asp Glu Leu Val Thr Lys Lys Glu Ala Asn Ala
        195                 200                 205

Thr Glu Asp Asp Leu Leu Gly Arg Gln Ile Leu Lys Gln Arg Glu Thr
    210                 215                 220
```

```
Gly Glu Ala Asp His Gly Glu Leu Val Gly Leu Ala Phe Leu Leu Leu
225                 230                 235                 240

Ile Ala Gly His Glu Thr Thr Ala Asn Met Ile Ser Leu Gly Thr Val
            245                 250                 255

Thr Leu Leu Glu Asn Pro Asp Gln Leu Ala Lys Ile Lys Ala Asp Pro
        260                 265                 270

Gly Lys Thr Leu Ala Ala Ile Glu Glu Leu Leu Arg Val Phe Thr Ile
    275                 280                 285

Ala Glu Glu Ala Thr Ser Arg Phe Ala Thr Ala Asp Val Glu Ile Gly
    290                 295                 300

Gly Thr Leu Ile Arg Ala Gly Glu Gly Val Val Gly Leu Ser Asn Ala
305                 310                 315                 320

Gly Asn His Asp Pro Asp Gly Phe Glu Asn Pro Asp Thr Phe Asp Ile
            325                 330                 335

Glu Arg Gly Ala Arg His His Val Ala Phe Gly Phe Gly Val His Gln
        340                 345                 350

Cys Leu Gly Gln Asn Leu Ala Arg Leu Glu Leu Gln Ile Val Phe Asp
    355                 360                 365

Thr Leu Phe Arg Arg Val Pro Gly Leu Arg Ile Ala Val Pro Val Asp
370                 375                 380

Glu Leu Pro Phe Lys His Asp Ser Thr Ile Tyr Gly Leu His Ala Leu
385                 390                 395                 400

Pro Val Thr Trp

<210> SEQ ID NO 93
<211> LENGTH: 23
<212> TYPE: DNA
<213> ORGANISM: Artifical Sequence
<220> FEATURE:
<223> OTHER INFORMATION: Designed primer sequence used for amplification
      and mutagenesis of Mutant 12 (T291E) to produce a double point
      mutant; Mutant 27 (T291E, M75A)

<400> SEQUENCE: 93
gttcccgctg gcggtcgcgc ggc                                             23

<210> SEQ ID NO 94
<211> LENGTH: 23
<212> TYPE: DNA
<213> ORGANISM: Artifical Sequence
<220> FEATURE:
<223> OTHER INFORMATION: Designed primer sequence used for amplification
      and mutagenesis of Mutant 12 (T291E) to produce a double point
      mutant; Mutant 27 (T291E, M75A)

<400> SEQUENCE: 94
gccgcgcgac cgccagcggg aac                                             23

<210> SEQ ID NO 95
<211> LENGTH: 1215
<212> TYPE: DNA
<213> ORGANISM: Amycolatopsis lurida

<400> SEQUENCE: 95
atgactgacg tcgaggaaac caccgcgacc ttgccgctgg cccggaaatg cccgttttcg     60
ccgccgcccg aatacgaacg gcttcgccgg gaaagtccgg tttcccgggt cggtctcccg    120
tccggtcaaa cggcttgggc gctcaccecgg ctcgaagaca tccgcgaaat gctgagcagc    180
ccgcatttca gttccgaccg gcagagcccg tcgttcccgc tggcggtcgc gcggcagatc    240
```

-continued

```
cgccgcgagg acaagccgtt ccgcccctcc ctcatcgcga tggatccgcc ggaacacagc      300
cgggccaggc gtgacgtcgt cggggaattc accgtcaagc ggatgaaggc gctccagccg      360
cgaattcagc agatcgtcga cgaacatctc gacgccctgc tcgcgggccc caaacccgcc      420
gatctcgtcc aggcgctttc cctgccgtt ccctcgctgg tgatctgcga actgctcggc       480
gtcccctatt cggaccacga gttcttccag tcctgcagtt ccaggatgct cagccgggag      540
gtcaccgccg aagaacggat gaccgcgttc gagcagctcg aaaactatct cgacgaactg      600
gtcaccaaga aggaggcgaa cgccaccgag gacgacctcc tcggccgtca gatcctgaaa      660
cagcgggaaa cgggcgaggc cgaccacggt gaactcgtcg ggctggcgtt cctgctgctc      720
atcgccggac acgagaccac ggcgaacatg atctcgctcg gcacggtgac cctgctggag      780
aatcccgatc agctcgcgaa gatcaaggca gaccccggca agaccctcgc cgccatcgag      840
gaactcctgc gggtcttcac gatcgcggaa gaagcgacct cacgcttcgc cacggcggac      900
gtcgagatcg gcggaacgct gatccgcgcg ggggaagggg tggtgggcct gagcaacgcg      960
ggcaaccacg atccggacgg cttcgagaac ccggacacct tcgacatcga acgcggcgcg     1020
cggcatcacg tcgcgttcgg attcggggtg caccagtgtc tcggccagaa cttggcgagg     1080
ttggaactcc agatcgtctt cgatacgttg ttccggcgag tgccgggcct ccggatcgcc     1140
gttccggtcg acgaactgcc gttcaagcac gattcgacga tctacggcct ccacgccctt     1200
ccggtcacct ggtag                                                     1215
```

<210> SEQ ID NO 96
<211> LENGTH: 404
<212> TYPE: PRT
<213> ORGANISM: Amycolatopsis lurida

<400> SEQUENCE: 96

```
Met Thr Asp Val Glu Glu Thr Thr Ala Thr Leu Pro Leu Ala Arg Lys
1               5                   10                  15

Cys Pro Phe Ser Pro Pro Glu Tyr Glu Arg Leu Arg Arg Glu Ser
            20                  25                  30

Pro Val Ser Arg Val Gly Leu Pro Ser Gly Gln Thr Ala Trp Ala Leu
        35                  40                  45

Thr Arg Leu Glu Asp Ile Arg Glu Met Leu Ser Ser Pro His Phe Ser
    50                  55                  60

Ser Asp Arg Gln Ser Pro Ser Phe Pro Leu Ala Val Ala Arg Gln Ile
65                  70                  75                  80

Arg Arg Glu Asp Lys Pro Phe Arg Pro Ser Leu Ile Ala Met Asp Pro
                85                  90                  95

Pro Glu His Ser Arg Ala Arg Arg Asp Val Val Gly Glu Phe Thr Val
            100                 105                 110

Lys Arg Met Lys Ala Leu Gln Pro Arg Ile Gln Gln Ile Val Asp Glu
        115                 120                 125

His Leu Asp Ala Leu Leu Ala Gly Pro Lys Pro Ala Asp Leu Val Gln
    130                 135                 140

Ala Leu Ser Leu Pro Val Pro Ser Leu Val Ile Cys Glu Leu Leu Gly
145                 150                 155                 160

Val Pro Tyr Ser Asp His Glu Phe Phe Gln Ser Cys Ser Ser Arg Met
                165                 170                 175

Leu Ser Arg Glu Val Thr Ala Glu Glu Arg Met Thr Ala Phe Glu Gln
            180                 185                 190
```

Leu Glu Asn Tyr Leu Asp Glu Leu Val Thr Lys Lys Glu Ala Asn Ala
        195                 200                 205

Thr Glu Asp Asp Leu Leu Gly Arg Gln Ile Leu Lys Gln Arg Glu Thr
    210                 215                 220

Gly Glu Ala Asp His Gly Glu Leu Val Gly Leu Ala Phe Leu Leu Leu
225                 230                 235                 240

Ile Ala Gly His Glu Thr Thr Ala Asn Met Ile Ser Leu Gly Thr Val
                245                 250                 255

Thr Leu Leu Glu Asn Pro Asp Gln Leu Ala Lys Ile Lys Ala Asp Pro
        260                 265                 270

Gly Lys Thr Leu Ala Ala Ile Glu Glu Leu Leu Arg Val Phe Thr Ile
        275                 280                 285

Ala Glu Glu Ala Thr Ser Arg Phe Ala Thr Ala Asp Val Glu Ile Gly
        290                 295                 300

Gly Thr Leu Ile Arg Ala Gly Glu Gly Val Val Gly Leu Ser Asn Ala
305                 310                 315                 320

Gly Asn His Asp Pro Asp Gly Phe Glu Asn Pro Asp Thr Phe Asp Ile
                325                 330                 335

Glu Arg Gly Ala Arg His His Val Ala Phe Gly Phe Gly Val His Gln
        340                 345                 350

Cys Leu Gly Gln Asn Leu Ala Arg Leu Glu Leu Gln Ile Val Phe Asp
        355                 360                 365

Thr Leu Phe Arg Arg Val Pro Gly Leu Arg Ile Ala Val Pro Val Asp
        370                 375                 380

Glu Leu Pro Phe Lys His Asp Ser Thr Ile Tyr Gly Leu His Ala Leu
385                 390                 395                 400

Pro Val Thr Trp

<210> SEQ ID NO 97
<211> LENGTH: 23
<212> TYPE: DNA
<213> ORGANISM: Artifical Sequence
<220> FEATURE:
<223> OTHER INFORMATION: Designed primer sequence used for amplification
      and mutagenesis of Mutant 12 (T291E) to produce a double point
      mutant; Mutant 28 (T291E, V315I)

<400> SEQUENCE: 97 ggaagggtg attggcctga gca                                              23

<210> SEQ ID NO 98
<211> LENGTH: 23
<212> TYPE: DNA
<213> ORGANISM: Artifical Sequence
<220> FEATURE:
<223> OTHER INFORMATION: Designed primer sequence used for amplification
      and mutagenesis of Mutant 12 (T291E) to produce a double point
      mutant; Mutant 28 (T291E, V315I)

<400> SEQUENCE: 98
tgctcaggcc aatcacccct tcc                                             23

<210> SEQ ID NO 99
<211> LENGTH: 1215
<212> TYPE: DNA
<213> ORGANISM: Amycolatopsis lurida

<400> SEQUENCE: 99

```
atgactgacg tcgaggaaac caccgcgacc ttgccgctgg cccggaaatg cccgttttcg    60
ccgccgcccg aatacgaacg gcttcgccgg gaaagtccgg tttccggggt cggtctcccg   120
tccggtcaaa cggcttgggc gctcacccgg ctcgaagaca tccgcgaaat gctgagcagc   180
ccgcatttca gttccgaccg gcagagcccg tcgttcccgc tgatggtcgc gcggcagatc   240
cgccgcgagg acaagccgtt ccgcccctcc ctcatcgcga tggatccgcc ggaacacagc   300
cgggccaggc gtgacgtcgt cggggaattc accgtcaagc ggatgaaggc gctccagccg   360
cgaattcagc agatcgtcga cgaacatctc gacgccctgc tcgcgggccc caaacccgcc   420
gatctcgtcc aggcgctttc cctgcccgtt ccctcgctgg tgatctgcga actgctcggc   480
gtcccctatt cggaccacga gttcttccag tcctgcagtt ccaggatgct cagccgggag   540
gtcaccgccg aagaacggat gaccgcgttc gagcagctcg aaaactatct cgacgaactg   600
gtcaccaaga aggaggcgaa cgccaccgag gacgacctcc tcggccgtca gatcctgaaa   660
cagcgggaaa cgggcgaggc cgaccacggt gaactcgtcg ggctggcgtt cctgctgctc   720
atcgccggac acgagaccac ggcgaacatg atctcgctcg gcacggtgac cctgctggag   780
aatcccgatc agctcgcgaa gatcaaggca daccccggca agaccctcgc cgccatcgag   840
gaactcctgc gggtcttcac gatcgcgaaa gaagcgacct cacgcttcgc cacggcggac   900
gtcgagatcg gcggaacgct gatccgcgcg ggggaagggg tgattggcct gagcaacgcg   960
ggcaaccacg atccggacgg cttcgagaac ccggacacct tcgacatcga acgcggcgcg  1020
cggcatcacg tcgcgttcgg attcggggtg caccagtgtc tcggccagaa cttggcgagg  1080
ttggaactcc agatcgtctt cgatacgttg ttccggcgag tgccgggcct ccggatcgcc  1140
gttccggtcg acgaactgcc gttcaagcac gattcgacga tctacggcct ccacgcccct  1200
ccggtcacct ggtag                                                   1215
```

<210> SEQ ID NO 100
<211> LENGTH: 404
<212> TYPE: PRT
<213> ORGANISM: Amycolatopsis lurida

<400> SEQUENCE: 100

```
Met Thr Asp Val Glu Glu Thr Thr Ala Thr Leu Pro Leu Ala Arg Lys
1               5                   10                  15

Cys Pro Phe Ser Pro Pro Glu Tyr Glu Arg Leu Arg Arg Glu Ser
            20                  25                  30

Pro Val Ser Arg Val Gly Leu Pro Ser Gly Gln Thr Ala Trp Ala Leu
        35                  40                  45

Thr Arg Leu Glu Asp Ile Arg Glu Met Leu Ser Ser Pro His Phe Ser
    50                  55                  60

Ser Asp Arg Gln Ser Pro Ser Phe Pro Leu Met Val Ala Arg Gln Ile
65                  70                  75                  80

Arg Arg Glu Asp Lys Pro Phe Arg Pro Ser Leu Ile Ala Met Asp Pro
                85                  90                  95

Pro Glu His Ser Arg Ala Arg Arg Asp Val Val Gly Glu Phe Thr Val
            100                 105                 110

Lys Arg Met Lys Ala Leu Gln Pro Arg Ile Gln Gln Ile Val Asp Glu
        115                 120                 125

His Leu Asp Ala Leu Leu Ala Gly Pro Lys Pro Ala Asp Leu Val Gln
    130                 135                 140
```

```
Ala Leu Ser Leu Pro Val Pro Ser Leu Val Ile Cys Glu Leu Leu Gly
145                 150                 155                 160

Val Pro Tyr Ser Asp His Glu Phe Phe Gln Ser Cys Ser Ser Arg Met
            165                 170                 175

Leu Ser Arg Glu Val Thr Ala Glu Arg Met Thr Ala Phe Glu Gln
        180                 185                 190

Leu Glu Asn Tyr Leu Asp Glu Leu Val Thr Lys Lys Glu Ala Asn Ala
            195                 200                 205

Thr Glu Asp Asp Leu Leu Gly Arg Gln Ile Leu Lys Gln Arg Glu Thr
210                 215                 220

Gly Glu Ala Asp His Gly Glu Leu Val Gly Leu Ala Phe Leu Leu Leu
225                 230                 235                 240

Ile Ala Gly His Glu Thr Thr Ala Asn Met Ile Ser Leu Gly Thr Val
            245                 250                 255

Thr Leu Leu Glu Asn Pro Asp Gln Leu Ala Lys Ile Lys Ala Asp Pro
            260                 265                 270

Gly Lys Thr Leu Ala Ala Ile Glu Glu Leu Leu Arg Val Phe Thr Ile
        275                 280                 285

Ala Glu Glu Ala Thr Ser Arg Phe Ala Thr Ala Asp Val Glu Ile Gly
290                 295                 300

Gly Thr Leu Ile Arg Ala Gly Glu Gly Val Ile Gly Leu Ser Asn Ala
305                 310                 315                 320

Gly Asn His Asp Pro Asp Gly Phe Glu Asn Pro Asp Thr Phe Asp Ile
            325                 330                 335

Glu Arg Gly Ala Arg His His Val Ala Phe Gly Phe Gly Val His Gln
            340                 345                 350

Cys Leu Gly Gln Asn Leu Ala Arg Leu Glu Leu Gln Ile Val Phe Asp
            355                 360                 365

Thr Leu Phe Arg Arg Val Pro Gly Leu Arg Ile Ala Val Pro Val Asp
            370                 375                 380

Glu Leu Pro Phe Lys His Asp Ser Thr Ile Tyr Gly Leu His Ala Leu
385                 390                 395                 400

Pro Val Thr Trp

<210> SEQ ID NO 101
<211> LENGTH: 23
<212> TYPE: DNA
<213> ORGANISM: Artificial Sequence
<220> FEATURE:
<223> OTHER INFORMATION: Designed primer sequence used for amplification
      and mutagenesis of Mutant 12 (T291E) to produce a double point
      mutant; Mutant 29 (T291E, V315A)

<400> SEQUENCE: 101
ggaaggggtg gcgggcctga gca                                          23

<210> SEQ ID NO 102
<211> LENGTH: 23
<212> TYPE: DNA
<213> ORGANISM: Artificial Sequence
<220> FEATURE:
<223> OTHER INFORMATION: Designed primer sequence used for amplification
      and mutagenesis of Mutant 12 (T291E) to produce a double point
      mutant; Mutant 29 (T291E, V315A)

<400> SEQUENCE: 102
tgctcaggcc cgccacccct tcc                                          23
```

<210> SEQ ID NO 103
<211> LENGTH: 1215
<212> TYPE: DNA
<213> ORGANISM: Amycolatopsis lurida

<400> SEQUENCE: 103

```
atgactgacg tcgaggaaac caccgcgacc ttgccgctgg cccggaaatg cccgttttcg      60
ccgccgcccg aatacgaacg gcttcgccgg gaaagtccgg tttccgggt cggtctcccg     120
tccggtcaaa cggcttgggc gctcacccgg ctcgaagaca tccgcgaaat gctgagcagc    180
ccgcatttca gttccgaccg gcagagcccg tcgttcccgc tgatggtcgc gcggcagatc    240
cgccgcgagg acaagccgtt ccgcccctcc ctcatcgcga tggatccgcc ggaacacagc    300
cgggccaggc gtgacgtcgt cggggaattc accgtcaagc ggatgaaggc gctccagccg    360
cgaattcagc agatcgtcga cgaacatctc gacgccctgc tcgcgggccc caaacccgcc    420
gatctcgtcc aggcgctttc cctgccgtt ccctcgctgg tgatctgcga actgctcggc    480
gtccctat cggaccacga gttcttccag tcctgcagtt ccaggatgct cagccgggag     540
gtcaccgccg aagaacggat accgcgttc gagcagctcg aaactatct cgacgaactg     600
gtcaccaaga aggaggcgaa cgccaccgag gacgacctcc tcggccgtca gatcctgaaa    660
cagcgggaaa cgggcgaggc cgaccacggt gaactcgtcg ggctggcgtt cctgctgctc    720
atcgccggac acgagaccac ggcgaacatg atctcgctcg gcacggtgac cctgctggag    780
aatcccgatc agctcgcgaa gatcaaggca gaccccggca agaccctcgc cgccatcgag    840
gaactcctgc gggtcttcac gatcgcggaa gaagcgacct cacgcttcgc cacggcggac    900
gtcgagatcg gcggaacgct gatccgcgcg ggggaagggg tggcgggcct gagcaacgcg    960
ggcaaccacg atccggacgg cttcgagaac ccggacacct tcgacatcga acgcggcgcg   1020
cggcatcacg tcgcgttcgg attcggggtg caccagtgtc tcggccagaa cttggcgagg   1080
ttggaactcc agatcgtctt cgatacgttg ttccggcgag tgccgggcct ccggatcgcc   1140
gttccggtcg acgaactgcc gttcaagcac gattcgacga tctacggcct ccacgccctt   1200
ccggtcacct ggtag                                                    1215
```

<210> SEQ ID NO 104
<211> LENGTH: 404
<212> TYPE: PRT
<213> ORGANISM: Amycolatopsis lurida

<400> SEQUENCE: 104

```
Met Thr Asp Val Glu Glu Thr Thr Ala Thr Leu Pro Leu Ala Arg Lys
1               5                   10                  15

Cys Pro Phe Ser Pro Pro Glu Tyr Glu Arg Leu Arg Arg Glu Ser
            20                  25                  30

Pro Val Ser Arg Val Gly Leu Pro Ser Gly Gln Thr Ala Trp Ala Leu
        35                  40                  45

Thr Arg Leu Glu Asp Ile Arg Glu Met Leu Ser Ser Pro His Phe Ser
    50                  55                  60

Ser Asp Arg Gln Ser Pro Ser Phe Pro Leu Met Val Ala Arg Gln Ile
65                  70                  75                  80

Arg Arg Glu Asp Lys Pro Phe Arg Pro Ser Leu Ile Ala Met Asp Pro
                85                  90                  95

Pro Glu His Ser Arg Ala Arg Arg Asp Val Val Gly Glu Phe Thr Val
            100                 105                 110
```

Lys Arg Met Lys Ala Leu Gln Pro Arg Ile Gln Gln Ile Val Asp Glu
            115                 120                 125

His Leu Asp Ala Leu Leu Ala Gly Pro Lys Pro Ala Asp Leu Val Gln
        130                 135                 140

Ala Leu Ser Leu Pro Val Pro Ser Leu Val Ile Cys Glu Leu Leu Gly
145                 150                 155                 160

Val Pro Tyr Ser Asp His Glu Phe Phe Gln Ser Cys Ser Ser Arg Met
                165                 170                 175

Leu Ser Arg Glu Val Thr Ala Glu Arg Met Thr Ala Phe Glu Gln
            180                 185                 190

Leu Glu Asn Tyr Leu Asp Glu Leu Val Thr Lys Lys Glu Ala Asn Ala
        195                 200                 205

Thr Glu Asp Asp Leu Leu Gly Arg Gln Ile Leu Lys Gln Arg Glu Thr
    210                 215                 220

Gly Glu Ala Asp His Gly Glu Leu Val Gly Leu Ala Phe Leu Leu Leu
225                 230                 235                 240

Ile Ala Gly His Glu Thr Thr Ala Asn Met Ile Ser Leu Gly Thr Val
                245                 250                 255

Thr Leu Leu Glu Asn Pro Asp Gln Leu Ala Lys Ile Lys Ala Asp Pro
            260                 265                 270

Gly Lys Thr Leu Ala Ala Ile Glu Glu Leu Leu Arg Val Phe Thr Ile
        275                 280                 285

Ala Glu Glu Ala Thr Ser Arg Phe Ala Thr Ala Asp Val Glu Ile Gly
    290                 295                 300

Gly Thr Leu Ile Arg Ala Gly Glu Gly Val Ala Gly Leu Ser Asn Ala
305                 310                 315                 320

Gly Asn His Asp Pro Asp Gly Phe Glu Asn Pro Asp Thr Phe Asp Ile
                325                 330                 335

Glu Arg Gly Ala Arg His His Val Ala Phe Gly Phe Gly Val His Gln
            340                 345                 350

Cys Leu Gly Gln Asn Leu Ala Arg Leu Glu Leu Gln Ile Val Phe Asp
        355                 360                 365

Thr Leu Phe Arg Arg Val Pro Gly Leu Arg Ile Ala Val Pro Val Asp
    370                 375                 380

Glu Leu Pro Phe Lys His Asp Ser Thr Ile Tyr Gly Leu His Ala Leu
385                 390                 395                 400

Pro Val Thr Trp

<210> SEQ ID NO 105
<211> LENGTH: 23
<212> TYPE: DNA
<213> ORGANISM: Artificial Sequence
<220> FEATURE:
<223> OTHER INFORMATION: Designed primer sequence used for amplification
    and mutagenesis of Mutant 12 (T291E) to produce a double point
    mutant; Mutant 30 (T291E, V315L)

<400> SEQUENCE: 105 ggaagggtg ctgggcctga gca                                    23

<210> SEQ ID NO 106
<211> LENGTH: 23
<212> TYPE: DNA
<213> ORGANISM: Artificial Sequence
<220> FEATURE:
<223> OTHER INFORMATION: Designed primer sequence used for amplification
    and mutagenesis of Mutant 12 (T291E) to produce a double point
    mutant; Mutant 30 (T291E, V315L)

<400> SEQUENCE: 106
tgctcaggcc cagcacccct tcc                                        23

<210> SEQ ID NO 107
<211> LENGTH: 1215
<212> TYPE: DNA
<213> ORGANISM: Amycolatopsis lurida

<400> SEQUENCE: 107
atgactgacg tcgaggaaac caccgcgacc ttgccgctgg cccggaaatg cccgttttcg    60
ccgccgcccg aatacgaacg gcttcgccgg gaaagtccgg tttcccgggt cggtctcccg   120
tccggtcaaa cggcttgggc gctcacccgg ctcgaagaca tccgcgaaat gctgagcagc   180
ccgcatttca gttccgaccg gcagagcccg tcgttcccgc tgatggtcgc gcggcagatc   240
cgccgcgagg acaagccgtt ccgcccctcc ctcatcgcga tggatccgcc ggaacacagc   300
cgggccaggc gtgacgtcgt cggggaattc accgtcaagc ggatgaaggc gctccagccg   360
cgaattcagc agatcgtcga cgaacatctc gacgccctgc tcgcgggccc caaacccgcc   420
gatctcgtcc aggcgctttc cctgccgttc cctcgctgg tgatctgcga actgctcggc   480
gtcccctatt cggaccacga gttcttccag tcctgcagtt ccaggatgct cagccgggag   540
gtcaccgccg aagaacggat gaccgcgttc gagcagctcg aaaactatct cgacgaactg   600
gtcaccaaga aggaggcgaa cgccaccgag gacgacctcc tcggccgtca gatcctgaaa   660
cagcgggaaa cgggcgaggc cgaccacggt gaactcgtcg ggctggcgtt cctgctgctc   720
atcgccggac acgagaccac ggcgaacatg atctcgctcg gcacggtgac cctgctggag   780
aatcccgatc agctcgcgaa gatcaaggca gaccccggca agaccctcgc cgccatcgag   840
gaactcctgc gggtcttcac gatcgcggaa gaagcgacct cacgcttcgc cacggcggac   900
gtcgagatcg gcggaacgct gatccgcgcg ggggaagggg tgctgggcct gagcaacgcg   960
ggcaaccacg atccggacgg cttcgagaac ccggacacct cgacatcga acgcggcgcg  1020 cggcatcacg tcgcgttcgg attcggggtg caccagtgtc tcggccagaa cttggcgagg  1080
ttggaactcc agatcgtctt cgatacgttg ttccggcgag tgccgggcct ccggatcgcc  1140
gttccggtcg acgaactgcc gttcaagcac gattcgacga tctacggcct ccacgccctt  1200
ccggtcacct ggtag                                                  1215

<210> SEQ ID NO 108
<211> LENGTH: 404
<212> TYPE: PRT
<213> ORGANISM: Amycolatopsis lurida

<400> SEQUENCE: 108

Met Thr Asp Val Glu Glu Thr Thr Ala Thr Leu Pro Leu Ala Arg Lys
1               5                   10                  15

Cys Pro Phe Ser Pro Pro Glu Tyr Glu Arg Leu Arg Arg Glu Ser
            20                  25                  30

Pro Val Ser Arg Val Gly Leu Pro Ser Gly Gln Thr Ala Trp Ala Leu
        35                  40                  45

Thr Arg Leu Glu Asp Ile Arg Glu Met Leu Ser Ser Pro His Phe Ser
    50                  55                  60

Ser Asp Arg Gln Ser Pro Ser Phe Pro Leu Met Val Ala Arg Gln Ile
65                  70                  75                  80

-continued

Arg Arg Glu Asp Lys Pro Phe Arg Pro Ser Leu Ile Ala Met Asp Pro
                85                  90                  95

Pro Glu His Ser Arg Ala Arg Arg Asp Val Val Gly Glu Phe Thr Val
            100                 105                 110

Lys Arg Met Lys Ala Leu Gln Pro Arg Ile Gln Gln Ile Val Asp Glu
        115                 120                 125

His Leu Asp Ala Leu Leu Ala Gly Pro Lys Pro Ala Asp Leu Val Gln
    130                 135                 140

Ala Leu Ser Leu Pro Val Pro Ser Leu Val Ile Cys Glu Leu Leu Gly
145                 150                 155                 160

Val Pro Tyr Ser Asp His Glu Phe Phe Gln Ser Cys Ser Ser Arg Met
                165                 170                 175

Leu Ser Arg Glu Val Thr Ala Glu Arg Met Thr Ala Phe Glu Gln
            180                 185                 190

Leu Glu Asn Tyr Leu Asp Glu Leu Val Thr Lys Lys Glu Ala Asn Ala
        195                 200                 205

Thr Glu Asp Asp Leu Leu Gly Arg Gln Ile Leu Lys Gln Arg Glu Thr
    210                 215                 220

Gly Glu Ala Asp His Gly Glu Leu Val Gly Leu Ala Phe Leu Leu Leu
225                 230                 235                 240

Ile Ala Gly His Glu Thr Thr Ala Asn Met Ile Ser Leu Gly Thr Val
                245                 250                 255

Thr Leu Leu Glu Asn Pro Asp Gln Leu Ala Lys Ile Lys Ala Asp Pro
            260                 265                 270

Gly Lys Thr Leu Ala Ala Ile Glu Glu Leu Leu Arg Val Phe Thr Ile
        275                 280                 285

Ala Glu Glu Ala Thr Ser Arg Phe Ala Thr Ala Asp Val Glu Ile Gly
    290                 295                 300

Gly Thr Leu Ile Arg Ala Gly Glu Gly Val Leu Gly Leu Ser Asn Ala
305                 310                 315                 320

Gly Asn His Asp Pro Asp Gly Phe Glu Asn Pro Asp Thr Phe Asp Ile
                325                 330                 335

Glu Arg Gly Ala Arg His His Val Ala Phe Gly Phe Gly Val His Gln
            340                 345                 350

Cys Leu Gly Gln Asn Leu Ala Arg Leu Glu Leu Gln Ile Val Phe Asp
        355                 360                 365

Thr Leu Phe Arg Arg Val Pro Gly Leu Arg Ile Ala Val Pro Val Asp
    370                 375                 380

Glu Leu Pro Phe Lys His Asp Ser Thr Ile Tyr Gly Leu His Ala Leu
385                 390                 395                 400

Pro Val Thr Trp

<210> SEQ ID NO 109
<211> LENGTH: 1418
<212> TYPE: DNA
<213> ORGANISM: Amycolatopsis lurida
<220> FEATURE:
<221> NAME/KEY: misc_feature
<222> LOCATION: (141)..(143)
<223> OTHER INFORMATION: n is a, c, g, or t
<220> FEATURE:
<221> NAME/KEY: misc_feature
<222> LOCATION: (223)..(225)
<223> OTHER INFORMATION: n is a, c, g, or t
<220> FEATURE:
<221> NAME/KEY: misc_feature
<222> LOCATION: (871)..(873)

<223> OTHER INFORMATION: n is a, c, g, or t
<220> FEATURE:
<221> NAME/KEY: misc_feature
<222> LOCATION: (943)..(945)
<223> OTHER INFORMATION: n is a, c, g, or t

<400> SEQUENCE: 109

```
atgactgacg tcgaggaaac caccgcgacc ttgccgctgg cccggaaatg cccgttttcg      60
ccgccgcccg aatacgaacg gcttcgccgg gaaagtccgg tttcccgggt cggtctcccg     120
tccggtcaaa cggcttgggc nnncacccgg ctcgaagaca tccgcgaaat gctgagcagc     180
ccgcatttca gttccgaccg gcagagcccg tcgttcccgc tgnnngtcgc gcggcagatc     240
cgccgcgagg acaagccgtt ccgcccctcc ctcatcgcga tggatccgcc ggaacacagc     300
cgggccaggc gtgacgtcgt cggggaattc accgtcaagc ggatgaaggc gctccagccg     360
cgaattcagc agatcgtcga cgaacatctc gacgccctgc tcgcgggccc caaacccgcc     420
gatctcgtcc aggcgctttc cctgccgtt ccctcgctgg tgatctgcga actgctcggc      480
gtcccctatt cggaccacga gttcttccag tcctgcagtt ccaggatgct cagccgggag     540
gtcaccgccg aagaacggat gaccgcgttc gagcagctcg aaaactatct cgacgaactg     600
gtcaccaaga aggaggcgaa cgccaccgag gacgacctcc tcggccgtca gatcctgaaa     660
cagcgggaaa cgggcgaggc cgaccacggt gaactcgtcg ggctggcgtt cctgctgctc     720
atcgccggac acgagaccac ggcgaacatg atctcgctcg gcacggtgac cctgctggag     780
aatcccgatc agctcgcgaa gatcaaggca gaccccggca agaccctcgc cgccatcgag     840
gaactcctgc gggtcttcac gatcgcggaa nnngcgacct cacgcttcgc cacggcggac     900
gtcgagatcg gcggaacgct gatccgcgcg ggggaagggg tgnnnggcct gagcaacgcg     960
ggcaaccacg atccggacgg cttcgagaac ccggacacct cgacatcga acgcggcgcg    1020
cggcatcacg tcgcgttcgg attcggggtg caccagtgtc tcggccagaa cttggcgagg    1080
ttggaactcc agatcgtctt cgatacgttg ttccggcgag tgccgggcct ccggatcgcc    1140
gttccggtcg acgaactgcc gttcaagcac gattcgacga tctacggcct ccacgccctt    1200
ccggtcacct ggtaggagga gccatgaaga tcatcgcgga caccgggaaa tgcgtgggcg    1260
cgggccagtg cgtgctcacc gatcccgatc tgttcgatca gagcgaggac gacggaacgg    1320
tcctcgtgct gaacgccgag cctgaaggcg aagaggcgga agaaaacgcc cgcaccgccg    1380
tgcacatctg cccggggcag gccttgtcgc tcgcttaa                            1418
```

<210> SEQ ID NO 110
<211> LENGTH: 404
<212> TYPE: PRT
<213> ORGANISM: Amycolatopsis lurida
<220> FEATURE:
<221> NAME/KEY: misc_feature
<222> LOCATION: (47)..(47)
<223> OTHER INFORMATION: Xaa can be any naturally occurring amino acid
<220> FEATURE:
<221> NAME/KEY: misc_feature
<222> LOCATION: (75)..(75)
<223> OTHER INFORMATION: Xaa can be any naturally occurring amino acid
<220> FEATURE:
<221> NAME/KEY: misc_feature
<222> LOCATION: (291)..(291)
<223> OTHER INFORMATION: Xaa can be any naturally occurring amino acid
<220> FEATURE:
<221> NAME/KEY: misc_feature
<222> LOCATION: (315)..(315)
<223> OTHER INFORMATION: Xaa can be any naturally occurring amino acid

<400> SEQUENCE: 110

```
Met Thr Asp Val Glu Glu Thr Thr Ala Thr Leu Pro Leu Ala Arg Lys
1               5                   10                  15
Cys Pro Phe Ser Pro Pro Glu Tyr Glu Arg Leu Arg Arg Glu Ser
            20                  25                  30
Pro Val Ser Arg Val Gly Leu Pro Ser Gly Gln Thr Ala Trp Xaa Leu
            35                  40                  45
Thr Arg Leu Glu Asp Ile Arg Glu Met Leu Ser Ser Pro His Phe Ser
50                  55                  60
Ser Asp Arg Gln Ser Pro Ser Phe Pro Leu Xaa Val Ala Arg Gln Ile
65                  70                  75                  80
Arg Arg Glu Asp Lys Pro Phe Arg Pro Ser Leu Ile Ala Met Asp Pro
                85                  90                  95
Pro Glu His Ser Arg Ala Arg Asp Val Val Gly Glu Phe Thr Val
            100                 105                 110
Lys Arg Met Lys Ala Leu Gln Pro Arg Ile Gln Gln Ile Val Asp Glu
            115                 120                 125
His Leu Asp Ala Leu Leu Ala Gly Pro Lys Pro Ala Asp Leu Val Gln
130                 135                 140
Ala Leu Ser Leu Pro Val Pro Ser Leu Val Ile Cys Glu Leu Leu Gly
145                 150                 155                 160
Val Pro Tyr Ser Asp His Glu Phe Phe Gln Ser Cys Ser Ser Arg Met
                165                 170                 175
Leu Ser Arg Glu Val Thr Ala Glu Glu Arg Met Thr Ala Phe Glu Gln
            180                 185                 190
Leu Glu Asn Tyr Leu Asp Glu Leu Val Thr Lys Lys Glu Ala Asn Ala
            195                 200                 205
Thr Glu Asp Asp Leu Leu Gly Arg Gln Ile Leu Lys Gln Arg Glu Thr
210                 215                 220
Gly Glu Ala Asp His Gly Glu Leu Val Gly Leu Ala Phe Leu Leu Leu
225                 230                 235                 240
Ile Ala Gly His Glu Thr Thr Ala Asn Met Ile Ser Leu Gly Thr Val
                245                 250                 255
Thr Leu Leu Glu Asn Pro Asp Gln Leu Ala Lys Ile Lys Ala Asp Pro
            260                 265                 270
Gly Lys Thr Leu Ala Ala Ile Glu Glu Leu Leu Arg Val Phe Thr Ile
            275                 280                 285
Ala Glu Xaa Ala Thr Ser Arg Phe Ala Thr Ala Asp Val Glu Ile Gly
            290                 295                 300
Gly Thr Leu Ile Arg Ala Gly Glu Gly Val Xaa Gly Leu Ser Asn Ala
305                 310                 315                 320
Gly Asn His Asp Pro Asp Gly Phe Glu Asn Pro Asp Thr Phe Asp Ile
                325                 330                 335
Glu Arg Gly Ala Arg His His Val Ala Phe Gly Phe Gly Val His Gln
            340                 345                 350
Cys Leu Gly Gln Asn Leu Ala Arg Leu Glu Leu Gln Ile Val Phe Asp
            355                 360                 365
Thr Leu Phe Arg Arg Val Pro Gly Leu Arg Ile Ala Val Pro Val Asp
370                 375                 380
Glu Leu Pro Phe Lys His Asp Ser Thr Ile Tyr Gly Leu His Ala Leu
385                 390                 395                 400
Pro Val Thr Trp
```

HYDROXYLATION TECHNIQUES

FIELD OF THE INVENTION

The present invention relates to the use of a cytochrome P450 enzyme for catalysing the hydroxylation of organic substrates.

BACKGROUND OF INVENTION

Cytochrome P450 (CYP) is a superfamily of haem-thiolate proteins named for the spectral absorbance peak of their carbon-monoxide bound species at 450 nm. They are found in all kingdoms of life such as animals, plants, fungi, protists, bacteria, archaea, and furthermore a putative P450 from giant virus *A. polyphaga* has been recently proposed, Lamb, D C; Lei, L; Warrilow, A G; Lepesheva, G I; Mullins, J G; Waterman, M R; Kelly, S L (2009). "*The first virally encoded cytochrome P450*". Journal of Virology. 83 (16): pp 8266-9. Cytochrome P450 have not been identified in *E. coli*, Roland Sigel; Sigel, Astrid; Sigel, Helmut (2007). The Ubiquitous Roles of Cytochrome P450 Proteins: Metal Ions in Life Sciences. New York: Wiley. ISBN 0-470-01672-8; Danielson P B (December 2002). "The cytochrome P450 superfamily: biochemistry, evolution and drug metabolism in humans". Curr. Drug Metab. 3 (6): pp 561-97.

Cytochrome P450 shows extraordinary diversity in their reaction chemistry supporting the oxidative, peroxidative and reductive metabolism of a diversity of a range of endogenous and xenobiotic substrates.

In humans, cytochrome P450 are best known for their central role in phase I drug metabolism where they are of critical importance for two of the most significant problems in clinical pharmacology: drug interaction and inter-individual variability in drug metabolism.

The most common reaction catalyzed by cytochromes P450 is a mono-oxygenase reaction. Cytochrome P450 mono-oxygenases use a haem group to oxidise molecules, often making them more water-soluble by either adding or unmasking a polar group. In general the reaction catalysed by these enzymes can be summarised as:

$$R\text{---}H + O_2 + 2e^- \rightarrow R\text{---}OH + H_2O$$

Where R—H is the substrate and R—OH is the oxygenated substrate. The oxygen is bound to the haem group in the core of the CYP enzyme, protons (H$^+$) are usually derived from the reduced cofactor NADH or NADPH through specific amino acids in the CYP enzyme. CYP enzymes can receive electrons from a range of redox partner proteins such as cytochrome b5, a ferredoxin reductase and a ferredoxin, and adrenodoxin reductase and adrenodoxin.

Although classification and nomenclature of cytochrome P450 is quite complex, they can be classified by their redox partner transfer protein system, proposed by I. Hanukoglu (1996). "*Electron Transfer Proteins of Cytochrome P450 Systems*". Advances in Molecular and Cell Biology. Advances in Molecular and Cell Biology. 14: 29-56. In summary, cytochromes P450 can be classified into the following groups:

Microsomal P450 systems which utilise cytochrome P540 reductase or cytochrome b5 to transfer electrons from cofactor to cytochrome P450;

Mitochondrial P450 systems which utilise adrenodoxin reductase and adrenodoxin to transfer electrons from reduced cofactor to cytochrome P450;

Bacterial P450 systems which utilise ferredoxin reductase and ferredoxin to transfer electrons from reduced cofactor to cytochrome P450;

CYB5R-cytb5-P450 systems, which utilise cytochrome b5 for the electron transfer from the cofactor to the cytochrome P450;

FMN-Fd-P450 systems in which the electron partner reductase is a fused FMN domain;

P450 only systems that do not require redox partner proteins, e.g., P450$_{BM-3}$.

Isolated bacterial cytochrome P450 enzymes are known, including P450$_{cam}$ from *Pseudomonas putida*, J Biol Chem (1974) 249, 94; P450$_{BM-1}$ and P450$_{BM-3}$ both from *Bacillus megaterium* ATCC 14581, Biochim Biophys Acta (1985) 838, 302, and J Biol Chem (1986) 261, 1986, 7160; P450a, P450b, and P450c from *Rhizobium japonicum*, Biochim Biophys Acta (1967) 147, 399; and P450npd from Nocardia NHI, Microbios (1974) 9, 119.

However, cytochrome P450 enzymes purified from Actinomycete microorganisms remain relatively unreported. The induction of a cytochrome P450 in *Streptomyces griseus* by soybean flour (P450$_{soy}$) is described in Biochem and Biophys Res Comm (1986) 141, 405. Other reported examples include the isolation and properties of two forms of a P450 effecting pesticide inactivation (P450$_{SU1}$ & $_{SU2}$) and two forms of 6-deoxyerythronolide B hydroxylase from *Saccharopolyspora erythraea* (originally classified as *Streptomyces erythraeus*) as described in Biochemistry (1987) 26, 6204. U.S. Pat. No. 6,884,608 describes enzymatic hydroxylation of epothilone B to epothilone F, effected with a hydroxylation enzyme produced by a strain of *Amycolatopsis orientalis* (originally classified as *Streptomyces orientalis*).

In the field of medicinal chemistry, modifications to chemical compounds are used to modify the properties of such chemical compounds. For example, tertiary butyl moieties are often used by medicinal chemists in the synthesis of drug-like molecules for introduction of hydrophobicity. However, further modifications thereof can be used to improve potency, selectivity and solubility profiles of such compounds, for example hydroxylations can be used. Hydroxylations are also the main route of metabolic degradation, another important aspect of pharmacology and medicinal chemistry. Methods for the production of these hydroxylated metabolites are sought using biotransformation with animal tissues.

It had previously been found that a cytochrome P450 enzyme found in *Amycolatopsis lurida* NRRL-2430 can be used for the hydroxylation of a wide range of organic substrates.

In particular, a cytochrome P450 enzyme having the SEQ ID NO: 2 can be used for the hydroxylation of organic compounds in order to activate or modify the compound's physicochemical and pharmacological properties. In a particularly preferred embodiment, the cytochrome P450 enzyme having the SEQ ID NO: 3 is used for the hydroxylation of isopropyl or tertiary butyl moieties, or chemicals containing such moiety, for the purposes of C—H activation or modification of the compound's physicochemical and pharmacological properties.

SUMMARY OF THE INVENTION

It has now been found that mutagenesis to alter the sequence of this enzyme shown in SEQ ID No: 110 at residue T291 produces modified cytochrome P450 enzymes with improved properties including altered regiospecificity for hydroxylation of aromatic substrates.

A first aspect of the invention provides the use of a cytochrome P450 enzyme comprising SEQ ID NO: 110, or a variant enzyme having at least 70% identity thereto and having CYP450 activity, for the hydroxylation of an organic compound, wherein the amino acid residue at position 291 is not threonine.

A second aspect of the invention provides a method for the production of a hydroxylated organic compound, comprising reacting the organic compound with an enzyme preparation containing in part the cytochrome P450 enzyme comprising SEQ ID NO: 110, or a variant enzyme having at least 70% identity thereto and having CYP450 activity, wherein the amino acid residue at position 291 is not threonine.

A third aspect of the invention provides a kit comprising i) a cytochrome P450 enzyme comprising SEQ ID NO: 110, or a variant enzyme having at least 70% identity thereto and having CYP450 activity, or ii) a microorganism that expresses a cytochrome P450 enzyme comprising SEQ ID NO: 110, or a variant enzyme having at least 70% identity thereto and having CYP450 activity, wherein the amino acid residue at position 291 is not threonine and wherein the kit further comprises instructions and other cofactor reagents for use for the hydroxylation of an organic compound.

BRIEF DESCRIPTION OF THE FIGURES

FIG. 1 shows various ID sequences. SEQ ID NO: 1 is the nucleic acid sequence of P450 aluC09, ferredoxin aluF03 and ferredoxin reductase SCF15A; SEQ ID NO: 2 is the amino acid sequence of P450 AluC09; SEQ ID NO: 3 is the amino acid sequence of ferredoxin AluF03; SEQ ID NO: 4 is the amino acid sequence of ferredoxin reductase SCF15A; SEQ ID NO: 7 is the nucleic acid sequence of aluC09M11; SEQ ID NO: 8 is the amino acid sequence of AluC09M11; SEQ ID NO: 11 is the nucleic acid sequence of aluC09M12; SEQ ID NO: 12 is the amino acid sequence of AluC09M12; SEQ ID NO: 15 is the nucleic acid sequence of aluC09M17; SEQ ID NO: 16 is the amino acid sequence of AluC09M17; SEQ ID NO: 19 is the nucleic acid of aluC09M18; SEQ ID NO: 20 is the amino acid sequence of AluC09M18; SEQ ID NO: 23 is the nucleic acid sequence of aluC09M19; SEQ ID NO: 24 is the amino acid sequence of AluC09M19; SEQ ID NO: 27 is the nucleic acid sequence of aluC09M20; SEQ ID NO: 28 is the amino acid sequence of AluC09M20; SEQ ID NO: 31 is the nucleic acid sequence of aluC09M21; SEQ ID NO: 32 is the amino acid sequence of AluC09M21; SEQ ID NO: 35 is the nucleic acid sequence of aluC09M31; SEQ ID NO: 36 is the amino acid sequence of AluC09M31; SEQ ID NO: 39 is the nucleic acid sequence of aluC09M32; SEQ ID NO: 40 is the amino acid sequence of AluC09M32; SEQ ID NO: 43 is the nucleic acid sequence of AluC09M33; SEQ ID NO: 44 is the amino acid sequence of AluC09M33; SEQ ID NO: 47 is the nucleic acid sequence of aluC09M34; SEQ ID NO: 48 is the amino acid sequence of AluC09M34; SEQ ID NO: 51 is the nucleic acid sequence of aluC09M35; SEQ ID NO: 52 is the amino acid sequence of AluC09M35; SEQ ID NO: 55 is the nucleic acid sequence of aluC09M36; SEQ ID NO: 56 is the amino acid sequence of AluC09M36; SEQ ID NO: 59 is the nucleic acid sequence of aluC09M37; SEQ ID NO: 60 is the amino acid sequence of AluC09M37; SEQ ID NO: 63 is the nucleic acid sequence of aluC09M38; SEQ ID NO: 64 is the amino acid sequence of AluC09M38; SEQ ID NO: 67 is the nucleic acid sequence of aluC09M39; SEQ ID NO: 68 is the amino acid sequence of AluC09M39; SEQ ID NO: 71 is the nucleic acid sequence of aluC09M40; SEQ ID NO: 72 is the amino acid sequence of AluC09M40; SEQ ID NO: 75 is the nucleic acid sequence of aluC09M22; SEQ ID NO: 76 is the amino acid sequence of AluC09M22; SEQ ID NO: 79 is the nucleic acid sequence of aluC09M23; SEQ ID NO: 80 is the amino acid sequence of AluC09M23; SEQ ID NO: 83 is the nucleic acid sequence of aluC09M24; SEQ ID NO: 84 is the amino acid sequence of AluC09M24; SEQ ID NO: 87 is the nucleic acid sequence of aluC09M25; SEQ ID NO: 88 is the amino acid sequence of AluC09M25; SEQ ID NO: 91 is the nucleic acid sequence of aluC09M26; SEQ ID NO: 92 is the amino acid sequence of AluC09M26; SEQ ID NO: 95 is the nucleic acid sequence of aluC09M27; SEQ ID NO: 96 is the amino acid sequence of AluC09M27; SEQ ID NO: 99 is the nucleic acid sequence of aluC09M28; SEQ ID NO: 100 is the amino acid sequence of AluC09M28; SEQ ID NO: 103 is the nucleic acid sequence of aluC09M29; SEQ ID NO: 104 is the amino acid sequence of AluC09M29; SEQ ID NO: 107 is the nucleic acid sequence of aluC09M30; SEQ ID NO: 108 is the amino acid sequence of AluC09M30; SEQ ID NO: 109 shows the nucleic acid sequence where the nucleotides at positions 141 to 143, 223 to 225, 871 to 873 and 943 to 945 are denoted as modified; SEQ ID NO: 110 shows the amino acid sequence of the enzyme of the invention, where the residue at position 47, 75, 291 and 315 are denoted as modified.

FIG. 2 shows carbon monoxide difference spectra for a specific AluC09 mutant as described in Example 4.

FIG. 7 shows UPLC chromatograms showing O-demethylation of indomethacin catalysed by P450 mutant aluC09M36.

DESCRIPTION OF THE PREFERRED EMBODIMENTS

Figure 3A:
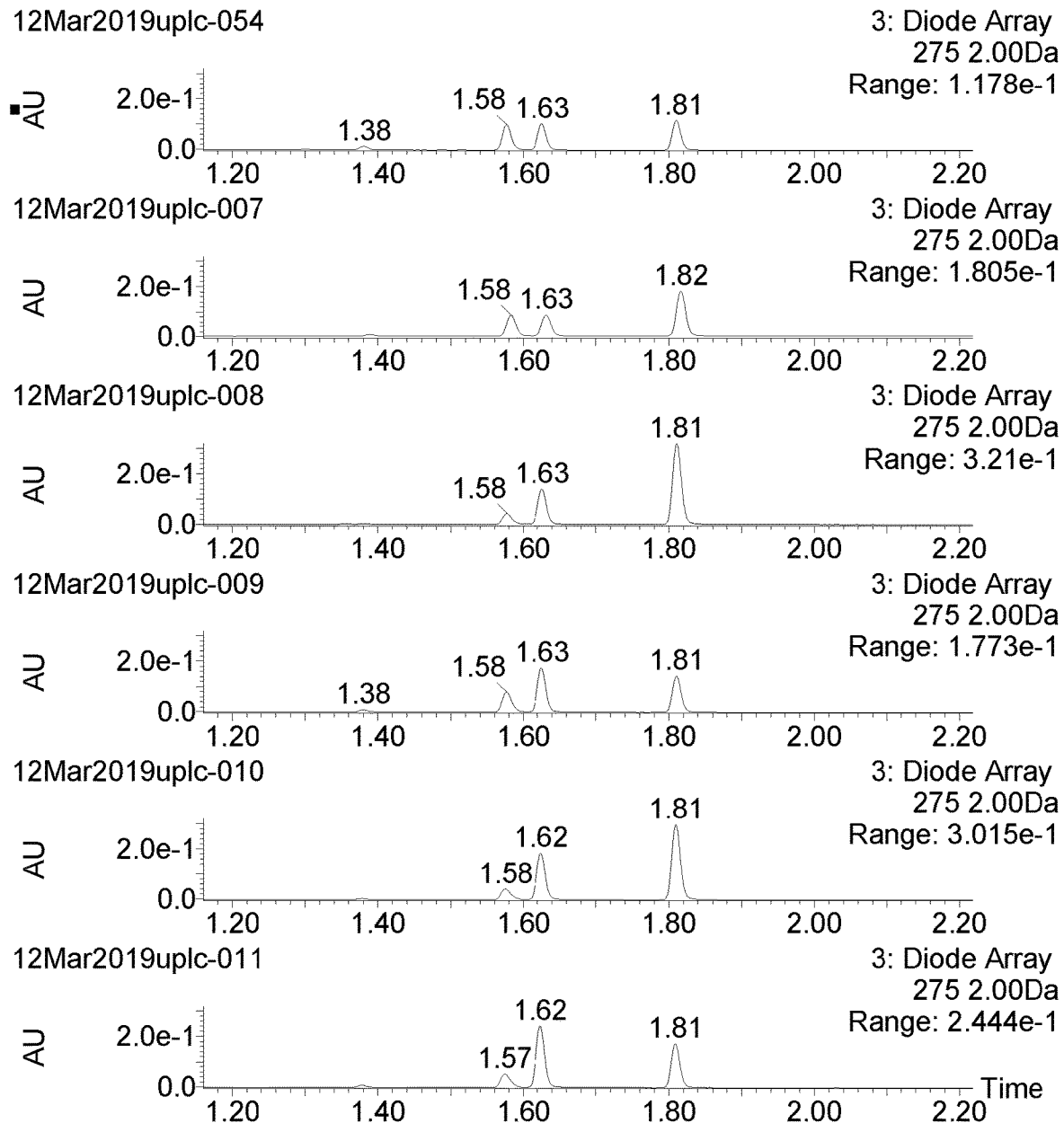
FIG. 3 shows example UPLC chromatograms monitoring the hydroxylation of diclofenac catalysed by AluC09 and various T291x mutants.

A first aspect of the invention provides the use of a cytochrome P450 enzyme comprising SEQ ID NO: 110, or a variant enzyme having at least 70% identity thereto and having CYP450 activity, for the hydroxylation of an organic compound, wherein the amino acid residue at position 291 is not threonine.

Specifically, the present invention provides the use of the enzyme cytochrome $P450_{aluC09}$ having a mutation at position 291. This enzyme has amino acid sequence as shown in SEQ ID NO: 110.

The parent enzyme is present in the strain *Amycolatopsis lurida*, deposited in the ARS Culture Collection, National Center for Agricultural Utilization Research, 1815 North University Street, Peoria, Ill. 61604, USA, under the Accession number NRRL 2430. The strain has also been deposited with the American Tissue Culture Collection, with the accession number ATCC 14930.

When the specific mutation of this enzyme, or a variant thereof, is combined with suitable reductase components, it is able to hydroxylate organic compounds.

The enzyme cytochrome P450$_{aluC09}$ can be extracted, with or without purification from the known *Amycolatopsis lurida* NRRL-2430, or other bacterial strain, or similarly extracted, with or without purification from a recombinant expression system via cloning of cytochrome P450$_{aluC09}$ into an expression system, such as *E. coli*, as will be understood by the skilled person.

Actinomycetes including *Amycolatopsis lurida* NRRL-2430 readily undergo mutation both through natural causes and as a result of artificial treatments such as UV irradiation, radiation treatment and chemical treatment. The present invention embraces all productive mutants of *Amycolatopsis lurida* NRRL-2430. These mutant strains also include any strains obtained by gene manipulation such as gene recombination, transduction and transformation. It is also well-known that the properties of Actinomycetes change in some degree even for the same strain after successive cultures. Therefore, strains cannot always be differentiated taxonomically because of a slight difference in culture properties. This invention embraces all strains that can produce one or more of the cytochromes P450 enzymes, and especially strains that cannot be clearly differentiated from strain NRRL-2430 or its mutants.

One of skill in the art will appreciate that the present invention can include variants of those particular amino acids sequences which are exemplified herein. Particularly preferred are variants having an amino acid sequence similar to that of the amino acid sequences disclosed herein, in which one or more amino acids residues are substituted, deleted or added in any combination. Especially preferred are silent substitutions, additions and deletions, which do not alter the properties and activities of the protein of the present invention. Various amino acids have similar properties, and one or more such amino acids of a substance can often be substituted by one or more other amino acids without eliminating a desired activity of that substance. Thus, the amino acids glycine, alanine, valine, leucine and isoleucine can often be substituted for one another (amino acids having aliphatic side chains). Of these possible substitutions it is preferred that glycine and alanine are used to substitute for one another (since they have relatively short side chains) and that valine, leucine and isoleucine are used to substitute for one another (since they have larger aliphatic side chains which are hydrophobic). Other amino acids which can often be substituted for one another include: phenylalanine, tyrosine and tryptophan (amino acids having aromatic side chains); lysine, arginine and histidine (amino acids having basic side chains); aspartate and glutamate (amino acids having acidic side chains); asparagine and glutamine (amino acids having amide side chains); and cysteine and methionine (amino acids having sulphur containing side chains). Variants include naturally occurring and artificial variants. Artificial variants may be generated using mutagenesis techniques, including those applied to nucleic acid molecules, cells or organisms. Preferably, the variants have substantial identity to the amino acid sequences exemplified herein. As used herein, the term "variant" or "mutant thereof" refers to amino acid sequences which have "substantial identity", preferably having at least 70%, 80%, 90%, 91%, 92%, 93%, 94%, 95% 96%, 97%, 98%, 98.1%, 98.2%, 98.3%, 98.4%, 98.5%, 98.6%, 98.7%, 98.8%, 98.9%, 99%, 99.1%, 99.2%, 99.3%, 99.4%, 99.5%, 99.6%, 99.1%, 99.8% or 99.9% identity with SEQ ID NO 110. Desirably, the term "substantial identity" indicates that said sequence has a greater degree of identity with any of the sequences described herein than with prior art amino acid sequences. One can use a program such as the CLUSTAL program to compare amino acid sequences. This program compares amino acid sequences and finds the optimal alignment by inserting spaces in either sequence as appropriate. It is possible to calculate amino acid identity or similarity (identity plus conservation of amino acid type) for an optimal alignment. A program like BLASTx will align the longest stretch of similar sequences and assign a value to the fit. It is thus possible to obtain a comparison where several regions of similarity are found, each having a different score. The above applies mutatis mutandis to all amino acid sequences disclosed in the present application.

"In a preferred embodiment, the term "variant" or "mutant thereof" generally refers to a sequence having at least 70% identity to SEQ ID No 110 and CYP450 activity, more preferably least 90% identity thereto or at least 95% identity thereto, further preferably 96% identity thereto, even more preferably 97% identity thereto, most preferably 100% identity thereto.

With regard to "variants" or "mutants", it will be understood that the amino acid at position 291 is not threonine. The mutation at residue position 291 (shown in SEQ ID NO: 110) may be any amino acid other than threonine. In preferred embodiments, the threonine residue in the parent sequence has been replaced with the amino acid glutamic acid (E), glutamine (Q), alanine (A) asparagine (N), aspartic acid (D), tyrosine (Y) or valine (V). Most preferably, the threonine is replaced with glutamic acid (E).

The invention also envisages one or more additional mutations being incorporated into the enzyme sequence. Additions, substitutions and deletions can all be made, as will be appreciated by the skilled person. Preferably, the enzyme may incorporate a replacement amino acid at one or more of positions A47, M75 and V315, based on the sequence shown as SEQ ID NO: 110.

A variety of different compounds can be hydroxylated using the claimed cytochrome P450 enzyme. In a preferred embodiment, the organic compound to be hydroxylated will have a rate of conversion to the hydroxylated derivative of at least 3%, more preferably at least 5%, more preferably at least 10%, more preferably at least 25%, more preferably at least 50%, even more preferably at least 70% and most preferably a rate of conversion to the hydroxylated derivative of 100%, using the same conditions described in Example 4 herein.

Preferably, the organic compound to be hydroxylated is not epothilone.

The compound to be hydroxylated by the cytochrome P450 enzyme may have an optionally substituted branched alkyl group, such as isopropyl or tert butyl, which is hydroxylated; or an aromatic group, such as an optionally substituted aryl or heteroaryl, which is hydroxylated.

There is a particularly high conversion rate from these compounds to their hydroxylated derivatives when using the claimed cytochrome P450 enzyme.

Preferably, the compound to be hydroxylated is of formula Ia or Ib:

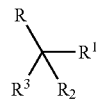

(Ia)

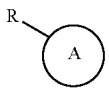
(Ib)

where R represents the rest of the compound, and where $R^1$, $R^2$ and $R^3$ are independently selected from H or $C_{1-12}$ alkyl or $C_{6-10}$ aryl, or wherein any two of $R^1$, $R^2$ and $R^3$ may be joined to form an optionally substituted cycloalkyl or heterocycloalkyl or $R^1$, $R^2$ and $R^3$ may be joined together with their bridging carbon to form an olefin, aryl or heteroaryl, and wherein A is optionally substituted benzyl, aryl or heteroaryl.

Preferably R is an optionally substituted alkyl; an optionally substituted olefin, an optionally substituted aryl, optionally substituted heteroaryl or optionally substituted heterocycloalkyl.

Preferably, A is benzyl, aryl or heteroaryl, optionally substituted with one or more halogen atoms, $C_1$-$C_8$ alkyl, $C_1$-$C_8$ alkoxy, —COOH, $C_1$-$C_8$—COOH, cyano, amino or alkylamino groups.

More preferably, A is benzyl, aryl or heteroaryl optionally substituted with one or more halogen atoms, $C_1$-$C_4$ alkyl, —COOH or $C_1$-$C_4$ Alkyl-COOH groups.

More preferably, A is $C_6$ aryl or $C_4$-$C_{20}$ bicyclic or tricyclic heteroaryl, optionally substituted with $C_1$-$C_8$ alkyl, $C_1$-$C_8$ alkoxy, —COOH, $C_1$-$C_8$—COOH, cyano, amino or alkylamino groups.

Most preferably, A is indolyl, isoindolyl, azaindolyl or a group having the formula.

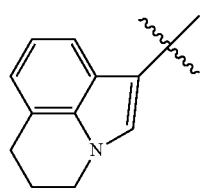 [SMILES: *c1cn2c3c(cccc13)CCC2]

As used herein "alkyl" means a $C_1$-$C_{10}$ alkyl group, which can be linear or branched or cyclic. Examples include propyl and butyl, pentyl, hexyl, cyclopentyl and cyclohexyl. Preferably, it is a $C_3$-$C_{10}$ alkyl moiety. More preferably it is a $C_5$-$C_6$ alkyl moiety. Preferably the alkyl is an optionally substituted cyclohexyl.

As used herein "alkoxy" means on alkyl group, as defined above, having an oxygen atom attached thereto.

As used herein "halogen" refers to fluorine, chlorine, bromine and iodine.

As used here the term "alkylamino" means at least one alkyl group, as defined herein, is appended to the parent molecular moiety though an amino group. By way of non-limiting example, suitable alkylamino groups include methlamino, ethlamino, proylamino, butylamino and hexylamino.

The term "alkenyl" means a straight or branched hydrocarbon chain containing at least one carbon-carbon double bond and from 1 to 10 carbon atoms.

For the avoidance of any doubt, the term cycloalkyl is a cyclic alkyl group.

As used herein "aryl" means an optionally substituted monocyclic, bicyclic or tricyclic aromatic radical, such as phenyl, biphenyl, napthyl, anthracenyl. Preferably the aryl is an optionally substituted $C_6$ aryl.

As used herein "heteroaryl" means an optionally substituted monocyclic, bicyclic or tricyclic aromatic radical containing at least one and up to four heteroatoms selected from oxygen, nitrogen and sulfur, such as furanyl, pyrrolyl, thiazolyl, isothiazolyl, tetrazolyl, imidazolyl, oxazolyl, isoxazolyl, thienyl, pyrazolyl, pyridinyl, pyrazinyl, pyrimidinyl, indolyl, azaindolyl, isoindolyl, quinolyl, isoquinolyl, triazolyl, thiadiazolyl, oxadiazolyl. Preferably the heteroaryl is an optionally substituted thioazole.

As used herein "heterocycloalkyl" means an optionally substituted cycloalkyl wherein one to four carbon atoms have been substituted with a heteroatom. Preferably, the heteroatoms are selected from nitrogen, oxygen, sulphur or phosphorous.

As used herein the term "optionally substituted" means an H has been removed from a compound and replaced with an organic fragment such as those those comprising a combination of any of carbon, hydrogen, nitrogen, oxygen and sulphur.

Preferably the compound of formula I has a molecular weight of from 50 to 2000, such as from 100 to 700, more preferably from 200 to 500.

Preferably at least 2 of $R^1$, $R^2$ and $R^3$ are selected from $C_{1-12}$ alkyl or $C_{6-10}$ aryl. Preferably, $R^1$, $R^2$ and $R^3$ are independently selected from H, $C_{1-6}$ alkyl or $C_{6-10}$ aryl, preferably with the proviso that either one or none of $R^1$, $R^2$ and $R^3$ is H. Most preferably, $R^1$, $R^2$ and $R^3$ are independently selected from H, methyl, ethyl, propyl, butyl, t-butyl, pentyl and hexyl preferably with the proviso that either one or none of $R^1$, $R^2$ and $R^3$ is H.

In a particularly preferred embodiment, the compound to be hydroxylated is of formula (II), where R represents the rest of the compound and where $R^1$ is $CH_3$ or H:

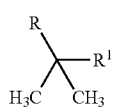
(II)

In this case, the cytochrome P450 enzyme catalyses the following reaction:

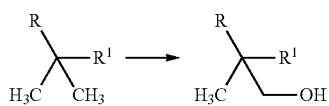

Where $R^1$ = H, $CH_3$

Therefore, in a particular preferred embodiment, the organic compound contains an isopropyl or tert-butyl group. Most preferably, the group to be hydroxylated is a tert-butyl moiety. The cytochrome P450 enzyme catalyses the conversion of a substrate compound with a tert-butyl moiety to a hydroxylated-tert-butyl derivative.

In a particularly preferred embodiment, the cytochrome P450 enzyme is reacted with a compound such as bosentan, diclofenac, buparvaquone, tivantinib, BIRB796 or ritonavir. Most preferably, the cytochrome P450 enzyme is reacted with bosentan, buparvaquone, BIRB796 or ritonavir.

The compounds of formula I are typically of the following structural formulae:

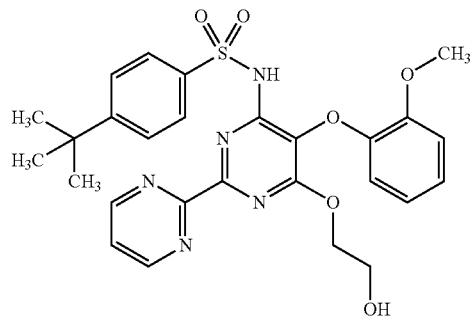

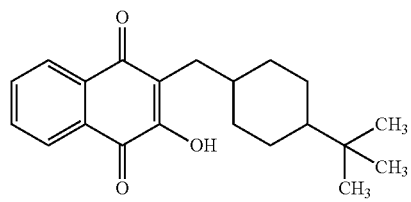

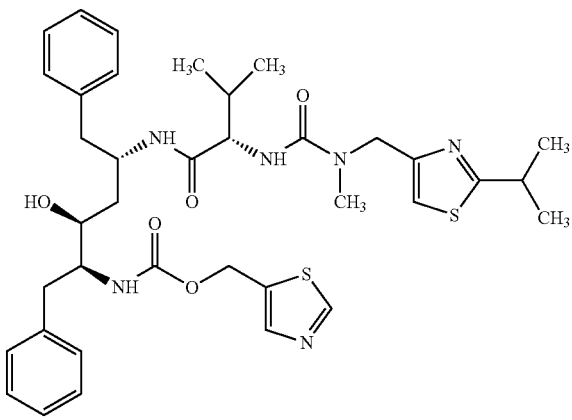

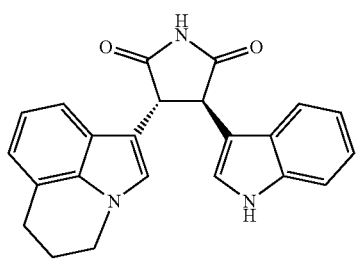

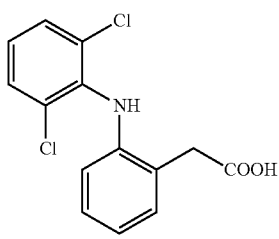

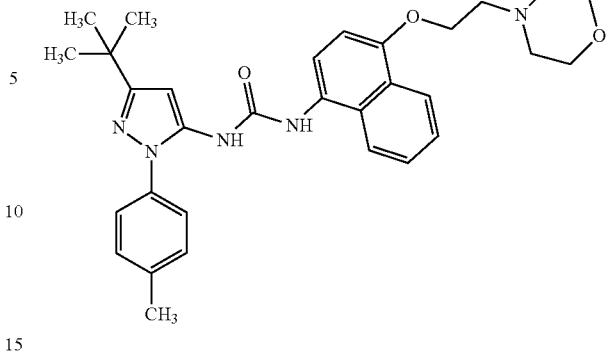

The mutated cytochrome P450 enzyme, or variants thereof, wherein the amino acid residue at position 291 is not threonine, may optionally be used in combination with reductase components, which activate the cytochrome P450. In a preferred embodiment, ferredoxin and ferredoxin reductase components are used. Any components which activate the cytochrome P450 may also be used, including small-molecule chemicals acting directly or indirectly, protein chemicals in solution or those fused directly or by peptide linkage, or electronic via electrode. In a particularly preferred embodiment, the enzyme cytochrome P450aluC09 having SEQ ID NO 110, or a variant enzyme having at least 70% identity thereto and having CYP450 activity, is combined with suitable ferredoxin and ferredoxin reductase components to give an effective system to convert a substrate compound to a hydroxylated derivative.

In a preferred embodiment, parent the cytochrome P450 enzyme or variant thereof is present in *Amycolatopsis lurida* (NRRL-2430) cells.

In another preferred embodiment, the cytochrome P450 enzyme or variant thereof is expressed by at least one recombinant microorganism comprising heterologous nucleic acid encoding the enzyme, derived from *Amycolatopsis lurida* (NRRL 2430). As used herein the term "comprising" is intended to mean containing at least the claimed sequence, but may include other sequences. In one embodiment, the recombinant microorganism comprises a heterologous nucleic acid encoding the enzyme or variant thereof. In an alternative embodiment, the recombinant microorganism also comprises a heterologous nucleic acid encoding a reductase agent.

In another aspect of the invention, there is provided a method for the production of a hydroxylated organic compound, comprising reacting the organic compound with a cytochrome P450 enzyme comprising SEQ ID NO: 110, or a variant enzyme having at least 70% identity thereto and having CYP450 activity.

The choice of compound to be hydroxylated is discussed above.

In a preferred embodiment, the enzyme is used to catalyse the hydroxylation of a propyl group or a butyl group, more preferably an isopropyl or isobutyl group or tert-butyl group. Most preferably, the enzyme is used to catalyse the hydroxylation of a tert-butyl moiety. The cytochrome P450 enzyme is able to catalyse the conversion of a substrate compound with a tert-butyl moiety to a hydroxylated-tert-butyl derivative.

In a particularly preferred embodiment, the compound to be hydroxylated is bosentan, diclofenac, tivantinib, buparvaquone, BIRB796 or ritonavir. Most preferably, the compound to be hydroxylated is bosentan, buparvaquone, BIRB796 or ritonavir.

Optionally, one or more additional component(s) may be used to activate the cytochrome P450 enzyme. In an embodiment according to the present invention, the cytochrome P450 enzyme is used in combination with reductase components, preferably with ferredoxin and ferredoxin reductase components.

The cells comprising the enzyme of the invention may be dosed with the organic compound to be hydroxylated. The method may optionally comprise an additional step wherein the cells are subsequently harvested and purified to obtain the hydroxylated compound.

Culture of the recombinant cells expressing the enzyme of the invention is suitably performed by seeding of a conventional culture medium containing nutrients well-known for use with such microorganisms. Thus, the culture medium contains sources of assimilable carbon and of assimilable nitrogen. The culture medium may also contain inorganic salts. Examples of sources of assimilable carbon include glucose, sucrose, starch, glycerin, millet jelly, molasses and soybean oil. Examples of sources of assimilable nitrogen include soybean solids (such as soybean meal or soybean flour), wheat germ, meat extracts, peptone, corn steep liquor, dried yeast and ammonium salts, such as ammonium sulphate. If required, inorganic salts, such as sodium chloride, potassium chloride, calcium carbonate and various phosphates, may also be included. The medium is preferably sterilized and has a pH adjusted to 5 to 8.

The skilled person will understand that the particular cultivation technique employed is not critical to the invention and any technique commonly used for the cultivation of the specific recombinant bacteria may equally be employed with the present invention. For example, the bacteria may be an Actinomycete, and suitable culture conditions will be apparent to the skilled person. In general the techniques employed will be chosen having regard to industrial efficiency. Thus, liquid culture is generally preferred and the submerged culture method is most convenient from the industrial point of view. Cultivation is preferably carried out under aerobic conditions.

The enzymes of this invention are inducible enzymes, and are not produced unless an induction agent is present. For preference, but not limited to, the induction agent is selected to be the same as the intended substrate for the isolated enzyme. When from 4 hours to 3 days have elapsed after inoculation, preferably 0.05 to 5 mM, more preferably 0.2 mM of induction agent is added, and then cultivation is continued for 2 hours to 1 week, preferably for about one day. The temperature of cultivation is typically 20° to 45° C., preferably 25° to 30° C., optimally about 27° C. Shake culture or aeration techniques can be adopted.

The cells obtained by the cultivation may be disrupted by cell disruption techniques such as high-pressure homogenisation in buffer solution. The supernatant obtained by centrifugation gives the crude enzyme solution. For example, the enzyme of the present invention can be obtained in a supernatant produced by centrifugation at 38,000×g for 20 minutes.

In an alternative embodiment, the cytochrome P450 enzyme or variant thereof wherein the amino acid residue at position 291 is not threonine is expressed by at least one recombinant microorganism comprising heterologous nucleic acid encoding the enzyme, derived from *Amycolatopsis lurida* (NRRL 2430).

Here, the at least one recombinant microorganism can be dosed with an organic compound to be hydroxylated. This method may optionally comprise a purification step to obtain the hydroxylated compound.

In a preferred embodiment, this can be achieved by the recombinant expression of the functional cytochrome P450aluC09 protein with intact haem. This can be expressed with any or all of the cofactor enzymes. In a particularly preferred embodiment, ferredoxin and ferredoxin reductase may be expressed. This can be achieved by polycistronic plasmid use or via fusion-protein, either via linkers or directly into a single protein product.

Alternatively, the functional mutant cytochrome P450aluC09 protein, or variant thereof, wherein the amino acid residue at position 291 is not threonine, may be expressed alone without mixing with cofactor enzymes. In a preferred embodiment, cofactor enzymes may be titrated in to provide the active enzyme reaction after material production. The cofactors may be obtained by extraction from wild-type or recombinant materials derived from plants or microbial fermentation. Hussain & Ward, Appl Environ Microbiol. 2003; 69(1):373-382, describe the cloning techniques that may be used.

The native organism, host strain expressing the recombinant enzyme or extracted enzyme is contacted directly with the substrate, preferably in an aqueous medium, either mono, bi or triphasic, with such multiphase systems being either in dispersed or layered form. Reaction conditions, including choice of pH and temperature will be evident to the skilled person, based on conventional techniques. For example, a selected microbial growth medium or phosphate buffer solution at a pH value in the range of from 5 to 12, more preferably 6.5 to 11.0, most preferably around 7.4 may be used. Of particular note is the activity of this recombinant enzyme at elevated pH values e.g., pH value of 11. The ability to catalyse reactions at such a pH affords a particular commercial advantage because increased substrate loading may be achieved for selected substrates with improved solubility at a higher pH, such as compounds with a carboxyl moiety. Other advantages of catalysis at higher pH are the ability to directly utilise the product from a prior step resulting in such products, such as chemical synthesis, base-catalysed hydrolysis of a feedstock, or reaction product from another enzyme where increasing pH has been used to stop that reaction. The reaction temperature is preferably within the range from 10° to 45° C., more preferably from 25° to 30° C. The concentration of the substrate in the reaction medium is preferably within the range from 0.01 to 5.0% by weight. The time allowed for the reaction is normally from 1 minute to 5 days, more usually from 1 hour to 16 hours, although this may vary, depending upon the concentration of substrate in the reaction mixture, the reaction temperature, and other factors. The extracted enzyme material can either be used directly after extraction, after storage in frozen solution. In a particularly preferred embodiment, the extracted enzyme material can be dried, preferably by lyophilisation, for later use with or without the addition of other components required for reaction, such as other enzyme cofactor components.

After completion of the conversion reaction, the hydroxylated compound can be isolated using conventional procedures, including, for instance, filtration, solvent extraction, chromatography, crystallization, and other isolation procedures. Such procedures will be selected having due regard to the identity of the product. Before, during or after the isolation, the product may or may not be derivatised, as desired.

The starting materials as substrates for the enzyme may by either derived from synthetic routes, naturally occurring, either via natural biomass such as plant material, or produced by fermentation, or by mixed routes thereof. Enzyme reactions can also be performed using pure or non-purified materials, the resulting reaction may be used to aid later purifications of reacted or unreacted components.

Of the substrate compounds used as starting materials, free bases, alkali metal salts, e.g. the sodium or potassium salts, or acid salts of organic or inorganic nature such as tosylate or hydrochlorides, are suitable for use.

After completion of the conversion reaction, the desired compound can be obtained from the reaction system, collected, isolated and purified by conventional means if required, or onward used directly in unpurified form. For example, the reaction product is centrifuged or filtered and the supernatant or filtrate is extracted with a hydrophobic resin, ion-exchange resin or water-immiscible organic solvent such as ethyl acetate. After evaporation of the solvent of the extract, the remaining crude hydroxylated compound, for example the remaining crude hydroxylated tert-butyl compound, may be purified by subjecting it to column chromatography using silica gel or alumina or reversed-phase stationary phase, and by eluting with a suitable eluent. If the starting material is a mixture, then the product can be isolated as a mixture of hydroxylated compounds which if desired can be separated using chromatography or other suitable techniques.

In general, the hydroxylated compounds may have improved pharmaceutical or agrochemical properties, such as bioactivity potency, improved solubility characteristics, reduced off-target interactions, or simply of further utility, such as for onward synthesis, or be useful for an analytical standard. Particularly preferred are the hydroxylated compounds of formulas (I) & (II) discussed above.

The present invention is further illustrated with reference to two classes of substrates of markedly different structure, namely aromatic-tBu compounds such as bosentan, and compounds in which the tBu is not directly bonded to an aromatic carbo-cycle system such as buparvaquone.

When the cytochrome P450 enzyme preparation of this invention is reacted with diclofenac as substrate at pH 7.4 for 5 minutes with (a) ferredoxin, (b) ferredoxin-$NADP^+$-reductase, (c) $NADP^+$, (d) NADPH regeneration system, and (e) dissolved oxygen, the temperature of reaction ranges at least from 4° C. to 60° C. The optimum pH for each cytochrome ranges from 6.5 to 11.0. Each cytochrome is stable when kept for 24 hours at 4° C. at pH 7.4.

The use of ferredoxin, ferredoxin-$NADP^+$-reductase, oxygen and NADPH is not essential. Any components which can activate the cytochrome P450 may be adopted.

Measurement of the enzyme activity is normally effected in one of two ways:

(i) Measurement on Cytochrome $P450_{aluC09}$

Measurement is performed according to the method of Omura and Sato et al. (J Biol Chem, 239. 1964, 2370). That is to say, cytochrome $P450_{aluC09}$ is analyzed quantitatively using the following formula, based on the difference in the absorbance of the reduced CO versus the reduced difference spectrum at 450 nm and 490 nm.

$$\text{Cytochrome P450 (mM)} = \frac{\text{Abs(450 nm)} - \text{Abs(490 nm)}}{91(\text{mM cm}^{-1}) \times l(\text{cm})}$$

(ii) Measurement of Rate of Formation of Hydroxylated Diclofenac Derivatives from Diclofenac The following cocktail of components is employed:

| | |
|---|---|
| Potassium phosphate buffer pH 7.4 | 50 mM |
| $MgCl_2$ | 5 mM |
| Enzyme solution containing expressed Fd, FdR, P450 concentration as extracted | native |
| $NADP^+$ | 1 mM |
| Glucose-6-phosphate | 5 mM |
| Glucose-6-phosphate dehydrogenase | 2 UN/ml |
| Diclofenac substrate | 0.125 mg/ml |
| Total volume | 0.50 ml |

To measure enzyme activity the components of the table are mixed, the solution is shaken at 30° C. for 16-20 hours, and then 500 μl of acetonitrile is added and the reaction stopped. The amount of hydroxy-diclofenac formed by the enzyme system is determined with HPLC or UPLC.

Using the test methods for determining activity, the loss of activity with change in temperature and pH can be determined.

For example, the cytochrome is fully inactivated at pH 7.4 and 70° C. for 60 minutes in the presence of 20% glycerol and 2 mM dithiothreitol. The cytochrome is inactivated at pH 3 or a more acidic pH.

In a further aspect, the invention provides a kit comprising i) a cytochrome P450 enzyme comprising SEQ ID NO: 110, or a variant enzyme having at least 70% identity thereto and having CYP450 activity, or ii) a microorganism that expresses a cytochrome P450 enzyme comprising SEQ ID NO: 110, or a variant enzyme having at least 70% identity thereto and having CYP450 activity, wherein the amino acid residue at position 291 is not threonine and wherein the kit further comprises instructions for use for the hydroxylation of an organic compound.

The kit allows the user to screen for the hydroxylation of compounds of interest.

In a preferred embodiment, the kit further comprises electron donating agents. The kit may preferably comprise as the electron donating agents ferredoxin reductase and a ferredoxin with cofactors NADH or NADPH or cofactor regeneration systems such as NAD+ or NADP+, glucose or glucose-6-phosphate, and glucose-dehydrogenase or glucose-6-phosphate dehydrogenase. However, any suitable electron donating agents may be used.

Optionally, the kit may further comprise a buffer, either separately or contained with the other components.

Preferably, the kit may further comprise one or more other CYP450 enzymes.

Preferably, the cytochrome P450 enzyme or microorganism is lyophilised or immobilised or tethered to other macromolecules or support materials such alginate beads, Nickel columns and electrochemical electrodes.

The methods of the present invention are demonstrated in the examples below. These examples are provided as an illustration only and should not be construed as limiting on the present invention.

EXAMPLES

Example 1: Cloning of $P450_{aluC09}$ T291 Mutants

PCR-Based Site Directed Mutagenesis

Site directed mutagenesis by PCR of position T291 in $P450_{aluC09}$ was performed in which the individual threonine codon was altered to a new amino acid. Seven new amino acids were chosen to modify position 291. The sequences of primers used for amplification and mutagenesis are shown in Table 1. Two 23 mer oligonucleotides were designed that are complementary to the sequences surrounding the ACG triplet encoding the threonine residue.

TABLE 1

| Mutant | Primer Sequences |
|---|---|
| Mutant 11 (T291D) | 5'-GATCGCGGAAGATGCGACCTCAC-3' (SEQ ID NO: 5) <br> 5'-GTGAGGTCGCATCTTCCGCGATC-3' (SEQ ID NO: 6) |
| Mutant 12 (T291E) | 5'-GATCGCGGAAGAAGCGACCTCAC-3' (SEQ ID NO: 9) <br> 5'-GTGAGGTCGCTTCTTCCGCGATC-3' (SEQ ID NO: 10) |
| Mutant 17 (T291N) | 5'-GATCGCGGAAAACGCGACCTCAC-3' (SEQ ID NO: 13) <br> 5'-GTGAGGTCGCGTTTTCCGCGATC-3' (SEQ ID NO: 14) |
| Mutant 18 (T291Q) | 5'-GATCGCGGAACAGGCGACCTCAC-3' (SEQ ID NO: 17) <br> 5'-GTGAGGTCGCCTGTTCCGCGATC-3' (SEQ ID NO: 18) |
| Mutant 19 (T291A) | 5'-GATCGCGGAAGCGGCGACCTCAC-3' (SEQ ID NO: 21) <br> 5'-GTGAGGTCGCCGCTTCCGCGATC-3' (SEQ ID NO: 22) |
| Mutant 20 (T291V) | 5'-GATCGCGGAAGTGGCGACCTCAC-3' (SEQ ID NO: 25) <br> 5'-GTGAGGTCGCCACTTCCGCGATC-3' (SEQ ID NO: 26) |
| Mutant 21 (T291Y) | 5'-GATCGCGGAATATGCGACCTCAC-3' (SEQ ID NO: 29) <br> 5'-GTGAGGTCGCATATTCCGCGATC-3' (SEQ ID NO: 30) |
| Mutant 31 (T291S) | 5'-GATCGCGGAAAGCGCGACCTCAC-3' (SEQ ID NO: 33) <br> 5'-GTGAGGTCGCGCTTTCCGCGATC-3' (SEQ ID NO: 34) |
| Mutant 32 (T291L) | 5'-GATCGCGGAACTGGCGACCTCAC-3' (SEQ ID NO: 37) <br> 5'-GTGAGGTCGCCAGTTCCGCGATC-3' (SEQ ID NO: 38) |
| Mutant 33 (T291I) | 5'-GATCGCGGAAATTGCGACCTCAC-3' (SEQ ID NO: 41) <br> 5'-GTGAGGTCGCAATTTCCGCGATC-3' (SEQ ID NO: 42) |
| Mutant 34 (T291M) | 5'-GATCGCGGAAATGGCGACCTCAC-3' (SEQ ID NO: 45) <br> 5'-GTGAGGTCGCCATTTCCGCGATC-3' (SEQ ID NO: 46) |
| Mutant 35 (T291P) | 5'-GATCGCGGAACCGGCGACCTCAC-3' (SEQ ID NO: 49) <br> 5'-GTGAGGTCGCCCGGTTCCGCGATC-3' (SEQ ID NO: 50) |
| Mutant 36 (T291F) | 5'-GATCGCGGAATTTGCGACCTCAC-3' (SEQ ID NO: 53) <br> 5'-GTGAGGTCGCAAATTCCGCGATC-3' (SEQ ID NO: 54) |
| Mutant 37 (T291W) | 5'-GATCGCGGAATGGGCGACCTCAC-3' (SEQ ID NO: 57) <br> 5'-GTGAGGTCGCCCATTCCGCGATC-3' (SEQ ID NO: 58) |

TABLE 1-continued

| Mutant | Primer Sequences |
|---|---|
| Mutant 38 (T291H) | 5'-GATCGCGGAACATGCGACCTCAC-3' (SEQ ID NO: 61) <br> 5'-GTGAGGTCGCATGTTCCGCGATC-3' (SEQ ID NO: 62) |
| Mutant 39 (T291K) | 5'-GATCGCGGAAAAAGCGACCTCAC-3' (SEQ ID NO: 65) <br> 5'-GTGAGGTCGCTTTTTCCGCGATC-3' (SEQ ID NO: 66) |
| Mutant 40 (T291R) | 5'-GATCGCGGAACGCGCGACCTCAC-3' (SEQ ID NO: 69) <br> 5'-GTGAGGTCGCGCGTTCCGCGATC-3' (SEQ ID NO: 70) |

This method used pQR368bb-aluC09-aluF03 as the template DNA and mutagenic primers. PCR reactions contained 12.5 µl of Phusion® High-Fidelity PCR Master Mix (1 U/µl; New England Biolabs), 2 ng of template DNA, 1.25 µl DMSO, 0.5 µM of each forward and reverse primer and the reaction was filled up to a total volume of 25 µl with MilliQ®-H$_2$O. Since the whole of the plasmid was amplified leading to long PCR products, reactions were supplemented with 5% DMSO. Amplification reactions were identical for all mutagenic reactions, with the exception of annealing temperatures which varied as follows: 58° C. for mutants 11, 12, 61° C. for mutant 17, 62° C. for mutants 18, 20, 64° C. for mutant 19, and 60° C. for mutant 21. Reactions were performed on a Techne™ TC-512 Thermal Cycler with the following cycling conditions: 98° C. for 30 seconds, 16 cycles (98° C. for 30 seconds, annealing temperature for 1 minute, 72° C. for 8 minutes), 72° C. for 10 minutes. Amplifications were then subjected to DpnI digestion.

DpnI Digestion

One microliter of DpnI (20 U/µl; New England Biolabs), 1 µl Cutsmart buffer (New England Biolabs) was added to 8 µl of the PCR reaction. Unmutated template DNA was digested for 60 min at 37° C.

Cloning of Mutants

DpnI reactions were used to transform 50 µl chemically competent E. coli DH5α cells. Clones were selected on lysogeny broth (LB) plates containing 100 µg/ml ampicillin after 16 hours of incubation at 37° C. Clones were picked and cultivated in 5 ml LB containing 100 µg/ml ampicillin for 16 hours at 37° C. and 250 rpm. Recombinant plasmids were isolated from these cultures using the QIAprep® Spin Miniprep Kit (Qiagen) and analysed via DNA sequencing.

DNA Sequencing and Analysis

DNA sequences of the cloned mutants and the reductase part of the pQR368bb vector backbone were confirmed by Sanger sequencing at Eurofins Genomics (Germany).

Example 2: Cloning of P450$_{aluC09}$ Double Point Mutants

PCR-Based Site Directed Mutagenesis

Site directed mutagenesis by PCR of position T291 in P450$_{aluC09}$ was performed in which the individual threonine codon was altered to a new amino acid. This created Mutant 12 (T291E) as described in Example 1. This mutant was then used as the template DNA for further site directed mutagenesis of positions A47, M75 and V315, thus producing the double point mutants 22-30. The sequences of primers used for amplification and mutagenesis are shown in Table 2. Two 23 mer oligonucleotides were designed that are complementary to the sequences surrounding the ACG triplet encoding the threonine residue.

This method used P450$_{aluC09}$ T291E (Mutant 12) as the template DNA and mutagenic primers. PCR reactions contained 12.5 µl of Phusion® High-Fidelity PCR Master Mix (1 U/µl; New England Biolabs), 2 ng of template DNA, 1.25 µl DMSO, 0.5 µM of each forward and reverse primer and the reaction was filled up to a total volume of 25 µl with MilliQ®-H$_2$O. Since the whole of the plasmid was amplified leading to long PCR products, reactions were supplemented with 5% DMSO. Amplification reactions were identical for all mutagenic reactions, with the exception of annealing temperatures which varied as follows: 52° C. for mutants 23, 24, 64° C. for mutants 22, 25, 28, 30, 66° C. for mutant 29, and 69° C. for mutants 26, 27. Reactions were performed on a Techne™ TC-512 Thermal Cycler with the following cycling conditions: 98° C. for 30 seconds, 16 cycles (98° C. for 30 seconds, annealing temperature for 1 minute, 72° C. for 8 minutes), 72° C. for 10 minutes. Amplifications were then subjected to the same DpnI digestion, cloning of mutants and DNA sequencing and analysis as in Example 1.

TABLE 2

| Mutant | Primer Sequences |
|---|---|
| Mutant 22 (T291E, A47W) | 5'-AACGGCTTGGTGGCTCACCCGGC-3' (SEQ ID NO: 73) <br> 5'-GCCGGGTGAGCCACCAAGCCGTT-3' (SEQ ID NO: 74) |
| Mutant 23 (T291E, A47F) | 5'-AACGGCTTGGTTTCTCACCCGGC-3' (SEQ ID NO: 77) <br> 5'-GCCGGGTGAGAAACCAAGCCGTT-3' (SEQ ID NO: 78) |
| Mutant 24 (T291E, A47I) | 5'-AACGGCTTGGATTCTCACCCGGC-3' (SEQ ID NO: 81) <br> 5'-GCCGGGTGAGAATCCAAGCCGTT-3' (SEQ ID NO: 82) |
| Mutant 25 (T291E, M75F) | 5'-GTTCCCGCTGTTTGTCGCGCGGC-3' (SEQ ID NO: 85) <br> 5'-GCCGCGCGACAAACAGCGGGAAC-3' (SEQ ID NO: 86) |
| Mutant 26 (T291E, M75W) | 5'-GTTCCCGCTGTGGGTCGCGCGGC-3' (SEQ ID NO: 89) <br> 5'-GCCGCGCGACCCACAGCGGGAAC-3' (SEQ ID NO: 90) |
| Mutant 27 (T291E, M75A) | 5'-GTTCCCGCTGGCGGTCGCGCGGC-3' (SEQ ID NO: 93) <br> 5'-GCCGCGCGACCGCCAGCGGGAAC-3' (SEQ ID NO: 94) |
| Mutant 28 (T291E, V315I) | 5'-GGAAGGGGTGATTGGCCTGAGCA-3' (SEQ ID NO: 97) <br> 5'-TGCTCAGGCCAATCACCCCTTCC-3' (SEQ ID NO: 98) |
| Mutant 29 (T291E, V315A) | 5'-GGAAGGGGTGGCGGGCCTGAGCA-3' (SEQ ID NO: 101) <br> 5'-TGCTCAGGCCCGCCACCCCTTCC-3' (SEQ ID NO: 102) |
| Mutant 30 (T291E, V315L) | 5'-GGAAGGGGTGCTGGGCCTGAGCA-3' (SEQ ID NO: 105) <br> 5'-TGCTCAGGCCCAGCACCCCTTCC-3' (SEQ ID NO: 106) |

Example 3: Expression of Mutants

Construction of the Recombinant Expression Strain

The strain *E. coli* BL21 (DE3) (Invitrogen) was used as a host for recombinant expression of mutant variants of P450$_{aluC09}$, ferredoxin$_{aluF03}$ and ferredoxin reductase$_{SCF15A}$. To construct this expression strain, *E. coli* BL21 (DE3) cells were transformed with plasmid using the heat shock procedure. Twenty five microliters of chemically competent cells were mixed with 1 µl (~100 ng) of mutant plasmid followed by incubation on ice for 30 minutes. Heat shock was performed for 30 seconds in a water bath at 42° C. and cells were subsequently chilled on ice for 2 min. After the addition of 950 µl LB Miller Media (Sigma), cells were incubated for 1 hour at 37° C. and 250 rpm in a New Brunswick Scientific Innova 4230. Two hundred microliters of the transformation mixture was plated on LB plates containing 100 µg/ml ampicillin. Plates were incubated at 37° C. for approximately 16 hours.

Expression of Recombinant Mutant AluC09, AluF03 and SCF15A

To prepare glycerol stocks of this expression strain, a streak of colonies were picked and inoculated into 5 ml LB containing 100 µg/ml ampicillin and cultivated at 37° C. and 250 rpm for approximately 16 hours. Five hundred microliter of this culture were mixed with 500 µl of 50% glycerol (weight: vol) in cryovials and stored at −80° C.

Preculture: Five milliliters of LB Miller media supplemented with 100 µg/ml of ampicillin was inoculated with a loop scraped from a cryovial containing of *E. coli* BL21 (DE3) harbouring the mutant plasmid. Cells were grown overnight at 37° C. and 250 rpm in a New Brunswick Scientific Innova 4230.

Seed: Into a 250 ml baffled flask, 50 ml of PCM8.1 media supplemented with 100 µg/ml of ampicillin was inoculated with the overnight preculture to an OD600 of 0.1 and incubated at 37° C. and 200 rpm until the end of the day. The components of PCM8.1 were MgSO$_4$ (0.49 gL$^{-1}$), Na$_2$HPO$_4$*7H$_2$O (6.7 gL$^{-1}$), KH$_2$PO$_4$ (3.4 gL$^{-1}$), NH$_4$Cl (2.68 gL$^{-1}$), Na$_2$SO$_4$ (0.71 gL$^{-1}$), arginine (0.2 gL$^{-1}$), histidine (0.15 gL$^{-1}$), lysine (0.2 gL$^{-1}$), phenylalanine (0.2 gL$^{-1}$), serine (0.2 gL$^{-1}$), threonine (0.2 gL$^{-1}$), tryptophan (0.2 gL$^{-1}$), methionine (0.2 gL$^{-1}$), monosodium glutamate (8 gL$^{-1}$), glucose (0.5 gL$^{-1}$), glycerol (10 gL$^{-1}$) and a 1000-fold diluted trace element solution with FeCl3 (81.1 gL$^{-1}$), CaCl$_2$*6H$_2$O (4.38 gL$^{-1}$), MnCl$_2$*4H$_2$O (1.98 gL$^{-1}$), ZnSO$_4$*7H$_2$O (2.88 gL$^{-1}$), CoCl$_2$*6H$_2$O (0.48 gL$^{-1}$), CuCl$_2$*2H$_2$O (0.34 gL$^{-1}$), NiCl$_2$*6H$_2$O (0.48 gL$^{-1}$), Na$_2$MoO$_4$*2H$_2$O (0.48 gL$^{-1}$), Na$_2$SeO$_3$ (0.35 gL$^{-1}$), and H$_3$BO$_3$ (0.12 gL$^{-1}$).

Production: At the end of the day, a 1 L baffled flask containing 200 mL of PCM8.1 media supplemented with 100 µg/ml of ampicillin, 23.8 µg/ml of IPTG, 320 µg/ml of 5'-aminolevulinic acid and 55 µg/ml of FeSO$_4$*7H$_2$O were inoculated with the seed cultures to an OD of 0.6. The induced production cultures were incubated at 27° C. and 200 rpm until the cultures had reached stationary phase (approximately 16-20 hours). The cultures were harvested by centrifugation at 3,000 rpm for 15 minutes. The pellets were washed with 30 mL of wash buffer (isotonic 0.85% NaCl with 5% glycerol) and transferred into a fresh 50 mL falcon tube. The cells were further centrifuged at 4,000 rpm for 25-35 minutes and the pellet was stored at −20° C. for processing.

Example 4: Extraction & Processing of Enzyme Materials

Suspended cell pellets were provided as described in Example 3, containing recombinant mutants of CYP450$_{aluC09}$, ferredoxin$_{aluF03}$ and ferredoxin reductases$_{CF15A}$ in 50 mM potassium phosphate buffer pH 7.4, 5 mM MgC$_2$, 0.1 mM TCEP, and 1 mM PMSF in a ratio of 15 ml of buffer per 1 g of cells. Lysed cells were produced by high pressure disruption using three cycles of 30 kpsi. Lysed material was centifuged at 38,000×g for 40 minutes (4° C.) and the supernatant was sterilized by passing through 0.22 micron filter to provide the enzyme preparation containing the recombinant mutant CYP450$_{aluC09}$ The crude extract was then dispensed into glass vials (0.5 ml per 2 ml vial), frozen and lyophilised using an Edwards Supermodulyo Freeze-dryer before being stored in a standard laboratory freezer at −20° C. until required for use.

Example 5: Biocatalytic Activity/Spectrum Testing

Lyophilised material of mutants of CYP450aluC09, ferredoxinaluF03 and ferredoxin reductaseSCF15A was made as described in examples 3 and 4 and suspended in water (0.5 mL per vial) and biocatalysis was performed at 27° C. in the following conditions: 50 mM potassium phosphate pH 7.4, 5 mM MgCl2, 0.125 mg/ml substrate compound such as diclofenac (Sigma-Aldrich, UK), Aceclofenac (Tokyo Chemical Industry UK Ltd, UK), Indomethacin (Sigma-Aldrich, UK), Flufenamic acid (Sigma-Aldrich, UK), Napropamide (Sigma-Aldrich, UK), celecoxib (LC Laboratories, USA), valsartan (Tokyo Chemical Industry UK Ltd, UK), ruxolitinib (LC Laboratories, USA), 4-pyrrolidylacetophenone (Sigma-Aldrich, UK), tofacitinib (LC Laboratories, USA), bosentan (CarboSynth Ltd, UK), buparvaquone (MedChemtronica, Sweden), BIRB796 (Stratech Scientific Limited, UK), epothilone B (LC Laboratories, USA), ritonavir (Tokyo Chemical Industry UK Ltd, UK) or tivantinib (MedChemtronica, Sweden), P450AluC09 (concentration as in Table 8), 5 mM G6P, 1 mM NADP, 2 UN/ml G6PDH in a final volume of 100 µL. After 16-20 hours at 200 rpm (5 cm orbital shaker, Kuhner AG, Switzerland), reactions were extracted with an equal volume of acetonitrile, centrifuged to remove precipitated proteins and conversion assessed by UPLC-MS analysis.

UPLC data was obtained as follows:

Column: Acquity UPLC BEH Shield RP18 1.7 µm 2.1 mm i.d. 50 mm length

Solvents: H2O, B: Acetonitrile, both with 0.1% Formic acid

Flow rate: 1.0 ml/min

Detector: Waters Acquity UPLC PDA (UV-Vis detection) and Waters Acquity UPLC QDA (MS)

Figure 3B:
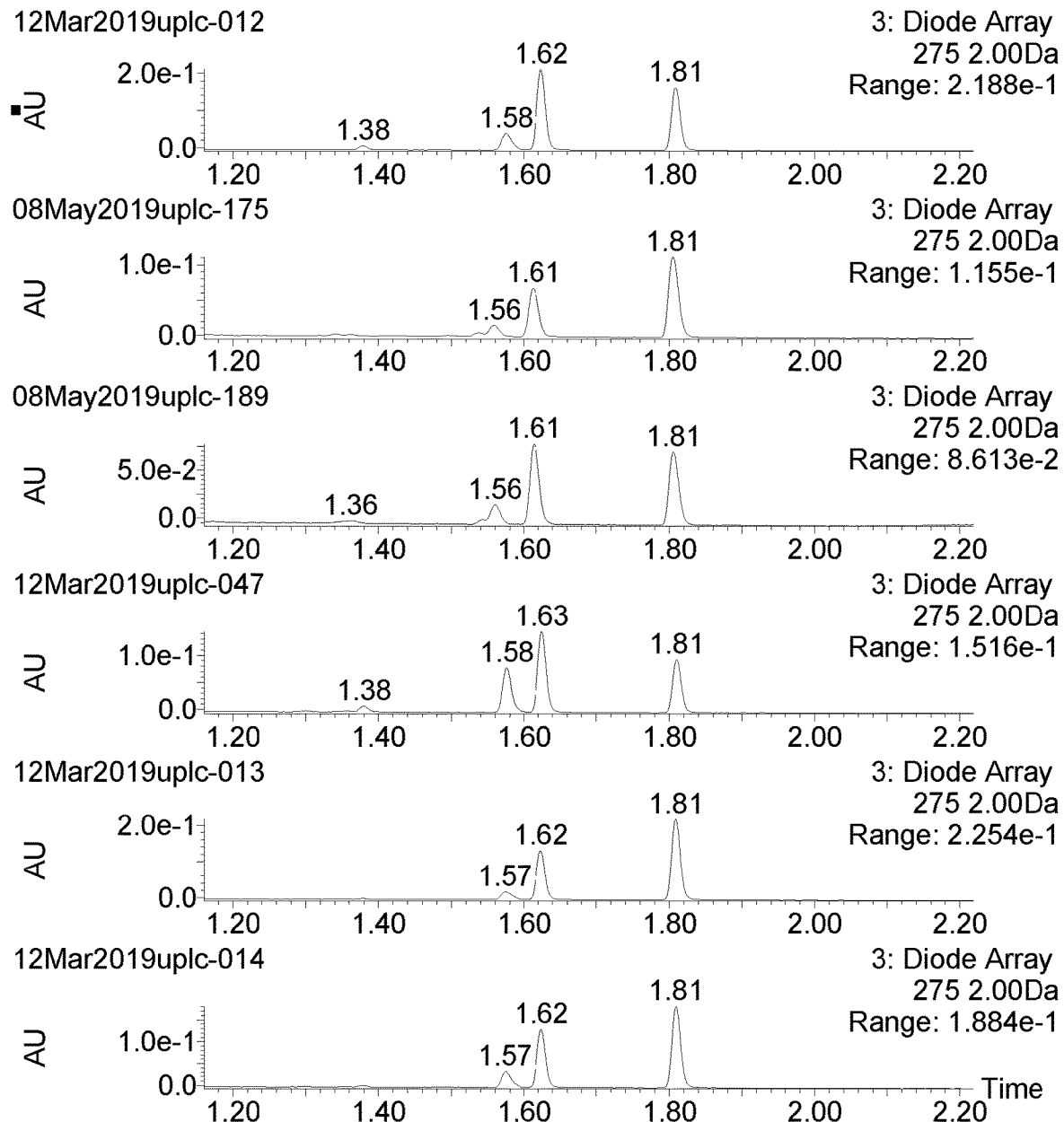
Figure 3C:
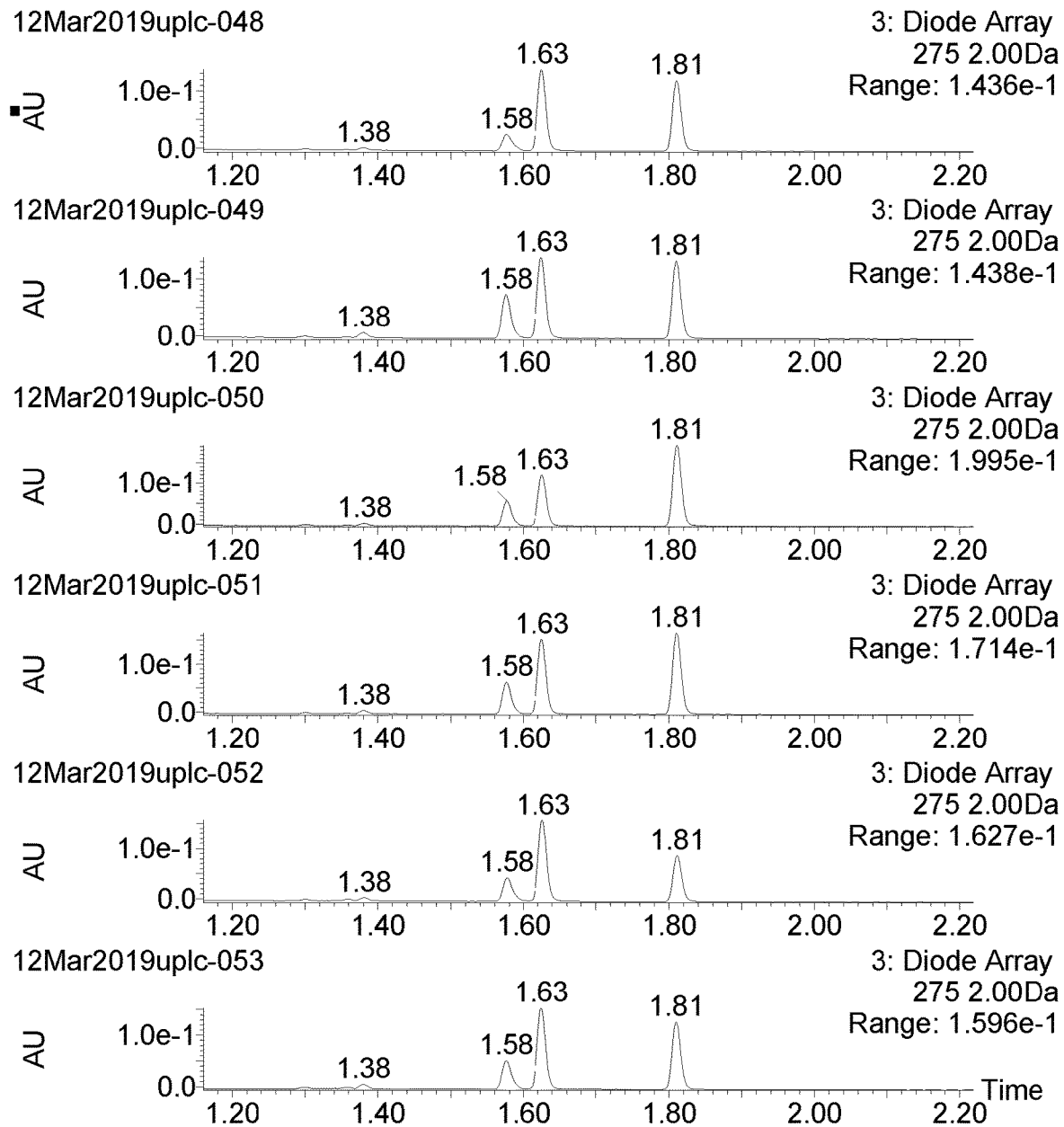

Illustrative results for the hydroxylation of diclofenac by CYP450aluC09 and selected T291x mutants are summarised below in Table 3 with representative chromatograms resented in FIG. 3a-c; retention times: diclofenac 1.85-1.88 minutes, 5-hydroxydiclofenac 1.60-1.63 minutes, 4'-hydroxydiclofenac 1.65-1.68 minutes, 4',5-dihydroxydiclofenac 1.40-1.42 minutes. The chromatographic retention times and mass spectra coincided with those of authentic samples. The change in the product ratio of 4'-hydroxydiclofenac (2): 5-hydroxydiclofenac (1) indicates an altered regioselectivity of aromatic hydroxylation for the catalysis for some of the mutants compared to CYP450aluC09, which is most notable for mutants M24, M33 and M35 showing over four-fold regioselectivity of hydroxylation.

Figure 4:
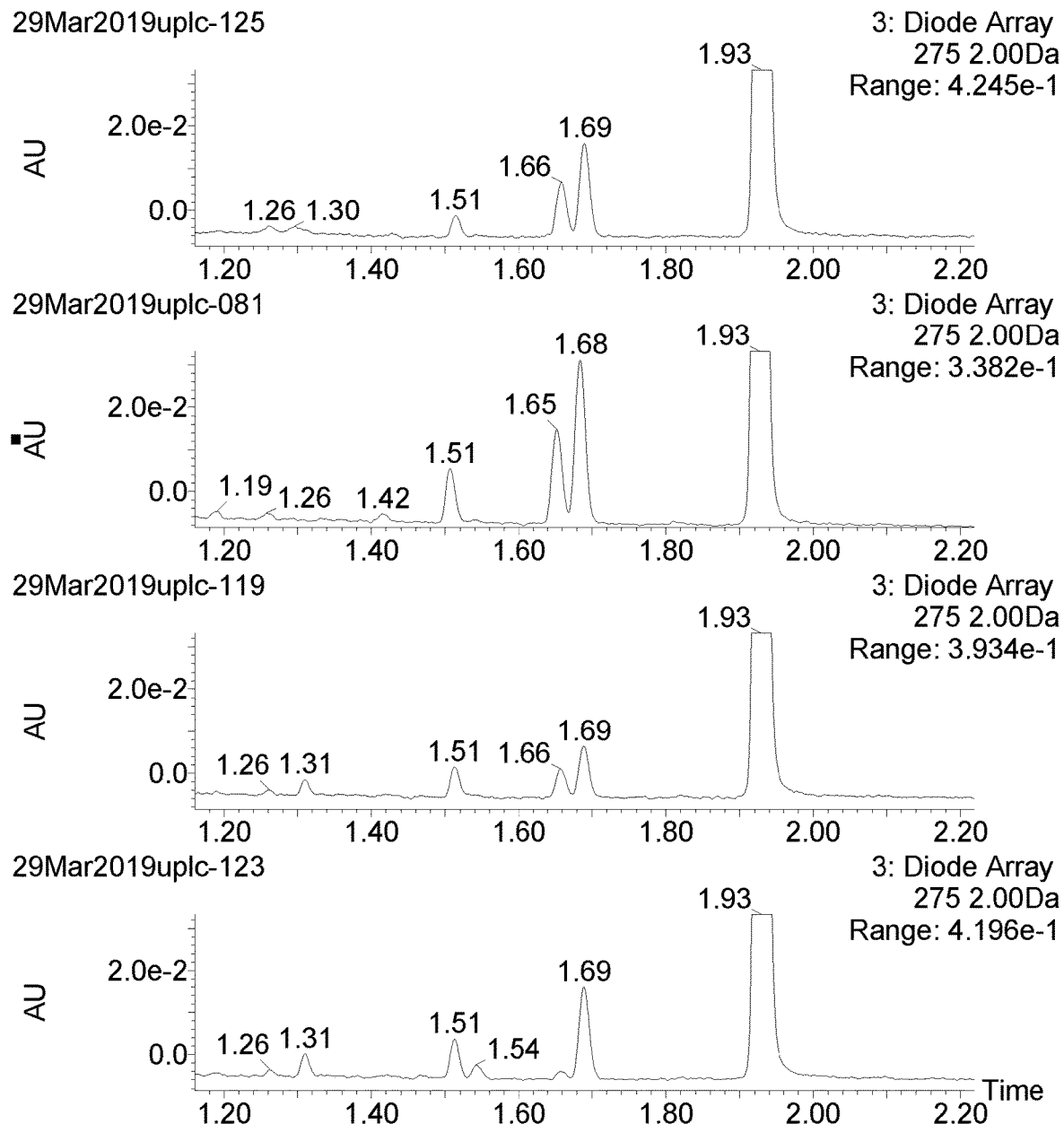
FIG. 4 shows UPLC chromatograms with UV detection at 275 nm showing the hydroxylation of flufenamic acid catalysed by, from top to bottom: cytochrome P450 aluC09 and mutants aluC09M18, aluC09M35 and aluC09M39.

Altered regioselectivity of aromatic hydroxylation is further demonstrated when using other substrates. Albeit of lower overall conversion yield, Table 4 show the changes in regioselectivity of hydroxylation of flufenamic acid, most notably illustrated in mutant M39 showing no detectable production of hydroxyl-flufenamic acid 2, absent at 1.65 minutes compared to the wild-type enzyme CYP450aluC09 and other mutants (FIG. 4). Flufenamic acid elutes at 1.93 minutes, hydroxy-flufenamic acid 1 elutes at 1.68 minutes and hydroxy-flufenamic acid 2 elutes at 1.65 minutes.

Figure 5A:
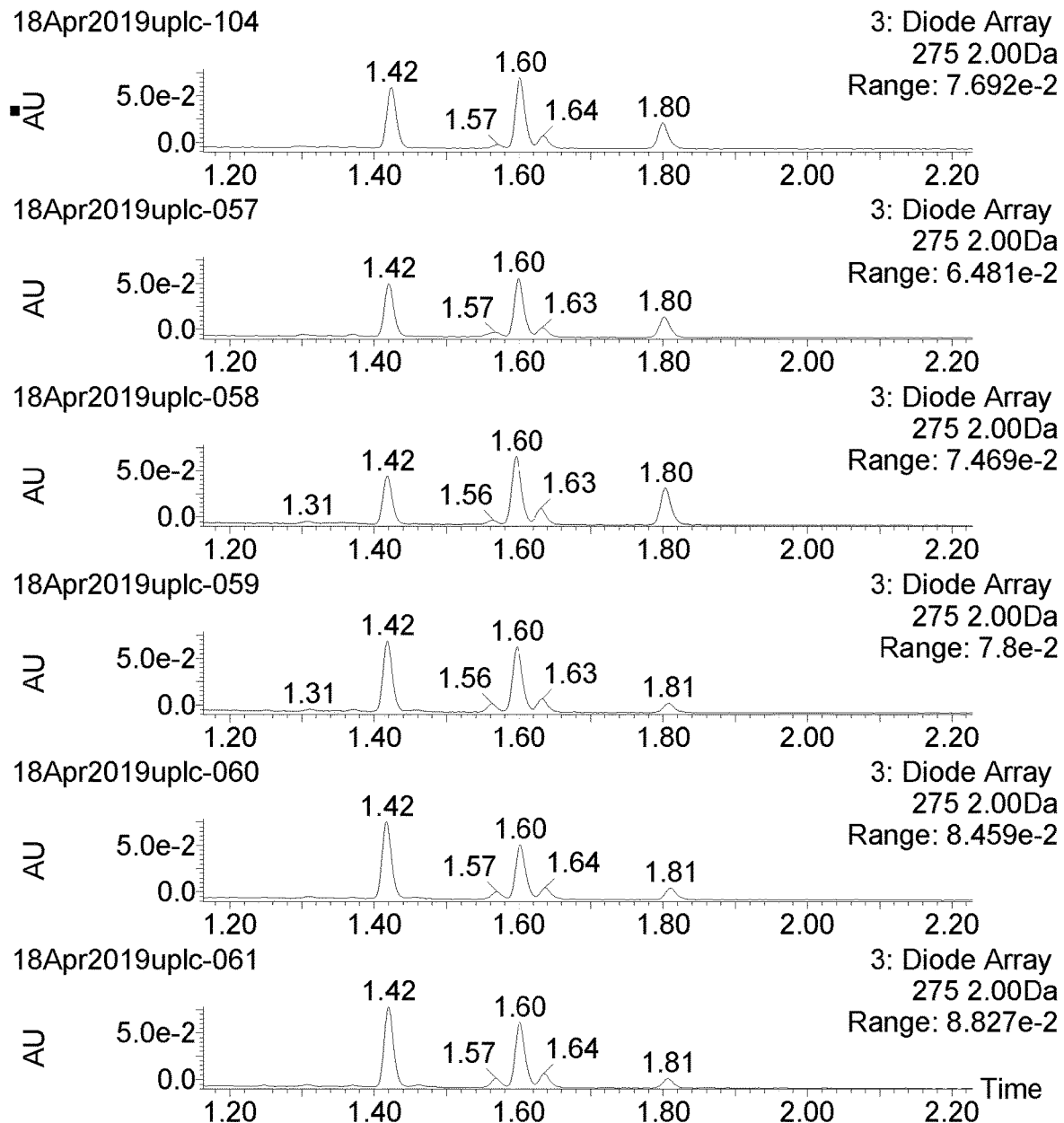
FIG. 5 shows UPLC chromatograms with UV detection at 275 nm for the hydroxylation of aceclofenac catalysed by various enzymes of the invention.
Figure 5B:
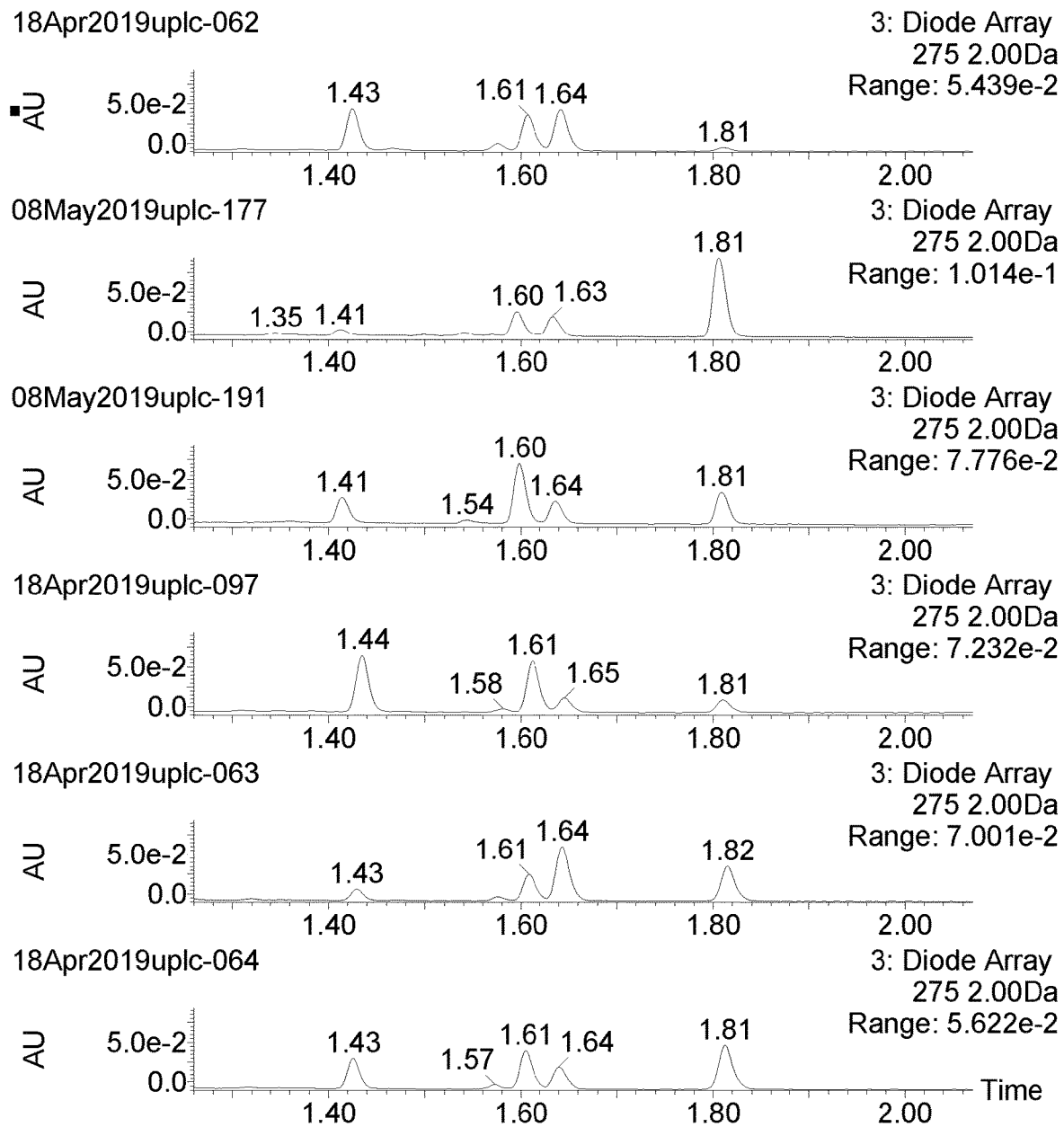
Figure 5C:
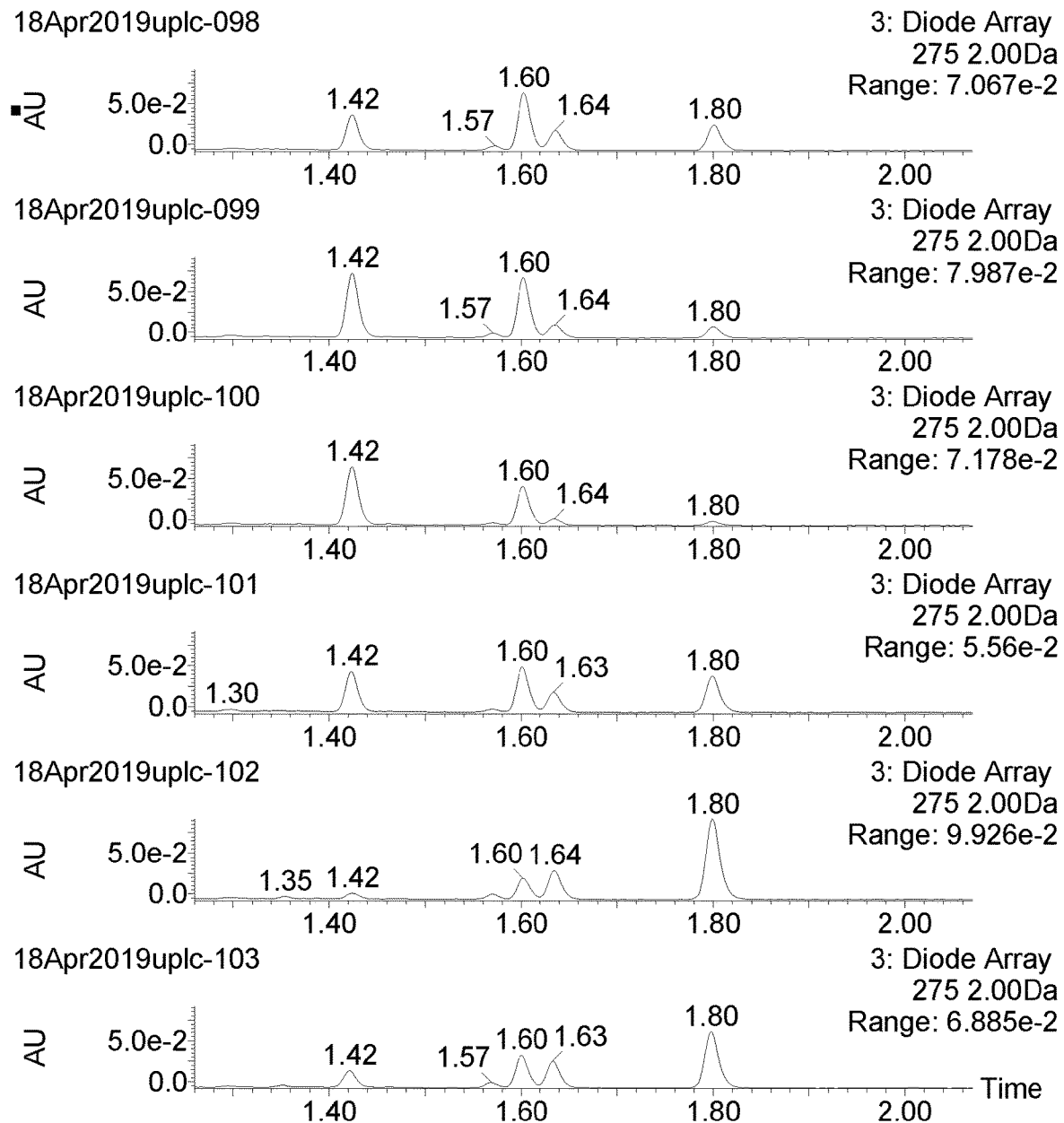

Table 5 show the changes in regioselectivity of hydroxylation of Aceclofenac, most notably illustrated in mutant M33 showing a reversal of the regioselectivity of hydroxylation of aceclofenac compared to the wild-type enzyme. Chromatograms are provided in FIGS. 5a-c; aceclofenac elutes at 1.80 minutes, hydroxy-aceclofenac acid 1 elutes at 1.64 minutes, hydroxy-aceclofenac acid 2 elutes at 1.60 minutes and dihydroxy-aceclofenac elutes at 1.42 minutes.

Figure 6:
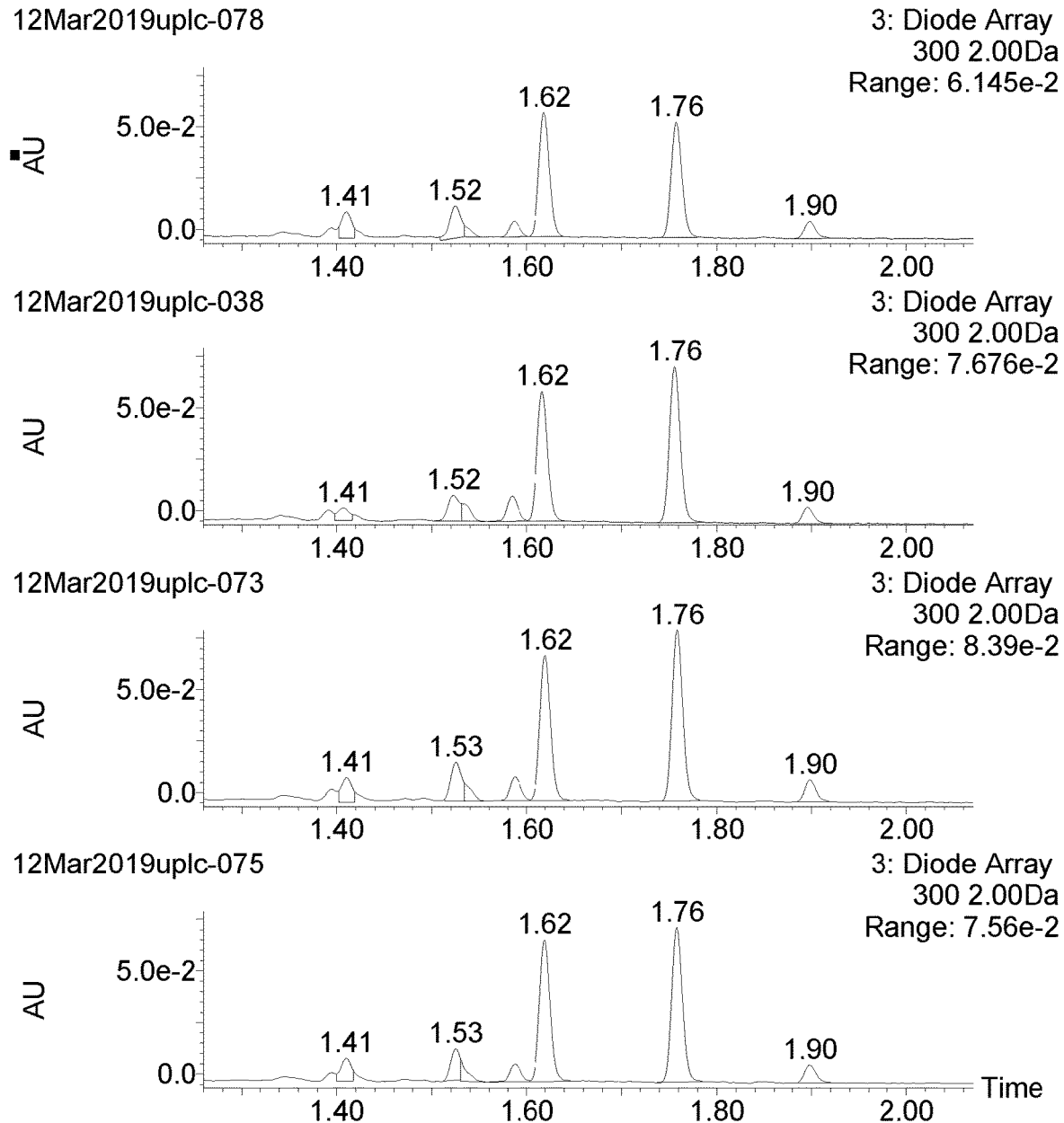
FIG. 6 shows UPLC chromatograms with UV detection at 300 nm for the metabolism of napropamide catalysed by various enzymes of the invention.

Despite the overriding reaction being the de-N-ethylation of the napropamide substrate, Table 6 show changes in regioselectivity of hydroxylation pattern of napropamide, most notably illustrated in mutants M34 and M38, showing changes in the ratio both downwards (1.1) and upwards (3.9), respectively, compared to the wild-type enzyme hydroxylation ration (2.1) whilst maintaining similar yield. Example chromatograms are provided in FIG. 6. Napropamide elutes at 1.76 minutes, unidentified metabolite (−2 Da) elutes at 1.90 minutes, desethyl-napropamide elutes at 1.62 minutes, hydroxy-napropamide 1 elutes at 1.53 minutes and hydroxy-napropamide 2 elutes at 1.52 minutes and the desethyl-hydroxy-napropamide product elutes at 1.41 minutes.

Further, the various mutants maintained ability to de-O-methylate indomethacin, as shown in Table 7 to varying degrees. Example UV and MS chromatograms are provided in FIG. 7.

Figure 8:
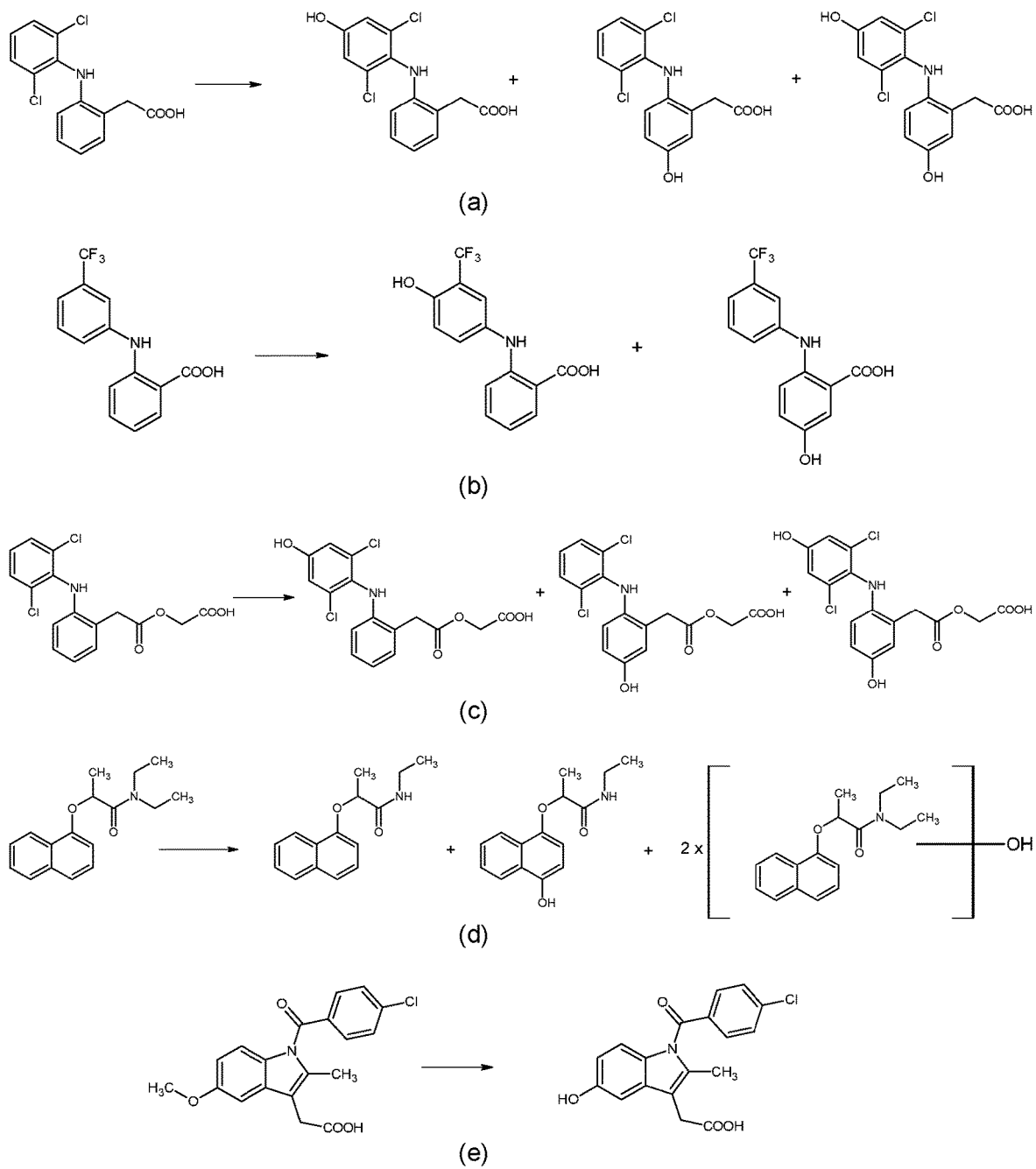
FIG. 8 shows the structural formulae of selected compounds utilised in Example 5.

Structural formulae of some of the substrates and products described above are provided in FIG. 8.

Furthermore, some of the mutants showed greater extent of reaction compared to the wild-type enzyme CYP450aluC09. Table 8 shows the extent of reaction for various additional substrates. The results demonstrate the influence the changing of the amino acid at residue T291 has on extent of substrate metabolism; the extent of reaction for a given mutation is substrate-dependent, no one mutation provides an improved conversion across the set of test substrates. However, of particular note when considering P450 concentration are the results for mutants M12, M20 and M34, as well as the deleterious impact on the range of substrate utility in mutants M39 and M40.

TABLE 3

Table 3: Hydroxylation of diclofenac catalysed by cytochrome P450 aluC09 mutants aluC09M11, aluC09M12, aluC09M17, aluC09M18, aluC09M19, aluC09M20, aluC09M24, aluC09M30, aluC09M31, aluC09M33, aluC09M34, aluC09M35, aluC09M36, aluC09M37, aluC09M38, aluC09M39, aluC09M40 compared to P450 aluC09 wild-type, as determined by UPLC-PDA-MS. Parent substrate and resulting products have altered UV absorption spectra due to the introduction of phenolic hydroxylation, therefore having different molar absorptivity at the selected wavelength; therefore percentages are for illustration purposes only.

| | | Diclofenac and metabolites % by UV peak area at 275nm | | | | |
|---|---|---|---|---|---|---|
| Cytochrome P450 | Mutation | Diclofenac (Substrate) 1.81 mins | 4'-hydroxy-diclofenac (1) 1.62 mins | 5-hydroxy-diclofenac (2) 1.58 mins | 4',5-dihydroxy-diclofenac 1.38 mins | Hydroxylated Ratio hydroxy 1:hydroxy 2 |
| aluC09M11 | T291D | 48.3 | 25.3 | 25.1 | 2.3 | 1.0 |
| aluC09M12 | T291E | 58.0 | 30.3 | 10.8 | 1.8 | 2.8 |
| aluC09M17 | T291N | 32.3 | 44.8 | 21.8 | 3.2 | 2.1 |
| aluC09M18 | T291Q | 41.6 | 45.5 | 12.3 | 1.9 | 3.7 |
| aluC09M19 | T291A | 34.8 | 50.0 | 14.2 | 2.4 | 3.5 |
| aluC09M20 | T291V | 34.8 | 50.1 | 13.7 | 3.1 | 3.7 |
| aluC09M24 | T291E, A47I | 57.0 | 34.2 | 8.0 | 1.8 | 4.3 |
| aluC09M30 | T291E, V315L | 41.6 | 43.4 | 13.0 | 3.6 | 3.3 |
| aluC09M31 | T291S | 32.3 | 43.3 | 22.8 | 3.3 | 1.9 |
| aluC09M33 | T291I | 63.3 | 29.5 | 6.7 | 1.1 | 4.4 |
| aluC09M34 | T291M | 53.6 | 35.3 | 10.4 | 1.3 | 3.4 |
| aluC09M35 | T291P | 48.2 | 41.3 | 9.9 | 0.9 | 4.2 |
| aluC09M36 | T291F | 33.0 | 42.8 | 23.0 | 3.6 | 1.9 |
| aluC09M37 | T291W | 51.8 | 31.4 | 15.9 | 1.9 | 2.0 |
| aluC09M38 | T291H | 35.6 | 44.5 | 18.9 | 2.9 | 2.4 |
| aluC09M39 | T291K | 41.4 | 42.8 | 14.6 | 2.1 | 2.9 |
| aluC09M40 | T291R | 48.8 | 35.7 | 14.3 | 2.2 | 2.5 |
| aluC09 | Wild Type | 45.2 | 27.0 | 26.2 | 3.1 | 1.0 |

TABLE 4

Hydroxylation of flufenamic acid catalysed by cytochrome P450 aluC09 mutants aluC09M11, aluC09M12, aluC09M17, aluC09M18, aluC09M19, aluC09M20, aluC09M24, aluC09M30, aluC09M31, aluC09M33, aluC09M34, aluC09M35, aluC09M36, aluC09M37, aluC09M38, aluC09M39, aluC09M40 compared to P450 aluC09 wild-type, as determined by UPLC-PDA-MS. Parent substrate and resulting products have altered UV absorption spectra due to the introduction of phenolic hydroxylation, therefore having different molar absorptivity at the selected wavelength; therefore percentages are for illustration purposes only.

| | | Flufenamic Acid and metabolites % by UV peak area at 275 nm | | | |
|---|---|---|---|---|---|
| Cytochrome P450 | Mutation | Flufenamic Acid (Substrate) 1.93 mins | Hydroxy-Flufenamic Acid (1) 1.69 mins | Hydroxy-Flufenamic Acid (2) 1.65 mins | Hydroxylated Ratio 1:2 |
| aluC09M11 | T291D | 94.7 | 3.4 | 1.9 | 1.8 |
| aluC09M12 | T291E | 95.9 | 2.0 | 2.1 | 0.9 |
| aluC09M17 | T291N | 94.4 | 3.4 | 2.2 | 1.6 |
| aluC09M18 | T291Q | 86.1 | 9.1 | 4.8 | 1.9 |
| aluC09M19 | T291A | 90.4 | 5.8 | 3.8 | 1.5 |
| aluC09M20 | T291V | 93.6 | 4.4 | 2.0 | 2.2 |
| aluC09M24 | T291E, A47I | 89.2 | 7.7 | 3.1 | 2.5 |
| aluC09M30 | T291E, V315L | 93.8 | 3.7 | 2.4 | 1.5 |
| aluC09M31 | T291S | 89.1 | 6.8 | 4.1 | 1.7 |
| aluC09M33 | T291I | 98.3 | 1.0 | 0.6 | 1.6 |
| aluC09M34 | T291M | 94.0 | 3.8 | 2.2 | 1.7 |
| aluC09M35 | T291P | 95.8 | 2.7 | 1.5 | 1.9 |
| aluC09M36 | T291F | 89.8 | 7.7 | 2.6 | 3.0 |
| aluC09M37 | T291W | 91.3 | 6.4 | 2.2 | 2.9 |
| aluC09M38 | T291H | 95.3 | 2.9 | 1.8 | 1.6 |
| aluC09M39 | T291K | 94.4 | 5.1 | 0.5 | 4.9 |
| aluC09M40 | T291R | 94.8 | 4.4 | 0.9 | 4.9 |
| aluC09 | Wild Type | 93.1 | 4.5 | 2.4 | 1.9 |

TABLE 5

Table 5: Hydroxylation of aceclofenac catalysed by cytochrome P450 aluC09 mutants aluC09M11, aluC09M12, aluC09M17, aluC09M18, aluC09M19, aluC09M20, aluC09M24, aluC09M30, aluC09M31, aluC09M33, aluC09M34, aluC09M35, aluC09M36, aluC09M37, aluC09M38, aluC09M39, aluC09M40 compared to P450 aluC09 wild-type, as determined by UPLC-PDA-MS. Parent substrate and resulting products have altered UV absorption spectra due to the introduction of phenolic hydroxylation, therefore having different molar absorptivity at the selected wavelength; therefore percentages are for illustration purposes only.

| | | Aceclofenac and metabolites % by UV peak area at 275 nm | | | | |
|---|---|---|---|---|---|---|
| Cytochrome P450 | Mutation | Aceclofenac (Substrate) (1.80 mins) | Hydroxy-Aceclofenac (1) (1.64 min) | Hydroxy-Aceclofenac (2) (1.60 min) | Dihydroxy-Aceclofenac (1.42 mins) | Hydroxylated Ratio 2:1 |
| aluC09M11 | T291D | 17.5 | 6.3 | 41.0 | 35.2 | 6.5 |
| aluC09M12 | T291E | 25.2 | 7.9 | 39.1 | 27.8 | 4.9 |
| aluC09M17 | T291N | 9.2 | 6.9 | 40.8 | 43.2 | 5.9 |
| aluC09M18 | T291Q | 10.2 | 5.9 | 34.9 | 49.1 | 5.9 |
| aluC09M19 | T291A | 6.7 | 6.5 | 38.5 | 48.3 | 5.9 |
| aluC09M20 | T291V | 4.2 | 33.1 | 27.6 | 35.1 | 0.8 |
| aluC09M24 | T291E, A47I | 63.4 | 14.3 | 17.4 | 5.0 | 1.2 |
| aluC09M30 | T291E, V315L | 24.1 | 15.0 | 42.5 | 18.4 | 2.8 |
| aluC09M31 | T291S | 12.3 | 8.5 | 36.1 | 43.1 | 4.2 |
| aluC09M33 | T291I | 30.8 | 41.7 | 18.6 | 8.8 | 0.4 |
| aluC09M34 | T291M | 36.6 | 15.2 | 26.8 | 21.3 | 1.8 |
| aluC09M35 | T291P | 21.8 | 12.2 | 39.4 | 26.6 | 3.2 |
| aluC09M36 | T291F | 9.3 | 7.2 | 38.9 | 44.6 | 5.4 |
| aluC09M37 | T291W | 4.2 | 4.5 | 35.3 | 56.0 | 7.8 |
| aluC09M38 | T291H | 29.8 | 11.9 | 29.4 | 28.9 | 2.5 |
| aluC09M39 | T291K | 63.7 | 18.6 | 13.3 | 4.4 | 0.7 |
| aluC09M40 | T291R | 46.3 | 19.7 | 21.4 | 12.7 | 1.1 |
| aluC09 | Wild Type | 18.0 | 5.7 | 39.8 | 36.5 | 7.0 |

TABLE 6

Table 6: Hydroxylation of napropamide catalysed by cytochrome P450 aluC09 mutants aluC09M11, aluC09M12, aluC09M17, aluC09M18, aluC09M19, aluC09M20, aluC09M31, aluC09M33, aluC09M34, aluC09M35, aluC09M36, aluC09M37, aluC09M38, aluC09M39, aluC09M40 compared to P450 aluC09 wild-type, as determined by UPLC-PDA-MS. Parent substrate and resulting products have altered UV absorption spectra due to the introduction of phenolic hydroxylation, therefore having different molar absorptivity at the selected wavelength; therefore percentages are for illustration purposes only.

| | | Napropamide and metabolites % by UV peak area at 275 nm | | | | | | |
|---|---|---|---|---|---|---|---|---|
| Cytochrome P450 | Mutation | Napropamide (substrate) | M-2Da (unidentified) (1.89 min) | Desethyl Napropamide (1.62 min) | Hydroxy-Napropamide (1) (1.53 min) | Hydroxy-Napropamide (2), (1.52 min) | Desethyl-hydroxy-Napropamide (1.41 min) | Hydroxylated Ratio 2:1 |
| aluC09M11 | T291D | 47.6 | 6.7 | 36.6 | 1.5 | 3.1 | 8.7 | 2.1 |
| aluC09M12 | T291E | 34.1 | 5.8 | 46.0 | 2.5 | 5.3 | 9.7 | 2.1 |
| aluC09M17 | T291N | 28.7 | 6.0 | 53.7 | 0.9 | 3.1 | 10.6 | 3.4 |
| aluC09M18 | T291Q | 38.3 | 5.7 | 49.5 | 1.4 | 2.5 | 4.1 | 1.8 |
| aluC09M19 | T291A | 34.3 | 6.1 | 50.1 | 2.3 | 3.9 | 4.9 | 1.7 |
| aluC09M20 | T291V | 25.3 | 4.7 | 56.2 | 2.1 | 6.1 | 7.6 | 2.9 |
| aluC09M31 | T291S | 37.9 | 7.0 | 44.8 | 2.4 | 5.1 | 4.6 | 2.1 |
| aluC09M33 | T291I | 56.0 | 5.1 | 30.6 | 1.8 | 4.1 | 5.7 | 2.3 |
| aluC09M34 | T291M | 44.0 | 5.3 | 40.7 | 3.4 | 3.7 | 5.3 | 1.1 |
| aluC09M35 | T291P | 51.0 | 5.3 | 36.6 | 1.2 | 3.6 | 4.8 | 3.0 |
| aluC09M36 | T291F | 46.8 | 6.3 | 40.5 | 1.2 | 3.5 | 3.1 | 3.0 |
| aluC09M37 | T291W | 47.3 | 6.0 | 40.1 | 1.6 | 3.3 | 3.3 | 2.1 |
| aluC09M38 | T291H | 41.1 | 6.2 | 45.6 | 1.0 | 3.9 | 3.8 | 3.9 |
| aluC09M39 | T291K | 78.2 | 2.3 | 16.3 | 1.4 | 1.6 | 0.7 | 1.2 |
| aluC09M40 | T291R | 80.6 | 2.4 | 12.9 | 2.3 | 1.8 | 0.4 | 0.8 |
| aluC09 | Wild Type | 39.3 | 6.6 | 44.8 | 2.0 | 4.0 | 5.4 | 2.1 |

TABLE 7

O-demethylation of indomethacin catalysed by cytochrome P450 aluC09 mutants aluC09M11, aluC09M12, aluC09M17, aluC09M18, aluC09M19, aluC09M20, aluC09M24, aluC09M30, aluC09M31, aluC09M33, aluC09M34, aluC09M35, aluC09M36, aluC09M37, aluC09M38, aluC09M39, aluC09M40 compared to P450 aluC09 wild-type, as determined by UPLC-PDA-MS. Parent substrate and resulting product have altered UV absorption spectra due to the resulting phenolic hydroxyl having different molar absorptivity at the selected wavelength; therefore percentages are for illustration purposes only.

| | | Indomethacin and metabolites % by UV peak area at 275 nm | |
|---|---|---|---|
| Cytochrome P450 | Mutation | Indomethacin (1.74 mins) | O-demethyl-Indomethacin (1.52 mins) |
| aluC09M11 | T291D | 92.6 | 7.4 |
| aluC09M12 | T291E | 94.6 | 5.4 |
| aluC09M17 | T291N | 84.4 | 15.6 |
| aluC09M18 | T291Q | 83.6 | 16.4 |
| aluC09M19 | T291A | 93.5 | 6.5 |
| aluC09M20 | T291V | 89.2 | 10.8 |
| aluC09M24 | T291E, A47I | 94.2 | 5.8 |
| aluC09M30 | T291E, V315L | 90.1 | 9.9 |
| aluC09M31 | T291S | 84.8 | 15.2 |
| aluC09M33 | T291I | 92.8 | 7.2 |
| aluC09M34 | T291M | 96.2 | 3.8 |
| aluC09M35 | T291P | 94.1 | 5.9 |
| aluC09M36 | T291F | 80.3 | 19.7 |
| aluC09M37 | T291W | 89.0 | 11.0 |
| aluC09M38 | T291H | 83.8 | 16.2 |
| aluC09M39 | T291K | 93.0 | 7.0 |
| aluC09M40 | T291R | 88.8 | 11.2 |
| aluC09 | Wild Type | 83.6 | 16.4 |

TABLE 8

Table 8: Metabolism of various substrates catalysed by cytochrome P450 aluC09 mutants aluC09M11, aluC09M12, aluC09M17, aluC09M18, aluC09M19, aluC09M20, aluC09M21, aluC09M24, aluC09M30, aluC09M31, aluC09M33, aluC09M34, aluC09M35, aluC09M36, aluC09M37, aluC09M38, aluC09M39, aluC09M40 compared to P450 aluC09 wild-type, as determined by UPLC-PDA-MS. Values are percent of each substrate being converted.

| | P450 Identity | | | | | | | | | | | | | | | | | | |
|---|---|---|---|---|---|---|---|---|---|---|---|---|---|---|---|---|---|---|---|
| | WT | M11 | M12 | M17 | M18 | M19 | M20 | M21 | M24 | M30 | M31 | M33 | M34 | M35 | M36 | M37 | M38 | M39 | M40 |
| [CYP]/μM | 9.7 | 15.3 | 6.4 | 8.2 | 8.9 | 10.5 | 9.9 | 24 | 4.8 | 6.1 | 17.9 | 1.6 | 3.8 | 4.1 | 11.5 | 11.1 | 12.6 | 6.4 | 6.4 |
| % conversions (avg) | | | | | | | | | | | | | | | | | | | |
| Ritonavir | 59.6 | 57.3 | 31.9 | 51.7 | 53.3 | 65.4 | 100 | 28.2 | 30.4 | 20.9 | 73.5 | 41.3 | 50.3 | 37.6 | 73.8 | 64.1 | 64.2 | 39.2 | 53.4 |
| Celecoxib | 2.5 | 3.2 | 5.4 | 8.1 | 3.7 | 4.5 | 2.2 | 1 | 3.6 | 3.9 | 3.6 | 2.8 | 6.8 | 1.5 | 5.7 | 7.2 | 2.3 | 0 | 0 |
| Epothilone B | 18.4 | 8.5 | 50.8 | 16.8 | 24.8 | 4.5 | 21.1 | 33.8 | 52.3 | 32.2 | 35.3 | 21.8 | 30.7 | 20.6 | 62.3 | 50.2 | 13.4 | 1.6 | 2.4 |
| Buparvaquone | 14 | 15.8 | 9.7 | 17.9 | nt | 17.1 | 15.4 | nt | nt | nt | 11.3 | 8.2 | 11.6 | 7.1 | 9.5 | 10.5 | 4.1 | 0 | 0 |
| BIRB796 | 13.4 | nt | 23 | 23.2 | 24.3 | 16.6 | 22.4 | nt | 18.9 | 18 | 15.3 | 13.5 | 18 | 4.6 | 20 | 10 | 13.6 | 0 | 0 |
| Bosentan | 98.8 | 100 | 100 | 100 | 100 | nt | nt | 59 | 100 | 80.4 | 99 | 98.9 | 99 | 98.4 | 99.5 | 98.6 | 98.7 | 85.1 | 76.5 |
| Valsartan | 28.9 | 26 | 38 | 21.9 | 27.1 | nt | 13.1 | 19 | 21.2 | 20 | 33.9 | 12.4 | 43.2 | 21.8 | 45.7 | 41 | 61.9 | 7.8 | 7.3 |
| Ruxolitinib | 46.6 | 35.7 | 48.9 | 33.9 | 38.5 | 50.8 | 70.7 | 19 | 37.7 | 37.5 | 41.7 | 30.6 | nt | 34.1 | 42.1 | 34.2 | 30.8 | 5.3 | 5.2 |
| 4-pyrrolidyl-acetophenone | 5.6 | 21.4 | 30.8 | 21.7 | 14.1 | 0.7 | nt | 15.8 | 7.6 | 16.6 | 4.9 | 7.9 | 7.3 | 3.3 | 6.8 | 7.3 | 2.9 | 1.5 | 1.7 |
| Tivantinib | 41.4 | 34.2 | 7.2 | 53.9 | 59.7 | 26.1 | 22.2 | 29.6 | 6.8 | 2.7 | 56 | 29.6 | 59.1 | 35.7 | 30.4 | 31 | 27.6 | 7.2 | 5.3 |
| Tofacitinib | 1.4 | 1.4 | 0 | 4.4 | 2.2 | 0 | 4.5 | 2.7 | 0 | 0 | 1.5 | 1.1 | 3.1 | 1.1 | 2.4 | 0.9 | 0.7 | 0 | 0.4 | nt: substrate not tested or no validated test data available

The invention claimed is:

1. A kit comprising:
   i) an enzyme having cytochrome P-450 activity and comprising the amino acid sequence set forth in SEQ ID NO: 110, or a sequence having at least 90% identity thereto, wherein the amino acid residue at the position corresponding to position 291 of SEQ ID NO: 110 is aspartic acid, glutamic acid, asparagine, glutamine, valine, methionine, phenylalanine, tryptophan, isoleucine, proline or histidine; or
   ii) a microorganism that expresses an enzyme as defined in (i); or
   iii) an extract of the microorganism of (ii).

2. The kit of claim 1, further comprising a reducing agent.

3. The kit of claim 1, further comprising one or more other cytochrome P-450 enzymes.

4. The kit of claim 1, wherein the cytochrome P-450 enzyme, microorganism or extract is lyophilised.

5. The kit of claim 1, wherein the amino acid at the position of the enzyme corresponding to position 291 of SEQ ID NO: 110 is glutamic acid.

6. The kit of claim 5, wherein the enzyme comprises the amino acid sequence set forth in SEQ ID NO: 12 or a sequence having at least 95% identity thereto.

7. The kit of claim 5, wherein the amino acid at the position of the enzyme corresponding to position 47 of SEQ ID NO: 110 is isoleucine, or the amino acid at the position of the enzyme corresponding to position 315 of SEQ ID NO: 110 is leucine.

8. The kit of claim 7, wherein the enzyme comprises the amino acid sequence set forth in SEQ ID NO: 84 or 108, or a sequence having at least 95% identity thereto.

9. The kit of claim 1, wherein the enzyme comprises the amino acid sequence set forth in SEQ ID NO: 8, 16, 20, 28, 44, 48, 52, 56, 60 or 64, or a sequence having at least 95% identity thereto.

10. An enzyme having cytochrome P-450 activity and comprising the amino acid sequence set forth in SEQ ID NO: 110, or a sequence with at least 90% sequence identity thereto, wherein the amino acid residue at the position corresponding to position 291 of SEQ ID NO: 110 is aspartic acid, glutamic acid, asparagine, glutamine, valine, methionine, phenylalanine, tryptophan, isoleucine, proline or histidine.

11. The enzyme of claim 10, wherein the amino acid at the position corresponding to position 291 of SEQ ID NO: 110 is glutamic acid.

12. The enzyme of claim 11, comprising the amino acid sequence set forth in SEQ ID NO: 12 or a sequence having at least 95% identity thereto.

13. The enzyme of claim 11, wherein the amino acid at the position corresponding to position 47 of SEQ ID NO: 110 is isoleucine, or the amino acid at the position corresponding to position 315 of SEQ ID NO: 110 is leucine.

14. The enzyme of claim 13, comprising the amino acid sequence set forth in SEQ ID NO: 84 or 108, or a sequence having at least 95% sequence identity thereto.

15. The enzyme of claim 10, comprising the amino acid sequence set forth in SEQ ID NO: 8, 16, 20, 28, 44, 48, 52, 56, 60 or 64, or a sequence having at least 95% identity thereto.

16. A method for the production of a hydroxylated organic compound, comprising reacting the organic compound with an enzyme according to claim 10.

17. The method according to claim 16, wherein the enzyme is used to catalyse the hydroxylation of a propyl group or a butyl group of the compound.

18. The method according to claim 16, wherein the P-450 enzyme is in purified form, part-purified form, a crude enzyme extract or a recombinant host cell.

19. The kit of claim 2, wherein the reducing agent is a ferredoxin reductase and a ferredoxin, wherein these are provided either as discrete components or linked within a single fusion protein construct.

20. The kit of claim 1, further comprising a buffer.

* * * * *